(12) United States Patent
Kawaoka et al.

(10) Patent No.: US 9,222,118 B2
(45) Date of Patent: Dec. 29, 2015

(54) SCREEN FOR INHIBITORS OF FILOVIRUS AND USES THEREFOR

(75) Inventors: Yoshihiro Kawaoka, Middleton, WI (US); Shinji Watanabe, Madison, WI (US); Yasuko Hatta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 546 days.

(21) Appl. No.: 13/127,951

(22) PCT Filed: Nov. 6, 2009

(86) PCT No.: PCT/US2009/006019
§ 371 (c)(1),
(2), (4) Date: Jul. 15, 2011

(87) PCT Pub. No.: WO2010/053573
PCT Pub. Date: May 14, 2010

(65) Prior Publication Data
US 2011/0263554 A1    Oct. 27, 2011

Related U.S. Application Data

(60) Provisional application No. 61/112,524, filed on Nov. 7, 2008, provisional application No. 61/150,486, filed on Feb. 6, 2009.

(51) Int. Cl.
| | |
|---|---|
| *A61K 31/56* | (2006.01) |
| *A01N 43/42* | (2006.01) |
| *A61K 31/44* | (2006.01) |
| *A01N 43/00* | (2006.01) |
| *A61K 31/445* | (2006.01) |
| *C12Q 1/18* | (2006.01) |
| *A61K 31/00* | (2006.01) |
| *A61K 31/05* | (2006.01) |
| *A61K 31/135* | (2006.01) |
| *A61K 31/351* | (2006.01) |
| *A61K 31/352* | (2006.01) |
| *A61K 31/365* | (2006.01) |
| *A61K 31/395* | (2006.01) |
| *A61K 31/40* | (2006.01) |
| *A61K 31/404* | (2006.01) |
| *A61K 31/4155* | (2006.01) |
| *A61K 31/433* | (2006.01) |
| *A61K 31/435* | (2006.01) |
| *A61K 31/438* | (2006.01) |
| *A61K 31/45* | (2006.01) |
| *A61K 31/451* | (2006.01) |
| *A61K 31/4535* | (2006.01) |
| *A61K 31/46* | (2006.01) |
| *A61K 31/573* | (2006.01) |
| *C12Q 1/70* | (2006.01) |

(52) U.S. Cl.
CPC . *C12Q 1/18* (2013.01); *A61K 31/00* (2013.01); *A61K 31/05* (2013.01); *A61K 31/135* (2013.01); *A61K 31/351* (2013.01); *A61K 31/352* (2013.01); *A61K 31/365* (2013.01); *A61K 31/395* (2013.01); *A61K 31/40* (2013.01); *A61K 31/404* (2013.01); *A61K 31/4155* (2013.01); *A61K 31/433* (2013.01); *A61K 31/435* (2013.01); *A61K 31/438* (2013.01); *A61K 31/45* (2013.01); *A61K 31/451* (2013.01); *A61K 31/4535* (2013.01); *A61K 31/46* (2013.01); *A61K 31/573* (2013.01); *C12Q 1/701* (2013.01); *G01N 2333/08* (2013.01); *G01N 2500/10* (2013.01)

(58) Field of Classification Search
USPC .......................................... 514/181, 278, 324
See application file for complete search history.

(56) References Cited

FOREIGN PATENT DOCUMENTS

| WO | WO-2010053573 A2 | 5/2010 |
|---|---|---|
| WO | WO-2010053573 A3 | 7/2010 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
"International Application Serial No. PCT/US2009/006019, Written Opinion mailed Jun. 10, 2010", 17 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 17 Pgs.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000, ISSN: 0166-3542, abstract, (Sep. 1, 2004), 209-215.
Halfmann, P., et al., "Generation of biologically contained Ebola viruses", Proceedings of the National Academy of Sciences of the United States of America, vol. 105, No. 4, XP002563467, ISSN: 1091-6490, the whole document, (Jan. 29, 2008), 1129-1133.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR. (Suppl 1), XP002574255, ISSN: 0022-1899, abstract, (Feb. 1999), 240-247.

(Continued)

*Primary Examiner* — Marcos Sznaidman
(74) *Attorney, Agent, or Firm* — Schwegman Lundberg & Woessner, P.A.

(57) ABSTRACT

The invention provides methods to identify agents useful to prevent, inhibit or treat viral infections, e.g. filovirus infections, as well as compositions having one or more agents to prevent, inhibit or treat viral infection.

16 Claims, 123 Drawing Sheets

(56) References Cited

OTHER PUBLICATIONS

Towner, J S, et al., "Generation of eGFP express ing recombinant Zaire ebolavirus for analysis of early pathogenesis events and high-throughput antiviral drug screening", Virology, Academic Press, Orlando, US, vol. 332, No. 1, XP004715289, ISSN: 0042-6822, the whole document, (Feb. 5, 2005), 20-27.

Watanabe, S., et al., "Ebola virus (EBOV) VP24 inhibits transcription and replication of the EBOV genome", J Infect Dis., 196(Suppl 2), (Nov. 15, 2007), S284-90.

* cited by examiner

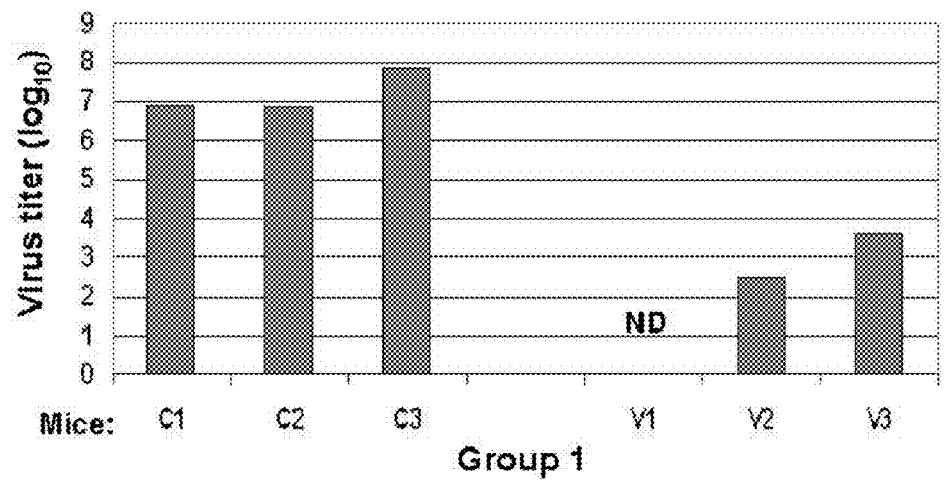
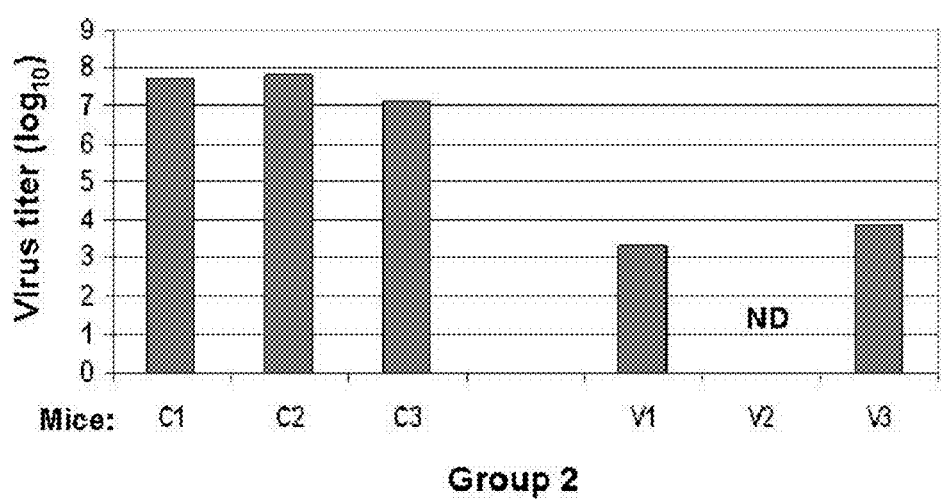
Fig. 5

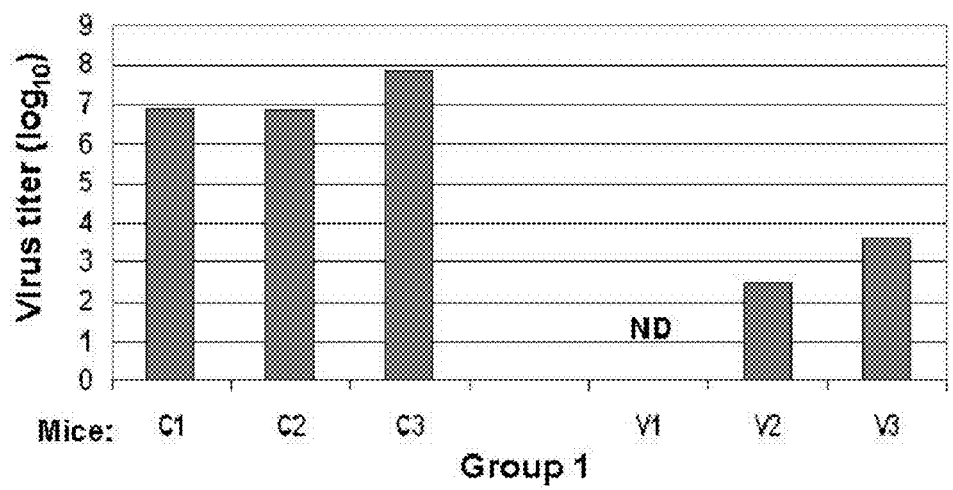
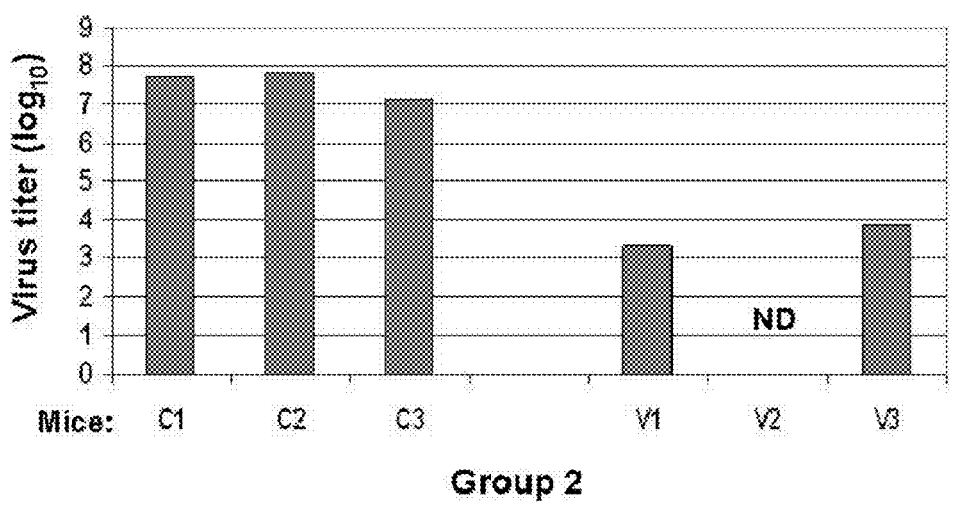
Fig. 9

NC_006432

1 cggacacaca aaaagaaaga aaagtttttt atacttttg tgtgcgaata actatgagga
61 agattaatca ttttcctcaa actcaaacta atattaacat tgagattgat ctcatcattt
121 accaattgga gacaatttaa ctagtcaatc ccccatttgg gggcattcct aaagtgttgc
181 aaaggtatgt gggtcgtatt gctttgcctt ttcctaacct ggctcctcct acaattctaa
241 cctgcttgat aagtgtgatt acctgagtaa tagactaatt tcgtcctggt aattagcatt
301 ttctagtaaa accaatacta tctcaagtcc taagagaagg tgagaagagg gtcccgaggt
361 atccctccag tccacaaaat ctagctaatt ttagctgagt ggactgatta ctctcatcac
421 acgctaacta ctaagggttt acctgagagc ctacaacatg gataaacggg tgagaggttc
481 atgggccctg ggaggacaat ctgaagttga tcttgactac cacaaaatat taacagccgg
541 gctttcggtc caacaaggga ttgtgcgaca aagagtcatc ccggtatatg ttgtgagtga
601 tcttgagggt atttgtcaac atatcattca ggcctttgaa gcaggcgtag atttccaaga
661 taatgctgac agcttccttt tactttatg tttacatcat gcttaccaag gagatcatag
721 gctcttcctc aaaagtgatg cagttcaata cttagagggc catggtttca ggtttgaggt
781 ccgagaaaag gagaatgtgc accgtctgga tgaattgttg cccaatgtca ccggtggaaa
841 aaatcttagg agaacattgg ctgcaatgcc tgaagaggag acaacagaag ctaatgctgg
901 tcagttttta tcctttgcca gtttgtttct acccaaaact gtcgttgggg agaaaagcgtg
961 tctggaaaaa gtacaaaggc agattcaggt ccatgcagaa caagggctca ttcaatatcc
1021 aacttcctgg caatcagttg gacacatgat ggtgatcttc cgtttgatga gaacaaactt
1081 tttaatcaag ttcctactaa tacatcaggg gatgcacatg gtcgcaggcc atgatgcgaa
1141 tgacacagta atatctaatt ctgttgccca agcaaggttc tctggtcttc tgattgtaaa
1201 gactgttctg gaccacatcc tacaaaaaac agatcttgga gtacgacttc atccactggc
1261 caggacagca aaagtcaaga atgaggtcag ttcattcaag gcagctcttg gctcacttgc
1321 caagcatgga gaatatgctc catttgcacg tctcctcaat ctttctggag tcaacaactt
1381 ggaacatggg ctttatccac aactctcagc cattgctttg ggtgttgcaa ctgcccacgg
1441 gagcacgctg gctggtgtta atgtaggggga gcaatatcag caactgcgtg aggctgctac
1501 tgaagctgaa aagcaactcc aacaatatgc tgaaacacgt gagttggaca accttgggct
1561 tgatgaacag gaaaagaaga ttctcatgag cttccaccag aagaagaatg agatcagctt
1621 ccagcaaact aacgcaatgg taaccctgag gaaagagcgg ctggccaaac tgaccgaagc
1681 catcacgact gcatcaaaga tcaaggttgg agatcgttat cctgatgaca atgatattcc
1741 atttcccggg ccgatctatg atgaaaccca ccccaaccct tctgatgata atcctgatga
1801 ttcacgtgat acaactatcc caggtggtgt tgttgacccg tatgatgatg agagtaataa
1861 ttatcctgac tacagaggatt cggctgaagg caccacagga gatcttgatc tcttcaattt
1921 ggacgacgac gatgacgaca gccaaccagg accaccagac aggggggcaga gcaaggaaag
1981 agcggctcgg acacatggcc tccaagatcc gaccttggac ggagcgaaaa aggtgccgga
2041 gttgacccca ggttcccacc aaccaggcaa cctccacatc accaagccgg gttcaaacac
2101 caaccaacca caaggcaata tgtcatctac tctccagagt atgaccccta tacaggaaga
2161 atcagagccc gatgatcaga aagatgatga tgacgagagt ctcacatcc ttgactctga
2221 aggtgacgaa gatgttgaga gcgtatcagg ggagaacaac ccaactgtag ctccaccagc
2281 accagtctac aaagatactg gagtagacac taatcagcaa aatggaccaa gcaatgctgt
2341 agatggtcaa ggttctgaaa gtgaagctct cccaatcaac cccgaaaagg gatctgcact
2401 ggaagaaaca tattatcatc tcctaaaaac acagggtcca tttgaggcaa tcaattatta
2461 tcacctaatg agtgatgagc ccattgcttt tagcactgaa agtggcaagg aatatatctt

*Fig. 10A*

```
2521 cccagattct cttgaagaag cctacccgcc ttggttgagt gagaaggagg ccttagagaa
2581 agaaaatcgt tatctggtca ttgatggcca gcaattcctc tggccagtaa tgagcctaca
2641 ggacaagttc cttgctgttc ttcaacatga ctgaggaccc atgattagta gattttgttt
2701 attctgagct tgattataat tgttttgata attcaagtat gagcaaccaa cccgaaatat
2761 aaaccctatt ttagttatga ggaaattaaa taaataatct gtaagttgta ggactatgaa
2821 gagctgcttg tgtcaattta tcacgggcta atacccatac cgcaagaata attatttagt
2881 aattttgatc agcttatgat atgtaccaat aggaaaacat tatagcatta aaacataaag
2941 tatccttcga tgagcttagg aggataatat cctgatgaat tctatagaac ttaggattaa
3001 gaaaaaattc atgatgaaga ttaaaacctt catcatcctt taaaaagaga gctattcttt
3061 atctgaatgt ccttattaat gtctaagagc tattattttg taccctctta gcctagacac
3121 tgcccagcat ataagccatg cagcaggata ggacttatag acatcatgga cccgaagtgt
3181 ctggctggtt ttctgagcaa ttaatgaccg gcaaaatacc gctaacagag gtgtttgttg
3241 atgttgaaaa caaaccaagt cctgccccga taaccattat tagtaagaat cccaagacaa
3301 cacgtaaaag tgataagcaa gtccaaacag atgatgccag tagcttattg acagaagaag
3361 tcaaggctgc cataaattcg gtgatatcag ctgtgcgtcg gcaaaccaat gctattgaat
3421 cactagaagg tcgagtaaca actcttgagg ccagcttaaa accegttcaa gacatggcaa
3481 agaccatatc atccctgaat cgcagctgtg ccgaaatggt tgcaaaatac gacctactgg
3541 tgatgaccac tgggcgagca actgccactg ctgcagcaac agaagcatat tggaatgaac
3601 atggacaagc acctccaggc ccatcattgt acgaggatga tgctattaag gctaaattga
3661 aagatccgaa cgggaaggtt ccagaaagtg tcaaacaggc ctacataaat ctagatagca
3721 caagtgccct caatgaggaa aatttcgggc gaccttacat ttcagcaaaa gatctcaagg
3781 aaatcatcta tgaccatctc ccaggatttg ggacagcttt tcatcagttg gtgcaggtta
3841 tctgcaaaat tggtaaggat aataatatcc tagacataat tcatgcagaa ttccaagcaa
3901 gcttggctga gggagactcc ccccagtgtg cattaatcca gataacaaaa cggatccctg
3961 ctttccaaga tgcctctcct ccaattgtgc atatcaagtc tcgaggagat atacccaaag
4021 cctgtcagaa aagcctccgg ccggtcccac cgtcaccaaa gatcgataga ggttgggtct
4081 gtatttttca attccaagac gggaaggccc ttgggctaaa aatatgatac agaagcaagg
4141 taagctcatt ttgcgatggc caaatgatac ttatgactgt ttaaaatcaa gttagactaa
4201 tagtctattg tgtcataagc ttataagtca gttttaaatt tcccctctat cctaatcaat
4261 tgataatgct gtcaataggg aaattccct gtattgtaat aagacctcat taacatattt
4321 cccctgctta gtactatgca gaaaccccg agcaaattaa aattgatgaa gattaagaaa
4381 aagagggatt ttctcaggaa aaatctttt tcttaccttc atctcattta aacaaattta
4441 ggactcagga aaaatgagaa gggtcactgt gccgactgca ccacctgcct atgctgacat
4501 tggctatcct atgagcatgc ttcccatcaa gtcaagcagg gctgtgagtg gaattcaaca
4561 gaaacaagag gtccttcctg gaatggatac accatcaaat tctatgagac ctgttgctga
4621 tgataacatt gatcatacaa gtcatacccc gaacggagtg gcctcagcat tcatcttgga
4681 ggcaactgtc aatgtgatct cggggcccaa agtcctcatg aaacaaatcc ctatttggtt
4741 gccactcgga attgctgacc aaaaaaacgta cagttttgac tcaacaacag cagcaattat
4801 gctcgcatct tatacgatca cccattttgg aaaggccaac aaccccctcg ttagagtgaa
4861 tcgacttggt cagggaatac cggatcaccc actcagattg ctcaggatgg ggaaccaggc
4921 tttccttcaa gagtttgtgc taccaccagt tcaactgccg caatatttca cttttgatct
4981 gactgcactc aaactagtga cacagcctct ccctgctgca acatggacag atgagactcc
5041 gagcaaacctt tcaggagccc ttcgtcccgg gctttcattt caccaaaagc tgagacccgt
5101 tctacttcca ggcaagacgg gaaagaaagg gcatgtttct gatctgactg ccccagacaa
5161 aattcagaca attgtgaacc tgatgcaaga tttcaaaatc gtgccaattg atccagctaa
5221 gagtatcatt gggatcgagg ttccagaatt gctggtccac aagctcactg ggaagaaaat
```

*Fig. 10B*

```
5281 gagtcagaag aatggacagc ctataattcc tgtcttactc ccaaaataca ttgggctaga
5341 tccaatctca cctggagacc tgactatggt cataacacca gattatgatg attgtcattc
5401 acctgccagt tgctcttatc tcagtgaaaa gtgattctca caaagtgaga gaaacacctc
5461 cagtaaagaa atcaaatctt atctatagca actcaatcga cttttaggaa gctagcagtc
5521 catatactat gggacaactc aaccctcttg ttaaaatgta ctaatcgggt caaggaactc
5581 tcactgatca agcctgaatc caagatagaa ccagcccaaa gggcctcccc agagtctctt
5641 acaagcttag ccaatcaatt aacatgcata agcgatccat acttcgccca atcagtgtcc
5701 gatgttcacc ccttcaagcc tccttcctag caaattgacc tagctgtacc aagagattcc
5761 ctcagcctcc ttctcaaata acctgatcct cgagggttac accttcacca ctctatgctc
5821 atttcaccca aacataaaat gaaatgtctt aacatgattg caccattaag aaaaacaaat
5881 ctgatgaaga ttaagcctga tgaaggccca accttcatct ttttaccata atcttgttct
5941 cagtaccatt tgataagggt acacttgcca atacgccccc atcctaaggg tctcgcaatg
6001 gggggtctta gcctactcca attgcccagg gacaaatttc ggaaaagctc tttctttgtt
6061 tgggtcatca tcttattcca aaaggccttt tccatgcctt tgggtgttgt gactaacagc
6121 actttagaag taacagagat tgaccagcta gtctgcaagg atcatcttgc atctactgac
6181 cagctgaaat cagttggtct caacctcgag gggagcggag tatctactga tatcccatct
6241 gcaacaaagc gttggggctt cagatctggt gttcctccca aggtggtcag ctatgaagcg
6301 ggagaatggg ctgaaaattg ctacaatctt gaaataaaga agccggacgg gagcgaatgc
6361 ttaccccac cgccagatgg tgtcagaggc tttccaaggt gccgctatgt tcacaaagcc
6421 caaggaaccg ggccctgccc aggtgactac gcctttcaca aggatggagc tttcttcctc
6481 tatgacaggc tggcttcaac tgtaatttac agaggagtca attttgctga gggggtaatt
6541 gcattcttga tattggctaa accaaaagaa acgttccttc agtcacccc cattcgagag
6601 gcagtaaact acactgaaaa tacatcaagt tattatgcca catcctactt ggagtatgaa
6661 atcgaaaatt ttggtgctca acactccacg acccttttca aaattgacaa taatactttt
6721 gttcgtctgg acaggcccca cacgcctcag ttccttttcc agctgaatga taccattcac
6781 cttcaccaac agttgagtaa tacaactggg agactaattt ggacactaga tgctaatatc
6841 aatgctgata ttggtgaatg ggctttttgg gaaaataaaa aaatctctcc gaacaactac
6901 gtggagaaga gctgtctttc gaagctttat cgctcaacga gacagaagac gatgatgcgg
6961 catcgtcgag aattacaaag ggaagaatct ccgaccgggc caccaggaag tattcggacc
7021 tggttccaaa gaattcccct gggatggttc cattgcacat accagaaggg gaaacaacat
7081 tgccgtctca gaattcgaca gaaggtcgaa gagtaggtgt gaacactcag gagaccatta
7141 cagagacagc tgcaacaatt ataggcacta acggcaacca tatgcagatc tccaccatcg
7201 ggataagacc gagctccagc caaatcccga gttcctcacc gaccacggca ccaagccctg
7261 aggctcagac ccccacaacc cacacatcag gtccatcagt gatggccacc gaggaaccaa
7321 caacaccacc gggaagctcc cccggcccaa caacagaagc acccactctc accaccccag
7381 aaaatataac aacagcggtt aaaactgtcc tgccacagga gtccacaagc aacggtctaa
7441 taacttcaac agtaacaggg attcttggga gtcttgggct tcgaaaacgc agcagaagac
7501 aaaactaacac caaagccacg ggtaagtgca atcccaactt acactactgg actgcacaag
7561 aacaacataa tgctgctggg attgcctgga tcccgtactt tggaccgggt gcggaaggca
7621 tatacactga aggcctgatg cataaccaaa atgccttagt ctgtggactt aggcaacttg
7681 caaatgaaac aactcaagct ctgcagcttt tcttaagagc cacaacggag ctgcggacat
7741 ataccatact caataggaag gccatagatt tccttctgcg acgatggggc gggacatgca
7801 ggatcctggg accagattgt tgcattgagc cacatgattg gacaaaaaac atcactgata
7861 aaatcaacca aatcatccat gatttcatcg acaaccccctt acctaatcag gataatgatg
7921 ataattggtg gacgggctgg agacagtgga tccctgcagg aataggcatt actggaatta
7981 ttattgcaat tattgctctt ctttgcgttt gcaagctgct ttgctgaata tcaatttgaa
```

*Fig. 10C*

```
8041 tcatcaattt aagcttgata catttctagc attttaaatt ataaaccgat actgatactt
8101 gaaaatcagg ctaatgccaa gttctgtgca aaacttgaaa gtaggtttac aaaaatcctt
8161 tggactggaa tgctttgata ctctttctca atactatata agttccttcc caagaataat
8221 attgatgaag attaagaaaa agtgacattg tgcccacttt tgtaatcttc atccacctac
8281 acattcatat tcaggaatct ttgaattaac cctcacactt gcttaggaaa gagcctatcc
8341 tctacaagaa tcccgaggcg gcaattcagt taatttcata tcaagataac atccatttcc
8401 aagaccacag ataactatat tattaatctt taccacaaat atggagaggg gtcgtgagcg
8461 cgggagatca aggaattcac gtgccgacca gcaaaattca acaggtcctc aatttaggac
8521 aagatccatt tcccgggata agacaacaac agactaccgt agtagtcgaa gtacttcgca
8581 agttagagtc cctacggttt tccataagaa aggtactggg acccttactg tcctccagc
8641 acctaaggat gtttgtccta ctctcagaaa aggatttcta tgtgatagta atttctgtaa
8701 aaaggaccat caacttgaaa gcctaaccga ccgggagctc ctacttctta tagcacggaa
8761 gacctgtgga tcaactgatt catcgcttaa tatagctgct cctaaagacc taagactagc
8821 aaatcctacg gctgatgact tcaagcaaga cggcagtcca aaattaaccc taaaattact
8881 agtcgagact gctgagtttt gggccaatca gaatattaat gaagtagatg atgcaaaact
8941 ccgtgctctc ttgacgttga gtgctgtctt agtgcggaaa ttctctaagt cacagcttag
9001 tcaattatgt gagagtcatc ttaggaggga aaacttagga caagaccaag ctgaatcagt
9061 tctcgaggtt tatcaacgtt tacatagtga caaaggaggt gcttttgagg cagcactatg
9121 gcaacagtgg gatagacaat cattaactat gtttatatct gcttcctcc atgtagcatt
9181 gcaactttcc tgtgagagct ccactgtagt gatatcaggc ctacgcttac ttgccccccc
9241 aagcgttaat gaagggctcc ctcctgcacc aggggaatat acttggtcag aagatagtac
9301 aacttagcct gtagggagga caagtaaaac aagatgccct tatcctctat agatggtatt
9361 tttagagagg gggacaggat aggaataaag ataatgacta aagccaatat aaagatacga
9421 acacaagtag aaattaaaat agaaatcaaa acaatctccc cttattcaat atgaaatata
9481 atagtgagta tttgtttcat gatgtcaatc atttattgtt aaaaataaac aaagtcagta
9541 agagtgttag gatcgttata ttgcaaggat cctccctaga agcgttgaat catctcaagt
9601 agcctagaac aagaacagca gagcattaaa ttgaaataga taataaggat attgcttgtt
9661 tttaagatag ttttaggaag tttaaaatta agaaaaagaa cccatggaca cactctagca
9721 ttgaggatgg ggttcccttg atgatagtat agtcttaggt atagggtagt cctacacgta
9781 ctatattata cagtctaaac ttgtaaaatt aaactacaag aacatgatga aaattaatga
9841 gaaggttcca agattgactt caatccaaac accttgctct gccaattttc atctccttaa
9901 gatatatgat tttgttcctg cgagataagg ttatcaaata gggtgtgtat ctcttttaca
9961 tatttgggct cccactaggc tagggtttat agttaaggaa gactcatcac attttttatt
10021 gaactagtct actcgcagaa tcctaccggg aatagaaatt agaacatttg tgatactttg
10081 actataggaa ataatttca acactacctg agatcaggtt attcttccaa cttattctgc
10141 aagtaattgt ttagcatcat aacaacaacg ttataattta agaatcaagt cttgtaacag
10201 aaataaagat aacagaaaga acctttatta tacgggtcca ttaattttat aggagaagct
10261 ccttttacaa gcctaagatt ccattagaga taaccagaat ggctaaagcc acaggccggt
10321 acaacttggt aacaccaaaa cgggagctag agcaaggagt tgtgtttagc gacctatgca
10381 acttcctagt gactccaact gtgcaaggat ggaaggttta ctgggctgga cttgagtttg
10441 atgtcaacca aaagggtatt accctgttaa atcgtcttaa agtgaatgat tttgctcctg
10501 catgggcgat gacccggaac ctcttcccac acttgttcaa aaaccaacag tctgaagtcc
10561 aaactcccat ttgggccttg agggtaattc ttgccgccgg gattcttgac caattaatgg
10621 atcattccct cattgagccg ctatcagggg ccctgaacct aattgctgat tggttactaa
10681 caacatctac taatcacttc aacatgagaa ctcaacgagt aaaggaccaa ctgagcatga
10741 ggatgttatc tcttataagg tcaaatatta ttaactttat aaataagctc gagactcttc
```

*Fig. 10D*

10801 atgtcgttaa ttacaaggga cttctaagca gtgttgagat aggaacacca agctatgcaa
10861 tcatcattac caggactaat atgggttatc ttgtcgaggt tcaggaacca gataaatctg
10921 cgatggatat acgacaccct ggtcctgtca aattctcctt actacatgaa tcgacactta
10981 aacctgttgc cactcctaaa ccatcaagca ttacttcatt gatcatggag ttcaacagtt
11041 ctttggcaat ttaattgccg taataaaaat tgtacgatag ggctaacatt gattccataa
11101 tccatcgtag gacagaatca ttttcctgta tgatcttagt ttaatctctc tttatacaat
11161 gattaataag gagcctgttt aaaatgttac aaaagtatac tgtttgaacc cctagtatcc
11221 ctgtaaatat cctcattcaa ttttttgctt ttacatgtgt agtcaccigt atagcatgac
11281 cctagtcatg cctttaatta atacttaatc taacagttaa tataatgtat aactttccat
11341 gttcaaagag tagtcaaaac aatgtgagat ccagtttcac tcacagcatc tattcactat
11401 ttacagtatg atgagcccaa attaacacgg tagaggtcta gatttattaa tagaacgagg
11461 aagattaaga aaaagtccat aatgctgggg aggcaatcct tgccaccata ggactttttc
11521 aattcctcta ttttatgatg gctacccaac atacacaata tcctgatgca agattgtctt
11581 ccccaattgt cttagaccaa tgtgacctag tgacaagagc atgtggactt tactctgagt
11641 attcgctgaa ccctaaacta aagacatgcc gtttaccgaa acatatctat agattaaaat
11701 atgacactat tgttttacga tttattagtg atgtccctgt agctacaatc ccaatagact
11761 acattgctcc gatgttaata aatgttctgg cagatagtaa aaatgtacca ttggaacctc
11821 cctgcttgag tttcttggat gaaatagtca attataccgt gcaggatgca gccttcctta
11881 attattacat gaatcagatt aaaacacagg aaggagtaat tacagatcaa ttaaaacaga
11941 acattcgtag ggtcattcac aaaaacagat atctatctgc tctattcttc tggcatgatc
12001 ttgccatcct cacccgtcga gggagaatga accgaggaaa tgtgcgctcc acttggtttg
12061 taacgaatga ggttgttgac attctaggat atggtgatta tatcttctgc aagatcccta
12121 ttgctctatt accaatgaac acagctaatg ttccacatgc atcaactgac tggtaccaac
12181 ctaatatctt caaggaggct attcaaggac acacacatat tatttcagtc tctacagccg
12241 aggtccttat tatgtgtaag gatcttgtca caagtcgttt taatacccct ctgattgctg
12301 agttagccag gttggaagat ccagtgtctg ctgattatcc actagtagat aatattcaat
12361 ctctgtataa cgcaggagac tacctgttgt ccatattggg atcagagggg tacaaaataa
12421 tcaaatatct cgaacctctg tgtttggcta agattcaact atgttcccaa tatacagaac
12481 gaaaagggcg gtttttaacc cagatgcatc ttgcagttat tcagacattg cgtgaactcc
12541 tccttaatag agggttgaaa aaatcacaat tgtctaaaat ccgcgagttt caccaactgt
12601 tgctcagact ccgatctaca ccacaacaat tatgtgaatt attttcaatc caaaaacact
12661 ggggccaccc agttctgcat agtgaaaagg ccatccaaaa ggttaaaaat catgcaacag
12721 ttctaaaggc attgcggccg attatcatct ttgaaacgta ttgtgtattc aagtatagtg
12781 ttgcaaaaca tttctttgat agtcaaggca cttggtacag tgtgatatca gaccgatgtt
12841 taacgccggg attgaattcc tacattaggc gaaatcaatt ccctccactt ccaatgatca
12901 aagatctttt atgggaattt taccatttgg atcatcctcc attattctcc acgaagatca
12961 ttagtgacct cagcattttc attaaagacc gcgcaacagc agttgaacaa acctgttggg
13021 atgcagtttt tgagcctaac gttttgggct acagtccacc ttatcgattc aataccaaac
13081 gtgtacctga acaattcctg gagcaagagg attttttctat tgagagtgtc ttacaatacg
13141 cccaagaact taggtactta ttgccccaga atcgaaattt ttcttttca ttgaaggaaa
13201 aagaattaaa tgttggtagg acatttggaa aattgcctta tttaaccagg aatgtccaaa
13261 ccctctgcga agcattactt gcagatggtt tggctaaagc ctttccaagc aatatgatgg
13321 ttgtcacaga gagggaacaa aaggagagcc tccttcacca agcatcctgg caccatacaa
13381 gtgatgattt cggagagcat gccacagttc gtggaagtag tttgtcaca gacctggaaa
13441 aatacaatct ggccttcagg tatgaattca cagctcccctt catcaaatat tgcaaccaat
13501 gctatggggt tcgcaatgtc tttgattgga tgcacttcct aattccgcaa tgttacatgc

```
13561 atgttagtga ttattataac ccaccacata atgtaacctt agagaatagg gaatatcccc
13621 ccgaaggacc aagtgcttat agaggccacc ttggcggtat tgaggggctt caacaaaagt
13681 tatggactag tatctcatgt gctcaaatct cattggtaga gatcaagacc gggttcaaat
13741 tgcgatcagc agtcatgggg gataatcaat gtattacagt attatcagtc tttccactag
13801 aatctagtcc gaatgagcag gagagatgcg cagaagacaa tgcagccaga gtggctgcta
13861 gcttggccaa agtcacaagt gcctgtggga tattcctcaa gcctgatgag actttcgtac
13921 actcaggctt tatctatttt ggcaaaaagc aatacttgaa cggaattcaa ttccctcaat
13981 cactcaagac agcagctagg atggcccctc tctcagatgc aattttgat gacttgcaag
14041 gtacacttgc cagtatagga actgcctttg agcgatcaat ctccgaaact agacatattt
14101 taccatgccg tgttgcagct gcctttcata catatttctc tgttcggatc ttacaacatc
14161 atcaccttgg tttccataag ggttcagacc ttggacaatt ggcaatcaat aaacctcttg
14221 atttcgggac cattgcacta tccttagcag ttcctcaggt attgggtgga ttatccttcc
14281 taaatccaga aaagtgcctt tatcgcaact tgggtgatcc tgtaacttca ggcctatttc
14341 agttgaagca ttatctgtca atggtgggta tgagtgatat ctttcatgca cttattgcaa
14401 aaagcccagg gaattgtagc gcaattgact ttgttctaaa cccaggcggg ttaaatgtcc
14461 ctggatcaca ggatttaaca tctttccttc gtcagattgt cagaaggagt atcacacttt
14521 cggcaaggaa caagttaatc aacacgttat ttcacgcttc tgcagatctt gaagacgaat
14581 tagtatgtaa atggttactt tcttcaacgc ccgtgatgag ccgttttgca gccgatattt
14641 tctcacgaac accaagcggg aaaagattac aaatcttggg atacctcgag ggaaccagaa
14701 ctttattagc atccaaaatg ataagcaata atgcagagac accaatcttg gagaggctca
14761 gaaaaataac acttcaaaga tggaatctat ggtttagtta cctagaccat tgtgacccag
14821 ctttaatgga agcaattcaa ccaattaagt gtactgttga tattgctcaa attcttagag
14881 aatactcctg ggctcatatc cttgatggta gacagttaat aggggcaaca ctgccatgta
14941 tacctgagca gttccaaacc acatggttaa aaccttacga gcaatgtgtg gaatgttcat
15001 ccacaaacaa ttctagtcca tatgtatcag ttgcattaaa aaggaacgtg gttagtgctt
15061 ggcctgatgc atctagattg gggtggacga ttggtgatgg gattccctac ataggctcaa
15121 gaactgagga caaaataggt cagcccgcta ttaagccgag gtgcccatca gctgcattaa
15181 gagaagctat tgaattgacc tctaggttga cctgggtcac tcaaggtagt gcaaacagcg
15241 atcagttaat tcgccctttt cttgaggcaa gagtaaactt gagtgtacaa gagattcttc
15301 aaatgacccc ctcacattac tccggtaata ttgtgcatcg gtataatgat cagtatagcc
15361 ctcactcctt tatggctaac cgcatgagta acacagcaac gcgcttgatg gtatctacca
15421 acacactagg agagttttcc ggagggggtc aggctgcacg tgatagcaac attatatttc
15481 aaaatgtgat taactttgca gtggccttgt atgacattag gtttcggaac acttgtacat
15541 cttctattca atatcacagg gcccatattc acctgacgaa ttgttgtacg agggaagtac
15601 cggcccaata cttaacatac acaaccacgc taaatctaga tttgagtaag taccgtaata
15661 atgaactgat ttatgattca gatccactaa gaggaggtct caactgcaac ttatcgattg
15721 acagtccttt gatgaagggc ccacgtttaa atattattga ggatgactta ataccggttgc
15781 cacatttatc cggctgggaa ttagcaaaaa cagtcttgca atcaataatc tctgatagta
15841 gcaattcatc aacagatccc attagcagcg gtgaaacaag atccttcaca accacttct
15901 taacgtatcc caaaataggg cttctataca gttttggagc cctcataagt ttttatttgg
15961 gtaatactat tctatgcacg aaaaagatcg gactcacaga atttctatac tatctccaga
16021 atcagatcca caacttatca catagatccc ttcgaatctt caaaccgaca tttagacact
16081 caagtgtcat gtccaggttg atggatatag accccaactt ctcaatatat attggtggga
16141 ctgcaggtga ccgtggatta tcggacgctg caagattatt tctccgaatt gcaatttcaa
16201 ctttcttgag ctttgttgag gagtgggtta tctttaggaa ggcaaacatc ccactatggg
16261 ttatctatcc tctcgaaggc caacgctctg atcctcctgg cgaattttg aaccgagtaa
```

*Fig. 10F*

```
16321 aatctctaat tgttgggact gaagatgata aaaataaagg ctctatactt tcaagatctg
16381 gagagaaatg ctcttcaaat ctagtttata attgcaagag tacagcaagc aattttttcc
16441 atgcatcatt ggcttactgg agaggtcgac atagacctaa gaagactata ggtgcaacta
16501 acgcgacaac agctccacat atcattttgc cactgggaaa ttctgatcga ccgcctggcc
16561 tagaccttaa taggaacaat gatactttca ttcctaccag aattaaacag atagtccaag
16621 gagactctag aaacgacaga acgaccacca cgagatttcc acccaaaagt aggtccactc
16681 caacatcagc aaccgagcct cctacaaaaa tgtatgaggg ttcgacaacc caccaaggga
16741 aattaacaga tacacatttg gatgaggatc acaatgccaa agagttccca tccaatccgc
16801 atcgtttagt agtaccattc tttaaattaa caaaagatgg ggaatacagc atcgaacctt
16861 ctcctgaaga aagccgcagt aatataaaag ggttacttca acatttaaga accatggttg
16921 atactaccat atattgtcgc ttcactggaa ttgtttcatc aatgcattat aagttagatg
16981 aagtactatg ggaatataat aaatttgaat cagctgtaac cctagcagaa ggggagggtt
17041 caggtgcctt actactgatc caaaaatacg gcgttaagaa gttattttg aatacacttg
17101 ctactgaaca tagtattgag agtgaagtga tatcaggtta caccactcca aggatgctac
17161 tcccaattat gcctaaaaca catcgtggtg agctagaggt catattaaat aactcagcta
17221 gtcaaataac tgatattaca catcgagatt ggttttcaaa tcaaaaaaat aggattccaa
17281 atgatgctga tattattacc atggatgctg aaactacaga aaacttagat cgttccagat
17341 tatatgaagc agtatatacg attatttgta atcatatcaa tcctaaaact ttgaaagtgg
17401 tcatcttaaa agtcttcctc agcgattgg atgggatgtg ctggattaac aattatcttg
17461 ctcctatgtt tggatcagga tatttaatca aacctataac atcaagtgca aagtcaagtg
17521 agtggtattt atgcttatct aatctacttt caaccttgag aactactcag catcaaaccc
17581 aggcaaactg tctccatgtc gtacaatgtg ctcttcaaca gcaagtacaa agagggtcat
17641 attggctaag tcatcttacc aaatacacca caagtagatt gcacaatagt tatattgcat
17701 ttggttttcc ttcattagag aaggtcctat atcataggta taaccttgtt gattcgagaa
17761 atggaccatt agtttctata acgagacacc ttgccctcct ccaaactgag atccgggagt
17821 tggtaactga ttataatcag ctgcgacaaa gtcgaaccca gacttatcat ttcataaaaa
17881 catccaaggg acggataact aaaactagtga atgattatct aagatttgag ttggttatac
17941 gggctcttaa aaataattct acatggcacc atgagttata cttgctacca gaacttatag
18001 gtgtttgcca tcgatttaat catacacgta actgtacatg cagtgaaagg ttcctggttc
18061 aaactttata tctacaccga atgagtgatg ctgagataaa acttatggac cggctcacca
18121 gcctagtcaa tatgttttcct gaaggtttca ggtctagttc agtctaattc taactgcacc
18181 aaaggctcta aaaatatttt aaataaccag gtgtatatca aagtcaatac aagtgtaaaa
18241 acaatatgca agggaccaca tttaggatca gtttattgac tcttccaata cacagagttg
18301 gaagcaccga ttcaaggttt ctaagacgcc ctatcgatta tgttgataat gtaaataata
18361 gcttttcctg tctattatga cttaaataat catatctata acgaccatca cagctaagtc
18421 gttgccctag ttcatatatt aaattaaaat ttagaagcta ggttgactct aattacataa
18481 gtattaagaa aaaattacta agactaaatc tctcatgcca agaactagta atgtgtttca
18541 catgacagat tatttctaac actaaattgc aatttcaatt ttaaagctaa gtttaacacc
18601 tatacagcca aaatatttca tagggccgat gggaataaca taagaggaac atgatcaatg
18661 aacccttat tccaactagg cagttgattg ataatctaca aattccataa gatgttctta
18721 cgatattctt ttgtttttaa tctcaatgtc aatgatttaa taagtaataa taaaaaaatc
18781 acattaaaga tgcaggaaga tcttgacctc gccaggaaaa ttaagcgcac acaaataaat
18841 taaaaaatct gtattttctc ttttttgtgt gtcca
```

(SEQ ID NO: 1)

MAKATGRYNLVTPKRELEQGVVFSDLCNFLVTPTVQGWKVYWAG
LEFDVNQKGITLLNRLKVNDFAPAWAMTRNLFPHLFKNQQSEVQTPIWALRVIL
AAGI
LDQLMDHSLIEPLSGALNLIADWLLTTSTNHFNMRTQRVKDQLSMRMLSLIRSNI
INF
INKLETLHVVNYKGLLSSVEIGTPSYAIIITRTNMGYLVEVQEPDKSAMDIRHPGP
VK
FSLLHESTLKPVATPKPSSITSLIMEFNSSLAI     (SEQ ID NO: 2)

NC_004161

```
   1 cggacacaca aaaagaaaaa aggtttttta agacttttg tgtgcgagta actatgagga
  61 agattaacag ttttcctcag tttaagatat acactgaaat tgagattgag attctcctct
 121 ttgctattct gtaactttcc ctggttgtga caattgaatc agttttatct attaccaatt
 181 accatcaaca tggtatgtct agtgatcttg ggactcttct tcatctggtt tttcctagag
 241 ctctgaatcc attttgcgag aagttcatcc aaacgaccca gtgtctgaaa atacaaaagg
 301 ttccccttc cgtcaagttt aaggggttgt tttgattgtg tgtagatttt ataatcctag
 361 agtgccaagg agttgcgtgt catcattgat tgggaagatc aaggaaacaa tttgttccaa
 421 taatatcgta catcttgact aagtcgaaca agggggaagtc gatatggatc gtgggaccag
 481 aagaatctgg gtgtcgcaaa atcaaggtga tactgattta gattatcata aaattttgac
 541 agctggcctt actgttcaac agggaattgt caggcagaaa ataattctg tatatcttgt
 601 tgataacttg gaggctatgt gtcaattggt aatacaagcc tttgaggccg gaattgattt
 661 ccaagaaaat gccgacagct tccttctgat gctttgccta catcatgctt accaaggtga
 721 ctataaattg ttcttggaga gcaatgctgt acagtatttg gaaggtcatg gattcaaatt
 781 tgagctccgg aagaaggacg gtgtcaatcg gctcgaggaa ttgcttcctg ctgcaacgag
 841 tggaaaaaac atcaggcgta cgttggccgc actgcctgaa gaggagacta cagaagcaaa
 901 tgcagggcaa tttctctcat ttgcgagttt gtttcttccc aaactggttg tgggagagaa
 961 ggcttgcttg gaaaaagtcc agcgacaaat tcaggttcat gcagaacagg gtttaattca
1021 atatcccact gcatggcaat cagttggaca catgatggta atcttcagat tgatgaggac
1081 taatttcttg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgcccctt tgctcgcctt ctcaatctct cgggagttaa
1381 caacctagaa catggtctct acccacagtt atcagcaatt gctcttggag ttgccacagc
1441 acatggtagc acccttgcag gagttaatgt tggtgagcag tatcagcagc ttagagaggc
1501 tgccactgaa gctgagaagc aactccaaca atatgctgag tccagagaac tcgacagcct
1561 aggcctggac gatcaggaaa gaagaatact aatgaacttc catcagaaga aaaacgaaat
1621 tagtttccag cagaccaatg caatggtaac ccttaggaaa gagcgactgg ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaattac aatggctatc atgatgatga agttgggacg gcaggtgact tggtcctgtt
1921 cgatcttgac gatcatgagg atgacaataa agcttttgag ccacaggaca gctcgccaca
1981 atcccaaagg gaaatagaga gagaaagatt aattcatcca ccccaggca acaacaagga
```

*Fig. 10H*

2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac acccttatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct ccccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga aagaacgact
2581 ggacaaagag aatcgctaca tttacataaa taatcaacag ttcttctggc ctgtcatgag
2641 tcccagagac aaatttcttg caatcttgca gcaccatcag taaccacagc acaaagcgcg
2701 gtccacttcg taaagctaaa tacacttaag acttgaccga ttcatctaca aaactaatc
2761 cattataact tattagtgct acttttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaattaagaa aaacatttga tgaagattaa aaccttcatc gccagtaaat gattatattg
3061 tctgtaggca ggtgtttact ccaccttaaa tttggaaata tcctaccttta ggaccattgt
3121 caagaggtgc ataggcatta ccaccccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgg acgggctact tcaactgcag ctgcagtaga
3601 tgcgtattgg aaagagcaca acagccacc accagggcca gcgttgtatg aagagaatgc
3661 gcttaaagga aaaatcgatg atccaaacag ctatgtacca gatgctgtgc aagaggctta
3721 caagaacctt gacagtacat cgaccctgac cgaggaaaat tttgggaaac cttatatatc
3781 tgctaaagac ctgaaggaga tcatgtatga tcatctacct ggttttggga ctgcctttca
3841 ccaacttgtt caagtgattt gtaaaatagg aaaggataac aaccttttgg acacaatcca
3901 tgctgagttc caggcaagtc tagcagatgg tgactctccc caatgtgcac tcatacagat
3961 aaccaaaagg gtcccaatct ttcaggatgt gccgccccg ataatccata ttagatcccg
4021 tggtgacatc ccacgagcat gccaaaagag tctccgacca gcaccaccat cacccaaaat
4081 tgatcgtggt tgggtttgtt tgtttaagat gcaagatggt aaaacgcttg gacttaagat
4141 ctaagaatca agatttattt aacaaggcaa gccacaacct tagatggaac ctcagccaga
4201 ctattgaact attgacgctg ttgatgataa tatataatta atggtcttat ttgaatatga
4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catcttctaa agtgagatat tttatcatca aaaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca agccatactc
4681 caagcggagt agcttctgcc tttatattgg aagctacagt gaatgtaatt tcgggaacaa
4741 aagtcctgat gaagcaaata cctatttggc ttccactggg tgtagctgat cagaagatat

*Fig. 101*

```
4801 acagctttga ttcaacaaca gccgcaatta tgttggcttc ctacacagtg acacacttcg
4861 ggaagatatc taacccgctg gtacgtgtca acaggctagg cccaggaata cccgatcatc
4921 cgctacgact cctaaggttg ggcaatcagg cattccttca agagtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca agaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatccgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gttttttaat ctaattttcc
5641 agtcttgagt aataatcatt tcttttgtaa ttaattatgc atttgttaac ttatcggtgc
5701 gagatttcct tgagaacccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tccccaaatt acctatacaa catggggtca ggatatcaac
6061 ttctccaatt gcctcgggaa cgttttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt ttcttgtat gatagattgg
6541 cctcaactgt catctaccga gggacaactt ttgctgaagg tgtcgtagct ttttaattc
6601 tgtcagagcc caagaagcat ttttggaagg ctacaccagc tcatgaaccg gtgaacacaa
6661 cagatgattc cacaagctac tacatgaccc tgacactcag ctacgagatg tcaaattttg
6721 ggggcaatga aagcaacacc cttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcatttccaa attccatcaa cccacaccaa caactcctca gatcagagcc cggcgggaac
7021 tgtccaagga aaaattagct accaccccacc cgccaacaac tccgagctgg ttcaacgga
7081 ttccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac agccgaacaa
7261 cacagcatcc attgaagact cccccccatc ggcaagcaac gagacaattt accactccga
7321 gatggatccg atccaaggct cgaacaactc cgcccagagc ccacagacca agaccacgcc
7381 agcacccaca acatccccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtcccac caggaaacaa aagcgatcgg ttcgacaaaa
```

*Fig. 10J*

```
7561 caccgctaat aaatgtaacc cagatcttta ctattggaca gctgttgatg aggggggcagc
7621 agtaggattg gcatggattc catatttcgg acctgcagca gaaggcatct acattgaggg
7681 tgtaatgcat aatcagaatg ggcttatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaatatt actgatgaaa ttaaccaaat
7921 taaacatgac tttattgaca atcccctacc agaccacgga gatgatctta atctatggac
7981 aggttggaga caatggatcc cggctggaat tgggattatt ggagttataa ttgctataat
8041 agccctactt tgtatatgta agattttgtg ttgatttatt ctgagatctg agagagaaaa
8101 atctcagggt tactctaagg agaaatatta tttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat ttaatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc
8641 cgaatctgtt ccatcggaaa aagactgatg cactcatagt tcctccggct cctaaagata
8701 tatgcccaac actcaaaaaa ggattcctct gcgatagcaa attttgcaaa aaagatcacc
8761 aattggatag cttaaatgat catgaattac tactgctaat tgcaagaaga acatgtggaa
8821 ttatcgagag caattcgcag attacatccc caaaagatat gcggttagcg aatccaacag
8881 ctgaagactt ctcacaaggt aatagtccta aattaacact tgcagtcctt cttcaaattg
8941 ctgaacattg ggcaaccaga gacctaaggc aaattgagga ctctaaactt agagctcttt
9001 taacccttg tgccgtatta acaaggaaat tttctaaatc ccaactgggt cttctatgtg
9061 agacccacct acggcatgag ggcctcggac aggaccaagc tgattctgta ttagaggtct
9121 accaaagact ccacagtgat aaaggaggga attttgaggc tgccctgtgg caacaatggg
9181 accgacagtc attaataatg ttcatctctg cttttctcaa cattgctctc cagatacctt
9241 gtgaaagttc tagtgtcgta gtctcaggtc ttgccacatt gtacccagca caagacaatt
9301 ctacaccatc cgaggcaact aatgatacca cctggtcaag tacagttgaa tagaaaacca
9361 ctggagctat ttttccacga ttgctctcag tcaataaatt aatatagata taatacgact
9421 tcggtgtgca attgtcaaga gttccattta gtaataatga ttcttaaaac aatctactat
9481 cgcaattatc gatggatcta ccctatttga cggtacatga cttgaatgta ataaggtaag
9541 ttggtatctg aggtattttg tctagagtat actcaaaatc gtatgtctag caaattatca
9601 atagcaaagt taaattctcc taacctcata ttttgatcaa gtaatcatga ttttatgata
9661 attcttttca gattatcggt ttaatcttta ttaagaaaaa atcatgattg tagacaattt
9721 actggtagtc cttgggtatc caagttttatg aatagagcta gagagaattt gctacttccg
9781 aggtataact ttattatttg ctacttcgaa tgcctaaaac cagtaatgca ggatgaagat
9841 taattgcgga ggaatcagga attcaacttt agttccttaa ggcctcgtcc gaatcttcat
9901 cagttcgtaa gttcttttat agaagtcatt agcttctaag gtgattatat tttagtatta
9961 aattttgcta attgcttgct ataaagttga aatgtctaat gcttaaatga acacttttt
10021 gaagctgaca tacgaataca tcatatcata tgaaaacatc gcaattagag cgtccttgaa
10081 gtctggcatt gacagtcacc aggctgttct cagtagtctg tccttggaag ctcttggggga
10141 gacaaaaaga ggtcccagag agtcccaaca ggttggcata aggtcattaa caccagcata
10201 gtcggctcga ccaagactgt aagcgagtcg atttcaacta aaaagattat ttcttgttgt
10261 ttaaacaaat tcctttttgtg tgagacatcc tcaaggcaca agatggctaa agccacaggc
```

```
10321 cgatacaatc tcgtgccccc aaagaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatcttttc ccacatctgt tccagaaccc aaattcggtt
10561 attcaatctc ccatctgggc tttgagggta attttggcag ccggattgca ggatcagttg
10621 ttagaccatt cattggttga gccattgaca ggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagttct cattacttca tgagtctgcc
10981 ttcaaacctt tcactcgtgt tccacaatct gggatgcaat cattaataat ggagttcaac
11041 agtttgttgg caatttaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttagagtgt atgaattgtg cagatttaaa
11221 cttgggtttt gccttatgct tcataggtgg tcttttgaa atggagatta tcagcatttc
11281 ttaaatggga ggagttagca atcagaaatt ggagataaat ggacatcggg atagaacaat
11341 gcctaactat tgggcggctt ccatttttac atgtgtatat aaccaatctt ttcctatctt
11401 tgcttatatt ggtgtaactt tatttaata acatgtcaat gctatactgt taagagaagg
11461 tctgaggaag attaagaaaa aggcctcgtg ttcacttggt tgccgtcaag tatcctgtgg
11521 ttttttttcta cctaacttcc tcatgccata tggctaccca gcataaccca gtacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacggggcac ggtgatagggc
11821 cattgacccc gacttgcaat caattccttg atgaaattat taattacact cttcatgatg
11881 cagcctttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt ttggctcgac gtgggcgtct gaatcgcggg aacaaccgtt
12061 caacctggtt tgttcatgat gaattcattg atattttagg atatggcgat tatattttt
12121 ggaaaatacc tttatcatta ttaccagtta ctatagacgg ggtcccacac gcagcaactg
12181 actggtatca accgactctt tttaaagaat ccatcctagg gcatagccaa atcctatctg
12241 tgtcaacagc tgaaatacta attatgtgta aagatattat cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataaagtac cttgaaccac tttgtttggc caaaatccaa ctttgctcta
12481 aattcacaga aagaaaaggt cgtttcctca cacagatgca tttatcagta ataaatgatc
12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttgggggcat ccaatttttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccttcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
```

*Fig. 10L*

```
13081 tctccactaa aagggtgccg gaacaatttc tagaacaaga ggattttca atcgaaagtg
13141 tcctgaatta tgcacaggaa ttacattatt tattaccaca gaataggaat ttttcctttt
13201 ctctcaaaga aaaggaatta aatattggac gaacatttgg gaagctacca tatctcacac
13261 ggaatgtcca aactttatgt gaggctctgt tagcagatgg actggccaag gccttcccca
13321 gtaacatgat ggtagtaact gaacgtgaac aaaaagagag ccttcttcat caggcatcat
13381 ggcaccacac cagtgatgat tttggagaga atgctaccgt tcgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat ttaatcccgc
13561 agtgttacat gcatgtaagt gattattata atccgcctca caatgttaat cttagcaatc
13621 gagaatatcc tcctgaaggc ccgagttcgt accgagggca cttaggaggc atagagggat
13681 tacaacaaaa actgtggacg agtatatcct gtgcacaaat ctccttagtg gaaattaaaa
13741 ctggttttaa gttacgatca gcggtcatgg gagacaatca gtgtataacc gtattgtctg
13801 ttttccact taaacagac cctgaagagc aggagcaaag cgccgaagac aatgctgcaa
13861 gagtagcagc aagtcttgca aaagtaacca gtgcatgtgg gatctttctt aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagctttcca tacgtatttc gccgttcgga
14161 ttttacaata tcaccatctt ggatttaata aaggcatcga tttaggacag ttgtcactta
14221 gtaaaccatt agactatggg actattactc taacattggc ggttccacaa gtccttgggg
14281 gattgtcttt tctaaatcca gaaaagtgtt tttatcgaaa cttcggagat cctgtgactt
14341 ctggacttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat ttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc accctacaaa gatggaatct gtggttcagt tatttggacc
14821 attgtgacca attactagca gatgctctac agaaaattag ttgcacggtg gatttggccc
14881 agattttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagtggac aatagggagt ggtgtcccct
15121 atataggggtc aagaaccgag gataaaatcg gacagcctgc tatcaagccg cgatgcccct
15181 catctgccct caaggaggct atagaattag catcaaggct cacttggggt acacaaggag
15241 gttctaatag tgaacaatta atccggcctt tcttggaagc gagagtcaac cttagtgtca
15301 gtgaagtcct gcaaatgaca ccatcacatt attcaggaaa tattgtccat cgatataacg
15361 accaatacag cccgcactca ttatggcga atcgcatgag caatactgcg accgtctca
15421 tagtgtcaac taatacactt ggagaatttt caggtggagg gcaggccgcc agggatagca
15481 atataattt ccagaatgtt ataaattag cagttgccct ttatgatatt agattccgga
15541 atacaaacac ctctgatata aggcataata gggctcatct tcacctgaca gagtgctgta
15601 ctaaagaggt cccgccccag tatttgacat atacaagtgc acttaatctg gatttaagcc
15661 gttatcgtga taatgaacta atatatgact caaatccact gaagggagga ttgaactgca
15721 atttaacaat agatagtcct ttagtgaagg gtcctaggct taacatgatt gaagatgatc
15781 ttctccgctt tccacacctt tctggatggg agttagcgaa aacggtggta caatccatca
```

*Fig. 10M*

15841 tctcagacaa tagcaactca tcaacagatc caatcagtag cggagaaaca cgctctttca
15901 caactcattt tctcacttac cctcagattg gccttcttta cagtttcgga gcagtattat
15961 gctttatct aggcaatact atcctatgga ctaaaaaact tgattacgaa cagtttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagtttttta caatttctta aaagctggat catcgatcgc caaaagacaa
16261 ttcctttatg gatagtatat ccgcttgaag gtcaacagcc ggaatccatc aatgaatttc
16321 tacataaaat tttgggtctg ctcaaacaag gccccaaaag tattccaaag gaggtcagca
16381 tccaaaatga tggacatttg gatttggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgaaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca agtggaatcc ctgcaaaatg ttaatggaga
16741 gtcaaagggg aactgttcta acagagggtg actactttca aaacaatact ccaccaacag
16801 atgatgtatc aagtcctcac cgactcattc taccattttt taaattggga aatcacaacc
16861 atgcacatga tcaagatgcc caagaattga tgaatcaaaa tattaaacag tacctacatc
16921 agctaaggtc tatgttggac accactatat attgtagatt cacagggatt gtctcatcca
16981 tgcattacaa attggacgaa gttcttctag aatacaatag tttcgattca gctatcacat
17041 tagctgaagg tgaggggtca ggggctctat tactttttgca aaaatatagt acaaggttat
17101 tattttgaa cacattggca acagaacaca gtatagaatc agaagttgta tcaggttttt
17161 ctactccgag aatgttgtta ccaataatgc aaaaggttca tgaaggacaa gtcactgtta
17221 tcttaaataa ttcagcaagt cagataactg acataactag ctcaatgtgg ttaagtaatc
17281 aaaaatataa tctaccttgt caagttgaaa tcattatgat ggatgctgaa acaacagaga
17341 acttaaacag gtcccaactc taccgagcag tatataactt aatacttgat cacattgatc
17401 cgcagtatct caaggtggtg gtactcaaag tatttctgag tgatatagaa ggaatatatt
17461 ggattaatga ttacttggct ccattattcg gggctggtta cttgattaaa ccgattacat
17521 caagtgcccg gtcaagtgaa tggtaccttt gcttatcaaa tttgatatct actaacagga
17581 gatcggccca tcagactcac aaggcatgtc ttggtgttat cagagatgct ttgcaagcac
17641 aagtccagcg aggcgtgtac tggttgagtc acatcgcaca gtatgctaca aagaatctcc
17701 attgtgaata cataggcctt ggtttcccat ctctagaaaa ggtcctatat cacaggtata
17761 atctagttga tactggactc ggtccattgt cgtcagttat tagacattta actaacctcc
17821 aggcagagat acgagactta gtattagatt ataacctgat gagggagagt cgcactcaaa
17881 cgtaccattt tattaagact gcaaaaggca gaatcacaaa gttagtcaat gactttctga
17941 agttttcttt aattgtccag gcactcaaaa ataattcttc ttggtatact gagcttaaaa
18001 aattacctga ggttattaat gtgtgtaatc gattttatca tactcacaat tgcgaatgtc
18061 aggaaaaatt ctttgtccag acgtttatt tacaacgcct acgcgatgca gaaatcaagc
18121 taattgaacg ccttaccggg ttaatgcgat tttatccaga agggttaata tattccaatc
18181 acacataggt actaaatcat catagtatga ggaataagat aatgataatt cctgacgaca
18241 gttttagttc cgattctaag tatatcggaa gagagtatgc caatcttaat tgttagaggt
18301 aacaagctat tagttattac ttattgataa gaatacactt tatcatagcg taacacatca
18361 taactttata acgatttttgc atttctaatc ctagtattta ttagaatgta ctaccagaga
18421 aatgaccccca gttcctatct ttaaataatg attgtgtgta ttaaattatt agtttattag
18481 gtttatgagt tggttacaca gtgagtatta gtaattgagg attatgtaga taggtaatct
18541 aacactgaat cacccatctg atgtcaccat atccaaatgt tgtgctagtc gcatttaaac

*Fig. 10N*

18601 atgctatctt cagttaagta acatagactg aaaatgctaa gaagagattg gagtaaaagt
18661 ataaaataaa tttaattaaa cttcaaagtg attaaatgat aatgatcttg ggaactcgat
18721 atgacctcaa gtcaaaaata atgtcaatat aattgtttag taatatgagt gataatgtaa
18781 attttgataa ctaactagct ttagtagtta agatcaaatg caaacattat aagaatgtta
18841 agcgcacaca aaaacattat aaaaaaccaa ttttttcctt tttgtgtgtc c (SEQ ID NO: 3)

VP30

MEHSRERGRSSNMRHNSREPYENPSRSRSLSRDPNQVDRRQPRS
ASQIRVPNLFHRKKTDALIVPPAPKDICPTLKKGFLCDSKFCKKDHQLDSLNDHE
LLL
LIARRTCGIIESNSQITSPKDMRLANPTAEDFSQGNSPKLTLAVLLQIAEHWATRD
LR
QIEDSKLRALLTLCAVLTRKFSKSQLGLLCETHLRHEGLGQDQADSVLEVYQRL
HSDK
GGNFEAALWQQWDRQSLIMFISAFLNIALQIPCESSSVVVSGLATLYPAQDNSTPS
EA
TNDTTWSSTVE (SEQ ID NO: 4)

AY769362

1 cggacacaca aaagaaaaa aggtttttta agactttttg tgtgcgagta actatgagga
61 agattaacag ttttcctcag tttaagatat acactgaaat tgagattgag attctcctct
121 ttgctattct gtaactttcc ctggttgtga caattgaatc agttttatct attaccaatt
181 accatcaaca tggtatgtct agtgatcttg ggactcttct tcatctggtt tttcctagag
241 ctctgaatcc atttcgcgag aagttcatcc aaacgaccca gtgtctgaaa atacaaaagg
301 ttccccttc cgtcaagttt aagggggttgt tttgattgtg tgtagatttt ataatcctag
361 agtgccaagg agttgcgtgt catcattgat tgggaagatc aaggaaacaa tttgttccaa
421 taatatcgta catcttgact aagtcgaaca cggggaagtc gatatggatc gtgggaccag
481 aagaatctgg gtgtcgcaaa atcaaggtga tactgattta gattatcata aaattttgac
541 agctgtcctt actgttcaac agggaattgt caggcagaaa ataatttctg tatatcttgt
601 tgataacttg gaggctatgt gtcaattggt aatacaagcc tttgaggccg gaattgattt
661 ccgagaaaat gccgacagct tccttctgat gctttgccta catcatgctt accaaggtga
721 ctataaattg ttcttggaga gcaatgctgt acagtatttg gaaggtcatg gattcaaatt
781 tgagctccgg aagaaggacg gtgtcaatcg gctcgaggaa ttgcttcctg ctgcaacgag
841 tggaaaaaac atcaggcgta cgttggccgc actgcctgaa gaggagacta cagaagcaaa
901 tgcagggcaa tttctctcat ttgcgagtct gtttcttccc aaactggttg tgggagagaa
961 ggcttgcttg gaaaaagtcc agcgacaaat tcaggttcat gcagaacagg gtttaattca
1021 atatcccact gcatggcaat cagttggaca catgatggta atcttcagat tgatgaggac
1081 taatttcttg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgccccttt tgctcgcctt ctcaatctct cgggagtaa
1381 caacctagaa catggtctct acccacagtt atcagcaatt gctcttggag ttgccacagc
1441 acatggtagc acccttgcag gagttaatgt tggtgagcag tatcagcagc ttagagaggc

*Fig. 100*

```
1501 tgccactgaa gctgagaagc aactccaaca atatgctgag tccagagaac tcgacagcct
1561 aggcctggac gatcaggaag gaagaatact aatgaacttc catcagaaga aaaacgaaat
1621 tagtttccag cagaccaatg caatggtaac ccttaggaaa gagcgactgg ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaaattac aatggctatc atgatgatga agttgggacg gcaggtgact gggtcctgtt
1921 cgatcttgac gatcatgagg atgacaataa agcttttgag ccacaggaca gctcgccaca
1981 atcccaaagg gaaatagaga gagaaagatt aactcatcca cccccaggca acaacaagga
2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac acccttatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct ccccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga aagaacgact
2581 ggacaaagag aatcgctaca tttacataaa taatcaacag ttctcctggc ctgtcatgag
2641 tcccagagac aaatttcttg caatcttgca gcaccatcag taaccacagc acaaagcgcg
2701 gtccacttcg taaagctaaa tacacttaag acttgaccga ttcatctaca aaaactaatc
2761 cattataact tattagtgct acttttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaaattaagaa aaacatttga tgaagattaa aaccttcatc gccagtaaat gattatattg
3061 tctgtaggca ggtgtttact ccaccttaaa tttggaaata tcctaccita ggaccattgt
3121 caagaggtgc ataggcatta ccacccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgg acgggctact tcaactgcag ctgcagtaga
3601 tgcgtattgg aaagagcaca aacagccacc accagggcca gcgttgtatg aagagaatgc
3661 gcttaaagga aaaatcgatg atcctaacag ctatgtacca gatgctgtgc aagaggctta
3721 caagaaccct gacagtacat cgaccctgac cgaggaaaat tttgggaaac cttatatatc
3781 tgctaaagac ctgaaggaga tcatgtatga tcatctacct ggttttggga ctgcctttca
3841 ccaacttgtt caagtgattt gtaaaatagg aaaggataac aacctttgg acacaatcca
3901 tgctgagttc caggcaagtc tagcagatgg tgactctccc caatgtgcac tcatacagat
3961 aaccaaaagg gtcccaatct ttcaggatgt gccgcccccg ataatccata ttagatcccg
4021 tggtgacatc ccacgagcat gccaaaagag tctccgacca gcaccaccat cacccaaaat
4081 tgatcgtggt tgggtttgtt tgtttaagat gcaagatggt aaaacgcttg gacttaagat
4141 ctaagaatca agatttattt aacaaggcaa gccacaacct tagatggaac ctcagccaga
4201 ctattgaact attgacgctg ttgatgataa tatataatta atggtcttat ttgaatatga
```

```
4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catcttctaa agtgagatat tttatcatca aaaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca agccatactc
4681 caagcggagt agcttctgcc tttatattgg aagctacagt gaatgtaatt tcgggaacaa
4741 aagtcctgat gaagcaaata cctatttggc ttccactggg tgtagctgat cagaagatat
4801 acagctttga ttcaacaaca gccgcaatta tgttggcttc ctacacagtg acacacttcg
4861 ggaagatatc taacccgctg gtacgtgtca acaggctagg cccaggaata cccgatcatc
4921 cgttccggct cctgaggttg ggcaaaaaag cgttccttcc cgggtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca agaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatacgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gttttttaat ctaattttcc
5641 agtcttgagt aataatcatt tcttttgtaa ttaattatgc atttgttaac ttatcggtgc
5701 gagatttcct tgagaacccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tcccaaatt acctatacaa catgggggtca ggatatcaac
6061 ttctccaatt gcctcgggaa cgttttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt tttcttgtat gatagattgg
6541 cctcaactgt catctaccga gggacaactt ttgctgaagg tgtcgtagct tttttaattc
6601 tgtcagagcc caagaagcat ttttggaagg ctacaccagc tcatgaaccg gtgaacacaa
6661 cagatgattc cacaagctac tacatgaccc tgacactcag ctacgagatg tcaaattttg
6721 ggggcaatga aagtaacacc cttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcatttccaa attctatcaa cccacaccaa caactcctca gatcagagcc cggcgggaac
```

*Fig. 10Q*

```
7021 tgtccaagga aaaattagct accacccacc cgccaacaac tccgagctgg ttccaacgga
7081 ttcccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac aaccgaacaa
7261 cacagcatcc attgaagact cccccccatc ggcaagcaac gagacaattt accactccga
7321 gatggatccg atccaaggct cgaacaactc cgcccagagc ccacagacca agaccacgcc
7381 agcacccaca acatccccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtcccac caggaaacaa aagcgatcgg ttcgacaaaa
7561 caccgctaat aaatgtaacc cagatcttta ctattggaca gctgttgatg aggggggcagc
7621 agtaggattg gcatggattc catatttcgg acctgcagca gaaggcatct acattgaggg
7681 tgtaatgcat aatcagaatg ggcttatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaatatt actgatgaaa ttaaccaaat
7921 taaacatgac tttattgaca atcccctacc agaccacgga gatgatctta atctatggac
7981 aggttggaga caatggatcc cggctggaat tgggattatt ggagttataa ttgctataat
8041 agccctactt tgtatatgta agattttgtg ttgatttatt ctgagatctg agagagaaaa
8101 atctcagggt tactctaagg agaaatatta tttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat ttaatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc
8641 cgaatctgtt ccatcggaaa aagactgatg cactcatagt tcctccgact cctaaagata
8701 tatgcccaac actcaaaaaa ggattcctct gcgatagcaa attttgcaaa aaagatcacc
8761 aattggatag cttaaatgat catgaattac tactgctaat tgcaagaaga acatgtggaa
8821 ttatcgagag caattcgcag attacatccc caaaagatat gcggttagcg aatccaacag
8881 ctgaagactt ctcacatggt aatagtccta aattaacact tgcagtcctt cttcaaattg
8941 ctgaacattg ggcaaccaga gacctaaggc aaattgagga ctctaaactt agagctcttt
9001 taaccctttg tgccgtatta acaaggaaat tttctaaatc ccaactgggt cttctatgtg
9061 agacccacct acggcatgag ggcctcggac aggaccaagc tgattctgta ttagaggtct
9121 accaaagact ccacagtgat aaaggaggga attttgaggc tgccctgtgg caacaatggg
9181 accgacagtc attaataatg ttcatctctg cttttctcaa cattgctctc cagatacctt
9241 gtgaaagttc tagtgtcgta gtctcaggtc ttgccacatt gtacccagca caagacaatt
9301 ctacaccatc cgaggcaact aatgatacca cctggtcaag tacagttgaa tagaaaaacca
9361 ctggagctat ttttccacga ttgctctcag tcaataaatt aatatagata taatacgact
9421 tcggtgtgca attgtcaaga gttccattta gtaataatga ttcttaaaac aatctactat
9481 cgcaattatc gatggatcta ccctatttga cggtacatga cttgaatgta ataaggtaag
9541 ttggtatctg agglatttg tctagagtat actcaaaatc gtatgtctag caaattatca
9601 atagcaaagt taaattctcc taacctcata ttttgatcaa gtaatcatga ttttatgata
9661 attcttttca gattatcggt ttaatctttta ttaagaaaaa atcatgattg tagacaattt
9721 actggtagtc cttgggtatc caagtttatg aatagagcta gagagaattt gctacttccg
```

*Fig. 10R*

```
9781 aggtataact ttattatttg ctacttcgaa tgcctaaaac cagtaatgca ggatgaagat
9841 taattgcgga ggaatcagga attcaactt agttccttaa ggcctcgtcc gaatcttcat
9901 cagttcgtaa gttctttat agaagtcatt agcttctaag gtgattatat tttagtatta
9961 aatttttgcta attgcttgct ataaagttga aatgtctaat gcttaaatga acactttt
10021 gaagctgaca tacgaataca tcatatcata tgaaaacatc gcaattagag cgtccttgaa
10081 gtctggcatt gacagtcacc aggctgttct cagtagtctg tccttggaag ctcttgggga
10141 gacaaaaaga ggtcccagag agtcccaaca ggttggcata aggtcattaa caccagcata
10201 gtcggctcga ccaagactgt aagcgggtcg atttcaacta aaaagattat ttcttgttgt
10261 ttaaacaaat tccttttgtg tgagacatcc tcaaggcaca agatggctaa agccacaggc
10321 cgatacaatc tcgtgccccc aaagaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatcttttc ccacatctgt tccagaaccc aaattcggtt
10561 attcaatctc ccatctgggc tttgagggta attttggcag ccggattgca ggatcagttg
10621 ttagaccatt cattggttga gccattgaca gggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagttct cattacttca tgagtctgcc
10981 ttcaaacctt tcactcgtgt tccacaatct gggatgcaat cattaataat ggagttcaac
11041 agtttgttgg caatttaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttggagtgt atgaattgtg cagatttaaa
11221 cttgggtttt gccttatgct tcataggtgg tcttttgaa atggagatta tcagcatttc
11281 ttaaatggga ggagttagca atcagaaatt ggagataaat ggacatcggg atagaacaat
11341 gcctaactat tgggcggctt ccattttac atgtgtatat aaccaatctt ttcctatctt
11401 tgcttatatt ggtgtaactt tatttaata acatgtcaat gctatactgt taagagaagg
11461 tctgaggaag attaagaaaa aggcctcgtg ttcacttggt tgccgtcaag tatcctgtgg
11521 ttttttcta cctaacttcc tcatgccata tggctaccca gcatacccag tacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacgggggcac ggtgataggc
11821 cattgaccc gacttgcaat caattccttg atgaaattat taattacact cttcatgatg
11881 cagccttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt ttggctcgac gtgggcgtct gaatcgcggg aacaaccgtt
12061 caacctggtt tgttcatgat gaattcattg atatttagg atatggcgat tatattttt
12121 ggagaatacc tttatcatta ttaccagtta ctatagacgg ggtcccacac gcagcaactg
12181 actggtatca accgactctt tttaaagaat ccatcctagg gcatagccaa atcctatctg
12241 tgtcaacagc tgaaatacta attatgtgta aagatattat cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataaagtac cttgaaccac tttgttggc caaaatccaa ctttgctcta
12481 aattcacaga aagaaaaggt cgtttcctca cacagatgcg tttatcagta ataaatgatc
```

```
12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttgggggcat ccaattttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccgtcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
13081 tctccactaa aagggtgccg gaacaatttc tagaacaaga ggatttttca atcgaaagtg
13141 tcctgaatta tgcacaggaa ttacattatt tattaccaca gaataggaat ttttcctttt
13201 ctctcaaaga aaaggaatta aatattggac gaacatttgg gaagctacca tatctcacac
13261 ggaatgtcca aactttatgt gaggctctgt tagcagatgg actggccaag gccttcccca
13321 gtaacatgat ggtagtaact gaacgtggac aaaaagagag ccttcttcat caggcatcat
13381 ggcaccacac cagtgatgat tttggagaga atgctaccgt tcgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat ttaatcccgc
13561 agtgttacat gcatgtaagt gattattata atccgcctca caatgttaat cttagcaatc
13621 gagaatatcc tcctgaaggc ccgagttcgt accgagggca cttaggaggc atagagggat
13681 tacaacaaaa actgtggacg agtatatcct gtgcacaaat ctcctagtg gaaattaaaa
13741 ctggttttaa gttacgatca gcggtcatgg gagacaatca gtgtataacc gtattgtctg
13801 ttttccact tgaaacagac cctgaagagc aggagcaaag cgccgaagac aatgctgcaa
13861 gagtagcagc aagtcttgca aaagtaacca gtgcatgtgg gatctttctt aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagctttcca tacgtatttc gccgttcgga
14161 ttttacaata tcaccatctt ggatttaata aaggcatcga tttaggacag ttgtcactta
14221 gtaaaccatt agactatggg actattactc taacattggc ggttccacaa gtccttgggg
14281 gattgtcttt tctaaatcca gaaaagtgtt tttatcgaaa cttcggagat cctgtgactt
14341 ctggacttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat ttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc accctacaaa gatggaatct gtggttcagt tatttggacc
14821 attgtgacca attactagca gatgctctac agaaaattag ttgcacggtg gatttggccc
14881 agatttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagttggac aatagggagt ggtgtcccct
15121 atataggtc aagaaccgag gataaaatcg gacagcctgc tatcaagccg cgatgccctt
15181 catctgccct caaggaggct atagaattag catcaaggct cacttgggtt acacaaggag
15241 gttctaatag tgaacaatta atccggcctt tcttggaagc gagagtcaac cttagtgtca
```

*Fig. 10T*

```
15301 gtgaagtcct gcaaatgaca ccatcacatt attcaggaaa tattgtccat cgatataacg
15361 accaatacag cccgcactca tttatggcga atcgcatgag caatactgcg acccgtctca
15421 tagtgtcaac taatacactt ggagaatttt caggtggagg gcaggccgcc agggatagca
15481 atataatttt ccagaatgtt ataaatttag cagttgccct ttatgatatt agattccgga
15541 atacaaacac ctctgatata aggcataata gggctcatct tcacctgaca gagtgctgta
15601 ctaaagaggt cccggcccag tatttgacat atacaagtgc acttaatctg gatttgagcc
15661 gttatcgtgg taatgaacta atatatgact caaatccact gaagggagga ttgaactgca
15721 atttaacaat agatagtcct ttagtgaagg gtcctaggct taacatgatt gaagatgatc
15781 ttctccgctt tccacacctt tctggatggg agttagcgaa aacggtggta caatccatca
15841 tctcagacaa tagcaactca tcaacagatc caatcagtag cggagaaaca cgctctttca
15901 caactcattt tctcacttac cctcagattg gccttcttta cagtttcgga gcagtattat
15961 gcttttatct aggcaatact atcctatgga ctaaaaaact tgattacgac cagtttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagttttttta caatttctta aaagctggat catcgatcgc caaaagacaa
16261 ttcctttatg gatagtatat ccgcttgaag gtcaacagcc ggaatccatc aatgaatttc
16321 tacataaaat tttgggtctg ctcaaacaag gccccaaaag tattccaaag gaggtcagca
16381 tccaaaatga tggacatttg gatttggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgcaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca agtggaatcc ctgcaaaatg ttaatggaga
16741 gtcaaagggg aactgttcta acagagggtg actactttca aaacaatact ccaccaacag
16801 atgatgtatc aagtcctcac cgactcattc taccattttt taaattggga aatcacaacc
16861 atgcacatga tcaagatgcc caagaattga tgaatcaaaa tattaagcag tacctacatc
16921 agctaaggtc tatgttggac accactatat attgtagatt cacagggata gtctcatcca
16981 tgcattacaa attggacgaa gttcttctag aatacaaatag tttcgattca gctatcacat
17041 tagctgaagg tgaggggtca ggggctctat tactttttgca aaaatatagt acaaggttat
17101 tatttttgaa cacattggca acagaacaca gtatagaatc agaagttgta tcaggttttt
17161 ctactccgag aatgttgtta ccaataatgc aaaaggttca tgaaggacaa gtcactgtta
17221 tcttaaataa ttcatcaagt cacataactg acataactag ctcaatgtgg ctaagtagta
17281 atcaaaaata taatctacct tgtcaagttg aaatcattat gatggatgct gaaacaacag
17341 agaacttaaa caggtcccaa ctctaccgag cagtatataa cttaatactt gatcacattg
17401 atccgcagta tctcaaggtg gtggtactca aagtatttct gagtgatata gaaggaatat
17461 tatggattaa tgattacttg gctccattat tcgggggctgg ttacttgatt aaaccgatta
17521 catcaagtgc ccggtcaagt gaatggtacc tttgcttatc aaatttgata tctactaaca
17581 ggagatcggc ccatcagact cacaaggcat gtcttggtgt tatcagagat gctttgcaag
17641 cacaagtcca gcgaggcgtg tactggttga gtcacatcgc acagtatgct acaaagaatc
17701 tccattgtga atacatatggc cttggtttcc catctctaga aaaggtccta tatcacaggt
17761 ataatctagt tgatactgga ctcggtccat tgtcgtcagt tattagacat ttaactaacc
17821 tccaggcaga gatacgagac ttagtattag attataacct gatgagggag agtcgcactc
17881 aaacgtacca ttttattaag actgcaaaag gcagaatcac aaagttagtc aatgactttc
17941 tgaagttttc tttaattgtc caggcactca aaaataattc ttcttggtat actgagctta
18001 aaaaattacc tgaggttatt aatgtgtgta atcgatttta tcatactcac aattgcgaat
```

*Fig. 10U*

18061 gtcaggaaaa attctttgtc cagacgcttt atttacaacg cctacgcgat gcagaaatca
18121 agctaattga acgccttacc gggttaatgc gattttatcc agaagggtta atatattcca
18181 atcacacata ggtactaaat catcatagta tgaggaataa gataatgata attcctgacg
18241 acagttttag ttccgattct aagtatatcg gaagagagta tgccaatctt aattgttaga
18301 ggtaacaagc tattagttat tacttattga taagaataca ctttatcata gcgtaacaca
18361 tcataacttt ataacgattt tgcatttcta atcctagtat ttattagaat gtactaccag
18421 agaaatgacc ccagttccta tctttaaata atgattgtgt gtattaaatt attagtttat
18481 taggtttatg agttggttac acagtgagta ttagtaattg aggattatgt agataggtaa
18541 tctaacactg aatcacccat ctgatgtcac catatccaaa tgttgtgcta gtcgcattta
18601 aacatgctat cttcagttaa gtaacatagg ctgaaaatgc taagaagaga ttggagtaaa
18661 agtataaaat aaatttaatt aaacttcaaa gtgattaaat gataatgatc ttgggaactc
18721 gatatgacct caagtcaaaa ataatgtcaa tataattgtt tagtaatatg agtgataatg
18781 taaattttga taactaacta gctttagtag ttaagatcaa atgcaaacat tataagaatg
18841 ttaagcgcac acaaaaacat tataaaaaac caattttttc cttttttgtgt gtcca (SEQ ID NO: 5)

VP 30 :

MMEHSRERGRSSNMRHNSREPYENPSRSRSLSRDPNQVDRRQPR
SASQIRVPNLFHRKKTDALIVPPTPKDICPTLKKGFLCDSKFCKKDHQLDSLNDHE
LL
LLIARRTCGIIESNSQITSPKDMRLANPTAEDFSHGNSPKLTLAVLLQIAEHWATR
DL
RQIEDSKLRALLTLCAVLTRKFSKSQLGLLCETHLRHEGLGQDQADSVLEVYQRL
HSD
KGGNFEAALWQQWDRQSLIMFISAFLNIALQIPCESSSVVVSGLATLYPAQDNST
PSE
ATNDTTWSSTVE (SEQ ID NO: 6)

AY142960

1 cggacacaca aaaagaaaga agaattttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaacctta atagaaacat
301 tattgttaaa ggacagcatt agttcacagt caaacaagca agattgagaa ttaaccttgg
361 ttttgaactt gaacacttag ggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaactttctt tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg

Fig. 10V

```
 961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgactttga accttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca cacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg ttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatccta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
```

*Fig. 10W*

3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt ctttttctc tcctaaatgt agaacttaac aaaagactca taatatactt
5641 gttttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattcttttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatgggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg

*Fig. 10X*

6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccagggga atttacacag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaaattgatc agattattca
7921 tgattttgtt gataaaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gatttttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat

*Fig. 10Y*

```
 9241 attgctctcc agttaccgtg tgaaagttct gctgtcgttg tttcagggtt aagaacattg
 9301 gttcctcaat cagataatga ggaagcttca accaacccgg ggacatgctc atggtctgat
 9361 gagggtaccc cttaataagg ctgactaaaa cactatataa ccttctactt gatcacaata
 9421 ctccgtatac ctatcatcat atatttaatc aagacgatat cctttaaaac ttattcagta
 9481 ctataatcac tctcgtttca aattaataag atgtgcatga ttgccctaat atatgaagag
 9541 gtatgataca accctaacag tgatcaaaga aaatcataat ctcgtatcgc tcgtaatata
 9601 acctgccaag catacctctt gcacaaagtg attcttgtac acaaataatg ttttactcta
 9661 caggaggtag caacgatcca tcccatcaaa aaataagtat ttcatgactt actaatgatc
 9721 tcttaaaata ttaagaaaaa ctgacggaac ataaattctt tatgcttcaa gctgtggagg
 9781 aggtgtttgg tattggctat tgttatatta caatcaataa caagcttgta aaaatattgt
 9841 tcttgtttca agaggtagat tgtgaccgga aatgctaaac taatgatgaa gattaatgcg
 9901 gaggtctgat aagaataaac cttattattc agattaggcc ccaagaggca ttcttcatct
 9961 cctttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaaccccttag caggagcccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca atacccagac gctaggttat catccaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
```

*Fig. 10Z*

```
12001 cagggcaatg aatttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccaccc tccactttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaactttc tattgagaat gttctttcct acgcacaaaa actcgagtat
13201 ctactaccac aatatcggaa ctttctcttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga tttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gttttttaatt ggatgcatta tacaatccca cagtgttata tgcatgtcag tgattattat
13621 aatccaccac ataacctcac actgagaat cgagacaacc cccccgaagg gctagttca
13681 tacaggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgtttatca gtcttcccct tagagactga cgcagacgag
13861 caggaacaga gcgccgaaga caatgcagcg agggtggccg ccagcctagc aaaagttaca
13921 agtgcctgtg gaatctttt aaaacctgat gaaacatttg tacattcagg ttttatctat
13981 tttggaaaaa aacaatattt gaatgggggtc caattgcctc agtcccttaa aacggctaca
14041 agaatggcac cattgtctga tgcaatttt gatgatcttc aagggaccct ggctagtata
14101 ggcactgctt ttgagcgatc catctctgag acacgacata tctttccttg caggataacc
14161 gcagcttcc atacgttttt ttcggtgaga atcttgcaat atcatcatct cgggttcaat
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta ccttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tctttcacg cacgccgagc
14701 gggaagcgat tgcaaattct aggatacctg gaaggaacac gcacattatt agcctctaag
```

Fig. 10AA

```
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaacccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgacccct
15361 tcacattact caggaaatat tgttcacagg tacaacgatc aatacagtcc tcattctttc
15421 atggccaatc gtatgagtaa ttcagcaacg cgattgattg tttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccatttcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat tttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagcccg
```

Fig. 10BB 17521 tttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagtttttta taattatcat tactttaatt tgtcgtttta aaaacggtga
18661 tagccttaat ctttgtgtaa aataagagat taggtgtaat aaccttaaca ttttgtcta
18721 gtaagctact atttcataca gaatgataaa attaaaagaa aaggcaggac tgtaaaatca
18781 gaaataccctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtcca  (SEQ ID NO: 7)

VP30

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAVVVSGLRTLVPQSDNEEA
STN
PGTCSWSDEGTP    (SEQ ID NO: 8)

AF522874

1 cggacacaca aaaagaaaaa aggtttttta agactttttg tgtgcgagta actatgagga
61 agattaacag ttttcctcag tttaagatat acactgaaat tgagattgag attctcctct
121 ttgctattct gtaactttcc ctggttgtga caattgaatc agttttatct attaccaatt
181 accatcaaca tggtatgtct agtgatcttg ggactcttct tcatctggtt tttcctagag
241 ctctgaatcc attttgcgag aagttcatcc aaacgaccca gtgtctgaaa atacaaaagg
301 ttcccctttc cgtcaagttt aaggggttgt tttgattgtg tgtagatttt ataatcctag

Fig. 10CC

```
 361 agtgccaagg agttgcgtgt catcattgat tgggaagatc aaggaaacaa tttgttccaa
 421 taatatcgta catcttgact aagtcgaaca aggggaagtc gatatggatc gtgggaccag
 481 aagaatctgg gtgtcgcaaa atcaaggtga tactgattta gattatcata aaattttgac
 541 agctggcctt actgttcaac agggaattgt caggcagaaa ataatttctg tatatcttgt
 601 tgataacttg gaggctatgt gtcaattggt aatacaagcc tttgaggccg gaattgattt
 661 ccaagaaaat gccgacagct tccttctgat gctttgccta catcatgctt accaaggtga
 721 ctataaattg ttcttggaga gcaatgctgt acagtatttg gaaggtcatg gattcaaatt
 781 tgagctccgg aagaaggacg gtgtcaatcg gctcgaggaa ttgcttcctg ctgcaacgag
 841 tggaaaaaac atcaggcgta cgttggccgc actgcctgaa gaggagacta cagaagcaaa
 901 tgcagggcaa tttctctcat ttgcgagttt gtttcttccc aaactggttg tgggagagaa
 961 ggcttgcttg gaaaaagtcc agcgacaaat tcaggttcat gcagaacagg gtttaattca
1021 atatcccact gcatggcaat cagttggaca catgatggta atcttcagat tgatgaggac
1081 taattctctg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgcccctt tgctcgcctt ctcaatctct cgggagttaa
1381 caacctagaa catggtctct acccacagtt atcagcaatt gctcttggag ttgccacagc
1441 acatggtagc acccttgcag gagttaatgt tggtgagcag tatcagcagc ttagagaggc
1501 tgccactgaa gctgagaagc aactccaaca atatgctgag tccagagaac tcgacagcct
1561 aggcctggac gatcaggaaa gaagaatact aatgaacttc catcagaaga aaaacgaaat
1621 tagtttccag cagaccaatg caatggtaac cctaggaaaa gagcgactgg ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaaattac aatggctatc atgatgatga agttgggacg gcaggtgact tggtcctgtt
1921 cgatcttgac gatcatgagg atgacaataa agcttttgag ccacaggaca gctcgccaca
1981 atcccaaagg gaaatagaga gagaaagatt aattcatcca cccccaggca acaacaagga
2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac accctatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct cccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga aagaacgact
2581 ggacaaagag aatcgctaca tttacataaa taatcaacag ttcttctggc ctgtcatgag
2641 tccagagac aaatttcttg caatcttgca gcaccatcag taaccacagc acaaagcgcg
2701 gtccacttcg taaagctaaa tacacttaag acttgaccga ttcatctaca aaaactaatc
2761 cattataact tattagtgct acttttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaattaagaa aaacatttga tgaagattaa aaccttcatc gccagtaaat gattatattg
3061 tctgtaggca ggtgtttact ccaccttaaa tttggaaata tcctacctta ggaccattgt
```

Fig. 10DD

```
3121 caagaggtgc ataggcatta ccacccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgg acgggctact tcaactgcag ctgcagtaga
3601 tgcgtattgg aaagagcaca acagccacc accagggcca gcgttgtatg aagagaatgc
3661 gcttaaagga aaaatcgatg atccaaacag ctatgtacca gatgctgtgc aagaggctta
3721 caagaaccct gacagtacat cgaccctgac cgaggaaaat tttgggaaac cttatatatc
3781 tgctaaagac ctgaaggaga tcatgtatga tcatctacct ggttttggga ctgcctttca
3841 ccaacttgtt caagtgattt gtaaaatagg aaaggataac aaccttttgg acacaatcca
3901 tgctgagttc caggcaagtc tagcagatgg tgactctccc caatgtgcac tcatacagat
3961 aaccaaaagg gtcccaatct ttcaggatgt gccgccccg ataatccata ttagatcccg
4021 tggtgacatc ccacgagcat gccaaaagag tctccgacca gcaccaccat cacccaaaat
4081 tgatcgtggt tgggtttgtt tgtttaagat gcaagatggt aaaacgcttg gacttaagat
4141 ctaagaatca agatttattt aacaaggcaa gccacaacct tagatggaac ctcagccaga
4201 ctattgaact attgacgctg ttgatgataa tatataatta atggtcttat ttgaatatga
4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catcttctaa agtgagatat tttatcatca aaaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca agccatactc
4681 caagcggagt agcttctgcc tttatattgg aagctacagt gaatgtaatt tcgggaacaa
4741 aagtcctgat gaagcaaata cctatttggc ttccactggg tgtagctgat cagaagatat
4801 acagctttga ttcaacaaca gccgcaatta tgttggcttc ctacacagtg acacacttcg
4861 ggaagatatc taacccgctg gtacgtgtca acaggctagg cccaggaata cccgatcatc
4921 cgctacgact cctaaggttg ggcaatcagg cattccttca agagtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca gaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatccgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gtttttaat ctaattttcc
5641 agtcttgagt aataatcatt tcttttgtaa ttaattatgc atttgttaac ttatcggtgc
5701 gagatttcct tgagaaccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
```

Fig. 10EE 5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tccccaaatt acctatacaa catggggtca ggatatcaac
6061 ttctccaatt gcctcgggaa cgttttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt ttcttgtat gatagattgg
6541 cctcaactgt catctaccga gggacaaactt ttgctgaagg tgtcgtagct tttttaattc
6601 tgtcagagcc caagaagcat ttttggaagg ctacaccagc tcatgaaccg gtgaacacaa
6661 cagatgattc cacaagctac tacatgaccc tgacactcag ctacgagatg tcaaatttttg
6721 ggggcaatga aagcaacacc cttttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcatttccaa attccatcaa cccacaccaa caactcctca gatcagagcc cggcgggaac
7021 tgtccaagga aaaattagct accacccacc cgccaacaac tccgagctgg ttccaacgga
7081 ttcccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac agccgaacaa
7261 cacagcatcc attgaagact ccccccccatc ggcaagcaac gagacaattt accactccga
7321 gatggatccg atccaaggct cgaacaactc cgcccagagc ccacagacca agaccacgcc
7381 agcacccaca acatccccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtcccac caggaaacaa aagcgatcgg ttcgacaaaa
7561 caccgctaat aaatgtaacc cagatcttta ctattggaca gctgttgatg agggggcagc
7621 agtaggattg gcatggattc catatttcgg acctgcagca gaaggcatct acattgaggg
7681 tgtaatgcat aatcagaatg ggcttatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaaatatt actgatgaaa ttaaccaaat
7921 taaacatgac tttattgaca atcccctacc agaccacgga gatgatctta atctatggac
7981 aggttggaga caatggatcc cggctggaat tgggattatt ggagttataa ttgctataat
8041 agccctactt tgtatatgta agattttgtg ttgatttatt ctgagatctg agagagaaaa
8101 atctcagggt tactctaagg agaaatatta ttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat taatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc

*Fig. 10FF*

```
 8641 cgaatctgtt ccatcggaaa aagactgatg cactcatagt tcctccggct cctaaagata
 8701 tatgcccaac actcaaaaaa ggattcctct gcgatagcaa attttgcaaa aaagatcacc
 8761 aattggatag cttaaatgat catgaattac tactgctaat tgcaagaaga acatgtggaa
 8821 ttatcgagag caattcgcag attacatccc caaaagatat gcggttagcg aatccaacag
 8881 ctgaagactt ctcacaaggt aatagtccta aattaacact tgcagtcctt cttcaaattg
 8941 ctgaacattg ggcaaccaga gacctaaggc aaattgagga ctctaaactt agagctcttt
 9001 taaccctttg tgccgtatta acaaggaaat tttctaaatc ccaactgggt cttctatgtg
 9061 agacccacct acggcatgag ggcctcggac aggaccaagc tgattctgta ttagaggtct
 9121 accaaagact ccacagtgat aaaggaggga attttgaggc tgccctgtgg caacaatggg
 9181 accgacagtc attaataatg ttcatctctg cttttctcaa cattgctctc cagatacctt
 9241 gtgaaagttc tagtgtcgta gtctcaggtc ttgccacatt gtacccagca caagacaatt
 9301 ctacaccatc cgaggcaact aatgatacca cctggtcaag tacagttgaa tagaaaacca
 9361 ctggagctat ttttccacga ttgctctcag tcaataaatt aatatagata taatacgact
 9421 tcggtgtgca attgtcaaga gttccattta gtaataatga ttcttaaaac aatctactat
 9481 cgcaattatc gatggatcta ccctatttga cggtacatga cttgaatgta ataaggtaag
 9541 ttggtatctg aggtattttg tctagagtat actcaaaatc gtatgtctag caaattatca
 9601 atagcaaagt taaattctcc taacctcata ttttgatcaa gtaatcatga ttttatgata
 9661 attcttttca gattatcggt ttaatcttta ttaagaaaaa atcatgattg tagacaattt
 9721 actggtagtc cttgggtatc caagtttatg aatagagcta gagagaattt gctacttccg
 9781 aggtataact ttattatttg ctacttcgaa tgcctaaaac cagtaatgca ggatgaagat
 9841 taattgcgga ggaatcagga attcaacttt agttccttaa ggcctcgtcc gaatcttcat
 9901 cagttcgtaa gttctttat agaagtcatt agcttctaag gtgattatat tttagtatta
 9961 aattttgcta attgcttgct ataaagttga aatgtctaat gcttaaatga acactttttt
10021 gaagctgaca tacgaataca tcatatcata tgaaaacatc gcaattagag cgtccttgaa
10081 gtctggcatt gacagtcacc aggctgttct cagtagtctg tccttggaag ctcttgggga
10141 gacaaaaaga ggtcccagag agtcccaaca ggttggcata aggtcattaa caccagcata
10201 gtcggctcga ccaagactgt aagcgagtcg atttcaacta aaaagattat ttcttgttgt
10261 ttaaacaaat tcctttgtg tgagacatcc tcaaggcaca agatggctaa agccacaggc
10321 cgatacaatc tcgtgccccc aaagaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatcttttc ccacatctgt tccagaaccc aaattcggtt
10561 attcaatctc ccatctgggc tttgagggta attttggcag ccggattgca ggatcagttg
10621 ttagaccatt cattggttga gccattgaca ggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagttct cattacttca tgagtctgcc
10981 ttcaaacctt tcactcgtgt tccacaatct gggatgcaat cattaataat ggagttcaac
11041 agtttgttgg caattaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttagagtgt atgaattgtg cagatttaaa
11221 cttgggtttt gcctatgct tcataggtgg tcttttgaa atggagatta tcagcatttc
11281 ttaaatggga ggagttagca atcagaaatt ggagataaat ggacatcggg atagaacaat
11341 gcctaactat tgggcggctt ccattttac atgtgtatat aaccaatctt ttcctatctt
```

Fig. 10GG

```
11401 tgcttatatt ggtgtaactt tattttaata acatgtcaat gctatactgt taagagaagg
11461 tctgaggaag attaagaaaa aggcctcgtg ttcacttggt tgccgtcaag tatcctgtgg
11521 tttttttcta cctaacttcc tcatgccata tggctaccca gcatacccag tacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacggggcac ggtgataggc
11821 cattgacccc gacttgcaat caattccttg atgaaattat taattacact cttcatgatg
11881 cagcctttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt ttggctcgac gtgggcgtct gaatcgcggg aacaaccgtt
12061 caacctggtt tgttcatgat gaattcattg atattttagg atatggcgat tatattttt
12121 ggaaaatacc tttatcatta ttaccagtta ctatagacgg ggtcccacac gcagcaactg
12181 actggtatca accgactctt tttaaagaat ccatcctagg gcatagccaa atcctatctg
12241 tgtcaacagc tgaaatacta attatgtgta aagatattat cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataaagtac cttgaaccac tttgtttggc caaaatccaa ctttgctcta
12481 aattcacaga aagaaaaggt cgtttcctca cacagatgca tttatcagta ataaatgatc
12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttgggggcat ccaattttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccttcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
13081 tctccactaa aagggtgccg gaacaatttc tagaacaaga ggattttca atcgaaagtg
13141 tcctgaatta tgcacaggaa ttacattatt tattaccaca gaataggaat tttcctttt
13201 ctctcaaaga aaaggaatta aatattggac gaacatttgg gaagctacca tatctcacac
13261 ggaatgtcca aactttatgt gaggctctgt tagcagatgg actggccaag gccttccca
13321 gtaacatgat ggtagtaact gaacgtgaac aaaaagagag ccttcttcat caggcatcat
13381 ggcaccacac cagtgatgat tttggagaga atgctaccgt tcgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat ttaatcccgc
13561 agtgttacat gcatgtaagt gattattata atccgcctca caatgttaat cttagcaatc
13621 gagaatatcc tcctgaaggc ccgagttcgt accgagggca cttaggaggc atagagggat
13681 tacaacaaaa actgtggacg agtatatcct gtgcacaaat ctccttagtg gaaattaaaa
13741 ctggttttaa gttacgatca gcggtcatgg gagacaatca gtgtataacc gtattgtctg
13801 tttttccact taaaacagac cctgaagagc aggagcaaag cgccgaagac aatgctgcaa
13861 gagtagcagc aagtcttgca aaagtaacca gtgcatgtgg gatctttctt aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagctttcca tacgtattc gccgttcgga
```

*Fig. 10HH*

```
14161 ttttacaata tcaccatctt ggatttaata aaggcatcga tttaggacag ttgtcacttg
14221 gtaaaccatt agactatggg actattactc taacattggc ggttccacaa gtccttgggg
14281 gattgtcttt tctaaatcca gaaaagtgtt tttatcgaaa cttcggagat cctgtgactt
14341 ctggactttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat tttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc accctacaaa gatggaatct gtggttcagt tatttggacc
14821 attgtgacca attactagca gatgctctac agaaaattag ttgcacggtg gatttggccc
14881 agattttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagttggac aatagggagt ggtgtcccct
15121 atatagggtc aagaaccgag gataaaatcg gacagcctgc tatcaagccg cgatgcccgtt
15181 catctgccct caaggaggct atagaattag catcaaggct cacttgggtt acacaaggag
15241 gttctaatag tgaacaatta atccggcctt tcttggaagc gagagtcaac cttagtgtca
15301 gtgaagtcct gcaaatgaca ccatcacatt attcaggaaa tattgtccat cgatataacg
15361 accaatacag cccgcactca tttatggcga atcgcatgag caatactgcg accgtctca
15421 tagtgtcaac taatacactt ggagaatttt caggtggagg gcaggccgcc agggatagca
15481 atataatttt ccagaatgtt ataaatttag cagttgccct ttatgatatt agattccgga
15541 atacaaacac ctctgatata aggcataata gggctcatct tcacctgaca gagtgctgta
15601 ctaaagaggt cccggcccag tatttgacat atacaagtgc acttaatctg gattaagcc
15661 gttatcgtga taatgaacta atatatgact caaatccact gaagggagga ttgaactgca
15721 atttaacaat agatagtcct ttagtgaagg gtcctaggct taacatgatt gaagatgatc
15781 ttctccgctt tccacacctt tctggatggg agttagcgaa aacggtggta caatccatca
15841 tctcagacaa tagcaactca tcaacagatc caatcagtag cggagaaaca cgctctttca
15901 caactcattt tctcacttac cctcagattg gccttcttta cagttcgga gcagtattat
15961 gcttttatct aggcaatact atcctatgga ctaaaaaact tgattacgaa cagtttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagttttta caatttctta aaagctggat catcgatcgc caaaagacaa
16261 ttcctttatg gatagtatat ccgcttgaag gtcaacagcc ggaatccatc aatgaatttc
16321 tacataaaat tttgggtctg ctcaaacaag gccccaaaag tattccaaag gaggtcagca
16381 tccaaaatga tggacatttg gatttggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgaaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca gtggaatcc ctgcaaaatg ttaatggaga
16741 gtcaaagggg aactgttcta acagagggtg actactttca aaacaatact ccaccaacag
16801 atgatgtatc aagtcctcac cgactcattc taccatttt taaattggga aatcacaacc
16861 atgcacatga tcaagatgcc caagaattga tgaatcaaaa tattaaacag tacctacatc
```

*Fig. 10H*

16921 agctaaggtc tatgttggac accactatat attgtagatt cacagggatt gtctcatcca
16981 tgcattacaa attggacgaa gttcttctag aatacaatag tttcgattca gctatcacat
17041 tagctgaagg tgaggggtca ggggctctat tactttgca aaaatatagt acaaggttat
17101 tattttgaa cacattggca acagaacaca gtatagaatc agaagttgta tcaggttttt
17161 ctactccgag aatgttgtta ccaataatgc aaaaggttca tgaaggacaa gtcactgtta
17221 tcttaaataa ttcagcaagt cagataactg acataactag ctcaatgtgg ttaagtaatc
17281 aaaaatataa tctaccttgt caagttgaaa tcattatgat ggatgctgaa acaacagaga
17341 acttaaacag gtcccaactc taccgagcag tatataactt aatacttgat cacattgatc
17401 cgcagtatct caaggtggtg gtactcaaag tatttctgag tgatatagaa ggaatattat
17461 ggattaatga ttacttggct ccattattcg gggctggtta cttgattaaa ccgattacat
17521 caagtgcccg gtcaagtgaa tggtaccttt gcttatcaaa tttgatatct actaacagga
17581 gatcggccca tcagactcac aaggcatgtc ttggtgttat cagagatgct ttgcaagcac
17641 aagtccagcg aggcgtgtac tggttgagtc acatcgcaca gtatgctaca aagaatctcc
17701 attgtgaata cataggcctt ggtttcccat ctctagaaaa ggtcctatat cacaggtata
17761 atctagttga tactggactc ggtccattgt cgtcagttat tagacattta actaacctcc
17821 aggcagagat acgagactta gtattagatt ataacctgat gagggagagt cgcactcaaa
17881 cgtaccattt tattaagact gcaaaaggca gaatcacaaa gttagtcaat gactttctga
17941 agttttcttt aattgtccag gcactcaaaa ataattcttc ttggtatact gagcttaaaa
18001 aattacctga ggttattaat gtgtgtaatc gattttatca tactcacaat tgcgaatgtc
18061 aggaaaaatt ctttgtccag acgctttatt tacaacgcct acgcgatgca gaaatcaagc
18121 taattgaacg ccttaccggg ttaatgcgat tttatccaga agggttaata tattccaatc
18181 acacataggt actaaatcat catagtatga ggaataagat aatgataatt cctgacgaca
18241 gttttagttc cgattctaag tatatcggaa gagagtatgc caatcttaat tgttagaggt
18301 aacaagctat tagttattac ttattgataa gaatacactt tatcatagcg taacacatca
18361 taactttata acgattttgc atttctaatc ctagtattta ttagaatgta ctaccagaga
18421 aatgacccca gttcctatct ttaaataatg attgtgtgta ttaaattatt agtttattag
18481 gtttatgagt tggttacaca gtgagtatta gtaattgagg attatgtaga taggtaatct
18541 aacactgaat cacccatctg atgtcaccat atccaaatgt tgtgctagtc gcatttaaac
18601 atgctatctt cagttaagta acatagactg aaaatgctaa gaagagattg gagtaaaagt
18661 ataaaataaa tttaattaaa cttcaaagtg attaaatgat aatgatcttg ggaactcgat
18721 atgacctcaa gtcaaaaata atgtcaatat aattgtttag taatatgagt gataatgtaa
18781 attttgataa ctaactagct ttagtagtta agatcaaatg caaacattat aagaatgtta
18841 agcgcacaca aaaacattat aaaaaaccaa ttttttcctt tttgtgtgtc c (SEQ ID NO: 10)

VP30

MEHSRERGRSSNMRHNSREPYENPSRSRSLSRDPNQVDRRQPRS
ASQIRVPNLFHRKKTDALIVPPAPKDICPTLKKGFLCDSKFCKKDHQLDSLNDHE
LLL
LIARRTCGIIESNSQITSPKDMRLANPTAEDFSQGNSPKLTLAVLLQIAEHWATRD
LR
QIEDSKLRALLTLCAVLTRKFSKSQLGLLCETHLRHEGLGQDQADSVLEVYQRL
HSDK
GGNFEAALWQQWDRQSLIMFISAFLNIALQIPCESSSVVVSGLATLYPAQDNSTPS
EA
TNDTTWSSTVE (SEQ ID NO: 11)

```
   1 cggacacaca aaaagaaaga agaattttta ggatcttttg tgtgcgaata actatgagga
  61 agattaataa ttttcctctc attgaaattt atatcggaat ttaaattgaa attgttactg
 121 taatcacacc tggtttgttt cagagccaca tcacaaagat agagaacaac ctaggtctcc
 181 gaagggagca agggcatcag tgtgctcagt tgaaaatccc ttgtcaacac ctaggtctta
 241 tcacatcaca agttccacct cagactctgc agggtgatcc aacaaccta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgattttcaa gagagtgcgg acggtttcct tctcatgctt tgtcttcatc atgcgtacca
 721 gggagattac aaacttttct tggaaagtgg cgcagtcaag tatttggaag ggcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctcctttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aattctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga accttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt ccctttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtaccgcca cattctaaga tcacaggggc catttgatgc
```

*Fig. 10KK*

2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttatttttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatccatta
3061 cgtcaattga attctctagc actcgaagct tattgtcttc aatgtaaaag aaaagctggt
3121 ctaacaagat gacaactaga acaaagggca ggggccatac tgtggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 tacccagta tttcacctt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttca

Fig. 10LL

```
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagtttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gtttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga ccagttggac
6241 tgaatctcga agggaatgga gtggcaactg acgtgccatc tgcaactaaa agatgggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaaccaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaaacaca caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacacag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
```

```
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gatttttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tggtcaaaga aaatcataat ctcgtatcgc tcgtaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaaccatggc taaagctacg ggacgataca atctaatatc
10381 gcccaaaaag gacctggaga aaggggttgt cttaagcgac ctctgtaact tcttagttag
10441 ccaaactatt caggggtgga aggtttattg ggctggtatt gagtttgatg tgattcacaa
10501 aggaatggcc ctattgcata gactgaaaac taatgacttt gcccctgcat ggtcaatgac
10561 aaggaatctc tttcctcatt tatttcaaaa tccgaattcc acaattgaat caccgctgtg
10621 ggcattgaga gtcatccttg cagcagggat acaggaccag ctgattgacc agtctttgat
10681 tgaaccctta gcaggagccc ttggtctgat ctctgattgg ctgctaacaa ccaacactaa
```

```
10741 ccatttcaac atgcgaacac aacgtgtcaa ggaacaattg agcctaaaaa tgctgtcgtt
10801 gattcgatcc aatattctca agtttattaa caaattggat gctctacatg tcgtgaacta
10861 caacggattg ttgagcagta ttgaaattgg aactcaaaat catacaatca tcataactcg
10921 aactaacatg ggttttctgg tggagctcca agaacccgac aaatcggcaa tgaaccgcat
10981 gaagcctggg ccggcgaaat tttccctcct tcatgagtcc acactgaaag catttacaca
11041 aggatcctcg acacgaatgc aaagtttgat tcttgaattt aatagctctc ttgctatcta
11101 actaaggtag aatacttcat attgagctaa ctcatatatg ctgactcaat agttatcttg
11161 acatctctgc tttcataatc agatatataa gcataataaa taaatactca tatttcttga
11221 taatttgttt aaccacagat aaatcctcac tgtaagccag cttccaagtt gacacccta
11281 caaaaaccag gactcagaat ccctcaaaca agagattcca agacaacatc atagaattgc
11341 tttattatat gaataagcat tttatcacca gaaatcctat atactaaatg gttaattgta
11401 actgaacccg caggtcacat gtgttaggtt tcacagattc tatatattac taactctata
11461 ctcgtaatta acattagata agtagattaa gaaaaaagcc tgaggaagat taagaaaaac
11521 tgcttattgg gtctttccgt gttttagatg aagcagttga aattcttcct cttgatatta
11581 aatggctaca caacataccc aataccaga cgctaggtta tcatcaccaa ttgtattgga
11641 ccaatgtgac ctagtcacta gagcttgcgg gttatattca tcatactccc ttaatccgca
11701 actacgcaac tgtaaactcc cgaaacatat ctaccgtttg aaatacgatg taactgttac
11761 caagttcttg agtgatgtac cagtggcgac attgcccata gatttcatag tcccagttct
11821 tctcaaggca ctgtcaggca atggattctg tcctgttgag ccgcggtgcc aacagttctt
11881 agatgaaatc attaagtaca caatgcaaga tgctctcttc ttgaaatatt atctcaaaaa
11941 tgtgggtgct caagaagact gtgttgatga acactttcaa gagaaaatct tatcttcaat
12001 tcagggcaat gaattttac atcaaatgtt tttctggtat gatctggcta ttttaactcg
12061 aaggggtaga ttaaatcgag gaaactctag atcaacatgg tttgttcatg atgatttaat
12121 agacatctta ggctatgggg actatgtttt ttggaagatc ccaatttcaa tgttaccact
12181 gaacacacaa ggaatccccc atgctgctat ggactggtat caggcatcag tattcaaaga
12241 agcggttcaa gggcatacac acattgtttc tgtttctact gccgacgtct tgataatgtg
12301 caaagattta attacatgtc gattcaacac aactctaatc tcaaaaatag cagagattga
12361 ggatccagtt tgttctgatt atcccaattt taagattgtg tctatgcttt accagagcgg
12421 agattactta ctctccatat tagggtctga tgggtataaa attattaagt tcctcgaacc
12481 attgtgcttg gccaaaaattc aattatgctc aaagtacact gagaggaagg gccgattctt
12541 aacacaaatg catttagctg taaatcacac cctagaagaa attacagaaa tgcgtgcact
12601 aaagccttca caggctcaaa agatccgtga attccataga acattgataa ggctggagat
12661 gacgccacaa caactttgtg agctattttc cattcaaaaa cactggggggc atcctgtgct
12721 acatagtgaa acagcaatcc aaaaagttaa aaaacatgct acggtgctaa aagcattacg
12781 ccctatagtg attttcgaga catactgtgt ttttaaatat agtattgcca aacattattt
12841 tgatagtcaa ggatcttggt acagtgttac ttcagatagg aatctaacac cgggtcttaa
12901 ttcttatatc aaaagaaatc aattccctcc gttgccaatg attaaagaac tactatggga
12961 atttaccac cttgaccacc ctccacttt ctcaaccaaa attattagtg acttaagtat
13021 ttttataaaa gacagagcta ccgcagtaga aaggacatgc tggggatgcag tattcgagcc
13081 taatgttcta ggatataatc cacctcacaa atttagtact aaacgtgtac cggaacaatt
13141 tttagagcaa gaaaactttt ctattgagaa tgttctttcc tacgcacaaa actcgagta
13201 tctactacca caatatcgga acttttcttt ctcattgaaa gagaaagagt tgaatgtagg
13261 tagaaccttc ggaaaattgc cttatccgac tcgcaatgtt caaacactt gtgaagctct
13321 gttagctgat ggtcttgcta aagcatttcc tagcaatatg atggtagtta cggaacgtga
13381 gcaaaaagaa agcttattgc atcaagcatc atggcaccac acaagtgatg attttggtga
13441 acatgccaca gttagaggga gtagctttgt aactgattta gagaaataca atcttgcatt
```

```
13501 tagatatgag tttacagcac cttttataga atattgcaac cgttgctatg gtgttaagaa
13561 tgttttaat tggatgcatt atacaatccc acagtgttat atgcatgtca gtgattatta
13621 taatccacca cataacctca cactggagaa tcgagacaac ccccccgaag ggcctagttc
13681 atacaggggt catatgggag ggattgaagg actgcaacaa aaactctgga caagtatttc
13741 atgtgctcaa atttctttag ttgaaattaa gactggtttt aagttacgct cagctgtgat
13801 gggtgacaat cagtgcatta ctgttttatc agtcttcccc ttagagactg acgcagacga
13861 gcaggaacag agcgccgaag acaatgcagc gagggtggcc gccagcctag caaaagttac
13921 aagtgcctgt ggaatctttt taaaacctga tgaaacattt gtacattcag gttttatcta
13981 ttttggaaaa aaacaatatt tgaatggggt ccaattgcct cagtccctta aaacgggctac
14041 aagaatggca ccattgtctg atgcaatttt tgatgatctt caagggaccc tggctagtat
14101 aggcactgct tttgagcgat ccatctctga gacacgacat atctttcctt gcaggataac
14161 cgcagcttt catacgtttt ttcggtgag aatcttgcaa tatcatcatc tcgggttcaa
14221 taaaggtttt gaccttggac agttaacact cggcaaacct ctggatttcg gaacaatatc
14281 attggcacta gcggtaccgc aggtgcttgg agggttatcc ttcttgaatc ctgagaaatg
14341 tttctaccgg aatctaggag atccagttac ctcaggctta ctccagttaa aaacttatct
14401 ccgaatgatt gagatggatg atttattctt accttaatt gcgaagaacc ctgggaactg
14461 cactgccatt gactttgtgc taaatcctag cggattaaat gtccctgggt cgcaagactt
14521 aacttcattt ctgcgccaga ttgtacgcag gaccatcacc ctaagtgcga aaaacaaact
14581 tattaatacc ttatttcatg cgtcagctga cttcgaagac gaaatggttt gtaaatggct
14641 attatcatca actcctgtta tgagtcgttt tgcggccgat atcttttcac gcacgccgag
14701 cgggaagcga ttgcaaaattc taggatacct ggaaggaaca cgcacattat tagcctctaa
14761 gatcatcaac aataatacag agacaccggt tttggacaga ctgaggaaaa taacattgca
14821 aaggtggagc ctatggtta gttatcttga tcattgtgat aatatcctgg cggaggcttt
14881 aacccaaata acttgcacag ttgatttagc acagattctg agggaatatt catgggctca
14941 tatttagag ggaagacctc ttattggagc cacactccca tgtatgattg agcaattcaa
15001 agtgtttgg ctgaaaaccct acgaacaatg tccgcagtgt tcaaatgcaa agcaaccagg
15061 tgggaaacca ttcgtgtcag tggcagtcaa gaaacatatt gttagtgcat ggccgaacgc
15121 atcccgaata agctggacta tcggggatgg aatccccatac attggatcaa ggacagaaga
15181 taagatagga caacctgcta ttaaaccaaa atgtccttcc gcagcctta gagaggccat
15241 tgaattggcg tcccgtttaa catgggtaac tcaaggcagt tcgaacagtg acttgctaat
15301 aaaaccattt tggaagcac gagtaaattt aagtgttcaa gaaatacttc aaatgacccc
15361 ttcacattac tcaggaaata ttgttcacag gtacaacgat caatacagtc ctcattcttt
15421 catggccaat cgtatgagta attcagcaac gcgattgatt gtttctacaa acactttagg
15481 tgagttttca ggaggtggcc agtctgcacg cgacagcaat attattttcc agaatgttat
15541 aaattatgca gttgcactgt tcgatattaa atttagaaac actgaggcta cagatatcca
15601 atataatcgt gctcaccttc atctaactaa gtgttgcacc cgggaagtac cagctcagta
15661 tttaacatac acatctacat tggatttaga tttaacaaga taccgagaaa acgaattgat
15721 ttatgacagt aatcctctaa aaggaggact caattgcaat atctcattcg ataatccatt
15781 tttccaaggt aaacggctga acattataga agatgatctt attcgactgc ctcacttatc
15841 tggatgggag ctagccaaga ccatcatgca atcaattatt tcagatagca acaattcatc
15901 tacagaccca attagcagtg gagaaacaag atcattcact accatttct taacttatcc
15961 caagatagga cttctgtaca gttttgggc ctttgtaagt tattatcttg gcaatacaat
16021 tcttcggact aagaaattaa cacttgacaa ttttttatat tacttaacta ctcaaattca
16081 taatctacca catcgctcat tgcgaatact taagccaaca ttcaaacatg caagcgttat
16141 gtcacggtta atgagtattg atcctcattt ttctgtttac ataggcggtg ctgcaggtga
16201 cagaggactc tcagatgcgg ccaggttatt tttgagaacg tccatttcat ctttcttac
```

Fig. 10PP 16261 atttgtaaaa gaatggataa ttaatcgcgg aacaattgtc cctttatgga tagtatatcc
16321 gctagagggt caaaacccaa cacctgtgaa taattttctc tatcagatcg tagaactgct
16381 ggtgcatgat tcatcaagac aacaggcttt taaaactacc ataagtgatc atgtacatcc
16441 tcacgacaat cttgtttaca catgtaagag tacagccagc aatttcttcc atgcatcatt
16501 ggcgtactgg aggagcagac acagaaacag caaccgaaaa tacttggcaa gagactcttc
16561 aactggatca agcacaaaca acagtgatgg tcatattgag agaagtcaag aacaaaccac
16621 cagagatcca catgatggca ctgaacggaa tctagtccta caaatgagcc atgaaataaa
16681 aagaacgaca attccacaag aaaacacgca ccagggtccg tcgttccagt cctttctaag
16741 tgactctgct tgtgggacag caaatccaaa actaaatttc gatcgatcga gacacaatgt
16801 gaaatttcag gatcataact cggcatccaa gagggaaggt catcaaataa tctcacaccg
16861 tctagtccta cctttcttta cattatctca agggacacgc caattaacgt catccaatga
16921 gtcacaaacc caagacgaga tatcaaagta cttacggcaa ttgagatccg tcattgatac
16981 cacagtttat tgtagattta ccggtatagt ctcgtccatg cattacaaac ttgatgaggt
17041 cctttgggaa atagagagtt tcaagtcggc tgtgacgcta gcagagggag aaggtgctgg
17101 tgccttacta ttgattcaga aataccaagt taagaccttta ttttcaaca cgctagctac
17161 tgagtccagt atagagtcag aaatagtatc aggaatgact actcctagga tgcttctacc
17221 tgttatgtca aaattccata atgaccaaat tgagattatt cttaacaact cagcaagcca
17281 aataacagac ataacaaatc ctacttggtt taaagaccaa agagcaaggc tacctaagca
17341 agtcgaggtt ataaccatgg atgcagagac aacagagaat ataaacagat cgaaattgta
17401 cgaagctgta tataaattga tcttacacca tattgatcct agcgtattga aagcagtggt
17461 cctaaagtc tttctaagtg atactgaggg tatgttatgg ctaaatgata atttagcccc
17521 gttttttgcc actggttatt taattaagcc aataacgtca agtgctagat ctagtgagtg
17581 gtatctttgt ctgacgaact tcttatcaac tacacgtaag atgccacacc aaaaccatct
17641 cagttgtaaa caggtaatac ttacggcatt gcaactgcaa attcaacgaa gcccatactg
17701 gctaagtcat ttaactcagt atgctgactg tgagttacat taagttata tccgccttgg
17761 ttttccatca ttagagaaag tactatacca caggtataac ctcgtcgatt caaaaagagg
17821 tccactagtc tctatcactc agcacttagc acatcttaga gcagagattc gagaattaac
17881 taatgattat aatcaacagc gacaaagtcg gactcaaaca tatcacttta ttcgtactgc
17941 aaaaggacga atcacacaaac tagtcaatga ttatttaaaa ttctttctta ttgtgcaaagc
18001 attaaaacat aatgggacat ggcaagctga gtttaagaaa ttaccagagt tgattagtgt
18061 gtgcaatagg ttctaccata ttagagattg caattgtgaa gaacgtttct tagttcaaac
18121 cttatattta catagaatgc aggattctga agttaagctt atcgaaaggc tgacagggct
18181 tctgagttta tttccggatg gtctctacag gtttgattga attaccgtgc atagtatcct
18241 gatacttgca aaggttggtt attaacatac agattataaa aaactcataa attgctctca
18301 tacatcatat tgatctaatc tcaataaaca actatttaaa taacgaaagg agtccctata
18361 ttatatacta tatttagcct ctctccctgc gtgataatca aaaaattcac aatgcagcat
18421 gtgtgacata ttactgccgc aatgaattta acgcaacata ataaactctg cactctttat
18481 aattaagctt taacgaaagg tctgggctca tattgttatt gatataataa tgttgtatca
18541 atatcctgtc agatggaata gtgttttggt tgataacaca acttcttaaa acaaaattga
18601 tctttaagat taagtttttt ataattatca ttactttaat ttgtcgtttt aaaaacggtg
18661 atagccttaa tctttgtgta aaataagaga ttaggtgtaa taaccttaac attttgtct
18721 agtaagctac tatttcatac agaatgataa aattaaaaga aaaggcagga ctgtaaaatc
18781 agaaatacct tctttacaat atagcagact agataataat cttcgtgtta atgataatta
18841 agacattgac cacgctcatc agaaggctcg ccagaataaa cgttgcaaaa aggattcctg
18901 gaaaaatggt cgcacacaaa aatttaaaaa taaatctatt tcttcttttt tgtgtgtcca (SEQ ID NO: 12)

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAVVVSGLRTLVPQSDNEEA
STN
PGTCSWSDEGTP (SEQ ID NO: 13)

L11365

```
   1 cggacacaca aaaagaaaga agaattttta ggatcttttg tgtgcgaata actatgagga
  61 agattaataa ttttcctctc attgaaattt atatcggaat ttaaattgaa attgttactg
 121 taatcacacc tggtttgttt cagagccaca tcacaaagat agagaacaac ctaggtctcc
 181 gaagggagca agggcatcag tgtgctcagt tgaaaatccc ttgtcaacac ctaggtctta
 241 tcacatcaca agttccacct cagactctgc agggtgatcc aacaacctta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgatttcaa gagagtgcgg acagtttcct tctcatgctt tgtcttcatc atgcgtacca
 721 gggagattac aaactttct tggaaagtgg cgcagtcaag tatttggaag ggcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctccttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga accttctgg
1381 agtaaataat cttgagcatg gtctttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
```

```
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttatttttg
2821 aatttaaagc tagccttatt attactagcc gttttcaaa gttcatttg agtcttaatg
2881 caaataggcg ttaagccaca gttatagcca taattgtaac tcaatattct aactagcgat
2941 ttatctaaat taaattacat tatgctttta taacttacct actagcctgc ccaacattta
3001 cacgatcgtt ttataattaa gaaaaaacta atgatgaaga ttaaaacctt catcatcctt
3061 acgtcaattg aattctctag cactcgaagc ttattgtctt caatgtaaaa gaaaagctgg
3121 tctaacaaga tgacaactag aacaaagggc aggggccata ctgcggccac gactcaaaac
3181 gacagaatgc caggccctga gctttcgggc tggatctctg agcagctaat gaccggaaga
3241 attcctgtaa gcgacatctt ctgtgatatt gagaacaatc caggattatg ctacgcatcc
3301 caaatgcaac aaacgaagcc aaacccgaag acgcgcaaca gtcaaaccca aacggaccca
3361 atttgcaatc atagtttga ggaggtagta caaacattgg cttcattggc tactgttgtg
3421 caacaacaaa ccatcgcatc agaatcatta gaacaacgca ttacgagtct tgagaatggt
3481 ctaaagccag tttatgatat ggcaaaaaca atctcctcat tgaacagggt ttgtgctgag
3541 atggttgcaa aatatgatct tctggtgatg acaaccggtc gggcaacagc aaccgctgcg
3601 gcaactgagg cttattgggc cgaacatggt caaccaccac ctggaccatc actttatgaa
3661 gaaagtgcga ttcggggtaa gattgaatct agagatgaga ccgtccctca aagtgttagg
3721 gaggcattca acaatctaaa cagtaccact tcactaactg aggaaaattt tgggaaacct
3781 gacatttcgg caaaggattt gagaaacatt atgtatgatc acttgcctgg ttttggaact
3841 gctttccacc aattagtaca agtgatttgt aaattgggaa aagatagcaa ctcattggac
3901 atcattcatg ctgagttcca ggccagcctg gctgaaggag actctcctca atgtgcccta
3961 attcaaatta caaaaagagt tccaatcttc aagatgctg ctccacctgt catccacatc
4021 cgctctcgag gtgacattcc ccgagcttgc cagaaaagct tgcgtccagt cccaccatcg
4081 cccaagattg atcgaggttg ggtatgtgtt tttcagcttc aagatggtaa aacacttgga
4141 ctcaaaattt gagccaatct cccttccctc cgaaagaggc gaataatagc agaggcttca
4201 actgctgaac tataggggtac gttacattaa tgatacactt gtgagtatca gccctggata
4261 atataagtca attaaacgac caagataaaa ttgttcatat ctcgctagca gcttaaaata
4321 taaatgtaat aggagctata tctctgacag tattataatc aattgttatt aagtaaccca
4381 aaccaaaagt gatgaagatt aagaaaaacc tacctcggct gagagagtgt ttttcatta
4441 accttcatct tgtaaacgtt gagcaaaatt gttaaaaata tgaggcgggt tatattgcct
4501 actgctcctc ctgaatatat ggaggccata taccctgtca ggtcaaattc aacaattgct
```

*Fig. 10SS*

4561 agaggtggca acagcaatac aggcttcctg acaccggagt cagtcaatgg ggacactcca
4621 tcgaatccac tcaggccaat tgccgatgac accatcgacc atgccagcca cacaccaggc
4681 agtgtgtcat cagcattcat ccttgaagct atggtgaatg tcatatcggg ccccaaagtg
4741 ctaatgaagc aaattccaat ttggcttcct ctaggtgtcg ctgatcaaaa gacctacagc
4801 tttgactcaa ctacggccgc catcatgctt gcttcataca ctatcaccca tttcggcaag
4861 gcaaccaatc cacttgtcag agtcaatcgg ctgggtcctg gaatcccgga tcatccctc
4921 aggctcctgc gaattggaaa ccaggctttc tccaggagt tcgttcttcc gccagtccaa
4981 ctaccccagt atttcacctt tgatttgaca gcactcaaac tgatcaccca accactgcct
5041 gctgcaacat ggaccgatga cactccaaca ggatcaaatg gggcgttgcg tccaggaatt
5101 tcatttcatc caaaacttcg ccccattctt ttacccaaca aaagtgggaa gaaggggaac
5161 agtgccgatc taacatctcc ggagaaaatc caagcaataa tgacttcact ccaggacttt
5221 aagatcgttc caattgatcc aaccaaaaat atcatgggaa tcgaagtgcc agaaactctg
5281 gtccacaagc tgaccggtaa gaaggtgact tctaaaaatg gacaaccaat catccctgtt
5341 cttttgccaa agtacattgg gttggacccg gtggctccag gagacctcac catggtaatc
5401 acacaggatt gtgacacgtg tcattctcct gcaagtcttc cagctgtgat tgagaagtaa
5461 ttgcaataat tgactcagat ccagttttat agaatcttct cagggatagt gcataacatc
5521 tatttagtaa tccgtccatt agaggagaca cttttaattg atcaatatac taaaggtgct
5581 ttacaccatt gtctttttc tctcctaaat gtagaactta acaaagact cataatatac
5641 ttgttttaa aggattgatt gatgaaagat cataactaat aacattacaa ataatcctac
5701 tataatcaat acggtgattc aaatgttaat ctttctcatt gcacatactt tttgccctta
5761 tcctcaaatt gcctgcatgc ttacatctga ggatagccag tgtgacttgg attggaaatg
5821 tggagaaaaa atcgggaccc atttctaggt tgttcacaat ccaagtacag acattgccct
5881 tctaattaag aaaaaatcgg cgatgaagat taagccgaca gtgagcgtaa tcttcatctc
5941 tcttagatta tttgttttcc agagtagggg tcgtcaggtc ctttcaatc gtgtaaccaa
6001 aataaactcc actagaagga tattgtgggg caacaacaca atgggcgtta caggaatatt
6061 gcagttacct cgtgatcgat tcaagaggac atcattcttt ctttgggtaa ttatcctttt
6121 ccaaagaaca ttttccatcc cacttggagt catccacaat agcacattac aggttagtga
6181 tgtcgacaaa ctagtttgtc gtgacaaact gtcatccaca aatcaattga gatcagttgg
6241 actgaatctc gaagggaatg gagtggcaac tgacgtgcca tctgcaacta aaagatgggg
6301 cttcaggtcc ggtgtcccac caaaggtggt caattatgaa gctggtgaat gggctgaaaa
6361 ctgctacaat cttgaaatca aaaaacctga cgggagtgag tgtctaccag cagcgccaga
6421 cgggattcgg ggcttccccc ggtgccggta tgtgcacaaa gtatcaggaa cgggaccgtg
6481 tgccggagac tttgccttcc ataaagaggg tgctttcttc ctgtatgatc gacttgcttc
6541 cacagttatc taccgaggaa cgactttcgc tgaaggtgtc gttgcatttc tgatactgcc
6601 ccaagctaag aaggacttct tcagctcaca cccttgaga gagccggtca atgcaacgga
6661 ggacccgtct agtggctact attctaccac aattagatat caggctaccg gttttggaac
6721 caatgagaca gagtacttgt tcgaggttga caaattgacc tacgtccaac ttgaatcaag
6781 attcacacca cagtttctgc tccagctgaa tgagacaata tatacaagtg ggaaaaggag
6841 caataccacg ggaaaactaa tttggaaggt caaccccgaa attgatacaa caatcgggga
6901 gtgggccttc tgggaaacta aaaaaaaacct cactagaaaa attcgcagtg aagagttgtc
6961 tttcacagtt gtatcaaacg gagccaaaaa catcagtggt cagagtccgg cgcgaacttc
7021 ttccgaccca gggaccaaca caacaactga agaccacaaa atcatggctt cagaaaattc
7081 ctctgcaatg gttcaagtgc acagtcaagg aagggaagct gcagtgtcgc atctaacaac
7141 ccttgccaca atctccacga gtccccaatc cctcacaacc aaaccaggtc cggacaacag
7201 cacccataat acacccgtgt ataacttga catctctgag gcaactcaag ttgaacaaca
7261 tcaccgcaga acagacaacg acagcacagc ctccgacact ccctctgcca cgaccgcagc

*Fig. 10TT*

```
 7321 cggaccccca aaagcagaga acaccaacac gagcaagagc actgacttcc tggacccogc
 7381 caccacaaca agtccccaaa accacagcga gaccgctggc aacaacaaca ctcatcacca
 7441 agataccgga gaagagagtg ccagcagcgg gaagctaggc ttaattacca atactattgc
 7501 tggagtcgca ggactgatca caggcgggag aagaactcga agagaagcaa ttgtcaatgc
 7561 tcaacccaaa tgcaaccota atttacatta ctggactact caggatgaag gtgctgcaat
 7621 cggactggcc tggataccat atttcgggcc agcagccgag ggaatttaca tagaggggct
 7681 aatgcacaat caagatggtt taatctgtgg gttgagacag ctggccaacg agacgactca
 7741 agctcttcaa ctgttcctga gagccacaac tgagctacgc acctttcaa tcctcaaccg
 7801 taaggcaatt gatttcttgc tgcagcgatg gggcggcaca tgccacattc tgggaccgga
 7861 ctgctgtatc gaaccacatg attggaccaa gaacataaca gacaaaattg atcagattat
 7921 tcatgatttt gttgataaaa cccttccgga ccaggggac aatgacaatt ggtggacagg
 7981 atggagacaa tggataccgg caggtattgg agttacaggc gttataattg cagttatcgc
 8041 tttattctgt atatgcaaat ttgtctttta gttttcttc agattgcttc atggaaaagc
 8101 tcagcctcaa atcaatgaaa ccaggattta attatatgga ttacttgaat ctaagattac
 8161 ttgacaaatg ataatataat acactggagc tttaaacata gccaatgtga ttctaactcc
 8221 tttaaactca cagttaatca taaacaaggt ttgacatcaa tctagttatc tctttgagaa
 8281 tgataaactt gatgaagatt aagaaaaagg taatctttcg attatcttta atcttcatcc
 8341 ttgattctac aatcatgaca gttgtcttta gtgacaaggg aaagaagcct ttttattaag
 8401 ttgtaataat cagatctgcg aaccggtaga gtttagttgc aacctaacac acataaagca
 8461 ttggtcaaaa gtcaatagaa atttaaacag tgagtggaga caacttttaa atggaagctt
 8521 catatgagag aggacgccca cgagctgcca gacagcattc aagggatgga cacgaccacc
 8581 atgttcgagc acgatcatca tccagagaga attatcgagg tgagtaccgt caatcaagga
 8641 gcgcctcaca agtgcgcgtt cctactgtat ttcataagaa gagagttgaa ccattaacag
 8701 ttcctccagc acctaaagac atatgtccga ccttgaaaaa aggatttttg tgtgacagta
 8761 gtttttgcaa aaaagatcac cagttggaga gtttaactga tagggaatta ctcctactaa
 8821 tcgcccgtaa gacttgtgga tcagtagaac aacaattaaa tataactgca cccaaggact
 8881 cgcgcttagc aaatccaacg gctgatgatt ccagcaagaa ggaaggtcca aaaattacct
 8941 tgttgacact gatcaagacg gcagaacact gggcgagaca agacatcaga accatagagg
 9001 attcaaaatt aagagcattg ttgactctat gtgctgtgat gacgaggaaa ttctcaaaat
 9061 cccagctgag tcttttatgt gagacacacc taaggcgcga ggggcttggg caagatcagg
 9121 cagaacccgt tctcgaagta tatcaacgat tacacagtga taaaggaggc agttttgaag
 9181 ctgcactatg gcaacaatgg gaccgacaat ccctaattat gtttatcact gcattcttga
 9241 atattgctct ccagttaccg tgtgaaagtt ctgctgcgtt gtttcagggt taagaacatt
 9301 ggttcctcaa tcagataatg aggaagcttc aaccaacccg gggacatgct catggtctga
 9361 tgagggtacc ccttaataag gctgactaaa acactatata accttctact tgatcacaat
 9421 actccgtata cctatcatca tatatttaat caagacgata tcctttaaaa cttattcagt
 9481 actataatca ctctcgtttc aaattaataa gatgagcatg attgccctaa tatatgaaga
 9541 ggtatgatac aaccctaaca gtgatcaaag aaaatcataa tctcgtatcg ctcgtaatat
 9601 aacctgccaa gcatacctct tgcacaaagt gattcttgtc cacaaataat gttttactct
 9661 acaggaggta gcaacgatcc atcccatcaa aaaataagta tttcatgact tactaatgat
 9721 ctcttaaaat attaagaaaa actgacggaa cataaattct ttatgcttca agctgtggag
 9781 gaggtgtttg gtattggcta ttgttatatt acaatcaata acaagcttgt aaaaatattg
 9841 ttcttgtttc aagaggtaga ttgtgaccgg aaatgctaaa ctaatgatga agattaatgc
 9901 ggaggtctga taagaataaa cctattatt cagattaggc cccaagaggc attcttcatc
 9961 tcctttagc aaagtactat ttcagggtag tccaattagt ggcacgtctt ttagctgtat
10021 atcagtcgcc cctgagatac gccacaaaag tgtctctaag ctaaattggt ctgtacacat
```

*Fig. 10UU*

10081 cccatacatt gtattagggg caataatatc taattgaact tagccgttta aaatttagtg
10141 cataaatctg ggctaacacc accaggtcaa ctccattggc tgaaaagaag cttacctaca
10201 acgaacatca ctttgagcgc cctcacaatt aaaaaatagg aacgtcgttc caacaatcga
10261 gcgcaaggtt tcaaggttga actgagagtg tctagacaac aaaatattga tactccagac
10321 accaagcaag acctgagaaa aaaacatggc taaagctacg ggacgataca atctaatatc
10381 gcccaaaaag gacctggaga aaggggttgt cttaagcgac ctctgtaact tcttagttag
10441 ccaaactatt caggggtgga aggtttattg ggctggtatt gagtttgatg tgactcacaa
10501 aggaatggcc ctattgcata gactgaaaac taatgacttt gccctgcat ggtcaatgac
10561 aaggaatctc tttcctcatt tatttcaaaa tccgaattcc acaattgaat caccgctgtg
10621 ggcattgaga gtcatccttg cagcagggat acaggaccag ctgattgacc agtctttgat
10681 tgaaccctta gcaggagccc ttggtctgat ctctgattgg ctgctaacaa ccaacactaa
10741 ccatttcaac atgcgaacac aacgtgtcaa ggaacaattg agcctaaaaa tgctgtcgtt
10801 gattcgatcc aatattctca agtttattaa caaattggat gctctacatg tcgtgaacta
10861 caacggattg ttgagcagta ttgaaattgg aactcaaaat catacaatca tcataactcg
10921 aactaacatg ggttttctgg tggagctcca agaacccgac aaatcggcaa tgaaccgcat
10981 gaagcctggg ccggcgaaat tttccctcct tcatgagtcc acactgaaag catttacaca
11041 aggatcctcg acacgaatgc aaagtttgat tcttgaattt aatagctctc ttgctatcta
11101 actaaggtag aatacttcat attgagctaa ctcatatatg ctgactcaat agttatcttg
11161 acatctctgc tttcataatc agatatataa gcataataaa taaatactca tatttcttga
11221 taatttgttt aaccacagat aaatcctcac tgtaagccag cttccaagtt gacaccctta
11281 caaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaaccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca ataccccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aa (SEQ ID NO: 14)

VP30

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAALFQG (SEQ ID NO: 15)

NC_001608

1 gacacacaaa aacaagagat gatgattttg tgtatcatat aaataaagaa gaatattaac
61 attgacattg agacttgtca gtctgttaat attcttgaaa agatggattt acatagcttg
121 ttagagttgg gtacaaaacc cactgcccct catgttcgta ataagaaggt gatattattt
181 gacacaaatc atcaggttag tatctgtaat cagataatag atgcaataaa ctcagggatt

*Fig. 10VV*

```
241 gatcttggag atcttctaga agggggtttg ctgacgttgt gtgttgaaca ttactataat
301 tccgataaag ataaattcaa cacaagtcct atcgcaaaat acttgcgtga tgcgggctat
361 gagtttgatg tcgtcaagaa tgcagatgca acccgctttc tggatgtgat tcctaacgaa
421 cctcattaca gtcctttaat tttggcccct aagacattgg aaagtactga atctcagagg
481 gggagaattg ggctcttttt gtcattttgc agtcttttc tcccgaaact tgttgtcgga
541 gatcgggcta gtatcgaaaa ggcttaaga caagtaacag tacatcaaga acaggggatc
601 gtcacatacc ctaatcactg gcttactaca ggccatatga aagtaatttt tgggattttg
661 aggtctagct ttatcttaaa atttgtgtta attcatcaag gagtaaattt ggtgacaggt
721 catgatgcct atgacagtat cattagtaat tcagtaggtc aaactagatt ctcaggactt
781 cttattgtga aaacagttct tgagttcatc ttgcaaaaaa ctgattcagg ggtgacacta
841 catcctttgg tgcggacctc caaagtaaaa aatgaagttg ctagtttcaa gcaggcgttg
901 agcaacctag cccgacatgg agaatacgca ccgttcgcac gggttctgaa tttatcaggg
961 attaacaacc tcgaacatgg actctatcct cagctttcgg cgattgcgct gggtgttgca
1021 acagcacacg gcagtacatt ggctggtgtc aatgttggcg aacagtatca acagctacga
1081 gaggcggcac atgatgcgga aataaaacta caaaggcgac atgaacatca ggaaattcaa
1141 gctattgcag aggatgatga ggagaggaag atattagaac aattccacct tcagaaaact
1201 gaaatcacac acagtcagac actagccgtc ctcagccaga aacgagaaaa attagctcgt
1261 cttgctgcag aaattgaaaa caatattgtg gaagatcagg gatttaaaca atcacagaat
1321 caggtgtcac agtcgttttt gaatgaccct acacctgtgg aagtaacggt tcaagccagg
1381 cccataaatc gaccaactgc tctgcctccc ccagttgaca acaaaattga gcacgaatct
1441 acagaagata gctcttcttc aagcagcttt gttgatctta atgatccatt tgcgctgctg
1501 aatgaggacg aagacactct tgacgacagt gtcatgatcc cgagcacaac atcgagagaa
1561 tttcaaggga ttccagcacc accaagacaa tctcaggacc tcaacaacag ccaaggaaag
1621 caggaagatg aatcaacaaa tccgattaag aaacagtttc tgagatatca agaactgcct
1681 ccggttcaag aggatgatga atcggaatac acaaccgact ctcaggagag tatcgaccaa
1741 ccaggatctg acaatgaaca aggagttgat cttccacctc ctccattgta cgctcaggaa
1801 aaaaggcaag atccaataca gcacccagca gtaagctctc aggatccctt tggcagtatt
1861 ggtgatgtaa atggtgatat cttagaaccc ataagatcac cttcttcacc atctgctcct
1921 caggaagaca caagggcaag agaagcctat gaattgtcgc ctgatttcac aaattatgag
1981 gacaatcagc agaattggcc acaaagagtg gtgacaaaga agggtaggac tttccttttat
2041 cctaatgatc ttctgcagac aaatcctcca gaatcactta taacagccct cgtagaggaa
2101 taccaaaatc ctgtctcagc taaggagctc caagcagatt ggcccgacat gtcatttgat
2161 gaaaggagac atgttgctat gaacttgtag tccagataac acagcacggt tacctactta
2221 tctactttga tccgattcgt cctcagatca cagtaatcaa atttatttga atattcaaac
2281 tacttttag gatcctatta cttgttacta ttgtgtgaga caacataagc tatcaaataa
2341 caatcacggg caagaaccgg gcatactatg gtgatgcgag ggcattattc agtgctacaa
2401 attcttttt caattgctat aatgatacaa ctacgaacct ccatacattt gccgcaatac
2461 tgtaatcaac actgctgtat ctctccttca agccatctga tttaacttaa taaacatgac
2521 ttgattcaga gagtgtgctg aaaatgttat tgattgagct tctcaaatgg tgcactatcc
2581 tactgttttg ctcagcctag tatactgtaa catataagtg gactctccac ttctcttctc
2641 gagtattccc tataagtgat ttacttgata gaatgtcaag tccactggtt tggagtttcc
2701 ttactctaat gattgtaata attaactgtt ggcttagatg ataacagata cgaggttata
2761 taattactca tagtataaag tataattctt gcctctgttt cttctgtttt ctctttcctt
2821 tgtaatatgc caattaagaa aaactaaaaa tcgaagaata ttaaaggttt tctttaatat
2881 tcagaaaagg tttttattc tcttctttct ttttgcaaac atattgaaat aataattttc
2941 acaatgtggg actcatcata tatgcaacaa gtcagtgagg ggttgatgac tggaaaagtt
```

*Fig. 10WW*

```
3001 cccatagatc aagtgtttgg tgccaatccc tcagagaagt tacacaagag aaggaaacca
3061 aaaggcacag ttggactaca atgcagccct tgtctaatgt caaaggcgac aagcactgat
3121 gatattgttt gggaccaact gatcgtgaag aaaacactag ctgatctact tataccgata
3181 aataggcaga tatcggacat tcaaagcact ctaaacgaag taacaacaag agtccatgaa
3241 attgagcggc aattacatga gataacccca gtgttaaaaa tgggaaggac actggaagca
3301 atttccaagg ggatgtcaga aatgttagcc aaatacgacc acctcgtaat ttcaactgga
3361 agaaccactg caccagctgc tgcctttgat gcttacttaa atgagcatgg tgtccctccc
3421 ccccaacctg cgattttcaa agatcttggg gttgctcaac aagcttgtag taaggggacc
3481 atggttaaaa atgaaacaac agatgcagcc gacaagatgt cgaaagttct tgaactcagt
3541 gaggagacgt tctccaagcc aaatctttca gctaaggatt tagcccttt gttgtttacc
3601 catctacccg gcaacaacac tccattccat atcctagctc aagtcctttc aaaaattgct
3661 tacaagtcag gaaagtccgg agcattttg gatgcatttc accagattct aagtgaagga
3721 gagaatgctc aggcagcatt gactcgacta agcagaacat ttgatgcttt cctcggagta
3781 gttcctccag tgataagagt caaaaacttc caaacagtcc ctcgcccatg tcaaaaaagt
3841 cttcgggctg ttcctcccaa cccaacaatt gacaaaggat gggtctgtgt ttattcatct
3901 gagcaaggtg agacacgggc cctgaaaatc taattctcat tgttaacagt tgcagggga
3961 gtgatctttc cgagttgata caaagacact aaacatttca aaagcatata tgtgggcaaa
4021 acgtgactag accatcttaa tagaagtagt aatttatttc tgtcttaagt gtgattttca
4081 ccttgaaaga gttaaatggt gatagattaa tccttgaagt aactttttta tatattatag
4141 aggaactaat attactaaca aaagggggtct acctaacagg tatgactgag tgatcagtat
4201 attttataaa ccaagcaatt gacttctcac tttttaagaa tcaactaaca acatagaaaa
4261 catatttatc cttgtgtaat tctcggctta gttggaatta acttttgttg caattcaaga
4321 cgcttattca tagtagatta tatgattttt tataagttta agatatctta aattataccc
4381 acaagagata ctgttttaat taagaaaaac tatgaagaac attaagaaga tctttctctc
4441 gtagtgttct tttactggaa ggagtatccc aatctcagct tgttgaatta attgttactt
4501 aagtcattct ttttaaaatt aattcacaca aggtagtttg ggtttatatc tagaacaaat
4561 tttaatatgg ccagttccag caattacaac acatacatgc aatacttgaa cccccctcct
4621 tatgctgatc acggtgcaaa ccagttgatc ccggcggatc agctatcaaa tcagcagggt
4681 ataactccaa attatgtggg tgacttaaac ctagatgatc agttcaaagg gaatgtctgc
4741 catgctttca ctttagaggc aataattgac atatctgcgt ataatgaacc aacagtcaaa
4801 ggtgttccag catggctgcc tctcgggatt atgagcaatt ttgaatatcc tttagctcat
4861 actgtggctg cgttgctcac aggcagctat acaatcaccc aatttactca taatgggcaa
4921 aaattcgtcc gtgtaaatcg actcggtaca ggaatcccag cacacccact cagaatgttg
4981 cgtgaaggaa atcaagcttt tattcagaat atggtgatcc ccagaaattt ttccactaat
5041 caattcacct acaatctcac taacttagta ttgagtgtgc aaaaagcttcc tgatgatgcc
5101 tggcgcccat ccaaggacaa attaattggg aacaccatgc atcccgcagt ctccatacac
5161 ccgaatttgc cacccattgt tctaccaaca gtcaagaagc aggcttatcg tcagcataaa
5221 aatcccaaca atggaccact gctggccata tctggcatcc ttcaccaact gagggtcgag
5281 aaagtcccag agaagacaag cctgtttagg atttcacttc ctgccgatat gttctcagta
5341 aaagaaggta tgatgaagaa aaggggagaa aattccccgg tggtttattt tcaagcacct
5401 gagaacttcc ctttgaatgg cttcaacaac agacaagttg tactagcgta tgcgaatcca
5461 acgctcagtg ccgtttgaaa taatgctcaa atgagacagg agtccatctg cataagaagc
5521 atggcctaaa tgggtgtctg ttaagttctc acaagattga tttgtattga tttcaataat
5581 gctttaacct tacattgctg ctttaaatgg ttaattaagc tgatcagctt gcaagatgta
5641 atctcttttg ggtcatcaga tctataatgg gtttactaga ttatataaaa gaaatagtaa
5701 tgttttataa acaattcttg cttagtttta ctttgattta ctaacatata tcattgtgcc
```

*Fig. 10XX*

5761 cttcattgct aagtaaactc aactgatgat gatattcctt ctgaaatagt aagaaaaact
5821 aatgaagaac attaattgcc gggtaagagt gattaagttc tttaaatttg accaaagtaa
5881 tgttttgtta gtgaatacat tcttatattg cttgattaaa aacaagaaat tatcctaaca
5941 tgaagaccac atgtctcttt atcagtctta tcttaatcca agggataaaa actctccta
6001 ttttagagat agctagtaac aatcaacccc aaaatgtgga ttcggtatgc tccggaactc
6061 tccagaagac agaagatgtc catctgatgg gattcacact gagtgggcaa aaagttgctg
6121 attcccttt ggaggcatcc aagcgatggg ctttcaggac aggtgtacct cccaagaatg
6181 ttgagtatac agaaggggag gaagccaaaa catgctacaa tataagtgta acggatccct
6241 ctggaaaatc cttgctgttg gatcctccta ccaacatccg tgactatcct aaatgcaaaa
6301 ctatccatca tattcaaggt caaaaccctc atgcgcaagg gatcgccctc catttgtggg
6361 gagcattttt cctgtatgat cgcattgcct ccacaacaat gtaccgaggc agagtcttca
6421 ctgaagggaa catagcagct atgattgtca ataagacagt gcacaaaatg attttctcga
6481 ggcaaggaca ggggtaccgt cacatgaatc tgacttctac taataaatat tggacaagta
6541 acaatggaac acaaacgaat gacactggat gcttcggtgc tcttcaagaa tacaactcca
6601 cgaagaatca aacatgtgct ccgtccaaaa taccctcacc actgcccaca gcccgtccag
6661 agatcaaacc cacaagcacc ccaactgatg ccaccacact caacaccaca gacccaaaca
6721 atgatgatga ggacctcata acatccggtt cagggtccgg agaacaggaa ccctatacaa
6781 cttcagatgc ggtcactaag caagggcttt catcaacaat gccacccact ccctcaccac
6841 aaccaagcac gccacagcaa gaaggaaaca acacagacca ttcccaaggt actgtgactg
6901 aacccaacaa aaccaacaca acggcacaac cgtccatgcc ccccacaac accactgcaa
6961 tctctactaa caacccctcc aagaacaact tcagcaccct ctctgtatca ctacaaaaca
7021 ccaccaatta cgacacacag agcacagcca ctgaaaatga acaaaccagt gccccctcga
7081 aaacaacccct gcctccaaca ggaaatctta ccacagcaaa gagcactaac aacacgaaag
7141 gccccaccac aacggcacca aatatgacaa atgggcattt aaccagtccc tcccccaccc
7201 ccaacccgac cacacaacat cttgtatatt tcagaaagaa acgaagtatc ctctggaggg
7261 aaggcgacat gtttcctttt ctggacgggt taataaatgc tccaattgat tttgatccag
7321 ttccaaatac aaagacgatc tttgatgaat cttctagttc tggtgcttcg gctgaggaag
7381 atcaacatgc ctcccccaat atcagtttaa ctttatccta ttttcctaat ataaatgaaa
7441 acactgccta ctctggagaa aatgagaacg attgtgatgc agagttaaga atttggagcg
7501 ttcaggagga tgacctggca gcagggctca gttggatacc gttttttggc cctggaaatcg
7561 aaggacttta tactgctggt ttaattaaaa accaaaacaa tttggtctgc aggttgaggc
7621 gtctagccaa tcaaactgcc aaatccttgg aactcttatt aagagtcaca accgaggaaa
7681 ggacattttc cttaattaat agacatgcca ttgactttct actcacaagg tggggaggaa
7741 catgcaaagt gcttggacct gattgttgca ttggaataga agacttgtcc aggaatattt
7801 cggaacaaat tgaccaaaatc aaaaaagatg aacaaaaaga ggggactggt tggggtctag
7861 gtggtaaatg gtggacatcc gactggggtg ttcttactaa cttgggcatt tgctactat
7921 tatccatagc tgtcttgatt gctctatcct gtatttgtcg tatctttacc aaatatatcg
7981 ggtaatatta agtgtgtatt gattaaagct ttaggacaat tgctactgag cccttcttct
8041 aatctactga aatcaacttg ggagatttt aagaagctga taatttaatg tgaatcagta
8101 gtttacgtat tgttgattgt tatggtttga tattcaattg ttatcatagt caagagtaac
8161 cttttctatt tgatgcatta atgttttaaa ctacctctta agcttttgtg gatggtttca
8221 atatgtgcgt agaggttaat ttaaagagat ttcttgttgc acagttttt gtattactta
8281 cttgggcttg aagacatagt taagactggc cgaaaatgct ctccagtcaa ctccattccc
8341 cctcagaaga gacgtgccgt tcaaagagtc ttgatttata actaaccatt gtaagaatta
8401 atttactctt tccgttatac ttatctacat taattccttg aatgtccagc atcattaacg
8461 acttgtctta attcaatctt ttggatgcaa accataagga aaaatgagcc actttccctc

*Fig. 10YY*

```
8521 tactctgaac taaggaaatt tctcttatca gcctaaaatc tgatccgtta ggtcatgggc
8581 ccttcataat ctgtttgagc atgaatgttg atcaaatgac caaataatag tgcatttgta
8641 tagattcaat tatcctttat taagaaaaag atagacagaa cacaaagaat tgataaaata
8701 ttactttgat caattttgcg aggaattata aaaatcttga gggacaaatt attgtaacgt
8761 agagtcgaag aacattaagt gttctttgtt agaattattc atccaagttg ttttgagtat
8821 actcgcttca atacaacttc ccttcatatt tgattcaaga tttaaaatgc aacaaccccg
8881 tggaaggagt cgaactcgca accaccaaac cgcatcatct atatatcatg aaactcagtt
8941 gccctccaaa cctcactaca ccaatcatca tccacgtgca agatcgatga gctcaacccg
9001 cagtagtgca gaaagcagtc ccaccaatca tattcccgt gctcgaccac cccaacatt
9061 caacttatcg aaaccccctc ctcctccaaa agacatgtgt aggaacatga aaattggatt
9121 gccgtgcact gatcccactt gtaatagaga tcatgacctt gataatctaa caaatcgtga
9181 actttgcta ttgatggccc gaaaaatgct ccccaataca gacaagactt ttagaagtct
9241 gcaggattgt gggtcaccgt ctctttctaa agggctctca aaagataaac aggagcaaac
9301 gaaagatgtg ttgaccttgg aaaatctagg acacattctg aactacctcc acagatcaga
9361 tattgggaaa ttggatgaga catcactccg tgcagcatta agtttgacgt gcgctggaat
9421 tcgaaagacg aatagatcct tgatcaacac catgaccgaa ttacacatta accatgaaaa
9481 tctcccgcaa gaccaaaacg gtgttatcaa acagacatat acaggtattc accttgacaa
9541 aggaggtcaa ttcgaagccg ccttatggca aggttgggat aagagatcga tatctttatt
9601 cgtacaagca gctttatatg taatgaacaa tatcccttgt gaatcatcaa ccagtgtgca
9661 agcctcatac gatcattta ttcttcctca aagtcaaagt aaaggacaat gattattgtt
9721 tgaaagttga caatcaaatc actttcagtt tttagtttca actcttattg cgagacttga
9781 acacaattct actaacttca ataagtgacc ccaaattcaa gtttactgaa gactacgacg
9841 ataataatca ccaattcatt gtaaattact cgattaaaat attcttaagc tatcttaaac
9901 ttgatgatgc agctctgttt caccttctg ttgatttcaa tgttacagct atatctaagt
9961 gtctaattaa caacttgtac ctctaaggaa aatcatgaag aacattaaga aaaaggatgt
10021 tcttattttt caactaaact tgcatatcct ttgttgatac ccttgagaga caacttttga
10081 cactagatca cggatcaagc atatttcatt caaacacccc aaatttttcaa tcatacacat
10141 aataaccatt ttagtagcgt tacctttcaa tacaatctag gtgattgtga aaagacttcc
10201 aaacatggca gaattatcaa cgcgttacaa cttgcctgca aatgttacgg aaaaaagcat
10261 aaatcttgac cttaattcca cagcacgatg gataaaagaa cccagtgttg ggggctggac
10321 agtgaagtgg ggaaactttg ttttccacat accaaatact gggatggcat tgttgcatca
10381 tttaaagtct aacttcgttg ttccagagtg gcaacaaaca aggaatctat tctcccacct
10441 ctttaaaaac ccaaagtcaa caattataga accgttcttg gctttgagga tcttgcttgg
10501 agttgctttg aaggatcaag aattacagca atcattaatt cctggattta gatctattgt
10561 tcatatgctt tcagaatggt tgctcctaga ggtaacgtcg gcaatccata ttagcccaa
10621 tctgttggga atctatttga cctcagacat gtttaagatt ctgatggcag gtgtgaaaaa
10681 tttcttttaat aagatgttca ctcttcatgt tgtaaatgac cacggaaaac ccagcagtat
10741 tgaaataaag ttaactggac aacagatcat tatcactcgt gttaatatgg ggtttctagt
10801 ggaagtcagg aggattgata ttgaaccttg ttgtggtgag acagtcctct cagaatcagt
10861 tgttttggg ctagtggctg aggcagttct aagagaacac agtcaaatgg agaagggcca
10921 acccctcgat ctgacacaat acatgaacag caaaattgct atataagtgg cttaaattag
10981 catggatatt catagtttaa ccacataata atgttggagg cacagtacat tatagttaat
11041 tatcctgtat aacaaagaat ataacctaccc tgatttatat ttactggtat aaaatagtgg
11101 tatcatctta ttaaatagtt gtcatataac aggctgttcc tataatctga ttgtgagatt
11161 ataaacttgt agaattaccg tggatcacaa ctgttgcata tcttccaaaa tatatctttt
11221 gcaagcgatg tgtgcttgaa tacgtcgata taatacatac taataacgat tgattaagaa
```

*Fig. 10ZZ*

```
11281 aaaccaatga tggatattaa atatccatca agcaggtgtc gcagaatacc aggggtttca
11341 tatgctgcca tatttactaa atcttacata ggattatatc attctcttcg atacacgtta
11401 tatctttagc aaagtaatga aaatagcctt gtcatgttag acgccagtta tccatcttaa
11461 gtgaatcctt tcttcaatat gcagcatcca actcaatatc ctgatgcaag gttgtcctcc
11521 cctataatcc tagaccagtg tgacttatta gccagaagtt tagggttgta tagtcattat
11581 tcacataatc cgaaattgcg taattgtagg attccacatc atatttaccg tttaaggaat
11641 tcgacagcat taaaaacatt tcttcagaac tgttcaatac tcaccgtccc ttttcattca
11701 atctgggatc atattttaac ttccattcaa tatgatgcaa ttaatcatgt tgatgatttt
11761 aaatacctat tgccctctga gctagtcaag tatgcaaatt gggacaacga gttcttgaag
11821 gcatatctta ataagatctt aggacttgac catgttttc cagcttctgc aaggtcacaa
11881 tgggaggatt tttctcctaa ggaaaatcct tattattggg ggatgctgtt actcgtgcat
11941 ttatctcaac ttgccaggag gataaaagga caaagagggt cattaagaag taactggaag
12001 tttataggaa cagatttaga gctgtttgga atagcagatt ttattatttt taaagttcca
12061 gtaaaaacaa taatccgaaa tgctgtaagc ttacaagctt caaaaccagg gttaagagta
12121 tggtaccgtg accaaaactt gaccccttat ctatgcgatg atgagtttat tgtaagcgtc
12181 gctagttatg aatgttttat catgattaaa gacgtcttca ttgagaggta taacacgtgg
12241 gaaatatgtg cccgcgcctg gctcgaagac agtgatggag ctgattatct ccctcttgat
12301 gtgttaggtg agttatacaa ccaggagat caaattattg ccatgtactt ggaagacggt
12361 ttcaaattga tcaaacactt ggaacccttg tgtgtcagct gtatacaaac acatggcatc
12421 tttacaccag gaaaatactg gttccaatca cagaggattg agtcatatta tgaggagctc
12481 tgtagtctca attggaaatt taaaatttca ggcaataaag ctgagtgtgc tcaaaacttt
12541 attaaaacta taattcaggg gaaattgact cctcaacaat actgtgaatt attctctcta
12601 caaaagcatt ggggtcaccc cgtttatac attgatgttg cactagataa ggttaaaaaa
12661 catgcgcaat ctgtaaaaat cttaaaacct aaagtcatgt ttgaaacttt ttgtgttttc
12721 aaatttatag tagcaaagaa tcattatcat tctcaaggat catggtataa aaccacaatg
12781 gatttgcatt taactccata tcttagacaa catattgtgt caaattcatt tccgtcacaa
12841 gccgaaattt atcagcatct ttgggagtgg tatttcgtgg agcatgaacc tcttttctca
12901 actaaaataa taagtgattt aagtattttt ataaaagaca gggctactgc tgtgaaccag
12961 gagtgttggg acagtgtttt cgatagaagt gtattaggg ataacccctcc tgttagattt
13021 cagtcaaaga gagtgccaga gcaattttg ggccaagcag acttttcctt gaatcaaata
13081 ttggattttg ctgaaaagtt agaatatttg gctccttctt ataggaattt ttccttctca
13141 ttaaaagaaa aagagttgaa tataggaaga acttttggga aattaccata tcgtgtcaga
13201 aatgtccaaa cactcgcaga agccttgcta gcagatggac tagcaaaagc attccctagc
13261 aacatgatgg ttgttactga gagggaacag aaagaagcat tattgcatca ggcttcttgg
13321 caccacaatt cagcaagcat aggggaaaac gctatagtaa ggggtgcaag ttttgttact
13381 gatcttgaga aatacaacct tgccttccga tatgaattta cacgacattt catagactac
13441 tgtaatcgat gttatggtgt gaagaattta ttcgattgga tgcactttt aataccacta
13501 tgttatatgc atgtcagtga ttttatagc ccaccacatt gcgtaacaga agataaccga
13561 aataacccac cggattgtgc taatgcttat cattatcact taggggggtat agagggactt
13621 caacagaaat tgtggacatg tatatcatgt gcccagatca cccttgtaga gttaaaaact
13681 aaattaaaat taaaatccag tgttatgggt gataatcaat gtataacaac tctaagtctt
13741 ttccaattg atgctcccga cgattatcaa gagaacgaag ctgaattaaa tgcggcacga
13801 gttgctgtcg aattagctat tactacgggt tatgatggta tattttgaa gcctgaagaa
13861 acatttgtcc attcagggtt catttatttt ggtaaaaagc aatacctcaa cggtgttcaa
13921 ctgccacaat cattgaaaac aatggcaaga tgtggaccct tatctgactc tatttttgat
13981 gatcttcaag gttccctggc cagtattggt acatccttg agagaggaac aagtgagaca
```

```
14041 cggcacattt ttccgagtcg ttggatagct tcatttcatt caatgttagc aataaattta
14101 ttaaatcaga atcaccttgg gtttcccta gggttcagta ttgatatttc ttgtttcaaa
14161 aagcctctta cctttcgga aaaattaatt gctcttataa cgccccaagt tctaggaggg
14221 ttatcatttt tgaatccgga gaaattgttc taccggaaca taagtgatcc gctcacttcg
14281 ggtctatttc aacttaagaa tgcattagaa tttcttgaaa aggaagaatt attctatatc
14341 ttgattgcta aaaaacctgg tttagcagat gcctcagatt tcgtcatgaa tccattaggc
14401 ttaaatgtac caggatcaag ggaaataata acgttcctta gacaaacagt tcgtgaaaat
14461 atcacgatca cgtcacaaaa tagaataata aattccctt tcacatagg ttctgattta
14521 gaggaccaaa gggtgtgtga gtggctttta tcatcaaacc ccgtaatgag tcgatttgct
14581 gctgacatct tttcaagaac gcctagtgga aaacggcttc aggtcttagg ctatctggaa
14641 ggaacaagaa cattactagc ttctcggaca ataagtttaa ctacagaagg gacaatgttg
14701 atgaaattaa gggaattaac aagaaaccga tggaaaagct ggttttctta tattgatgca
14761 ttggacgatg atttatctga gtccttagaa aaattcacat gtactgttga tatagctaat
14821 ttcttgaggg catattcatg gctcgacgtc ttaaagggga aaaggctaat tggtgccaca
14881 ttgccatgtt tactagagca atttaaggta aagtggatta atttgtctga ggatttaagg
14941 gaacaattta atatgtcttc agaatcagaa tcaactataa atttattgcc gtatgactgc
15001 aaggaactgc gacttggaag aagcaatgac acagagttaa actatgtcag ttgtgctctc
15061 gaccggaaag ttgtccagaa acatccctct gttaatcgtc tggcttggac aataggaaat
15121 cgagcaccgt atataggatc acggacagaa gacaagatcg gttatcctcc cttaagagta
15181 aattgtccat cagcggcact taaagaagcc attgagatgg tttctagatt gttgtgggtg
15241 actcaaggca ctgcagaccg agaaaaattg cttattcctc tcctcaattc gagggtaaat
15301 ctggactatc agacagtgct taacttttta cctacacact actcaggcaa catagttcat
15361 agatataatg accaatatgg acaacattcc tttatggcaa acaggatgag taatacatct
15421 acacgtgcaa ttatatcaac taacacactg ggcaaatatg ctgggggggg tcaagctgct
15481 gttgatagta atataatctt ccaaaatact atcaatttag gagtggcagt tttagatatt
15541 gcattatctc ttgctaaatt gtcgtcagca tcaaatgtca ctttccgttt gatgttaaat
15601 aagtgctgca cgcggcatgt gccatctgaa tacctatttt ttgataaacc tttagatgtg
15661 gatttgaaca agtatatgga caatgagtta gtttatgaca atgaccctct ttgcagtggg
15721 attaaaggga gattaggcag agtatcccga tcaacacactct cgttgagttt gaatgtcagt
15781 gacattggtt cttatgactt tccaactatt gctgcatgga cactaggaga aactatagtc
15841 ggaagcattt tttctgatga gtcttctcaa agtacagatc caataagttc aggttgcaca
15901 aaaactttcg tcacacattt ccttgtgtat ccagttgaga gtatttttta tgcattcggg
15961 gctaacttaa tagtagaaag tttaagtcta agtaggatca aatcaattaa gaacctctca
16021 gatttgacat tccttatatc atccacaatc aggaatttat cacatagatc acttcggatt
16081 cttcaatcta ccttccgaca tgaattggta ctcacccgac tagcccacca catacccgtta
16141 atttctttaa tgttagggggg ttctgcagga gagaaaagtt catcagatgc tgttcggcta
16201 tttcttacag caagttacca gaatttcatc aacaacttca gttgtttgat gaaaaagggc
16261 cagtcatcac taccggtttg gctttactttt cctagtgaag ggcaacaatt aaaacctata
16321 ttaaaaatct tacagagatt atcagacttg ttatcacctg acaaagttca aaagcatcaa
16381 atcttagctg acacctgttg tccaattgac agcttttggg tctatccaag caagtccaca
16441 aggactaacc actattatgc aagccttaat tattggagag acaaagctaa taaggtcaag
16501 aatactcctt tttcgcattt gataaattgt tcatttcttg aacttctttc acacaccagt
16561 tcggtctctt ctaatcaaca agtgaccaat tcgaaatata ttgttcatcc agagaatatc
16621 cctgaaataa atgcaagaac caaattaata gattatggat caacagctct acaggggatg
16681 gatatcaaga tgcactctct ggagcaaaat ctggttggaa attgtcgacc atcaaagggc
16741 attagattca aggacaatcc aaaaacaaca aaacatgacc agggatttgt gggggaaggac
```

*Fig. 10BBB*

16801 tcttcaccgc gaccaatgtc ccctgaagac aacatgcaga ctcctgcata catacatagt
16861 tccccccat atcaaaccct tacaaaatca ccagatgtac atgaggactt tgatgcctcg
16921 aaggtaatct taaattctga aataaataac cttaacctta cggattgtac gcttaataca
16981 aagtcattga caactcctac cgggacagaa atcttaggta taagtccgtt cagatcctct
17041 agatattcat caacttccag ggaacggtct cgactatcta gagaacaagc ttcatatttg
17101 tatgttgatt gcagtaatat tccctctatc tctctagacc cgggttttca gaatatgtct
17161 gatcagaatc aagttcaaat gttaatcaat acctacaaac gtgatttaca tgcttgtttt
17221 gatagcaatc aattctgtcg gtttacaggg gtagtctcat caatgcatta caagcttat
17281 gatctcttgc ctccaggtga attgagaaag gcaatttgct tggccgaagg agaaggaagt
17341 ggtgctcggt tactttgaa gtggaagaag acggattatt tattttcaa cactttggct
17401 acggattcac agcaagaagc agagatttta agtggccggg taataccgag aatgttatat
17461 aacatagata ggtaaatgc tttgcttgaa tcaagaagat taatattgaa caacctaact
17521 atccaaatta cagatattac aagtccacta tggctagatt ctgtaataca atacttacct
17581 gaagatagcg acattcttac aatggacgca gagaccacta aagatgaaac aagggaacag
17641 ctttataaga ctattgtgaa tatttggaca cgtacttctc ctaatattcc aaaaattagc
17701 atcatcaagg tattttatt agactatgaa gggactttgt tcttaatgag gaatgccatt
17761 cagtattatg ggcaggttca actcaagaaa ccatatagct caaatgcaaa aaactcagaa
17821 tggtacttgt gttgcggtaa acgaagaatt caacgactca aaattgattt ctcagaccag
17881 gtaggaattt ttctgatttg taaagcaatg tcgcgccaaa gacaagcaat tccttactgg
17941 ttaaaacata tagaaaagaa ttatcctgct tcattacata agttttcct aactttgggt
18001 ttcccttctt tagagtcatc tttctgccat cgttatacta ttccattcag tgaaggaaag
18061 gctctttttc ataaggtcca atcttatgtt cgtcaaggca aacaacattt acattctctt
18121 atgttggatt atgaaaacaa ttcacctcta ctagacttga gaaatcactt tatttgctca
18181 ttgaggggaa agataactaa gtattacaat gatatattaa agttaaatct agttatcaag
18241 gcagtagaga aaggtaaaaa ttggtcacaa cttgttgaga cccttcctaa tatgcattca
18301 gtctgcatag tacacgtgga tcatgagtgc tttggatgtg agaaacggtt actactcaaa
18361 tggatttta ttagaaacac aaagatcgca gaacaaaaat tacttaatag agtaatcggg
18421 tatattttat tctttccgtt cggtctgttt aaatctgaat cattaacagc ataactttaa
18481 caaagagaac ttcatttaat tcacgaaaat aatctattta aaaatgaggg ttacatttc
18541 tagagtattg tatgagaaat aataaaataa acaagaagaa gaaaaaacta ttagacagct
18601 tgctttacac aagataatct tatatcgtct caaaccgtac acaagtaggg aaatcacgcg
18661 cacaaattaa cttgtgattg aacgttcggt cacaccagtg gtaactttc aatgttagtt
18721 actcaaatat tattgctcat aattggtatt gatattggta cattgggtga gtccttgagc
18781 tttatcctta atataatgta agaaattagg gaaatactga gatatactag ttgaattgag
18841 ttatgacata ccatatatca taaatataaa agaacgatct gctgtaatct ataagcatct
18901 ctttacata cattggggaa agaactaggt tatcgttgag attaaaaga ctacgttacg
18961 ttttctctga tgacaagtga caaaatttcg tagttaaatt tctagaatgt caatgtgaat
19021 gtaaattaag aaaaaccaat atataaaatt aaaaaattaa aaaactttga tataagtaac
19081 acaaaacatt cttcatcttt tttgtgtgtc ca  (SEQ ID NO: 18)

VP30

MQQPRGRSRTRNHQTASSIYHETQLPSKPHYTNHHPRARSMSST
RSSAESSPTNHIPRARPPPTFNLSKPPPPPKDMCRNMKIGLPCTDPTCNRDHDLDN
LT

*Fig. 10CC

NRELLLLMARKMLPNTDKTFRSLQDCGSPSLSKGLSKDKQEQTKDVLTLENLGH
ILNY
LHRSDIGKLDETSLRAALSLTCAGIRKTNRSLINTMTELHINHENLPQDQNGVIKQ
TY
TGIHLDKGGQFEAALWQGWDKRSISLFVQAALYVMNNIPCESSTSVQASYDHFI
LPQS
QSKGQ (SEQ ID NO: 19)

DQ447652

```
   1 agacacacaa aaacaagaga tgatgatttt gtgtatcata taaataaaga agaatattaa
  61 cattgacatt aagactagtc attttgttaa tattctttaa aagatggatt tacatagttt
 121 gctagaatta ggtacaaaac ccacagcccc tcatgttcgt aataagaagg tgatattgtt
 181 tgatacaaac catcaggtta gtatctgtaa ccagataata gatgcaataa actcagggat
 241 cgatttagga gatctttttgg aaggcggctt gttgacatta tgtgttgaac attattacaa
 301 ttctgacaaa gataaattca atacaagtcc tattgcaaaa tatctgcggg acgcgggcta
 361 tgagtttgat gtcatcaaga atcctgatgc aactcgcttt ctagaggtta ttcccaatga
 421 acctcattac agcccttttga ttttggctct caaaaccttta gaaagcactg aatctcaaag
 481 ggggaggatt gggctcttttc tgtcatttttg cagtctttt ctcccgaaac tcgttgtcgg
 541 agaccgagct agcatcgaaa aggccctgag acaagtaaca gtgcatcagg aacaagggat
 601 tgtaacatac cccaatcatt ggctcactac aggtcacatg aaagtaatct tgggatttt
 661 aagatctagc ttcattttaa agtttgtctt aatccatcag ggagtaaact tggtgacagg
 721 tcatgatgcc tatgacagta tcatcagtaa ttcagtagga caaactagat tctcagggct
 781 tcttattgtg aaaacagttc tagagttcat cctacaaaaa actgattcag gggtggcatt
 841 gcatccactt gtgcggacct caaaagtaaa aaatgaagtt gcaagcttca aacaggcatt
 901 gagtaactta gctcgtcatg gagagtacgc accatttgca cgggttttga atttatcagg
 961 gatcaataac cttgagcatg ggctctatcc tcagctttca gcaattgcac tgggcgttgc
1021 aacagcacat ggcagtacat ggctgtgt taacgttggc gaacaatacc aacaactgcg
1081 agaagcagca catgatgcag aagtaaaatt acaaaggcga catgaacacc aggaaattca
1141 ggccatcgcc gaggatgacg aagagagaaa aatattagaa cagttccatc tccagaagac
1201 tgagattaca cacagtcaga cattggccgt cctcagccaa aaacgagaga aactagctcg
1261 tcttgctgca gaaattgaaa acaacattgc agaggatcag gggttcaaac aatcgcagaa
1321 tcaggtgtca caatctttct taaatgatcc cacacctgta gaagtgacag tccaagccag
1381 gtctataaat cgaccaacag ccctgccccc cccagtcgac aacaaaattg agcatgaaac
1441 tgaagaggac agctcctcat caagtagttt tgttgacttg aatgatccat ttgcactgct
1501 aaacgaagac gaggatactc ttgaaaatag tgtcatggcc ccaagcacta ctttgagaga
1561 acccaaagaa gtttccgaac cactaaggca aactcaggac cttgatatta gccaaaagaa
1621 acagggaaat gaatcaacag atccagcaag aaaacaattc ttgcgatatc aagaattacc
1681 tcctgttcaa gaagacgatg aatcagaata cacaactgat tctcaggaaa gtgacgatca
1741 accaggatct gataatgaac aaggcgttga tctcccacca cctccattat atgctcagga
1801 aaagagacag gatcccatac agcatccaga cgtgagctcc caagatccct ttggcagtat
1861 tggagatgta gatggtgata ttttggaacc tataagatcg ccttcttcac cgtctgctcc
1921 tcaggaggac acaaggatgg gagaagccta tgaattatca cctgattta caagctatga
1981 ggataatcag cagaattggc cacagagagt ggtaacaaag aaaggcagga ccttccttta
2041 tcctaatgac cttttacaga cgagtcctcc agagtcatta ataacagccc ttgttgaaga
2101 gtaccaaaac cctgtctcag caaaagagct tcaagcggat tggcctgaca tgtcatttga
```

*Fig. 10DDD*

```
2161 tgagaggagg catgttgcta tgaacttata atttcgacaa cacagcacga ctactcattt
2221 atttacttca atatatttta cctccgaaac ataatagtca aatttattta aatatctaga
2281 ccactttcaa ataccttgct atatatcact gttatgtgag atggtgcaaa cctagaatg
2341 ataaccaaag gtaggaactg gttatatgac agtacctcga aggtgttatt caatggttta
2401 gatctctcct ctaattgcta cgagaataca actacaaacc tctttaccit ggttacaata
2461 ctgtaataga tatgattgta tttctttctt aaatcatctg attcaacttg atagatataa
2521 cttgattcag agaacatttt gggaacgtca ttaactaaat tctctaaatg atgtactgta
2581 ttactgtttc acccgactaa ttatatagta gcatattaat ggatccttta cctctcctcc
2641 tatgctcttc ttataagtca ctcaaccggt gaaacgccga gtttgttggc ttagagtttt
2701 cctgttttac tgaatgtagt aattaatgat tgacttgagt gttgatggaa tcaagatagt
2761 gcgatgattc atattataag gtacaatttc cattcctgtt ttgccaatgt atcttcttcc
2821 ttatcacatg ccaattaaga aaaacaaaga gtcgaagaat attaaagatt ctcttttaata
2881 ttcaaaaaca gttcttaatt cttttccttt cctttattaa tataatatat cgataaatct
2941 tacaatgtgg gactcgtcat acatgcaaca agtgagtgag ggactgatga ctggaaaagt
3001 tccaatagat caagtgttcg gcactaatcc cttagaaaag ttatataaga gaagaaagcc
3061 gaaagggaca gtgggattac aatgtagtcc ttgcttaata tcaaaatcaa caagtactga
3121 cgacattgtt tgggatcagc taatcgtaaa gaaaacattg gctgacttgc ttatacctat
3181 aaataggcaa atgtcggaca ttcaaagcac cctaagcgaa atgacaacaa aagtccatga
3241 gatcgagcgt caactacatg atatcacccc agttgtaaaa atgggaaaaa cgctagaagc
3301 aatttccaaa ggaatgtcag agatgctagc taagtacgat catctcgtga tttcaactgg
3361 aagaaccacc gcaccagctg ctgcctttga tgcttactta aacgagcatg gagtccccc
3421 ccctcagcct gcaatcttca aagatcttgg agttgcccaa caagcctaca gtcaaaagac
3481 tatggtcaaa aaccaaacaa cagatgcagc tgacaaaatg tcaaaggttc tggaactcag
3541 tgaagaaaca ttttccaagc caaaccttc agctaaggat ttggctctat tattatttac
3601 tcatctccct ggcaacaaca ctccattcca catactcgcc caagtccttt caaaaattgc
3661 ttacaaatca ggaaagtctg gagcattctt ggatgcattc catcagattt taagcgaagg
3721 ggagaatgct caggctgcat taactcgatt aagcagaaca ttcgatgctt tccttggagc
3781 agttcctcca gtaataaaag ttaaaaactt tcaaacggtc cccgccctt gtcaaaaaag
3841 cctccgagct gttcccccaa atccaacaat tgacaaggga tgggtctgtg tctattcatc
3901 tgaacagggt gaaacccggg ctcttaaaat ctaatccttg cgattcattc ttgaacaaag
3961 aatgatcttt ctaggttaat aaaaaaccac taaacatttc aagagtttgt ggatgattta
4021 agcatatttg ggtaaattta atcaggggtag tagtttaaat ttgtttaag cgtgattttc
4081 attaagagag ggttaattag ttatagattg atctttagtg tactccatat gcataatata
4141 gagaaattaa tattactaac aaaaagggtt ttaaacgg atttgattaa tagatcagta
4201 tatctcaaaa gccaaataat tgacttctta ctctttggga atttactaac aatataggaa
4261 agatatttat tcttacgtaa tccttggccc aacggaaact aacctccatg gtcattcaat
4321 atgcttgctc atgatatatt cagagatttt ttataagttc aaaacgttgt aaattatact
4381 tgcataaaat actgttttaa ttaagaaaaa ctatgaagaa cattaagtgg attttccctt
4441 cttagtgttc ttttacaaag caaggtttt aaattcaagt agatcaagtc tactcttgct
4501 gaacttactt ctttaaaaat taatttacac taaacaattc gttttgttg acggaacaaa
4561 ttcagatatg gccagttcca gcaattataa tacgtatatg caataccgtga accctccccc
4621 ttatgctgat catggtgcaa atcagttaat cccagcagat cagctatcaa atcaacatgg
4681 tataactccg aattatgtgg gcgatttgaa tctagatgat cagtttaaag ggaatgtttg
4741 tcacgccttc actttggaag caataattga tatatctgct tataatgagc ggacggtcaa
4801 aggagtccca gcgtggctgc ctcttgggat catgagcaat ttgaatacc ctttagccca
4861 cactgttgct gcattgctta cagggagcta cacgattacc caattcacgc acaatgggca
```

*Fig. 10EEE*

```
4921 aaaatttgtt cgtgttaatc gacttgggac aggaatccca gcacatccac tcagaatgct
4981 gcgggaagga aaccaagctt ttgtccaaaa catggtgatt cccaggaact tttctacaaa
5041 tcagtttacg tacaatctta ctaatctagt attgagcgtg caaaagcttc ctgatgatgc
5101 ttggcgcccg tccaaagaca aattaatcgg aaacaccatg caccctgcgg tttctgtaca
5161 cccaaacctg ccgcctattg tcctaccaac agttaaaaaa caagcctatc gtcagcataa
5221 gaatcctaac aatggaccac tgctggccat atctggcatc cttcatcaac tgagggttga
5281 aaaagtccca gagaagacga gcttattcag gatttcactt cctgccgaca tgttctcagt
5341 aaaagagggc atgatgaaga aaagaggaga aggttctccg gtagtttatt ccaagcgcc
5401 tgagaatttt ccttttgaatg gcttcaacaa ccggcaagtt gtgctagcat atgctaaccc
5461 gacactcagt gctgtttaat aagataattg ggtaagacaa tggcccttct gtacaaaggg
5521 tctgattcag atagatattt gtcagattca tgcaggatca ttttaagttg attttaatag
5581 tgctttaacc cttcactgct accctaaagg attgattgag ctgattaacc tataatgtat
5641 aacttctttt aaaccgctaa atcaatcata agtttgtcag atcatatagg atgaatgtta
5701 atacgtgata aatggttcct attcagtttt actttaacct catagtaaat cttataagac
5761 tactcatctt caagttgatc aattcaaaga taatttccct tctaaaataa taagaaaaac
5821 taatgaagaa cattaattgc taggtaaagg caattaagtt ctttgaactt tgcaaaagta
5881 aggtttcact agtgagtaaa ttcctgtatt agcagattaa aaccaaggaa gcaccccgac
5941 atgaagacca tatactttct gattagtctc attttaatcc aaagtataaa aactctccct
6001 gttttagaaa ttgctagtaa cagccaacct caagatgtag attcagtgtg ctccggaacc
6061 ctccaaaaga cagaagatgt tcatctgatg ggatttacac tgagtgggca aaaagttgct
6121 gattcccctt tggaagcatc taaacgatgg gctttcagga caggtgttcc tcccaagaac
6181 gttgagtata cggaaggaga agaagccaaa acatgttaca atataagtgt aacagaccct
6241 tctggaaaat ccttgctgct ggatcctccc agtaatatcc gcgattaccc taaatgtaaa
6301 actgttcatc atattcaagg tcaaaaccct catgcacagg ggattgccct ccatttgtgg
6361 ggggcatttt tcttgtatga tcgcgttgcc tctacaacaa tgtaccgagg caaggtcttc
6421 actgaaggaa atatagcagc tatgattgtt aataagacag ttcacagaat gatttttct
6481 aggcaaggac aaggttatcg tcacatgaac ttgacctcca ccaataaata ttggacaagc
6541 agcaatgaaa cgcggagaaa tgatacggga tgttttggca tcctccaaga atacaactcc
6601 acaaacaatc aaacatgctc tccatctctt aaacctccat ccctgcccac agtaactccg
6661 agcattcact ctacaaatac tcaaattaat actgctaaat ctggaactat gaacccaagt
6721 agcgacgatg aggacctat gatttccggc tcaggatctg gagaacaggg gccccacaca
6781 actcttaatg tagtcactga acagaaacaa tcgtcaacaa tattgtccac tccttcacta
6841 catccaagca cctcacaaca tgagcaaaac agtacgaatc cttcccgaca tgctgtaact
6901 gagcacaatg gaaccgaccc aacaacacaa ccagcaacgc tcctcaacaa tactaatgca
6961 actcccacct ataacactct caagtacaac ctcagtactc cttccccctcc aaccgcaac
7021 atcaccaata atgatacaca acgtgaacta gcagaaagcg aacaagccaa tgctcagttg
7081 aacacaactc tagatcctac agaaaatccc accacagcac aagcaccaa cagcacaacc
7141 aacatcgtca tgacgacatc agatataaca agcaaacacc ccacaaattc ttctccggat
7201 tctagtccga caacccgccc tcctatatac ttagaaaga aacgaagcat tttctggaaa
7261 gaaggtgata tattcccgtt tttagatggg ttaataaata ctgaaattga tttgatcca
7321 atcccaaaca cagaaacaat ctttgatgaa tcccccagct ttaatactic aactaatgag
7381 gaacaacaca cttccccgaa tatcagttta acttictctt atttcctga taaaaatgga
7441 gatactgcct actctgggga aaacgaggat gattgtgatg cagagttgag gatttggagt
7501 gtgcaggagg acgatttggc ggcagggctt agctggatac catttttgg ccctggaatc
7561 gaaggactct atactgccgg tttaatcaaa aatcagaaca attttagttig taggttgagg
7621 cgcttagcta atcaaactgc taaatccttg gagctcttgt taagggtcac aactgaggaa
```

*Fig. 10FFF*

```
7681 aggacatttt ccttaatcaa taggcatgca attgactttt tgcttacgag gtggggcgga
7741 acatgcaagg tgctaggacc tgattgttgc ataggaatag aagatctatc taaaaatatc
7801 tcagaacaaa ttgacaaaat cagaaaggat gaacaaaagg aggaaactgg ctggggtcta
7861 ggtggcaaat ggtggacatc tgactggggt gttctcacca atttgggcat cctgctacta
7921 ttgtctatag ctgttctgat tgctctgtcc tgtatctgtc gtatcttcac taaatacatt
7981 ggatgacata aagtttacaa tggttagagc tttaggaaag ttgctgctga gccctttgtc
8041 taatctactg aaatcgactt aaagaatcct cagggagctt ataactcaat gtgaatcgat
8101 tccctatata ttgttgattg tgctgatata gcagtcaagt gtcaccatca ttaggagcaa
8161 ttcttctgat ccaatgcatt gaagtcacta attacttcta aaatccttat cttttaatccg
8221 aatattcaca tagaaatcaa ttttgggaaa attccagtag tgcgtctttt catgtcactt
8281 ctctgaacct aagaccataa taaatattgg ttaaagaggt cagctggtca atcttctatt
8341 ttcatattaa agatatactg ctcagaaact cctagtttgc aacccaatct tggaaaaaga
8401 aacctcctct tttgatcata actatctcta tcaatgtctt gaacacttaa tattattaac
8461 aacttatttt tatttaatct tttaaatgca aatcaaaaga ggacatgagc caccctcact
8521 ttacttcaat acgaaggaat tcttcttctc agcctacatt ttaatttacc aggtgataaa
8581 cttatggtaa tttaccttaa cataggtgct gataagatga ttggatgata acacatttac
8641 cgagatttaa tcgtatctca ttaagaaaaa gataattaga acactggaaa ttgataaact
8701 tctatttttga tcaatgtaga aaagaattat aaaaatctta gtaaataaat tactgcaaag
8761 taaaaacgaa gaacattaag tgttctttat taaagttgtt catccttttt gcttttgatt
8821 atatttgatc aaatacaact tcatttggta ttcattccaa gattcagaat gcaacagcct
8881 cgtgggagaa gccgaaatcg tagccaccaa gttgcactat ccacatacca tgaaaatcaa
8941 ttaccctcta aacctcaata cattaaccat catccacgtg caagatcaat gagttcaacc
9001 cgtagtagta cagaaggtag ccctactaat catgcttcc gtgctcgacc actttcaaca
9061 tttaatctat cgaaacctcc tcccccccg aaagacatgt gcaggaacat gaaaattggg
9121 ttaccctgta ctgaccccgc ttgcaacagg gatcatgacc ttgataatct aacaaatcgt
9181 gaactcttgc tgttgatggc acggaagatg ctccccaata cagataaggc tttcaaaagt
9241 cagcaggact gtggatcgcc atctcttttcc aaagggcttt caaaggacaa gcaggaacaa
9301 gcaaaggatg tactgacttt ggaaaatcta gggcacatat tgaattatct tcatagatca
9361 gaaatcggaa aattggacga gacatcactc cgtgcagcat tgagtttaac atgtgccgga
9421 atccgaaaga caaataggtc tttgattaat actatgacag aattgcatat caaccatgag
9481 aatcttccac aggaccaaaa tggtgttatt aagcagacat atacaggtat tcatcttgac
9541 aaaggggggtc aatttgaagc tgccttatgg cagggctggg acaagaagtc aatatcttttg
9601 tttgtgcaag ctgcattata tgtgatgaat aatatcccct gtgaatcgtc catcagtgtg
9661 caggcctcat atgatcactt tattctccct cgaaatcagg gtgaaagaca atgattgtca
9721 tttcaaaatc aacgatataa ttattgttaa cattctacct tggttcttat tgtaagactt
9781 gtacactctc ctatcaactg tgattactag ttcaaaatta aaactcacaa aaattcaatc
9841 gcattgtaat caattattta tcatcgatta tttagtttga gggattccac atcatcttaa
9901 atccaataac acgattttgt ttgatttttc tttttaattc tacaccataa caacatacaa
9961 gtgtctgacg aacaacctgt gtttctatgg aaaaacatga agaacattaa gaaaaaggat
10021 gttcttgtat ttcaaccaag gttgtatata tttggccgat atcctcggag aataattgtc
10081 aatatctgac aattgatcat acacattcca ataatacatt atagactttt tatcagatat
10141 agaactggga ttctaatagt tctacttctt agtgcagtac aggtttttgc aaagaaactt
10201 ctgagtatgg cagaactgtc aacacgttac aacttaccaa caaatattac agagaagagc
10261 ataaatcttg atctcaattc tactgcacgg tgggtaaaag agcccagtgt tgggggctgg
10321 acagtgaaat gggggaattt tatctttcac atcccaaata ccggaatgac attgttgcat
10381 catttaaaat ctaattttgt tgttccagaa tggcaacaaa caaggagtct cttctcccat
```

*Fig. 10GGG*

```
10441 ctctttaaaa acccaaaatc aaccatcatg gagcctttct tggctttgag gatcttactt
10501 ggcgttgctt tgaaagatca agaattgcag caatcattga ttcccggatt tagatccatt
10561 gtgcatatgc tttcagaatg gctgctttta gaagttacgt cagctatcca tatcagtcct
10621 aacctgttgg ggatctattt gacctcagac atgtttaaaa tcctaatggc aggtgtgaaa
10681 aacttttta ataagctgtt taccctccat gttgtaaatg atcatggaaa acctagcagt
10741 attgaaataa aattaaccgg acaacagatc ataatcactc gagttaacat ggggttctta
10801 gtagaagtta ggaggattga cattgaacct tgctgcggcg agactgtcct ctcagaatca
10861 gttgtgtttg ggctagtagc tgaagcagtc ctaagggaac acagccagat tgagagaggt
10921 caacctctta atttgacaca atacatgaac agcaaaattg ctatttagac agcttgattc
10981 ggcatctaaa gctttaattc agctgtataa ggatattgag aagacagtgg atcataatca
11041 attgcccttt ataataaaag atgtagttgc cctaatttgt attcactaac ctaaaataat
11101 agtattatca cactagatag tcatcacata ataagttgtt tctatgaatt aatcatgata
11161 gtataatctt gtagaattac tatgggttct atatacggca tttattccgg actgtatcct
11221 ttgtaaacaa tgcatgctta agtattctca tatcatacat gttatcactg cctgattaag
11281 aaaaaccaat gatggatatt aaacatcctt caattgactg ttttgagact ttaaaatctt
11341 acaggctgtc ttgatcttta aattctctac gggattatac agtcacctt agcatacatt
11401 atgcttctcg cgaaataata taagtgactc tatgacattc cgagccaggt ctttatcttg
11461 aattaaccct cttttggta tgcaacaccc gactcaatat ccagatgcaa gattatcttc
11521 tcccataatt ttagatcagt gtgatttatt gaccagaagt ctagggttgt atagtcatta
11581 ctcacacaat ccaaaactac gtaattgtag gattccatac cacatttatc gcttgaggaa
11641 ttctacagca ttaaagacat ttcttcagaa ctgttcgata ctcacagttc cttttcactc
11701 aatttgggat cacatcataa cttcaattca acacgatgca attaatcata tcaatgattt
11761 caaataccta ttaccatcag aactcataaa gtatgctaat tgggacaatg agttcttaag
11821 agtattcctt aacaagatct tgagactcga tcatgctttt acaaattctg caaagttaca
11881 acgtgaggat ttctctccca aagagaatcc ttattattgg gggatgttat tgctcgtgca
11941 tttatctcaa cttgccagaa ggattaaggg acaaagaggg tctttaagga gcaactggaa
12001 gtttatagga gttgatttgg aactatttgg aatagcagat tttgttattt ttaaagttcc
12061 gctaaaagca ataattcgga atgctacaag tttacaggcc tcaaaaccag ggttaaagac
12121 atggtaccgt gatcaaaact taactcctta tctgtgtgat gatgaatttg ttgtaagcat
12181 cgctagttat gaatgtttta tcatgattaa agatgtcttc atcgaaaggt acaacacatg
12241 ggagatctgt gctcgcgctt gggtcgaaga taatgaagaa gctgattacc cacctcttgg
12301 tatattaaga gatttgtaca atcaagggga ccaaattata accatgtatc tagaggatgg
12361 tttcaaatta ataaaacact tagaaccttt atgtgtcagt tgtatacaaa cgtacggtat
12421 ttttacgccg aggaagtact ggtttcaatc tcagtgatt aaatcatatt atgacgaact
12481 tcgaagtctt aacctaaaac ttcagattcc ggataatagg actgaatgtg cacagaactt
12541 tattaaaacc ataattcagg caaaactgac tcctcaacaa tactgtgaat tgttctcttt
12601 acaaaaacat tggggtcacc cagttttata caatgatgtt gcactagaca aagtgaagaa
12661 acatgcccaa tcaacaaaaa tttaaaaacc taaagtcatg ttgaaaactt tttgtgtctt
12721 taagtttata gtggcaaaaa atcattatca ctctcaagga tcgtggtaca aaaccacaca
12781 tgatctacat ttgacccat atctacggca gcacattgtg tcaaattcat ttccatcgca
12841 agccgagatt tatcagcacc tctgggaatg gtactttgta gagcatgaac ctcttttttc
12901 tacaaaaata ataagtgatt tgagtatttt cataaaagat agagctactg ctgtaaatcg
12961 agagtgttgg gacagcgttt ttgataggag tgtgctagga taacatcccc ctgtcagatt
13021 tcaatcaaag agggtacctg agcaattctt aggtcaagca gatttctctt taaatcaaat
13081 actggatttt gctgagaaat tagagtatct agctccttca tatagaaact tttcctttttc
13141 attaaaggaa aaagaattga atattgggag aacattcggg aagttgccct atcgtgtcag
```

Fig. 10HHH

```
13201 aaatgtccaa acacttgcag aagccttatt agcagatgga ctagcgaagg cattccctag
13261 taatatgatg gttgttactg agagagagca gaaagaagct ctattgcatc aagcctcttg
13321 gcaccataat tcagcaagta taggggagaa tgccatagta agaggtgcaa gttttgttac
13381 tgatcttgag aaatacaatc ttgcctttag atatgagttt acacgacatt tcatagacta
13441 ctgtaataga tgttacggtg ttaaaaattt attcgactgg atgcatttct taataccact
13501 atgctatatg catgtcagtg actttatag ccctcctcac tgcgtgacag aaaataaccg
13561 aaataaccca cctgattgtg ccaatgctta tcattatcat ttaggaggta tagaaggact
13621 acaacagaaa ttgtggacat gtatatcatg tgctcaaatc acgcttgtag aactgaaaac
13681 taagttaaaa ttgaaatcca gtgtcatggg tgataatcaa tgtataacaa ctctaagtct
13741 tttccctatt gatgctccca atgattatca agaaaatgag gcagaattaa atgctgcacg
13801 agttgctgtt gaattagcta ttactacagg ctatagtggg atattcttaa aacctgaaga
13861 gacatttgtg cattcagggt ttatttactt tggtaaaaag caatacctaa atggtgttca
13921 attaccacaa tcattgaaga caatggcaag gtgtggacct ttatcagatt ccatttcga
13981 tgatcttcaa ggttcactag ccagtattgg cacatcattt gagagagggg caagcgagac
14041 acggcatatt tttccaagtc gttggatagc tgcatttcat tccatgttag ccataaattt
14101 gttaaatcag aatcacctcg gatttcccct aggatttagt attgatgtat cctgttttaa
14161 aaagcctctt actttctcgg agaaattaat tgctttgatc acacctcaag tgctaggggg
14221 attatctttc ttaaacccgg agaaattatt ctatcggaac atcagtgatc ctcttacttc
14281 agggttattt caactcagga atgcattaga gttccttaga aaggaagagt tgttctacat
14341 cttgattgct aaaaaacccg gtttagctga tgcttcagat ttcgttatga atccattagg
14401 tttaaatgtg ccaggatcta gggaaataat aacgtttctc aggcaaacag ttcgtgaaaa
14461 cataacgatt acatcacaaa atagaataat aaattctctt tttcacatag gttccgactt
14521 agaggatcaa agagtatgtg aatggctttt atcatcaaac cccgtaatga gccgatttgc
14581 tgctgatatt ttttcacgaa cacctagtgg aaaaagactt caagttttag gttacttgga
14641 agggaccaga acgttattag cttcccgcac gatcagttta accactgagg gtacaatgtt
14701 gatgagatta agagagttaa ctaagagtcg atggaagagt tggttttctt atattgatgc
14761 attagatgat gatttgtctg agtctcttga aaagttcata tgcactgttg atgtggctaa
14821 tttcttgaga gcatattcat ggtcagatgt cttgaaagga aagaagttaa ttggtgccac
14881 actaccatgt ttactggagc aattcaatgt aaagtgggtc aacttgtctg aagacttaaa
14941 ggagcaattt aagctatctt cagatctggg atcacctacg gatttattgc agtacgattg
15001 caatggactg cattcaaagg gggccgataa cgcagaatta aattatgtga gttgtgccct
15061 tgaccggaaa attgttcaaa agcatccatc tgacaatcgc ctggcatgga caataggaaa
15121 tcgagcaccg tatatagggt cacgaacaga agatasaatt ggttaccctc ctttaagagt
15181 aaactgccca tcggcagccc ttaaagaagc tattgaaatg gtctctagac tattgtgggt
15241 gactcaaggc accgcagatc gagaaaaatt gctcattcct cttctcaatt caagagttaa
15301 tttagactat cagacagtgc tcaacttcct gcccactcac tactcaggca atatagttca
15361 cagatacaat gatcaatatg gacaacactc ctttatggca aatagaatga gcaatacatc
15421 cactcgtgca atcatatcaa ctaacacact agggaaatat gctggagggg gtcaagctgc
15481 tgttgatagt aatataatct tccagaacac tattaattta ggtgttgcag tttggacat
15541 tgcattgtct ctttctaaat tgtcatcaac atcaaatgtt tctttccgtt taatgttaag
15601 taaatgttgc acacggcatg taccgtctga gtatttattc tttgataaac ctttagatgt
15661 ggatttgaac aagtacatgg acaacgagtt agttacgat aatgatcctc tctgtagtgg
15721 aataaaggga agattaggta gagtatcaag atcaacactc tcattgagtc taaatgtaag
15781 cgatattgga tcttacgact ttccgactat tgctgcgtgg actttaggag agacaattat
15841 tggaagtatt ttttctgatg aatcttctca aagtacagac cctataagtt caggctgtac
15901 aaaaacttt gtaacacact ttcttgtgta tccagttgag agtattttt atgcctttgg
```

*Fig. 10III*

15961 agctaatcta atagtggaaa gtttaagttt aagcaggatc aattcaatca agagcctctc
16021 agatttaaca tttcttatat catccacaat cagaaatttg tcacacagat cacttcgaat
16081 tcttcaatct actttccgac atgaattggt attaactaga ctagctcatc atataccatt
16141 gatttcctta atgctaggag gttctgcggg tgagaaaagt tcatcggatg ctgtccgact
16201 atttcttacg gcaagttatc aaaactttat caataatttc agttgtttga tgagaaagaa
16261 ccaatcacca ttaccagttt ggctttattt ccctagtgaa gggcaacaac taaaacctat
16321 tttaaaaatt ttgcaaaggt tatcatgttt attaacaact aaaaaggctc aaaatcacag
16381 acctgtagct gatacttgtt ttttgactga taattttttgg gtctatccaa gcaaatcaac
16441 gagaactaat cattattatg caagtcttaa ttattggaga gacaaagcta ataagattaa
16501 gaatacttca ttttcacatt tgataaaacta ttcattttct gaaccctctc tacatgcgag
16561 ctctatctct tctagtcaag aagtggtcaa tttaaaacac actagtcgtt tagatgaaac
16621 acctaatatg agtgaaaggg ctcaatcaac aaatcatgag ccaacagctt tacaagaggt
16681 gtgcactgag ataccctct cggaacaaga tccagccaaa agttatttgc tgttagagaa
16741 cactagattc agggataatc agaaaatatt aagacatgat cagaacgctg agaggggtga
16801 acctctttca ttgcaagtgt cttctagggg ttgcctgcag gctcttactt gccctcatca
16861 cccctcccca tctcaaacca ccacagaacc actaagcatg cttaggaatt gtgacgccat
16921 aaaagcagcc ttacgttctg agacgaatga tccccgtctt atgagcagta tccttgatat
16981 gagatcattg aaaactccca tgagaataga atctcgaaac acgagtctat tgcaaccttc
17041 tgagtgtctg tcaacttcta agggaaaatc tgtactgtct agagaacagg cttcatacct
17101 gtatgttgat tgcagtaata tctcttctat ttctctggat tcaggttttc gaaatatgtc
17161 tgatagaaat caagtccaaa tgctaataaa tacttacaaa cgcgacttat acacttgttt
17221 tgatagtaac caattctgca ggtttacagg ggtcgtttca tcaatgcatt ataagcttta
17281 tgatcttttg ccagcaggca aactcggaaa ggcaatctgc ctagccgaag gggaagggag
17341 tggcgctcga ctactcttga agtggaagga gacagattat ttattcttca atactttggc
17401 cacagattca caacaggaag cagaaatttt gagtggtcga gttattccaa ggatgttgta
17461 taacatagat aagctaagtg ttttacttga atccagaaaa ttaatcttga ataatctaac
17521 tattcaaatc acggatatta cacaccccact atggctggac tctgtcatac aatacctacc
17581 tgaagatagt gacattctaa caatggatgc agagaccact aaagaagaga caagagagca
17641 actctataaa actatcataa atatttgggc acgtacttct cctaatatcc ctaaaaccag
17701 catcattaaa gtgttttat tagattatgg gggaaccttg ttcttaatga agaatgctat
17761 tcaatattat ggacaagttc aacttaagaa accatatagt tcaatgcaa aaaattcaga
17821 atggtactta tgttgtggaa aacgaagagt tcaacgactc cgagttgatt tccagacca
17881 agtaggaata ttcttgatct gtaaagcaat gtcacgtcag aggcaagcaa ttccttactg
17941 gctaaagcac atagaaaaga attaccctgc ttcattgcac gagttcttta aactttagg
18001 ttttccttct ttagagtcat ctttctgcca tgctacacc attccgttca ctgagggaac
18061 ggctctcttt cacaaaggtcc agtcttacgt ccgacaaggt agacaacacc tacactctct
18121 tatgttagat tacgaaaata attcacccct cctagatctg agaaatcact tcatatgctc
18181 attgaggga aagatagcca agtattcaa tgacatattg aaattaagtt tagtagtgag
18241 agcagtagaa agagggaaaa attggtcgca actcgttgag tcccttccta atatgcactc
18301 agtatgcata acacatgttg atcacgaatg tattggctgt gagagacggt tattacttaa
18361 attggacttt gtcagaaata caaagatagc agaacaaaag ttactcaata gggtaattgg
18421 gtatattcta tctttccctt tggttctc cagacccaag tgactacaga tatattcttc
18481 aataaaggaa gctcagtcta actcacagaa ataatccact tcaaaacaag gatcacccat
18541 tttggaacat tgtataagaa actgcaagac aaataataag gaaaggatac tactgtataa
18601 cttgttatat ccaaaaggat cttgggtcat tttaagcatg atgcaaataa aaaatcgtct
18661 acatagccga actgaccgct cagtacttat tcacaatcat gctaactttt agtttaat

Fig. 10JJJ 18721 tgtgcaaaaa ttactaagaa taattaatat tgatattaaa acattaaatg gacatttgag
18781 ttttatgcct agaataatat aaagaaattt aagagatatt tagatatatc agttgaattg
18841 atttatgaca catagtgcat catgaataca aagagaaaaa tcgttgcaat tcaggaatat
18901 cttatttaaa tgtattagag agaaagtcag attattatca aaatcaagca aaatacaata
18961 ggtttttca aagaataggt ggtaaagcct tatggttatt ttttaaagat gtcaatgtga
19021 atttttatta agaaaaagta atgcatgaaa ttaaaaaatt aaagaacttt gatataagta
19081 acacaaaaca ctcttcatct ttttagtgtg tcca (SEQ ID NO: 20)

VP30

MQQPRGRSRNRSHQVALSTYHENQLPSKPQYINHHPRARSMSST
RSSTEGSPTNHASRARPLSTFNLSKPPPPPKDMCRNMKIGLPCTDPACNRDHDLD
NLT
NRELLLLMARKMLPNTDKAFKSQQDCGSPSLSKGLSKDKQEQAKDVLTLENLG
HILNY
LHRSEIGKLDETSLRAALSLTCAGIRKTNRSLINTMTELHINHENLPQDQNGVIKQ
TY
TGIHLDKGGQFEAALWQGWDKKSISLFVQAALYVMNNIPCESSISVQASYDHFIL
PRN
QGERQ (SEQ ID NO: 21)

DQ447649

1 agacacacaa aaacaagaga tgatgatttt gtgtatcata taaataaaga agaatattaa
61 cattgacatt aagactagtc attttgttaa tattctttaa aagatggatt tacatagttt
121 gctagaatta ggtacaaaac ccacagcccc tcatgttcgt aataagaagg tgatattgtt
181 tgatacaaac catcaggtta gtatctgtaa ccagataata gatgcaataa actcagggat
241 cgatttagga gatcttttgg aaggcggctt gttgacatta tgtgttgaac attattacaa
301 ttctgacaaa gataaattca atacaagtcc tattgcaaaa tatctgcggg acgcgggcta
361 tgagtttgat gtcatcaaga atcctgatgc aactcgcttt ctagaggtta ttcccaatga
421 acctcattac agcccctttga ttttggctct caaaacctta gaaagcactg aatctcaaag
481 ggggaggatt gggctctttc tgtcattttg cagtcttttt ctcccgaaac tcgttgtcgg
541 agaccgagct agcatcgaaa aggccctgag acaagtaaca gtgcatcagg aacaagggat
601 tgtaacatac cccaatcatt ggctcactac aggtcacatg aaagtaatct ttgggatttt
661 aagatctagc ttcattttaa agtttgtctt aatccatcag ggagtaaact tggtgacagg
721 tcatgatgcc tatgacagta tcatcagtaa ttcagtagga caaactagat tctcagggct
781 tcttattgtg aaaacagttc tagagttcat cctacaaaaa actgattcag ggtggcatt
841 gcatccactt gtgcggacct caaaagtaaa aaatgaagtt gcaagcttca aacaggcatt
901 gagtaactta gctcgtcatg gagagtacgc accatttgca cgggttttga atttatcagg
961 gatcaataac cttgagcatg ggctctatcc tcagctttca gcaattgcac tgggcgttgc
1021 aacagcacat ggcagtacat tggctggtgt taacgttggc gaacaatacc aacaactgcg
1081 agaagcagca catgatgcag aagtaaaatt acaaaggcga catgaacacc aggaaattca
1141 ggccatcgcc gaggatgacg aagagagaaa aatattagaa cagttccatc tccagaagac
1201 tgagattaca cacagtcaga cattggccgt cctcagccag aaacgagaga aactagcccg
1261 tcttgctgca gaaattgaaa acaacattgc agaggatcag gggttcaaac aatcgcagaa

Fig. 10KKK

```
1321 tcaggtgtca cagtctttct taaatgatcc cacacctgta gaagtgacag tccaagccag
1381 gtctataaat cgaccaacag ccctgccccc cccagtcgac aacaaaattg agcatgaaac
1441 tgaagaggac agctcctcat caagtagttt tgttgacttg aatgatccat ttgcactgct
1501 gaacgaagac gaggatactc ttgaaaatag tgtcatggcc ccaagcacta ctttgagaga
1561 acccaaagaa gtttccgaac cactaaggca aactcaggac cttgatatta gccaaaagaa
1621 acagggaaat gaatcaacag atccagcaag aaaacaattc ttacgatatc aagaattacc
1681 tcctgttcaa gaagacgatg aatcagaata cacaactgat tctcaggaaa gtgacgatca
1741 accaggatct gataatgaac aaggtgttga tctcccacca cctccattat atgctcagga
1801 aaagagacag gatcccatac agcatccagc cgtgagctcc caagatccct tggcagtat
1861 tggtgatgta gatggtgata ttttggaacc tataagatcg ccttcctcac cgtctgctcc
1921 tcaggaggac acaaggatgg gagaagccta tgaattatca cctgatttta caagctatga
1981 ggataatcag cagaattggc cacagagagt ggtaacaaag aaaggcagga ccttcctta
2041 tcctaatgac cttttacaga cgagtcctcc agagtcatta ataacagccc ttgttgaaga
2101 gtaccaaaac cctgtctcag caaaagagct tcaagcggat tggcctgaca tgtcatttga
2161 tgagaggagg catgttgcta tgaacttgta atttcgacaa cacagcacga ctactcattt
2221 atttacttca atatatttta cctccgaaac ataatagtca aatttattta aatatctaga
2281 ccactttcaa ataccttgtt atatatcact gttatgtgag atggtgcaaa ccttagaatg
2341 ataaccaaag gtaggaactg gttatatgac agtacctcga aggtgttatt caatggttta
2401 gatctctcct ctaattgcta cgataataca actacaaacc tctttacctt ggttacaata
2461 ctgtaataga tatgattgta tttcttttctt aaatcatctg attcaacttg atagatataa
2521 cttgattcag agaacatttt gggaacgtca ttaactaaat tctctaaatg atgtactgta
2581 ttactgtttc acccgactaa ttatatagta gcatattaat ggatccttta cctctcctcc
2641 tatgctcttc ttataagtca ctcaaccggt gaaacgccga gtttgttggc ttagagtttt
2701 cctgttttac tgaatgtagt aattaatgat tgacttgagt gttgatggaa tcaagatagt
2761 gcgatgattc atattataag gtacaatttc catttctgtt ttgccaatgt atcctcttcc
2821 ttatcacatg ccaatcaaga aaaacaaaga gtcgaagaat attaaagatt ctctttaata
2881 ttcaaaaaca gttcttaatt cttttccttt cctttattaa tataatatat cgataaatct
2941 tacaatgtgg gactcgtcat acatgcaaca agtgagtgag ggactgatga ctggaaaagt
3001 tccaatagat caagtgttcg gcactaatcc cttagaaaag ttatataaga gaagaaagcc
3061 gaaagggaca gtgggattac aatgtagtcc ttgcttaata tcaaaatcaa caagtactga
3121 cgacattgtt tgggatcagc taatcgtaaa gaaaacattg gctgacttgc ttatacctat
3181 aaataggcaa atgtcggaca ttcaaagcac cctaagcgaa atgacaacaa aagtccatga
3241 gatcgagcgt caactacatg atatcacccc agttgtaaaa atgggaaaaa cgctagaagc
3301 aatttccaaa ggaatgtcag agatgctagc taagtacgat catctcgtga tttcaactgg
3361 aagaaccacc gcaccagctg ctgcctttga tgcttactta aacgagcatg gagtcccccc
3421 ccctcagcct gcaatcttca aagatcttgg agttgcccaa caagcctaca gtcaaaagac
3481 tatggtcaaa aaccaaacaa cagatgcagc tgacaaaatg tcaaaggttc tgaactcag
3541 tgaagaaaca ttttccaagc caaacctttc agctaaggat ttagctctat tattatttac
3601 tcatctccct ggcaacaaca ctccattcca catactcgcc caagtcctt caaaaattgc
3661 ttacaaatca ggaaagtctg gagcattctt ggatgcattc catcagattt taagcgaagg
3721 ggagaatgct caggctgcat taacccgatt aagcagaaca ttcgatgctt tccttggagc
3781 agttcctcca gtaataaaag ttaaaaactt tcaaacggtc ccccgccctt gtcaaaaaag
3841 cctccgagct gttcccccaa atccaacaat tgacaaggga tgggtctgtg tctattcatc
3901 tgaacagggt gaaacccggg ctcttaaaat ctaatccttg cgattcattc ttgaacaaag
3961 aatgatcttt ctaggttaat acaaaaacac taaacatttc aagagtttgt ggatgattta
4021 agcatatttg ggtaaattta atcaggatag tagtttaaat ttgttttaag cgtgatttttc
```

Fig. 10LLL

```
4081  attaagagag ggttaattag ttatagattg atctttagtg tactccatac gcataatata
4141  gagaaattaa tattactaac aaaaagggtt ttttaaacgg atttgattaa tagatcagta
4201  tatctcaaaa gccaaataat tgacttctta ctctttggga atttactaac aatataggaa
4261  agatatttat tcttacgtaa tccttggccc aacggaaact aacctcaatg gtcattcaat
4321  atgcttgctc atgatatatc cagagatttt ttataagttc aaaacgttgt aaattatact
4381  tgcataaaat actgttttaa ttaagaaaaa ctatgaagaa cattaagtgg attttccctt
4441  cttagtgttc ttttacaaag caaggtttt aaattcaagt agatcaagtc tactcttgct
4501  gaacttactt cttttaaaaat taatttacac taaacaattc gtttttgttg acggaacaaa
4561  ttcagatatg gccagttcca gcaattataa tacgtatatg caataacctga accctcccc
4621  ttatgctgat catggtgcaa atcagttaat cccagcagac cagctatcaa atcaacatgg
4681  tataactccg aattatgtgg gcgacttgaa tctagatgat cagtttaaag ggaatgtttg
4741  tcacgccttc actttggaag caataattga tatatctgct tataatgagc ggacggtcaa
4801  aggagtccca gcgtggctgc ctcttgggat catgagcaat tttgaatacc ctttagccca
4861  cactgttgct gcattgctta cagggagcta cacgattacc caattcacgc acaatggaca
4921  aaaatttgtt cgtgttaatc gacttgggac aggaatccca gcacatccac tcagaatgct
4981  gcgggaagga aaccaagctt ttgtccaaaa catggtgatt cccaggaact ttctacaaa
5041  tcagtttacg tacaatctta ctaatctagt attgagcgtg caaaagcttc ctgatgatgc
5101  ttggcgcccg tccaaagaca aattaatcgg aaacaccatg caccctgcgg tttctgtaca
5161  cccaaacctg ccgcctattg tcctaccaac agttaaaaaa caagcctatc gtcagcataa
5221  gaatcctaac aatggaccac tgctggccat atctggcatc cttcatcaac tgagggttga
5281  aaaagtccca gagaagacga gcttattcag gatttcactt cctgccgaca tgttctcagt
5341  aaaagagggc atgatgaaga aaagaggaga aggttctccg gtagtttatt tccaagcgcc
5401  tgagaattttt cctttgaatg gcttcaacaa ccggcaagtt gtgctagcat atgctaaccc
5461  gacactcagt gctgtttaat aagataattg ggtaagacaa tggcccttct gtacaaaggg
5521  tctgattcag atagatattt gtcagattca tgcaggatca ttttaagttg attttaatag
5581  tgctttaacc cttcactgct accctaaagg attgattgag ctgattaacc tataatgtat
5641  aacttctttt aaaccgctaa atcaatcata agtttgtcag atcatatagg atgaatgtta
5701  atacgtgata aatggttcct attcagtttt actttaacct catagtaaat cttataagac
5761  tactcatctt caagttgatc aattcaaaga taatttccct tctaaaataa taagaaaaac
5821  taatgaagaa cattaattgc taggtaaagg caattaagtt ctttgaactt tgcaaaagta
5881  aggtttcact agtgagtaaa ttcctgtatt agtagattaa aaccaaggaa gcaccccgac
5941  atgaagacca tatattttct gattagtctc attttaatcc aaagtataaa aactctccct
6001  gttttagaaa ttgctagtaa cagccaacct caagatgtag attcagtgtg ctccggaacc
6061  ctccaaaaga cagaagatgt tcatctgatg ggatttacac tgagtgggca aaaagttgct
6121  gattcccctt tggaagcatc taaacgatgg gctttcagga caggtgttcc tcccaagaac
6181  gttgagtata cggaaggaga agaagccaaa acatgttaca atataagtgt aacagaccct
6241  tctggaaaat ccttgctgct ggatcctccc agtaatatcc gcgattaccc taaatgtaaa
6301  actgttcatc atattcaagg tcaaaaccct catgcacagg ggattgccct ccatttgtgg
6361  ggggcatttt tcttgtatga tcgcgttgcc tctacaacaa tgtaccgagg caaggtcttc
6421  actgaaggaa atatagcagc tatgattgtt aataagacag ttcacagaat gattttttct
6481  aggcaaggac aaggttatcg tcacatgaac ttgacctcca ccaataaata ttggacaagc
6541  agcaatgaaa cgcagagaaa tgatacggga tgttttggca tcctccaaga atcaactcc
6601  acaaacaatc aaacatgccc tccatctctt aaacctccat ccctgcccac agtaactccg
6661  agcattcact ctacaaatac tcaaattaat actgctaaat ctggaactat gaacccaagt
6721  agcgacgatg aggaccttat gatttccggc tcaggatctg gagaacaggg gccccacaca
6781  actcttaatg tagtcactga acagaaacaa tcgtcaacaa tattgtccac tccttcacta
```

*Fig. 10MMM*

6841 catccaagca cctcacaaca tgagcaaaac agtacgaatc cttcccgaca tgctgtaact
6901 gagcacaatg gaaccgaccc aacaacacaa ccagcaacgc tcctcaacaa tactaataca
6961 actcccacct ataacactct caagtacaac ctcagtactc cttcccctcc aacccgcaac
7021 atcaccaata atgatacaca acgtgaacta gcagaaagcg aacaaaccaa tgctcagttg
7081 aacacaactc tagatccaac agaaaatccc accacaggac aagacaccaa cagcacaacc
7141 aacatcatca tgacgacatc agatataaca agcaaacacc ccacaaattc ttctccggat
7201 tctagtccga caacccgccc tcctatatac tttagaaaga aacgaagcat tttctggaaa
7261 gaaggtgata tattcccgtt tttagatggg ttaataaata ctgaaattga ttttgatcca
7321 atcccaaaca cagaaacaat ctttgatgaa tctcccagct ttaatacttc aactaatgag
7381 gaacaacaca ctccccccgaa tatcagttta actttctctt attttcctga taaaaatgga
7441 gatactgcct actctgggga aaacgagaat gattgtgatg cagagttgag gatttggagt
7501 gtgcaggagg acgatttggc ggcagggctt agctggatac cattttttgg ccctggaatc
7561 gaaggactct atactgccgg tttaatcaaa aatcagaaca atttagtttg taggttgagg
7621 cgcttagcta atcaaactgc taaatccttg gagctcttgt taagggtcac aaccgaggaa
7681 aggacatttt ccttaatcaa taggcatgca attgactttt tgcttacgag gtggggcgga
7741 acatgcaagg tgctaggacc tgattgttgc ataggaatag aagatctatc taaaaatatc
7801 tcagaacaaa tcgacaaaat cagaaaggat gaacaaaagg aggaaactgg ctggggtcta
7861 ggtggcaaat ggtggacatc tgactggggt gttctcacca atttgggcat cctgctacta
7921 ttatctatag ctgttctgat tgctctgtcc tgtatctgtc gtatcttcac taaatacatt
7981 ggatgacata aagttacaa tggttagagc tttaggaaag ttgctgctga gcccttttgtc
8041 taatctactg aaatcgactt aaagaatcct cagggagctt ataactcaat gtgaatcgat
8101 tccctatata ttgttgatcg tgatgatata gcagtcaagt gtcaccatca ttaggagcaa
8161 ttcttctgat ccaatgcatt gaagtcacta attacttcta aaatccttat ctttaatccg
8221 aatattcaca tagaaatcaa ttttgggaaa attccagtag tgcgtctttt catgtcactt
8281 ctctgaacct aagaccataa taaatattgg ttaaagaggt cagctggtca atcttctatt
8341 ttcatattaa agatatactg ctcagaaact cctagtttgc aacccaatct tggaaaaata
8401 aacctcctct tttgatcata actatctcta tcaatgtctt gaacacttaa tattattaac
8461 aactatttt tatttaatct tttaaatgca aatcaaaaga ggacatgagc cacccctcatt
8521 ttacttcaat acgaaggaat tcttcttctc agcctacatt ttaatttacc aggtgataaa
8581 cttttggtaa tttaccttaa cataggtgct gataagatga ttggatgata acacatttac
8641 cgagatttaa tcgtatctca ttaagaaaaa gataattaga acactggaaa ttgataaact
8701 tctatttga tcaatgtaga aaagaattat aaaaatctta gtaaataaat tactgcaaag
8761 taaaaacgaa gaacattaag tgttctttat taaaattgtt catccttttc gcttttgatt
8821 atatttgatc aaatacaact tcatttggta ttcattccaa gattcagaat gcaacagcct
8881 cgtgggagaa gccgaaatcg tagccaccaa gttgcactat ccacatacca tgaaaatcaa
8941 ttaccctcta aacctcagta cattaaccat catccacgtg caagatcaat gagttcaacc
9001 cgtagtagta cagaaggtag ccctactaat catgcttccc gtgctcgacc actttcaaca
9061 tttaatctat cgaaacctcc tccccccccg aaagacatgt gcaggaacat gaaaattggg
9121 ttaccctgta ctgacccgc ttgcaacagg gatcatgacc ttgataatct aacaaatcgt
9181 gaactttgc tgttgatggc acggaagatg ctccccaata cagataaggc tttcaaaagt
9241 cagcaggact gtggatcgcc atctctttcc aaagggcttt caaaggacaa gcaggaacaa
9301 gcaaaggatg tactgacttt ggaaaatcta gggcacatat tgaattatct tcatagatca
9361 gaaatcggaa aattggacga gacatcactc cgtgcagcat tgagttaac atgtgccgga
9421 atccgaaaga caaataggtc tttgattaat actatgacag aattgcatat caaccatgag
9481 aatcttccac aggaccaaaa tggtgttatt aagcagacat atacaggtat tcatcttgac
9541 aaagggggtc aatttgaagc tgccttatgg cagggctggg acaagaagtc aatatcgttg

```
 9601 tttgtgcaag ctgcattata tgtgatgaat aatatccct gtgaatcgtc catcagtgtg
 9661 caggcctcat atgatcactt tattctccct cgaaatcagg gtgaaagaca atgattgtca
 9721 tttcaaaatc aacgatataa ttattgttaa cattctacct tggttcttat tgtaagactt
 9781 gtatactctc ctatcaactg tgactactag ttcaaaatta aaactcacaa aaattcaatc
 9841 gcattgtaat caattattta tcatcgattg tttagtttga gggattccac atcatcttaa
 9901 atccaataac acgattttgt ttgattttc ttttaatttc tacaccacaa caacatacaa
 9961 gtgtctgacg aacgacctgt gtttctatgg aaaaacatga agaacattaa gaaaaaggat
10021 gttcttgtat ttcaaccaag gttgtatata tttggccgat atcctcggag aataattgtc
10081 aatatctgac aattgatcat acacattcca ataatacatt atagacttt tatcatatat
10141 agaactggga ttctaatagt tctacttctt agtgcagtac aggttttgc aaagaaactt
10201 ctgagtatgg cagaactgtc aacacgttac aacttaccaa caaatattac agagaagagc
10261 ataaatcttg atctcaattc tactgcacgg tgggtaaaag agcccagtgt tgggggctgg
10321 acagtgaaat gggggaattt tatctttcac atcccaaata ccggaatgac attgttgcat
10381 catttaaaat ctaattttgt tgttccagaa tggcaacaaa caaggagtct cttctcccat
10441 ctctttaaaa acccaaaatc aaccatcatg gagcctttct tggctttgag gatcttactt
10501 ggcgttgctt tgaaggatca agaattgcag caatcattga ttcctggatt tagatccatt
10561 gtgcatatgc tttcagaatg gctgctttta gaagttacgt cagctatcca tatcagtcct
10621 aacctgttgg ggatctattt gacctcagac atgtttaaaa tcctaatggc aggtgtgaaa
10681 aacttttca ataagctgtt taccctccat gttgtaaatg atcatggaaa acctagcagt
10741 attgaaataa aattaaccgg acaacagatc ataatcactc gagttaacat ggggttctta
10801 gtagaagtta ggaggattga cattgaaacct tgctgcggcg agactgtcct ctcagaatca
10861 gttgtgtttg ggctagtagc tgaagcagtc ctaagggaac acagccagat tgagagaggt
10921 caacctctta atttgacaca atacatgaac agcaaaattg ctatttagac agcttgattc
10981 ggcatctaaa gctttaattc agctgtataa ggatattgag aagacagtgg atcataatca
11041 attgcccttt ataataaaag atgtagttgc cctaatttgt attcactaac ctaaaataat
11101 agtattatca cactagatag tcatcacata ataagttgtt tctatgaatt aatcatgata
11161 gtataatctt gtagaattac tatgggttct atatacggca tttattccgg actgtatcct
11221 ttgtaaacaa tgcatgctta agtattctca tatcatacat gttatcactg cctgattaag
11281 aaaaaccaat gatggatatt aaacatcctt caattgactg ttttgagact ttaaaatctt
11341 acaggctgtc ttgatttta aattctctac gggattatac agtcacctt agcatacatt
11401 atgcctctcg cgaaataata taagtgactc tatgacattc cgagccaggt ctttatcttg
11461 aattaaccct cttttggta tgcaacaccc gactcaatat ccagatgcaa gattatcttc
11521 tcccataatt ttagatcagt gtgatttatt gaccagaagt ctagggttgt atagtcatta
11581 ctcacacaat ccaaaactac gtaattgtag gattccatac cacatttatc gcttgaggaa
11641 ttctacagca ttaaagacat ttcttcagaa ctgttcgata ctcacagttc cttttcactc
11701 aatttgggat cacatcataa cttcaattca acacgatgca attaatcata tcaatgattt
11761 caaataccta ttaccatcag aactcataaa gtatgctaat tgggacaatg agttcttaag
11821 agtattcctt aacaagatct tgagactcga tcatgctttt acaaattctg caaagttaca
11881 atgtgaggat ttctctccca aagagaatcc ttattattgg gggatgttat tgctcgtgca
11941 tttatctcaa cttgccagaa ggattaaggg acaaagaggg tctttaagga gcaactggaa
12001 gtttatagga gttgatttgg aactatttgg aatagcagat tttgttattt ttaaagttcc
12061 gataaaagca ataattcgga atgctacaag tttacaggcc tcaaaaccag ggttaaagac
12121 atggtaccgt gatcaaaact taactcctta tctgtgtgat gatgaatttg ttgtaagcat
12181 cgctagttat gaatgtttta tcatgattaa agatgtcttc atcgaaaggt acaacacgtg
12241 ggagatctgt gctcgcgctt gggtcgaaga taatgaagaa gctgattacc cacctcttgg
12301 tatattaaga gatttgtaca atcaagggga ccaaattata accatgtatc tagaggatgg
```

*Fig. 10000*

```
12361 tttcaaatta ataaaacact tagaaccctt atgtgtcagt tgtatacaaa cgtacggtat
12421 ttttacgccg aggaagtact ggtttcaatc tcagatgatt aaatcatatt atgatgaact
12481 tcaaagtctt aacctaaaac ttcagattcc agataatagg actgaatgtg cacagaactt
12541 tattaaaacc ataattcagg caaaactgac tcctcaacaa tactgtgaat tgttctcttt
12601 acaaaaacat tggggtcacc cagttttata caatgatgtt gcactagaca aagtgaagaa
12661 acatgcccaa tcaacaaaaa ttttaaaacc taaggtcatg tttgaaactt tttgtgtctt
12721 taagtttata gtggcaaaaa atcattatca ctctcaagga tcgtggtaca aaaccacaca
12781 tgatctacat ttgaccccat atctacggca gcacattgtg tcaaattcat ttccatcgca
12841 agccgagatt tatcagcacc tctgggaatg gtactttgta gagcatgaac ctcttttttc
12901 tacaaaaata ataagtgatt tgagtatttt cataaaagat agagctactg ctgtaaatcg
12961 agagtgttgg gacagcgttt ttgataggag tgtgctagga tacaatcccc ctgtcagatt
13021 tcaatcaaag agggtacctg agcaattctt aggtcaagca gatttctctt taaatcaaat
13081 attggatttt gctgagaaat tagagtatct agctccttca tatagaaact tttccttttc
13141 attaaaggaa aaagaattga atattgggag aacattcggg aagttgccct atcgtgtcag
13201 aaatgtccaa acacttgcag aagccttatt agcagatgga ctagcgaagg cattccctag
13261 taatatgatg gttgttactg agagagagca gaaagaagct ctattgcatc aagcctcttg
13321 gcaccataat tcagcaagta taggggagaa tgccatagta gagggtgcaa gttttgttac
13381 tgatcttgag aaatacaatc ttgcctttag atatgagttt acacgacatt tcatagaacta
13441 ctgtaatcga tgttacggtg ttaaaaattt attcgactgg atgcatttct taataccact
13501 atgctatatg catgtcagtg actttatatag ccctcctcac tgcgtgacac aaaataaccg
13561 aaataaccca cctgattgtg ccaatgctta tcattatcat ttaggaggta tagaaggact
13621 acaacagaaa ttgtggacat gtatatcatg tgctcaaatc acgcttgtag aactgaaaac
13681 taagttaaaa ttgaaatcca gtgtcatggg tgataatcaa tgtataacaa ctctaagtct
13741 tttccctatt gatgctccca atgattatca agaaaatgag gcagaattaa atgctgcacg
13801 agttgctgtt gaattagcta ttactacagg ctatagtggg atattcttaa aacctgaaga
13861 gacatttgtg cattcagggt ttatttactt tggtaaaaag caataccataa atggtgttca
13921 attaccacaa tcattgaaga caatggcaag gtgtggacct ttatcagatt ccattttcga
13981 cgatcttcaa ggttcactag ccagtattgg cacatcattt gagagagggg caagcgagac
14041 acggcatatt tttccaagtc gttggatagc tgcattcat tccatgttag ccgtaaattt
14101 gttaaatcag aatcacctcg gatttcccct aggatttagt attgatgtat cctgttttaa
14161 aaagcctctt actttctcgg agaaattaat tgctttgatc acacctcaag tgctaggggg
14221 attatctttc ttaaacccgg agaaattatt ctatcggaac atcagtgatc ctcttacttc
14281 agggttattt caactcagga atgcattaga gttccttaga aaggaagagt tgttctacat
14341 cttgattgct aaaaaaaccccg gtttagctga tgcttcagatt ttcgttatga atccattagg
14401 tttaaatgtg ccaggatcta gggaaatat aacgtttctc aggcaaacag ttcgtgaaaa
14461 caaacaatt acatcacaaa atagaataat aaattctctt tttcacatag gttccgactt
14521 agaggatcaa agagtatgtg aatggctttt atcatcaaaac cctgtaatga gccgatttgc
14581 tgctgatatt tttcacgaa cacctagtgg aaaaagactt caagttttag gttacttgga
14641 aggaaccaga acgttattag cttcccgcac gatcagttta accactgagg gtacaatgtt
14701 gatgagatta agagagttaa ctaagagtcg atggaagagt tggtttttctt acattgatgc
14761 attagatgat gatttgtctg agtctcttga aaagttcata tgcactgttg atgtggctaa
14821 tttcttgaga gcatattcat ggtcagatgt cttgaaagga aaaaggttaa ttggtgccac
14881 actaccatgt ttactggagc aattcaatgt aaagtgggtc aacttgtctg aagacttaaa
14941 ggagcaattt aagctatctt cagatctggg atcacctacg gattattgc agtacgattg
15001 caatggactg cattcaaagg gggccgataa cgcagaatta aattatgtga gttgtgccct
15061 tgaccggaaa attgttcaaa agcatccatc tgacaatcgc ctggcatgga caataggaaa
```

*Fig. 10PPP*

```
15121 tcgagcaccg tatataggtt cacgaacaga agataaaatt ggttaccctc ctttaagagt
15181 aaactgccca tcggcagccc ttaaagaagc tattgaaatg gtctctagac tattgtgggt
15241 gactcaaggc accgcagatc gagaaaaatt gctcattcct cttctcaatt caagagttaa
15301 tttagactat cagacagtgc tcaacttcct gcccactcac tactcaggca atatagttca
15361 cagatacaat gatcaatatg gacaacactc ctttatggca aatagaatga gcaatacatc
15421 cactcgtgca atcatatcaa ctaacacact agggaaatat gctggagggg gtcaagctgc
15481 tgttgatagt aatataatct tccagaacac tattaattta ggtgttgcag ttttggacat
15541 tacattgtct ctttctaaat tgtcatcaac atcaaatgtt tctttccgtt taatgttaag
15601 taaatgttgc acacggcatg taccgtctga gtatttattc tttgataaac ctttagatgt
15661 ggatttgaac aagtacatgg acaacgagtt agtttacgat aatgatcctc tctgtagtgg
15721 aataaaggga agattaggta gagtatcaag atcaacactc tcattgagtc taaatgtaag
15781 cgatattgga tcttacgact ttccgactat tgctgcgtgg actttaggag agacaattat
15841 tggaagtatt ttttctgatg aatcttctca aagtacagac cctataagtt caggctgtac
15901 aaaaactttt gtaacacact ttcttgtgta tccagttgag agtatctttt atgcctttgg
15961 agctaatcta atagtgggaaa gtttaagttt aagcaggatc aattcaatca agagcctctc
16021 agatttaaca tttcttatat catccacaat cagaaatttg tcacacagat cacttcgaat
16081 tcttcaatct acttccgac atgaattggt attaactaga ctagctcatc atataccatt
16141 gatttcctta atgctagag gttctgcggg tgagaaaagt tcgtcggatg ctgtccgact
16201 atttcttacg gcaagttatc aaaatttat caataattc agttgtttga tgagaaagaa
16261 ccaatcacca ttaccagttt ggctttattt ccctagtgaa gggcaacaac taaaacctat
16321 ttttaaaaatt ttgcaaaggt tatcatgttt attaacaact aaaaaggttc aaaatcacag
16381 acctgtagct gatacttgtt ttttgactga taattttgg gtctatccaa gcaaatcaac
16441 gagaactaat cattattatg caagtcttaa ttattggaga gacaaagcta ataagattaa
16501 gaatacttca ttttcacatt tgataaacta ttcattttct gaaccctctc tacatgcgag
16561 ctctatctct tctagtcaag aagtggtcaa tttaaaacac accagtcgtt tagatgaaac
16621 acctaatatg agtgaaaggg ctcaatcaac aaatcatgag ccaacagctt tacaagaggt
16681 gtgcactgag ataccctact cggaacaaga tccagccaaa agttatttgc tgttagagaa
16741 tactagattc agggatgatc agaaaatatt aagacatgat cagaaagctg agaggggtga
16801 acctctttca ttgcaagtgt cttctagggg ttgcctgcag gctcttactt gccctcatca
16861 ccccctcccca tctcaaacca ccacagaacc actaagcatg cttaggaatt gtgacgccat
16921 aaaagcagcc ttacgttctg agacgaatga tccccgtctt atgagcagta tccttgatat
16981 gagatcattg aaaactccca tgagaataga atctcgaaac acgagtctat tgcaaccttc
17041 tgagtgtctg tcaacttcta agggaaaatc tgtactgtct agagaacagg cttcatacct
17101 gtatgttgat tgcagtaata tctcttctat ttctctggat tcaggttttc gaaatatgtc
17161 tgatagaaat caagtccaaa tgctaataaa tacttacaaa cgtgacttat acacttgtt
17221 tgatagtaac caattctgca ggtttacagg ggtcgtttca tcaatgcatt ataagcttta
17281 tgatcttttg ccagcaggca aactcggaaa ggcaatctgc ctagccgaag gggaagggag
17341 tggcgctcga ctactcttga agtggaagga gacagattat ttattcttca atacttttggc
17401 cacagattca caacaggaag cagaaatttt gagtggtcga gttattccaa ggatgttgta
17461 taacatagat aagctaagtg ttttacttga atccagaaaa ttaatcttga ataatctaac
17521 tattcaaatc acggatatta caaacccact atggctggac tctgtcatac aatacctacc
17581 tgaagatagt gacattctaa caatggatgc agagaccact aaagaagaga caagagagca
17641 actctataaa actatcataa atatttgggc acgtacttct cctaatatcc ctaaaaccag
17701 catcattaaa gtgttttat tagattatgg gggaacctta ttcttaatga agaatgctat
17761 tcaatatat ggacaagttc aacttaagaa accatatagt tcaaatgcaa aaaattcaga
17821 atggtactta tgttgtggaa aacgaagagt tcaacgactc cgagttgatt ttcagacca
```

*Fig. 10QQQ*

```
17881 agtaggaata ttcttgatct gtaaagcaat gtcacgtcag aggcaagcaa ttccttactg
17941 gctaaagcac atagaaaaga attaccctgc ttcattgcac gagttcttta taactttagg
18001 ttttccttct ttagagtcat ctttctgcca tcgctacacc attccgttca ctgagggaac
18061 ggctctcttt cacaaggtcc agtcttatgt ccgacaaggt agacaacacc tacactctct
18121 tatgttagat tacgaaaata attcacccct cctagatctg agaaatcact tcatatgctc
18181 attgagggga aagataacca agtattacaa tgcatatattg aaattaaatc tagtagtgag
18241 agcagtagaa agagggaaaa attggtcgca actcgttgag tcccttccta atatgcactc
18301 agtatgcata acacatgttg atcacgaatg tattggctgt gagagacggt tattacttaa
18361 attggactt gtcagaaata caaagatagc agaacaaaag ttactcaata gggtaattgg
18421 gtatattcta ttcttccctt ttggtttctc cagacccaag tgactacaga tatattcttc
18481 aataaaggaa gctcagtcta actcacagaa ataatctact tcaaaacaag gatcacccat
18541 tttggaacat tgtataagaa actgcaagac aaataataag gaaaggatac tactgtataa
18601 cttgttatat ccaaaaggat cttgggtcat tttaagcatg atgcaaataa aaaatcgtct
18661 acatagccga actgaccgct cagtacttat tcacaatcat gctaactttt agttttaat
18721 tgtgcaaaaa ttactaagaa taattaatat tgatattaaa acattaaatg gacatttgag
18781 ttttatgcct agaataatat aaagaaattt aagagacatt tagatatatc agttgaattg
18841 atttatgaca catagtgcat catgaataca aagagaaaaa ttgttgcaat tcaggaatat
18901 cttatttaaa tgtattagag agaaagtcag attattatca aaatcaagca aaatacaata
18961 ggttttttca aagaataggt ggtaaagcct tatggttatt ttttaaagat gtcaatgtga
19021 attttatta agaaaaagta atgcatgaaa ttaaaaaatt aaagaacttt gatataagta
19081 acacaaaaca ctcttcatct ttttagtgtg tcca  (SEQ ID NO: 22)
```

VP30

MQQPRGRSRNRSHQVALSTYHENQLPSKPQYINHHPRARSMSST
RSSTEGSPTNHASRARPLSTFNLSKPPPPPKDMCRNMKIGLPCTDPACNRDHDLD
NLT
NRELLLLMARKMLPNTDKAFKSQQDCGSPSLSKGLSKDKQEQAKDVLTLENLG
HILNY
LHRSEIGKLDETSLRAALSLTCAGIRKTNRSLINTMTELHINHENLPQDQNGVIKQ
TY
TGIHLDKGGQFEAALWQGWDKKSISLFVQAALYVMNNIPCESSISVQASYDHFIL
PRN
QGERQ (SEQ ID NO: 23)

AB050936

```
  1 gggacacaca aaagaaaaag gttttttaag attttttgtg tgcgagtaac tatgaggaag
 61 attaacagtt ttcctcagtt taaggtatac actgaaattg agattgagat tctcctctt
121 gctattctgt aactttccct ggttgtgaca attgaatcag ttttatctat taccaattac
181 catcaacatg gtatgtctag tgatcttggg actcttcttc atctggtttt tcctagagct
241 ctgaatctat tttgtgagaa gttcatccaa acgacccagt gtctgaaaat acaagaggtt
301 cccctttccg tcaagtttaa ggggttgttt tgattgtgtg tagattttat aatcctagag
361 tgccaaggag ttgcgtgtca tcattaattg ggaagatcaa ggaaacaatt tgttccaata
421 atatcgtaca tcttgactaa gtcgaacaag gggaagtcga tatggatcgt gggaccagaa
```

*Fig. 10RRR*

```
 481 gaatctgggt gtcgcaaaat caaggtgata ctgatttaga ttatcataaa attttgacag
 541 ctggccttac tgttcaacag ggaattgtca ggcagaaaat aatttctgta tatcttgttg
 601 ataacttgga ggctatgtgt caattggtaa tacaagcctt tgaggccgga attgatttcc
 661 aagaaaatgc cgacagcttc cttctgatgc tttgcctaca tcatgcttac caaggtgact
 721 ataaattgtt cttggagagc aatgctgtac agtatttgga aggtcatgga ttcaaatttg
 781 agctccggaa gaaggacggt gtcaatcggc tcgaggaatt gcttcctgct gcaacgagtg
 841 gaaaaaacat caggcgtacg ttggccgcac tgcctgaaga ggagactaca gaagcaaatg
 901 cagggcaatt tctctcattt gcgagttttgt ttcttcccaa actggttgtg ggagagaagg
 961 cttgcttgga aaaagtccag cgacaaattc aggttcatgc agaacagggt ttaattcaat
1021 atcccactgc atggcaatca gttggacaca tgatggtaat cttcagattg atgaggacta
1081 atttcttgat taaatattta ctgatccacc agggtatgca tatggtagct ggccacgatg
1141 ccaatgatgc tgtcattgct aattcagttg ctcaggctcg cttttcagga ctcctaattg
1201 tcaaaaccgt tcttgatcat attctgcaga aaaccgacca aggagtaaga cttcacccct
1261 tggcccgaac agccaaagtg cgtaatgagg ttaatgcatt taaggccgcc ctaagctcac
1321 ttgctaagca tggggagtat gccccttttg ctcgccttct caatctctcg ggagttaaca
1381 acctagaaca tggtctctac ccacagttat cagcaattgc tcttggagtt gccacagcac
1441 atggtagcac ccttgcagga gttaatgttg gtgagcagta tcagcagctt agagaggctg
1501 ccactgaagc tgagaagcaa ctccaacaat atgctgagtc cagagaactc gacagcctag
1561 gcctagacga tcaggaaaga agaatactaa tgaacttcca tcagaagaaa aatgaaatta
1621 gtttccagca gaccaatgca atggtaaccc ttaggaaaga gcgactggct aaaattaacag
1681 aagctataac gctggcctca agacctaacc tcgggtctag acaagacgac gacaatgaaa
1741 taccgttccc tgggcctata agcaacaacc cagaccaaga tcatctggag gatgatccta
1801 gagactccag agacactatc attcctaata gtgcaattga ccccgaggat ggtgattttg
1861 aaaattacaa tggctatcat gatgatgaag ttgggacggc aggtgacttg gtcttgttcg
1921 atcttgacga tcatgaggat gacaataaag cttttgagct acaggacagc tcaccacaat
1981 cccaaaggga aatagagaga gaaagattaa ttcatccacc cccaggcaac aacaaggacg
2041 acaatcgggc ctcagacaac aatcaacaat cagcagattc tgaggaacaa gaaggtcaat
2101 acaacaggca ccgaggccca gaacgtacga ccgccaatcg aagactctca ccagtgcacg
2161 aagaggacac ccctatagat caaggcgatg atgatccctc aagcccacct ccgctggaat
2221 ctgatgatga cgatgcatca agtagccaac aagatcccga ttatacagct gttgcccctc
2281 ctgctcctgt ataccgcagt gcagaagccc acgagcctcc ccacaaatcc tcgaacgagc
2341 cagctgaaac atcacaattg aatgaagacc ctgatatcgg tcaatcaaag tctatgcaaa
2401 aattaggaga gacatatcac catctgctga gaactcaagg tccatttgaa gctatcaatt
2461 attatcacat gatgaaggat gagccggtaa tatttagcac tgatgatggg aaggaataca
2521 cctacccgga ttcacttgag gaagcctatc tccatggct caccgagaaa gaacgactgg
2581 acaatgaaaa tcgatacatt tacataaata atcaacagtt cttctggcct gtcatgagtc
2641 ccagagacaa atttcttgca atcttgcagc accatcagta accacagcac aaagcgcggt
2701 ccacttcgta aagctaaata cacttaaagc ttgaccgatt catctacaaa aactaatcca
2761 ttataactta ttagtgctac ttttctataa gtgattctca atctaaggcc attaagagtt
2821 taagcaatat acatatacac ttacaccggt ctatccaaga tgtggctcaa tgttcttaat
2881 ttgaacatag tcataagggg ataaataata ctttatattt ctgattgtgg actgacccat
2941 tctgcttaaa atgcttcgcc cattaaaaat gtgatctaat agatagccct gactagacca
3001 attaagaaaa acatttgatg aagattaaaa ccttcatcgc cagtaaatga ttatattgtc
3061 tgtaggcagg tgtttactcc accttaaagt cggaaatatc ctaccttagg accattgtta
3121 agaggtgcat aggcattacc atccttgaga acatgtataa tgataaattg aagatatgtt
3181 caggcccaga aacaactgga tggatttctg agcaactaat gacaggtaag attccagtaa
```

*Fig. 10SSS*

```
3241 ctgatatatt cattgatatt gataacaagc cagatcaaat ggaagtccgg ctcaaaccat
3301 catcaaggag ctcaaccaga acttgtacaa gtagcagtca gacggaggtc aactatgtac
3361 ctctccttaa aaaggttgag gatacattaa ctatgctagt gagtgcaacc agtcgtcaga
3421 atgctgcaat cgaggccctt gaaaaccgcc tcagcacact tgagagtagc ttaaagccaa
3481 tccaagacat gggtaaagtg atttcatcat tgaatcgcag ttgtgccgaa atggtggcaa
3541 aatatgatct tctagttatg acaactggac gggctacttc aaccgcagct gcagtagatg
3601 cgtactggaa agagcacaaa cagccaccac cagggccagc gttgtatgaa gagaatgcgc
3661 ttaaaggaaa aatcgatgat ccaaacagct atgtaccaga tgctgtgcag gaggcttaca
3721 agaaccttga cagtacatcg accctgaccg aggaaaattt tgggaaacct tatatatctg
3781 ctaaagatct gaaggagatc atgtatgatc atctacctgg ttttgggact gccttcacc
3841 aacttgttca agtgatttgt aaaataggaa aggataacaa cctcttggac acaatccatg
3901 ctgagttcca ggcaagtcta gcagatggtg actctcccca atgtgcactc atacagataa
3961 ccaaaagagt cccaatcttt caggatgtgc cgccccgac aatccacatt agatcccgtg
4021 gtgatatccc acgagcatgc caaaagagtc tccgaccagc accaccatca cccaaaattg
4081 atcgtggttg ggtttgtttg tttaagatgc aagatggtaa aacgcttgga cttaagatct
4141 aaggatcaag atttatttaa caaggcaagc cacaacctta gatagaacct cagccagact
4201 attgaactat tgacgctgtt gatgataata tataattaat ggtcatattt gaatatgaca
4261 acatcttgct tcttgttttg ccttgtatct cttgagttg gaagatcatt ccaaacttac
4321 aaacatgcac aagatgttat ggtttagcaa agaattgata ggagtactgg tatataatgt
4381 aaatataaca agtgatgaag attaagaaaa accagtcggt attttccaga cttggcattt
4441 cttatcttca tcttctaaag tgagatattt tatcatcaaa aaatgagacg cggagtgtta
4501 ccaacggctc ctccagcata taatgatatt gcatactcta tgagcatact cccaacccga
4561 ccaagtgtca tagtcaatga gaccaaatca gatgtactgg cagtgccagg agcagatgtt
4621 ccatcaaact ccatgagacc agtggctgat gataacattg atcactcaag ccatactcca
4681 agcggagtag cttctgcctt tatattggaa gctaaagtga atgtaatttc gggaacaaaa
4741 gtcctgatga agcaaatacc tatttggctt ccactggggtg tagctgatca gaagatatac
4801 agctttgatt caacaacagc cgcaattatg ttggcttcct acacagtgac acacttcggg
4861 aagatatcta acccgctggt acgtgtcaac aggctaggcc caggaatacc cgatcatccg
4921 ctacgactcc taaggttggg caatcaggca ttccttcaag agtttgttct tccaccagtc
4981 cagcttcccc agtatttcac atttgatcta acagctctaa agctcatcac tcaaccattg
5041 ccagctgcaa cctggacaga cgaaactcca gcaggagcag tcaatgctct tcgtcctggg
5101 ctctcactcc atcccaagct tcgtccaatt cttctaccgg ggaagatagg aaagaaaggt
5161 catgcttcag acttaacatc acctgacaaa attcaaacaa tcatgaatgc aataccggac
5221 ctcaaaattg tcccgattga tccaatcaag aacatagttg gaattgaggt tccagaatta
5281 ctagttcaaa ggctgaccgg caaaaaacca caaccaaaaa atggccaacc aattattcca
5341 gttcttcttc cgaaatatgt tggacttgat cctatatcgc caggggactt aactatggtt
5401 atcacccagg attgtgattc atgccactct ccagccagcc atccgtatca catggacaag
5461 caggatagtt accaataatt taaattccat tcgagctatt attctgctag taattccgac
5521 gggatcaata gactaaaaat ctgattgtat agaattataa agaatcaag cagaggcaac
5581 agactcacag cttacgccta gatgactaat attaaggagt tttttaatct aattttccag
5641 tcttaagtaa taatcatttc ttttgtaatt aattatgcat ttgttaactt atcggtgcga
5701 gatttccttg agaacccggc ggggcttcta ctatctgtag taaccagaag agaagttcaa
5761 cccagtcaaa actaaaccaa gcaatattct gaatgctcta tagtctattc taatcagagg
5821 tataacaatg gctaagattt caatgactcg ttaacaatcg ctagtaattt taatctccag
5881 attaagaaaa agatatacga tgaagattaa ggcgacaacg agccgaaact tcatctcttt
5941 taaagatcta acattatctg ttccaaagtc atacaaggac acattcaaat cagggattgt
```

*Fig. 10TTT*

```
6001 aagctgctat ttcttacctc cccaaatcac ctatacaaca tggggtcagg atatcaactt
6061 ctccaattgc ctcgggaacg ttttcgtaaa acttcgttct tagtatgggt aatcatcctc
6121 ttccagcgag caatctccat gccgcttggt atagtgacaa atagcactct caaagcaaca
6181 gaaattgatc aattggtttg tcgggacaaa ctgtcatcaa ccagtcagct caagtctgtg
6241 gggctgaatc tggaaggaaa tggaattgca accgatgtcc catcagcaac aaaacgctgg
6301 ggattccgtt caggtgtgcc tcccaaggtg gtcagctatg aagccggaga atgggcagaa
6361 aattgctaca atctggagat caaaaagtca gacggaagtg agtgcctccc tctccctccc
6421 gacggtgtac ggggattccc tagatgtcgc tatgtccaca aagttcaagg aacaggtcct
6481 tgtcccggtg acttagcttt ccataaaaat ggggcttttt tcttgtatga tagattggcc
6541 tcaactgtca tctaccgtgg gacaactttt gctgaaggtg tcatagcttt tttaattctg
6601 tcagagccca agaagcattt ttggaaggct acaccagctc atgaaccggt gaacacaaca
6661 gatgattcca caagctacta catgaccctg acactcagct acgagatgtc aaattttgga
6721 ggcgaggaaa gtaacaccct ttttaaggta gacaaccaca catatgtgca actagatcgt
6781 ccacacactc cgcagttcct tgttcagctc aatgaaacac ttcgaagaaa taatcgcctt
6841 agcaacagta cagggagatt gacttggaca gtggatccca aaattgaacc agatgttggt
6901 gagtgggcct tctgggaaac taaaaaaact tttcccaaca acttcatgga gaaaacttgc
6961 atttccaaat tctatcaacc cacaccaaca actcctcaga tcagagcccg gcgggaactg
7021 tccaaggaaa aattagctac cacccaccca ccaacaactc cgagctggtt ccaacggatt
7081 cccctccagt ggtttcagtg ctcactgcag gacggacaga ggaaatgtcg acccaaggtc
7141 taactaacgg agagacaatc acaggtttca ccgcgaaccc aatgacaacc accattgccc
7201 caagtccaac catgacaagc gaggttgata acaatgtacc aagtgaacaa ccgaacaaca
7261 cagcatccat tgaagactcc ccccatcgg caagcaacga gacaattgac cactccgaaa
7321 tgaattcgat ccaaggctcg aacaactccg cccagagccc acagaccaag gccacgccag
7381 cgcccacagc atccccgatg acccctggacc cgcaagagac ggccaacatc agcaaaccag
7441 gaaccagccc aggaagcgca gccggaccaa gtcagcccgg actcactata aatacaataa
7501 gtaaggtagc tgattcactg agtcccacca ggaaacaaaa gcgatcggtt cgacaaaaca
7561 ccgctaataa atgtaaccca gatcttcact attggacagc tgttgatgag ggggcagcag
7621 caggattggc atggattcca tatttggac ctgcagcaga aggcatctac attgagggtg
7681 taatgcataa tcagaatggg cttatttgcg ggctacgtca gctagccaat gaaactaccc
7741 aggctcttca attattctg cgggccacaa cagaactgag gacttactca cttcttaaca
7801 gaaaagctat tgattttctt cttcaacgat ggggaggtac ctgtcgaatc ctaggaccat
7861 cttgttgcat tgagccacat gattggacaa aaatattac tgatgaaatt aaccaaatta
7921 aacatgactt tattgacaat cccctaccag accacggaga tgatcttaat ctatggacag
7981 gttggagaca atggatcccg gctggaattg ggattattgg agttataatt gctataatag
8041 ccctactttg tatatgtaag attttgtgtt gatttattct gagatctgag agaaaaaaat
8101 ctcagggtta ctctaaggag aaatattatt tttaaaattt acttaaatgc tgaccactta
8161 tcttaaatga gcaattaata atatgttttt ctgcttcttt gcttgattta caatatgata
8221 tttctcttaa taatgattaa tatattaaga aaaacttatg acgaagatta aaggggagga
8281 tcgttaacgg gaaaatctcc catctcgttc gtcgaagcca cgttggtggt gcttgcagct
8341 gagaacaact ccagagattg taggtagaaa ggaccagcat ttataggtag gggtcagaaa
8401 gcaacaatag ccataaaagg agagcctgac attgctattt aatatcctag aacctgattt
8461 ctaggttcta gttgtacaat ccggatgatg gagcattcaa gagaacgggg tagatctagc
8521 aacatgcgac ataatagccg ggaaccatac gaaaatccat caaggtctcg ctcattatct
8581 cgggacccta atcaggttga tcgtaggcag cctcgaagtg catcccaaat tcgtgttccg
8641 aatctgttcc atcggaaaaa gactgatgca ctcatagttc ctccggctcc caaagatata
8701 tgcccaacac tcaaaaaagg attcctctgc gatagtaaat tttgcaaaaa agatcaccaa
```

*Fig. 10UUU*

```
 8761 ttggatagct taaatgatca tgaattacta ctgctaattg caagaagaac atgtggaatt
 8821 atcgagagca attcgcagat tacatcccca aaagatatgc ggttagcgaa tccaacagct
 8881 gaagacttct cacaaggtaa tagtcctaaa ttaacacttg cagtccttct tcaaattgct
 8941 gaacattggg caaccagaga cctaaggcaa attgaggact ctaaacttag agctctttta
 9001 acccttttgtg ccgtattaac aaggaaattt tctaaatccc aactgggtct tctatgtgag
 9061 acccacctac ggcatgaggg cctcggacag gaccaagctg attctgtatt agaggtctac
 9121 caaagactcc acagtgataa aggagggaat tttgaggctg ccctgtggca acaatgggac
 9181 cgacagtcgt taataatgtt catctctgct tttctcaaca ttgctctcca gacaccttgt
 9241 gaaagttcta gtgtcgtagt ctcaggtctt gccacattgt acccagcaca agacaattct
 9301 acaccgtccg aggcaactaa tgataccacc tggtcaagta cagttgaata gaaaaccact
 9361 ggagctattt tccacgatt gctctcagtc aataaattaa tatagatata atacgacttc
 9421 ggtgtgcaat tgtcaagggt tccatttggt aataatgatt cttaaaacaa tctactatcg
 9481 taattatcga tggatctacc ctatttgacg gtacatgact tgaatgtaat aaggtaagtt
 9541 ggtatctgag gtattttgtc tagagtatac tcaaaatcgt atgtctagca aattatcaat
 9601 agcaaagtta aattctccta acctcatatt ttgatcaagt aatcatgatt ttatggtaat
 9661 tctttgcaga ttatcggttt aatctttatt aagaaaaaat catgattgta gacaatttac
 9721 tggtagtccc tgggtatcca agtttatgaa cagagctaga gagaatttgc tacttccgag
 9781 gtataacttt attatttgct acttcgaatg cctaaaacca gtaatgcagg atgaagatta
 9841 attgcggagg aatcaggaat tcaactttag ttccttaagg cctcgtctga atcttcatca
 9901 gttagtaagt tcttttatag aagtcattag cttctaaggt gattatattt tagtattaaa
 9961 ttttgttaat tgcttgctat aaagttgaaa tgtctaatgc ttaaatgaac atttctttga
10021 agctgacata cgaatacatc atatcatatg aaaacatcgc aattagagcg tccttgaagt
10081 ctggcattga cagtcaccag gctgttctca gtagtctgtc cttggaagct cttggggaga
10141 caagaagagg tcccagagag tcccaacagg ttggcataag gtcattaaca ccagcatagt
10201 cagctcgatc aagactgtaa gcgagtcgat tgcaactaaa aagattattt cttgttgttt
10261 aaacaaattc cttttgtgtg agacaccctc aaggcacaag atggctaaag ccacaggccg
10321 atacaatctc gtgcccccaa agaaagatat ggaaaaggga gtgatttta gtgatctttg
10381 taatttcttg attactcaaa ccctgcaagg ttggaaggtt tattgggcag gaattgagtt
10441 tgatgtaagt caaaaaggca tggctcttct gacaagactc aaaacaaatg actttgctcc
10501 tgcctgggcg atgacaagaa atctcttccc acatctgttc caaaacccaa attcggttat
10561 tcaatctccc atctgggctt tgagggtgat tttggcagcc ggattgcagg atcagttgtt
10621 agaccattca ttggttgagc cattgacagg ggctctcggt ctaatttctg attggctcct
10681 aactacaacg tcaacacatt tcaatcttcg tactagaagc gtaaaggacc agcttagtct
10741 tcgtatgtta tctttgatca ggtcaaacat cttgcagttc atcaacaagc ttgacgccct
10801 gcatgttgtc aattacaatg gtttactcag tagtattgag atcgggactt ctacacacac
10861 aatcattata actcgtacaa atatggggttt tctcgtggaa gttcaggagc ctgacaaatc
10921 agctatgaat tctaagcgcc caggaccagt caagttctca ttacttcatg agtctgcctt
10981 caaaccttc actcgtgttc cacaatctgg gatgcaatca ttaataatgg agttcaacag
11041 tttgttggca atttaacaag gtgatcttaa aataagtaca tgaatgagaa ttagttgtgg
11101 gtcttaccta gcattgttga gttagctatc taatctattt tcactaattg cattgagcac
11161 tgctagtagg tttgcaccac gttaaagatt cagagtgtat gaattgtgca gatttaaact
11221 tgggttttgc cttatgcttc acaggtggtc tttttaaaat ggagattatc agcatttctt
11281 caatgggagg agttagcaat cagaaattgg agataaatgg acatcgggat agaacaatgc
11341 ctaactattg ggcggctttc atttttaaat gtgtatataa ccaatctttt cctatctttg
11401 cttatattgg tgtaaacttta cttaataac atgtcaatgc tatactgtta agagaaggtc
11461 tgaggaagat taagaaaaag gtctcgtgtt cacttggttg ccgtcaagta tcctgtggtt
```

*Fig. 10VVV*

```
11521 tttttctacc taacttcctc atgccatatg gctacccagc atacccagta cccggatgca
11581 cgtttatctt cacctatagt cctggatcaa tgtgatttgg taactcgagc atgtgggtta
11641 tattcatctt attctctaaa tcctcagcta aggcaatgta aattaccaaa acatatatat
11701 cgacttaagt tcgacacaat agtatccaaa ttcctaagtg atacacctgt agcaacactg
11761 ccgatagact atttagtacc aattctcctg cgttccctaa cggggcacgg tgataggccg
11821 ttgaccccga cttgtaatca attccttgat ggaattatta attacactct tcatgatgca
11881 gcctttcttg attactatct caaggcaaca ggtgcacagg accatttgac aaacattaca
11941 actagagaga agcttaaaaa cgaaattcta aacaatgatt atgtccatca attgttcttc
12001 tggcatgacc tgtctatttt ggctcgacgt gggcgtctga atcgcgggaa caaccgttca
12061 acctggtttg ttcatgatga attcattgat attttaggat atggcgatta tattttttgg
12121 aaaataccctt tatcattatt accagttact atagacgggg tcccacacgc ggcaactgac
12181 tggtatcaac cgactctttt taaagaatcc atcctagggc acagccaaat cctatctgtg
12241 tcgacagctg aaatactaat tatgtgtaaa gatattatca cctgtaggtt taatacatca
12301 ctgattgcat ccattgcaaa attagaggat gtagatgtgt ctgattatcc tgacccgagt
12361 gatattctta agatatacaa tgctggagac tatgtaatat ctattcttgg ctcagaaggt
12421 tataagataa taaagtacct tgaaccactt tgtttggcca aaatccaact ttgctctaaa
12481 ttcacagaaa gaaaaggtcg tttcctcaca cagatgcatt tatcagtaat aaatgatctt
12541 cgggagttga tttctaaccg caggttaaag gactatcagc aagagaagat tagggatttt
12601 cacaaaatat tattacaatt gcaattatct cctcaacagt tttgtgaatt attctctgtt
12661 caaaaacatt gggggcatcc aattttacat agtgagaaag ctatacaaaa agtaaaacgg
12721 catgcaacca tccttaaggc tctcagacct aatgtcattt ttgagacata ttgtgtattc
12781 aagtacaata ttgccaagca ctatttcgac agccaaggaa cttggtacag tgtaatctca
12841 gacaggaatt taactccagg actcaactcc ttcataaaac gtaatcactt tccttcacta
12901 cccatgatta aggatcttct atgggaattc tatcatctta atcaccctcc gttattctct
12961 acaaaggtga ttagtgactt aagtattttc atcaaggata gggccacagc tgttgaacag
13021 acatgttggg atgcagtctt tgaacccaat gtgctaggtt acaatcctcc aaacaaattc
13081 tccactaaaa gggtgccgga acaatttcta gaacaggagg attttttcaat cgaaagtgtc
13141 ctgaattatg cacaggaatt acattattta ttaccacaga ataggaattt ttccttttct
13201 cttaaagaaa aagaattaaa tattggacga acattggta agctaccata tctcacacgg
13261 aatgtccaaa ctttatgtga ggctctgtta gcagatggac tggctaaggc cttccccagt
13321 aacatgatgg tagtaactga acgtgaacaa aaagagagcc ttcttcatca ggcatcatgg
13381 caccacacca gtgatgattt tggagagaat gctaccgttc gagggagtag ttttgtaact
13441 gatttagaga agtacaatct tgcatttcgc tatgagttca ctgcaccatt tattgagtac
13501 tgcaaccatt gctatggtgt gcgtaatgtc tttaattgga tgcattattt aatcccgcag
13561 tgttacatgc atgtaagtga ttattataat ccgcctcaca atgttaatct tagcaatcga
13621 gaatatcctc ctgaaggccc gagttcgtac cgagggcact taggaggcat agagggatta
13681 caacaaaaac tgtggacgag tatatcctgt gcacaaatct ccttagtgga aattaaaact
13741 ggttttaagt tacgatcagc ggtcatggga gacaatcagt gtataaccgt attgtctgtt
13801 tttccacttg aaacagacc tgaagagcag gagcaaagcg ccgaagacaa tgctgcaaga
13861 gtagcagcaa gtcttgcaaa agtaaccagt gcatgtggga tcttcttaa accagaagag
13921 acattcgtac actcaggttt catttatttc ggaaaaaaac aatatctcaa tggtgtacaa
13981 ttaccgcaat cactcaaaac agcagcaaga atggcgccac tctctgatgc tatattcgat
14041 gatctacaag gaacacttgc cagtattgga actgccttcg aacgtgctat atcggaaacg
14101 cgacatatcc tccatgtcg tattgtagca gctttccata cgtatttcgc cgttcggatt
14161 ttacaatatc accatcttgg atttaataaa ggcatcgatt tagggcagtt gtcacttagt
14221 aaaccattag actatgggac tattactcta acattggcgg ttccacaagt ccttggggga
```

Fig. 10WWW

```
14281 ttgtcttttc taaatccaga aaagtgtttt tatcgaaact tcggagatcc tgtgacttct
14341 ggacttttcc agctacgggt gtacctagaa atggttaaca tgaaagacct attttatcca
14401 ttaatatcga aaaatccagg aaattgtagt gccattgatt ttgtcttaaa tccatccgga
14461 ttaaatgttc caggatcaca agacttgaca tccttttgc gacagatcgt taggcgtagt
14521 attacactaa ctgcaagaaa taagttaatt aacactctct tccatgcctc tgctgatttg
14581 gaagatgaga tggtttgtaa atggctcctt tcatcaaacc ctgtcatgag tcgctttgca
14641 gcggatattt tttccaggac acctagtggt aaacgtctcc aaatattagg ttatcttgaa
14701 gggaccagga ctctattggc ctccaaaatc ataaacaaca acagtgagac acctgtactt
14761 gataagctga ggaagatcac cctacaaaga tggaatctgt ggttcagtta tttggaccat
14821 tgtgaccaat tactagcaga tgctctacag aaaattagtt gcacggtgga tttggcccag
14881 attttgcgtg agtatacatg gtcacacatc ttagagggta gaccattgat cggagcgaca
14941 ttaccatgta tggtggagca attcaaagtt aagtggctaa gacaatatga accttgtcca
15001 gaatgcctca acaaaaaagg ctcaaatgct tatgtctcag ttgcagtcaa agatcaagtg
15061 gtcagtgctt ggcctaatac ttctcgaata agttggacaa tagggagtgg tgtcccctat
15121 ataggggtcaa gaaccgagga taaaatcgga cagcctgcaa tcaagccgcg atgcccttca
15181 tctgcccctca aggaggctat agaattagca tcaaggctca cttgggttac acaaggaagt
15241 tctaatagtg aacaattaat ccggcctttc ttagaagcga gagtcaacct tagtgtcagt
15301 gaagtcctgc aaatgacacc atcacattat tcaggaaata ttgtccatcg atataacgac
15361 caatatagcc cgcactcatt tatggcgaat cgcatgagca atactgcgac ccgtctcata
15421 gtgtcaacta atacacttgg agaattttca ggtggagggc aggccgccag ggatagcaat
15481 ataattttcc agaatgttat aaatttagca gttgccctt atgatattag attccggaat
15541 acgaacacct ctgatataag gcataatagg gctcatcttc acctgacaga gtgctgtact
15601 aaagaggtcc cggcccagta tttgacatat acaagtgcac tcaatctgga tttaagccgt
15661 tatcgtgata atgaactaat atatgactca aatccactga ggggaggatt gaactgcaat
15721 ttaacaatgg atagtccttt agtgaagggt cctaggctta acatgattga agatgatctt
15781 ctccgctttc cacacctttc tggatgggag ttagcgaaaa cggtggtaca atccatcatc
15841 tcagacaata gcaactcatc aacagatcca atcagtagcg gagaaacacg ctctttcaca
15901 actcattttc tcacttaccc tcagattggc cttctttaca gtttcggggc agtattatgc
15961 tttatctag gcaatactat cctatggact aaaaaacttg attatgaaca gtttctatat
16021 tatttgcata accagctgca caacttacct catcgagcac tccgtgtttt taaaccaaca
16081 tttaagcatg ccagtgtgat gtcccgatta atggaaattg attccaactt ctcaattat
16141 attggcggga catctggaga tcgagggctg tctgatgctg ctcgactgtt tcttcggaca
16201 gcaatcgcga gttttttaca atttcttaaa agctggatca tcgatcgcca aaaggcaatt
16261 cctttatgga tagtatatcc gcttgaaggt caacagccgg aatccatcaa tgaatttcta
16321 cataaaattt ttggtctgct caaacaaggc cccaaaaata ttccaaagga ggtcagcatt
16381 caaaatgatg gacatttgga tttggcagaa aataattatg tttacaatag taagagcact
16441 gctagtaatt tcttccatgc atccttagct tactggagaa gtaggaaatc tcggaaaact
16501 caagaccata atgatttctc aagaggggat ggaacactta cagaacccgt gtgtaagttc
16561 tcaagcaatc atcagtcaga tgaaaagtac tacaatgtga catgtggaaa gtcaccgaag
16621 ccgcaagaac gcaaagactt ctcgcaatac agactcagca ataacgggca aacaatgagt
16681 aatcatcgta agaaagggaa gttccacaag tggaatccct gcaaagtgtt aatggagagt
16741 caaaggggaa ctgttctaaa agagggtgac tactttcaaa acaatactcc accaacagat
16801 gatgtatcaa gtcctcaccg actcattcta ccatttttta aattgggaaa tcacaaccat
16861 gcacatgatc aagatgccca agaattgata aatcaaaata ttaaacagta cctacatcag
16921 ctaaggtcta tgttggacac cactatatat tgtagattca caggggattgt ctcatccatg
16981 cattacaaat tggacgaagt tcttctagaa tacaatagtt tcgattcagc tatcacatta
```

Fig. 10XXX

```
17041 gctgaaggtg aggggtcagg ggctctatta cttttgcaga aatatagtac aaggttatta
17101 tttttgaaca cattggcaac agaacacagt atagagtcag aagttgtatc aggtttttct
17161 actccgagaa tgttgttacc aataatgcaa aaggttcatg aaggacaagt cactgttatc
17221 ttaaataatt cagcaagtca gataactgac ataactagct caatgtggtt aagtaatcaa
17281 aaatataatc taccttgtca agttgaaatc attacgatgg atgctgaaac aacagagaac
17341 ttaaacaggt cccaactcta ccgagcagta tataacttaa tacttgatca cattgatccg
17401 cagtatctca aggtggtggt actcaaagta tttctgagtg atatagaagg aatattatgg
17461 attaatgatt acttggctcc attattcggg gctggttact tgattaaacc gattacatca
17521 agtgcccggt caagtgaatg gtaccttttgc ttatcaaatt tgatatctac taacaggaga
17581 tcggcccatc agactcacaa ggcatgtctt ggtgttatca gagatgcttt gcaagcacaa
17641 gtccagcgag gcgtgtactg gttgagtcac atcgcacagt atgctacaaa gaatctccat
17701 tgtgaataca tatgccttgg ttttcccacct ctagaaaagg tcctatatca caggtataat
17761 ctagttgata ctggactcgg tccattgtcg tcagttatta gacatttaac taacctccag
17821 gcagagatac gagacttagt attagattat accctgatga gagagagtcg cactcaaacg
17881 taccatttta ttaagactgc aaaaggcaga atcacaaagt tagtcaatga ctttctgaag
17941 ttttctttaa ttgtccaggc actcaaaaat aattcttctt ggtatactga gcttaaaaaa
18001 ttacctgagg tgattaatgt gtgtaatcga ttttatcata ctcacagttg cgaatgtcag
18061 gaaaaattct ttgtccagac gctttattta caacgcctac gcgatgcaga aatcaagcta
18121 attgaacgcc ttaccggggtt aatgcgattt tatccagaag ggttaatata ttccaatcac
18181 acataggtac taaatcatca tagtatgagg aataaaataa tgataattcc tgacgacagt
18241 tttagttccg attctaagta tatcggaaga gagtatgcca atcttaatta ttaaaggtaa
18301 caagctatta gttattactt attgataaga ataaacttta tcatagcgta acacatcata
18361 actttatagc gattttgcat ttctaatcct agtatttatt agaatgtact atcagagaaa
18421 tgaccccagt tcctatcttt aaataatgat tgtgtgtatt aaattattag tttattaggt
18481 ttatgagttg gttacacagt gagtattagt aattgaggat tatgtagata ggtaatctaa
18541 cactgaatca cccatctgat gtcaccatat ccaaatattg tgctagtcgc attttaaacat
18601 gctatcttca gttaagtaac atagactgaa aatgctaaga agagattgga gtaaaagtat
18661 aaaataaatt taattaaact tcaaagtgat taaatgataa tgatcttggg aactcgatat
18721 gacctcaagt caaaaataat gtcaatataa ttgtttagta atatgagtta taatgtgaat
18781 tttgataact aactagcttt agtagttaag atcaaatgca aacattctaa gaatgttaag
18841 cgcacacaaa aacattataa aaaaccaatt ttttcctttt tgtgtgtccc
```
(SEQ ID NO: 24)

VP30

MEHSRERGRSSNMRHNSREPYENPSRSRSLSRDPNQVDRRQPRSASQIRVPNLFH
RKKTDALIVPPAPKDICPTLKKGFLCDSKFCKKDHQLDSLNDHELLLLIARRTCGI
IESNSQITSPKDMRLANPTAEDFSQGNSPKLTLAVLLQIAEHWATRDLRQIEDSKL
RALLTLCAVLTRKFSKSQLGLLCETHLRHEGLGQDQADSVLEVYQRLHSDKGGN
FEAALWQQWDRQSLIMFISAFLNIALQTPCESSSVVVSGLATLYPAQDNSTPSEA
TNDTTWSSTVE (SEQ ID NO: 25)

NC002549

1 cggacacaca aaaagaaaga agaattttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc

Fig. 10YYY

```
 181 gaagggagca agggcatcag tgtgctcagt tgaaaatccc ttgtcaacac ctaggtctta
 241 tcacatcaca agttccacct cagactctgc agggtgatcc aacaacctta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgattttcaa gagagtgcgg acagtttcct tctcatgctt tgtcttcatc atgcgtacca
 721 gggagattac aaactttct tggaaagtgg cgcagtcaag tatttggaag ggcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctcctttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt ccgtttgat
1081 gcgaacaaat ttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactcctta aggctgcact
1321 cagctccctg gccaagcatg gagagtatgc tcctttcgcc cgacttttga accttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca cacccagtc
2401 agaacactct tttgaggaga tgtatcgcca cattctaaga tcacagggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg ttttttcaaag ttcaatttga gtcttaatgc
2881 aaataggcgt taagccacag ttatagccat aattgtaact caatattcta actagcgatt
```

*Fig. 10ZZZ*

```
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact ataggggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcggggt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aagggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagtttttata gaatcttctc agggatagtg ataacatcta
5521 tttagtaatc cgtccattag aggagacact tttaattgat caatatacta aaggtgcttt
5581 acaccattgt ctttttctc tcctaaatgt agaacttaac aaaagactca taatatactt
5641 gtttttaaag gattgattga tgaaagatca taactaataa cattacaaat aatcctacta
```

*Fig. 10AAAA*

```
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 acccccaaaa gcagagaaca ccaacacgag caagagcact gacttcctgg acccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg atacggcag gtattggagt tacaggcgtt ataattgcag ttatcgcttt
8041 attctgtata tgcaaatttg tcttttagtt ttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agtatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
```

*Fig. 10BBBB*

```
 8461 gtcaaaaagt caatagaaat ttaaacagtg agtggagaca actttttaaat ggaagcttca
 8521 tatgagagag gacgcccacg agctgccaga cagcattcaa gggatggaca cgaccaccat
 8581 gttcgagcac gatcatcatc cagagagaat tatcgaggtg agtaccgtca atcaaggagc
 8641 gcctcacaag tgcgcgttcc tactgtattt cataagaaga gagttgaacc attaacagtt
 8701 cctccagcac ctaaagacat atgtccgacc ttgaaaaaag gattttttgtg tgacagtagt
 8761 ttttgcaaaa aagatcacca gttggagagt ttaactgata gggaattact cctactaatc
 8821 gcccgtaaga cttgtggatc agtagaacaa caattaaata taactgcacc caaggactcg
 8881 cgcttagcaa atccaacggc tgatgatttc cagcaagagg aaggtccaaa aattaccttg
 8941 ttgacactga tcaagacggc agaacactgg gcgagacaag acatcagaac catagaggat
 9001 tcaaaattaa gagcattgtt gactctatgt gctgtgatga cgaggaaatt ctcaaaatcc
 9061 cagctgagtc ttttatgtga gacacaccta aggcgcgagg ggcttgggca agatcaggca
 9121 gaacccgttc tcgaagtata tcaacgatta cacagtgata aaggaggcag ttttgaagct
 9181 gcactatggc aacaatggga ccgacaatcc ctaattatgt ttatcactgc attcttgaat
 9241 attgctctcc agttaccgtg tgaaagttct gctgtcgttg tttcagggtt aagaacattg
 9301 gttcctcaat cagataatga ggaagcttca accaacccgg ggacatgctc atggtctgat
 9361 gagggtaccc cttaataagg ctgactaaaa cactatataa ccttctactt gatcacaata
 9421 ctccgtatac ctatcatcat atatttaatc aagacgatat cctttaaaac ttattcagta
 9481 ctataatcac tctcgtttca aattaataag atgtgcatga ttgccctaat atatgaagag
 9541 gtatgataca accctaacag tgatcaaaga aaatcataat ctcgtatcgc tcgtaatata
 9601 acctgccaag catacctctt gcacaaagtg attcttgtac acaaataatg ttttactcta
 9661 caggaggtag caacgatcca tcccatcaaa aaataagtat ttcatgactt actaatgatc
 9721 tcttaaaata ttaagaaaaa ctgacggaac ataaattctt tatgcttcaa gctgtggagg
 9781 aggtgtttgg tattggctat tgttatatta caatcaataa caagcttgta aaaatattgt
 9841 tcttgtttca agaggtagat tgtgaccgga aatgctaaac taatgatgaa gattaatgcg
 9901 gaggtctgat aagaataaac cttattattc agattaggcc ccaagaggca ttcttcatct
 9961 ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagtttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaaccccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
```

*Fig. 10CCCC*

```
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca atacccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aatttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actggggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aagaaatca attccctccg ttgccaatga ttaaagaact actatgggaa
12961 ttttaccacc ttgaccaccc tccacttttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaacttttc tattgagaat gttctttcct acgcacaaaa actcgagtat
13201 ctactaccac aatatcggaa ctttttcttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa tttctttagt tgaaattaag actggttta agttacgctc agctgtgatg
13801 ggtgacaatc agtgcattac tgtttatca gtcttcccct tagagactga cgcagacgag
13861 caggaacaga gcgccgaaga caatgcagcg agggtggccg ccagcctagc aaaagttaca
13921 agtgcctgtg gaatcttttt aaaacctgat gaaacatttg tacattcagg ttttatctat
```

Fig. 10DDDD

```
13981 tttggaaaaa aacaatattt gaatggggtc caattgcctc agtcccttaa aacggctaca
14041 agaatggcac cattgtctga tgcaattttt gatgatcttc aagggaccct ggctagtata
14101 ggcactgctt ttgagcgatc catctctgag acacgacata tctttccttg caggataacc
14161 gcagctttcc atacgttttt ttcggtgaga atcttgcaat atcatcatct cgggttcaat
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaaccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgttaac atgggtaact caaggcagtt cgaacagtga cttgctaata
15301 aaaccatttt tggaagcacg agtaaattta agtgttcaag aaatacttca aatgacccct
15361 tcacattact caggaaatat tgttcacagg tacaacgatc aatacagtcc tcattctttc
15421 atggccaatc gtatgagtaa ttcagcaacg cgattgattg ttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacatca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccatttcatc tttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca agtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
```

*Fig. 10EEEEE*

16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat tttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 ttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcacttat tcgtactgca
17941 aaaggacgaa tcacaaaact agtcaatgat tatttaaaat tcttttcttat tgtgcaagca
18001 ttaaaacata tgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagtttttta taattatcat tactttaatt tgtcgtttta aaaacggtga
18661 tagcctaaat cttgtgtaa aataagagat taggtgtaat aaccttaaca tttttgtcta
18721 gtaagctact atttcataca gaatgataaa attaaaagaa aaggcaggac tgtaaaatca
18781 gaaataccttc tttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtcca (SEQ ID NO: 26)

VP30

MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ

NC_001608

1 agacacacaa aaacaagaga tgatgatttt gtgtatcata taaataaaga agaatattaa
61 cattgacatt gagacttgtc agtctgttaa tattcttgaa gagatggatt tacacagttt
121 gttggagttg ggtacaaaac ccactgcccc tcatgttcgt aataagaaag tgatattatt
181 tgacacaaat catcaggtta gtatctgtaa tcagataata gatgcaataa actcagggat
241 tgatcttgga gatctcctag aaggggggttt gctgacgttg tgtgttgagc attactataa
301 ttctgataag gataaattca acacaagtcc tatcgcgaag tacttacgtg atgcgggcta
361 tgaatttgat gtcatcaaga atgcagatgc aacccgcttt ctggatgtga ttcctaatga
421 acctcattac agccctttaa ttctagccct taagacattg gaaagtactg aatctcagag
481 ggggagaatt gggctctttt tatcattttg cagtctttc ctcccaaaac ttgtcgtcgg
541 agaccgagct agtatcgaaa aggctttaag acaagtaaca gtgcatcaag aacaggggat
601 cgtcacatac cctaatcatt ggcttaccac aggccacatg aaagtaattt tcgggatttt
661 gaggtccagc ttcattttaa agtttgtgtt gattcatcaa ggagtaaatt tggtgacagg
721 tcatgatgcc tatgacagta tcattagtaa ttcagtaggt caaactagat tctcaggact
781 tcttatcgtg aaaacagttc tcgagttcat cttgcaaaaa actgattcag gggtgacact
841 acatcctttg gtgcggacct ccaaagtaaa aaatgaagtt gctagtttca agcaggcgtt
901 gagcaaccta gcccgacatg gggaatacgc accatttgca cgggttctga atttatcagg
961 gattaacaac ctcgaacatg gactctatcc tcagctttca gcaattgcgc tgggtgtggc
1021 aacagcacac ggcagtacat tggctggtgt caatgttggc gaacaatatc aacaactacg
1081 agaggcggca catgatgcgg aagtaaaaact acaaaggcga catgaacatc aggaaattca
1141 agctattgcc gaggatgacg aggaaaggaa gatattagaa caattccacc ttcagaaaac
1201 tgaaatcaca cacagtcaga cactagccgt cctcagccag aaacgagaaa aattagctcg
1261 tctcgctgca gaaattgaaa acaatattgt ggaagatcag ggatttaagc aatcacagaa
1321 tcgggtgtca cagtcgtttt tgaatgaccc tacacctgtg gaagtaacgg ttcaagccag
1381 gcccatgaat cgaccaactg ctctgcctcc cccagttgac gacaagattg agcatgaatc
1441 tacagaagat agctcttctt caagtagctt tgttgacttg aatgatccat ttgcactgct
1501 gaatgaggac gaggatactc ttgatgacag tgtcatgatc ccgggcacaa catcgagaga
1561 atttcaaggg attcctgaac cgccaagaca atcccaagac ctcaataaca gccaaggaaa
1621 gcaggaagat gaatccacaa atccgattaa gaaacagttt ctgagatatc aagaattgcc
1681 tcctgttcaa gaggatgatg aatcggaata cacaactgac tctcaagaaa gcatcgacca
1741 accaggatcc gacaatgaac aaggagttga tcttccacct cctccgttgt acgctcagga
1801 aaaaagacag gacccaatac agcacccagc agcaaaccct caggatccct tcggcagtat
1861 tggtgatgta aatggtgata tcttagaacc tataagatca ccttcttcac catctgctcc
1921 tcaggaagac acaaggatga gggaagccta tgaattgtcg cctgatttca caatgatga
1981 ggataatcag cagaattggc cacaaagagt ggtgacaaag aagggtagaa ctttccttta
2041 tcctaatgat cttctgcaaa caaatcctcc agagtcactt ataacagccc tcgttgagga
2101 ataccaaaat cctgtctcag ctaaggagct tcaagcagat tggcccgaca tgtcatttga
2161 tgaaaggaga catgttgcga tgaacttgta gtccagataa cacagcacgg ttactcactt
2221 atctattttg atatgactca tcctcagatc acagcaatca aatttatttg aatatttgaa
2281 ccacctttta gtatcctatt acttgttact attgtgtgag acaacataag ccatcaaata
2341 acaatcacgg gcaaggactg ggcatactat ggtggtctta gagcattgtc cagtgctaca
2401 aattcttttt tcaattgcta taattataca actacaaacc tccatacatt tgccgcaaca
2461 ctgtaatcaa cactgctgta tctcttcttc aagccatctg atttaactta ataaacatga
2521 cttgattcaa agaatatact gacaatgtta ctgtttgaat ttctcaagtg gtgcactatc

*Fig. 10GGGG*

2581 ctactgtttt gctcagctta gtatattgta atatgtaagt ggactctccc cttctcctct
2641 cgtgtattct ttataaatca cttacttgat agaatgtcga gtctactggt ttggagtttc
2701 cttactctaa tggatgtaat aattaactgt tggcctagat gataacagat atgaggttat
2761 ataattactc atagtgtaaa gtataattct tacctctgtt tcttctgttt tcccttctt
2821 ttataatatg ccaattaaga aaaactaaaa atcgaagaat attaaagatt ttctttaata
2881 ttcagaaaag gcttttatt ctattctttc tttttacaaa cgtattgaaa tagtaattct
2941 cacaatgtgg gactcatcat acatgcagca agtcagcgaa gggttgatga ctggaaaagt
3001 acccatagat caagtgtttg gtgccaatcc cttagagaag ttatacaaga gaagaaaacc
3061 aaaaggcaca gttggactac aatgtagccc ttgtctaatg tcaaaggcga caagtactga
3121 tgatattatt tgggaccaac tgatcgtgaa gagaacacta gctgatctac ttataccgat
3181 aaataggcag atatcagaca ttcaaagcac tctaagcgaa gtaacaacaa gagtccatga
3241 aattgagcgg caattacatg agattacccc agttttaaaa atgggaagga cactggaagc
3301 aatttccaag gggatgtcag aaatgttagc caaatacgac caccttgtaa tttcaactgg
3361 aagaaccact gcaccagctg ctgcctttga tgcctactta aatgagcatg gtgtccctcc
3421 ccctcaaccc gcgattttca aagatcttgg ggttgcccaa caagcttgta gtaaggggac
3481 catggttaaa aatgcaacaa cagatgcagc cgacaagatg tcgaaggttc ttgaactcag
3541 tgaggaaacg ttctccaagc caaaccttc agctaaggat ttagcccttt tattgtttac
3601 ccatctaccc ggcaacaaca ctccattcca tatcctagct caggtccttt caaaaattgc
3661 ttacaagtca ggaaaatccg gagcattctt ggatgcattt caccagattc taagtgaagg
3721 agagaatgct caggcggcat taactcgact aagcagaaca tttgacgctt tccttggagt
3781 ggttcctcca gtgataagag tcaaaaactt ccaaacagtc cctcgtccat gtcaaaaaag
3841 tcttcgggct gtccctccaa atccaacaat tgacaaagga tgggtctgtg tttattcatc
3901 tgagcaaggt gaaacacggg cccttaaaat ctaattctca ttgttcatag ttgcaaggga
3961 agtgatcttt ccgagttgat acaaagacac taaacatttc aaaagcatgt atgtggacaa
4021 aacataatta gaccatctta attggagtag taatttattt ctgtcttaaa tgtgattttc
4081 actttaaaag cgttaaatgg tgatagatta atccttgaag ttactcttct atatattata
4141 gagaaaccaa tgttactaac aaaaggggtc tacctaacgc atatgattga gtaatccgta
4201 tattttataa accaaacaat taacttctta cttttaaga atcaactaac aacatagaaa
4261 agacatttat cctatgtaa tcctcggctt agttgaaatt aacttttgtt ggacctcaag
4321 acgcttattc atagtatatt atatgatttt ttataagttt aagatatctt aaattatacc
4381 cacaaaagat actgttttaa ttaagaaaaa ctatgaagaa cattaagaag atctttcttt
4441 cgtagtgttc ttttactgga aggagtattc caatttcagc ttgttggatt aattgttact
4501 taaattgtcc tttttgaaat taattcacac aaggtagttt aaatttatat ccaaaataaa
4561 ttttgatatg gccagttcca gcaattacaa cacatacatg caatacttga acccccctcc
4621 ttatgctgat cacggtgcaa accagttgat cccggcggat cagctatcaa atcagcaggg
4681 tataactcca aattacgtgg gtgatttaaa cctagatgat cagttcaaag ggaatgtctg
4741 ccatgcttc actttagagg caataattga catatctgca tataacgagc gaacagtcaa
4801 aggcgttccg gcatggctgc ctcttgggat tatgagcaat tttgaatatc ctttagctca
4861 tactgtggcc gcgttgctca caggcagcta tacaatcacc caattactc acaacgggca
4921 aaaattcgtc cgtgttaatc gacttggtac aggaatccca gcacaccac tcagaatgtt
4981 gcgtgaagga aatcaagctt ttattcagaa tatggtgatc cccaggaatt tttcaactaa
5041 tcaattcacc tacaatctca ctaatttagt attgagtgtg caaaaacttc ctgatgatgc
5101 ctggcgccca tccaaggaca aattaattgg gaacactatg catcccgcag tctccatcca
5161 cccgaatctg ccgcctattg ttctaccaac agtcaagaag caggcttatc gtcagcacaa
5221 aaatcccaac aatggaccat tgctggccat atctggcatc ctccatcaac tgagggtcga
5281 aaaagtccca gagaagacga gcctgtttag gatctcgctt cctgccgaca tgttctcagt

*Fig. 10HHHH*

5341 aaaagagggt atgatgaaga aaaggggaga aaattccccc gtggtttatt ttcaagcacc
5401 tgagaacttc cctttgaatg gcttcaataa cagacaagtt gtgctagcgt atgcgaatcc
5461 aacgctcagt gccgtttgaa atgatgctca aatgagacag gagtccatct gtataagaag
5521 tatggcttaa atggatattt gtcaaattct tacaagatta gtttgtattg atttcaacaa
5581 tgctttaacc ttacattgct gctttaaata gttgattaag ctgatcagct tgtaatatgt
5641 aatctcttct gggccatcag atccataatg ggtttactag actatataag agaaatagta
5701 atattttata aacaattctt gctcagtttt actgtgattt aataacatat gtcattgtgc
5761 cctccattgc taagtcaact caactgacga taatactcct tctgaaatag taagaaaaac
5821 taatgaagaa cattaattgc tgggtaaaag tgattaattt ctttaaattt gaccagaata
5881 atattttgtc agtgaatata ttctcatatc acttgattaa aaacagaaaa ttaccctaac
5941 atgaagacca catgtttcct tatcagtctt atcttaattc aagggacaaa aaatctcccc
6001 attttagaga tagctagtaa taatcaaccc caaaatgtgg attcggtatg ctccggaact
6061 ctccagaaga cagaagacgt ccatctgatg ggattcacac tgagtgggca aaaagttgct
6121 gattcccctt tggaggcatc caagcgatgg gctttcagga caggtgtacc tcccaagaat
6181 gttgagtaca cagaggggga ggaagccaaa acatgctaca atataagtgt aacggatccc
6241 tctggaaaat ccttgctgtt agatcctcct accaacatcc gtgactatcc taaatgcaaa
6301 actatccatc atattcaagg tcaaaaccct catgcacagg ggatcgccct tcatttatgg
6361 ggagcatttt ttctgtatga tcgcattgcc tccacaacaa tgtaccgagg caaagtcttc
6421 actgaaggga acatagcagc tatgattgtc aataagacag tgcacaaaat gattttctcg
6481 cggcaaggac aagggtaccg tcatatgaat ctgacttcta ctaataaata ttggacaagt
6541 agtaacggaa cgcaaacgaa tgacactgga tgtttcggcg ctcttcaaga atacaattct
6601 acaaagaacc aaacatgtgc tccgtccaaa atacctccac cactgcccac agcccgtccg
6661 gagatcaaac tcacaagcac cccaactgat gccaccaaac tcaataccac ggacccaagc
6721 agtgatgatg aggacctcgc aacatccggc tcagggtccg gagaacgaga accccacaca
6781 acttctgatg cggtcaccaa gcaagggctt tcatcaacaa tgccacccac tccctcacca
6841 caaccaagca cgccacagca aggaggaaac aacacaaacc attccaaga tgctgtgact
6901 gaactagaca aaaataacac aactgcacaa ccgtccatgc ccctcataa cactaccaca
6961 atctctacta acaacacctc caaacacaac ttcagcactc tctctgcacc attacaaaac
7021 accaccaatg acaacacaca gagcacaatc actgaaaatg agcaaaccag tgcccccctcg
7081 ataacaaccc tgcctccaac gggaaatccc accacagcaa agagcaccag cagcaaaaaa
7141 ggccccgcca caacggcacc aaaacacgaca aatgagcatt tcaccagtcc tcccccacc
7201 cccagctcga ctgcacaaca tcttgtatat ttcagaagaa agcgaagtat cctctggagg
7261 gaaggcgaca tgttcccttt tctggatggg ttaataaatg ctccaattga ttttgaccca
7321 gttccaaata caaaaacaat ctttgatgaa tcctctagtt ctggtgcctc ggctgaggaa
7381 gatcaacatg cctccccccaa tattagttta actttatctt attttcctaa tataaatgag
7441 aacactgcct actctggaga aaatgagaat gattgtgatg cagagttaag aatttggagc
7501 gttcaggagg atgacctggc cgcagggctc agttggatac cgttttttgg ccctggaatt
7561 gaaggacttt acactgctgt tttaattaaa aatcaaaaca atttggtctg caggttgagg
7621 cgtctagcca atcaaactgc caaatccttg gaactcttat tgagagtcac aactgaggaa
7681 agaacattct ccttaatcaa tagacatgct attgactttc tactcacaag atggggagga
7741 acatgcaaag tgcttggacc tgattgttgc atcgggatag aagacttgtc caaaaatatt
7801 tcagagcaaa ttgaccaaat taaaaaggac gaacaaaaag aggggactgg ttggggtctg
7861 ggtggtaaat ggtggacatc cgactggggt gttcttacta acttgggcat tttgctacta
7921 ttatccatag ctgtcttgat tgctctatcc tgtatttgtc gtatctttac taaatatatc
7981 ggataacgtt aaatgtgtaa tgattaggac tttaggacaa ttgctactga gccctttttc
8041 taatctactg aaatcaactt gggagatttt taagaagctg ataacttaat gtgaatcaat

*Fig. 10IIII*

```
8101 agtttatgta ttatcgatta ttatggtttg atattcaatt gttattattg tcaggagtga
8161 cctttctat ttgatgcatt aatgttttaa actacctctt aagcctttga gggcggtccc
8221 aatatgtgcg tagggggttaa tttaaaggga tttcttattg tacagttttc tgtattactt
8281 atttgggctt gaagacatag ttaagatttg ccgaaaatgc tctccagtca attccatccc
8341 ctctcagaaa agacgtgctg ttcaaagagt cttaatttat aaccaactat tgcaagaatt
8401 aatttacttt ttccgttata cttagttaca ttaatctttt gactgttcag cattattaac
8461 gacttgtctt aattcaatcg ttcggatgaa attcataagg aaaaatgagc ctccttcccc
8521 ctattctggg ctgagaaaat ttctcttatc cgcctaaaat ctgatctgtt aggtcatggg
8581 tccttcataa tctgtttgag catgaatatt gatcaaatga ccaaatgata gtgcatttgt
8641 atagactcaa ttatccttta ttaagaaaaa gataaataga acacaaagaa ttgacaaaat
8701 tttactttga ttgatttgc aaggagttat aaaaatcttg aaggataaat tgttataaag
8761 tagagtcgaa gaacattaaa tgttctttgt tagaattatt catctaagtt gtttttgagt
8821 atattcgctt caatacaact cctctttata tttgatttaa gtttaaaat gcaacaacct
8881 cgcggaagaa gtcgaacccg caaccaccaa gtcacaccga ctatatatca tgaaactcaa
8941 ttgccctcca aacctcatta taccaattat catccacgtg caagatcgat gagctcaacc
9001 cgtagtagtg cagaaagtag tcccaccaat catattcccc gtgctcgacc accctcaaca
9061 ttcaacttat cgaaaccccc tcctcctcca aaagacatgt gcaggaacat gaaaattgga
9121 ttgccgtgcg ctgatcccac ttgtaataga gatcatgacc ttgataatct aacaaatcgt
9181 gaacttttgc tattgatggc ccgaaaaatg ctccccaata cagacaagac ctttagaagt
9241 ccgcaggact gtggatcacc gtctctttct aaaggtctct caaaagataa acaggagcaa
9301 acgaaagatg tgttgacctt ggaaaatcta ggacacattc tgagctatct ccacagatca
9361 gaaattggga aattggatga gacatcactt cgtgcagcat taagtctgac gtgtgctgga
9421 attcgaaaga cgaatagatc cttgatcaac accatgacag aattacacat gaaccatgaa
9481 aatctcccgc aagaccaaaa cggtgttatc aagcagacct atacaggtat tcaccttgac
9541 aaaggaggtc aattcgaagc cgccttatgg caaggttggg ataagagatc gatatctcta
9601 ttcgtacaag cagctttata tgtaatgaac aatatcccct gtgaatcatc aatcagtgtg
9661 caagcctcat acgatcattt tattcttcct caaagtcaag gtaaaggaca gtgattattg
9721 ttcgaaagtt gacaatttga tcactttcag ttttcagttt caaccttat cgcgagactt
9781 gaatacaatc ctactaactt caataagtga ccccaaattc aagtttgctg aaagctaaga
9841 tgacaatgat cactagttca ttgtaaatta ctcgatcaaa atgttcttaa gctatcttaa
9901 gcttactgat gcggctctgc ttcacttttc ttttgatttt aaagccatag ctatatctaa
9961 gtgtctaatt aacaacttgt acctctaagg aaaaacatga agaacattaa gaaaaaggat
10021 gttcttattc tttgactaaa cctgcatatt ctttgttgat accctcgaga gacaactttt
10081 gacaccagat cacggatcaa gcacacttca atcaagcacc ctaaatttc aatcatacac
10141 ataataacca ttttagtagc gttgcctttc agtacagtct aggtgattgt tgaaagactt
10201 ccaagcatgg cagaattatc aacgcgttac aacttgcctg caaatgttac ggaaaatagt
10261 ataaatcttg accttaattc cacagcacga tggataaaag aacccagtgt tgggggctgg
10321 acagtgaagt gggggaaactt tgttttccat ataccaaata ctggaatgac attgttgcat
10381 catttaaagt ctaacttcgt tgttccagag tggcaacaaa caaggaatct attctcccac
10441 ctcttttaaaa acccaaaatc aacaattata gaaccgtttt tggccctgag gattttgctt
10501 ggagttgctt tgaaggatca agaattacag caatcattga ttcctggatt tagatctatt
10561 gttcatatgc tatcagaatg gctgctcctg gaggtcacgt cggcaatcca tattagccct
10621 aatctgttgg gaatctattt gacttcagac atgtttaaaa ttctgatggc aggtgtgaaa
10681 aatttcttca ataagatgtt cactcttcat gttgtaaatg accacggaaa acccagcagt
10741 attgaaataa agttaactgg acaacagatc attatcactc gtgttaatat ggggtttcta
10801 gtggaagtca ggaggattga tattgaacct tgctgtggtg agacagtcct ctcagaatca
```

Fig. 10JJJJ

```
10861 gttgtttttg gactagtggc tgaggcagtt ctaagagaac acagtcaaat ggagaagggc
10921 caacctctca atctgacaca atacatgaac agcaaaattg ctatataagt ggcttaaatt
10981 agcatgggta ttcctagttc gaccacataa taatgttgga ggcacagtac attatagtta
11041 attgtcttgt atactaaggg atatacctaa cctgatttat atttactggt ataaaatagt
11101 agcatcatct tattgaatag ttatcataca ataggctgtt cctataatct gattgtgaga
11161 ttataaactt gtagaattac cgtgggtcac aactgttgca tatcctccaa aatatatctt
11221 ttgcaagtga tgtgtgcttg aatacttcga tataatacat actaataacg attgattaag
11281 aaaaatcaat gatggatatt aaatgtccat caagcaagtg ttgtagaata ccaggggttt
11341 cacaggctgc taaacttact aaattttaca taggattata taattctttt cgatacacgt
11401 tatatcttta gcaaagtgag gaaaacagct ttatcatgtt agatgccagt tatccatttt
11461 aagtgaatcc tttcctcaac atgcagcatc caactcaata tcctgatgca aggttgtcct
11521 ctcctataat cctagaccag tgtgacttat tagccagaag tttagggttg tatagtcatt
11581 attcacataa tccgaaattg cgtaattgta ggattccaca tcacatttac cgtttaagga
11641 attcgacagc attaaagaca tttcttcaga attgttcgat actcaccgtt cctttcatt
11701 caatttggga tcatatttta acttccattc aatatgatgc aattaatcat gttgatgatt
11761 ttaaatacct attgccatct gagctagtca agtatgcgaa ttgggacaac gagttcttaa
11821 aagcatatct taataagatc ttaggacttg accatgtttt ttcagcttct gcaaggtcac
11881 agtgtgagga tttttctcct aaggaaaaatc cttattattg ggggatgtta ttactcgtgc
11941 atctatctca actlgccagg aggataaaag gacaaagagg gtcattaaga agtaactgga
12001 aatttatagg aacagatttg gagctgtttg gaatagcaga ttttgttatt tttaaggttc
12061 cagtaaaaac aataatccga aatgctgtaa gcttacaagc ttcaaaaccg ggattaagaa
12121 tatggtaccg tgaccaaaac ttaccccctt atctatgcga cgatgagttt attgtaagcg
12181 tcgctagtta tgaatgtttt atcatgatta aagacgtctt cattgagagg tataacacat
12241 gggaaatctg tgcccgcgct tggctcgaag acagtgatgg agctgattat cctcctcttg
12301 atgtgttagg tgaattatac aaccagggag accaaattat tgccatgtac ctggaggacg
12361 gtttcaaatt gattaaacac ttagaaccct tgtgtgtcag ctgtatacaa acacatggca
12421 tctttacacc aagaaaatac tggttccaat cacagatgat taagtcatat tatgatgaac
12481 tccatgatct caatttgaaa cttcaaattt cagacaataa ggctgagtgt gcccaaaact
12541 ttattaaaac tatagttcag gcgaaattga ctcctcaaca atactgtgaa ttattctccc
12601 tacaaaagca ttgggggtcat cccgttttat acaatgatgt tgcactagat aaggttaaaa
12661 aacatgcgca atcgacaaaa atcttaaaac ctaaagtcat gtttgaaact ttttgtgttt
12721 tcaaatttat agtagcaaag aatcattatc attctcaagg atcatggtat aaaaccacac
12781 atgatttgca tttgactcca tatcttagac aacatattgt gtcaaattca tttccatcac
12841 aagccgaaat ttatcagcat ctttgggagt ggtatttcgt ggagcatgaa cctcttttct
12901 caactaaaat aataagtgat ttaagtatct ttataaaaga cagggctacc gctgtgaacc
12961 aggagtgttg ggacagtgtc ttcgatagaa gtgtattagg atataaccct cctgttagat
13021 ttcaatcaaa gagagtgcca gagcaatttt tgggtcaagc agactttcc ttgaatcaaa
13081 tattagagtt tgctgaaaag ttagagtatt tggctccttc ttataggaat ttcctict
13141 cattaaaaga aaaagagttg aatataggaa gaacttttgg gaagttaccg tatcgtgtca
13201 gaaatgtcca aacactcgca gaagccctgc tagcagatgg actggcaaaa gcattcccta
13261 gtaacatgat ggttgtcact gagagggaac agaaagaagc attattacat caggcttctt
13321 ggcaccacaa ttcagcaagc atagggggaga acgctatagt gagggtgca agttttgtta
13381 ctgatcttga gaaatacaac ctcgccttcc gatatgaatt tacacggcat tcatagact
13441 actgtaatcg atgttatggt gtgaagaatt tattgattg gatgcatttt ttaataccac
13501 tatgttatat gcatgtcagt gactttata gcccaccaca ttgtgtgaca gaagataatc
13561 gaaataaccc acctgattgt gctaatgctt atcattatca cttaggaggt atagagggac
```

```
13621 ttcagcagaa attgtggaca tgcatatcat gtgcccaaat cacccttgtg gagttaaaaa
13681 ctaaattaaa attgaagtcc agcgtcatgg gtgataatca atgtataaca actctaagtc
13741 tttttccaat tgatgctccc aacgattatc aagagaacga ggctgaattg aatgcggcac
13801 gagttgctgt cgaattagct attactacag gttatagtgg tatattttta aagcctgagg
13861 aaacatttgt ccattcaggg ttcatttatt ttggtaaaaa gcaatatctc aacggtgttc
13921 aactgccgca atcattgaaa acaatggcaa ggtgtggacc cttatctgac tctattttcg
13981 atgatcttca aggttctctg gccagtattg gtacatcctt tgagagagga acaagcgaga
14041 cacggcacat ttttccgagc cgttggatag cttcattcca ttcaatgtta gcaataaatt
14101 tattaaatca gaatcacctt gggtttcctc tagggttcaa tattgatatt tcttgtttca
14161 aaaagcctct taccttctcg gaaaaattaa ttgctctcat aacgccccaa gttttaggag
14221 ggttatcatt tttaaatcca gaaaaattgt tctaccggaa cataagtgat cctctcactt
14281 caggtctatt tcaactcaag aatgcattgg aatttcttga aaaggaagaa ttattctata
14341 tcttgatttc taaaaaacct ggtttagcag atgcctcaga ttttgtcatg aatccattag
14401 gcttaaatgt accaggatca aaggaaataa taacgttcct tagacaaaca gttcgcgaaa
14461 atatcacgat cacgtcacaa aatagaataa taaattctct tttccacata ggttctgatt
14521 tagaggacca aagagtgtgt gagtggcttt tatcatcaaa ccctgtaatg agccgatttg
14581 ctgctgacat cttttcaaga acacctagtg gaaaacggct tcaagtctta ggctatctag
14641 aaggaacaag aacattacta gcttctcgga caatcagttt aactacagaa ggaacaatgt
14701 tgatgaaatt aagagaatta acgagaaacc gatggaaaag ttggttttct tatattgatg
14761 cactggacga tgatttatct gagtccttgg aaaagttcac atgtactgtt gatgtggcta
14821 atttcttgag ggcatattca tggtctgacg tcttaaaagg gaaaaggcta attggtgcca
14881 cactgccatg tttactagag caatttgagg taaagtggat taatttatct gaggatttaa
14941 gggaacaatt taatctatct tcagactcaa aatcaactat aaacttgttg ccgtatgact
15001 gtaaggaact gcgacttgaa ggaagcaatg acacagagtt aaattatgtc agttgtgctc
15061 ttgaccggaa agttgtccag aaacatccct ctgttaatcg tctagcttgg acgataggaa
15121 atcgagcacc gtatattggc tcacggacag aagataagat cggttatcct cccttaagag
15181 taaattgccc atcagcagca cttaaagaag ctattgagat ggtttctaga ttgttatggg
15241 tgactcaagg cactgcagac cgagaaaaat tgcttattcc tcttctcaat tcaagagtaa
15301 atctggacta tcagacggtg cttaactttt tacctacaca ctactcaggc aacatagttc
15361 atagatataa tgatcaatat ggacaacatt cctttatggc aaacaggatg agtaatacat
15421 ctacacgtgc aattatatca actaacacac tgggtaaata tgctgggggga ggtcaagctg
15481 ctattgatag taatataatc tttcaaaata ctattaattt aggagttgca gttttagata
15541 ttgcattgtc tcttgctaaa ttgtcgtcag catcaaatgt cactttccgt ttaatgttaa
15601 ataagtgctg cacgcggcat gtaccgtccg aataccta tttgataaa cctttagatg
15661 tggatttgaa caagtatatg gacaatgagt tggtttatga caatgaccct cttgcagtg
15721 ggattaaagg gagattaggc agagtatctc gatcaacact cacattgagt ttgaatgtca
15781 gtgacattgg ttcttatgac tttccaacta ttgctgcatg gacactagga gaaactatag
15841 tcggaagcat tttttctgat gaatcttctc aaagtacgga tccaataagc tcaggttgca
15901 caaaaacttt cgtcacacat ttccttgtgt atccagttga gagtatattt tatgcattcg
15961 gagctaactt aatagttgaa agtttaagtc taagtaggat caaatcaatt aagaacctct
16021 cagatttgac attcctata tcatccacaa tcaggaattt atcacataga tcacttcgga
16081 ttcttcaatc tactttccga catgaattgg tgctcaccca actagcccac cacataccgt
16141 taatttctt aatgttaggg ggctctgcag gagagaagag ttcatcagat gctgttcggc
16201 tatttcttac agcaagttat cagaatttta tcaataattt cagttgtctg atgaagaagg
16261 gtcagtcatc gctaccggtt tggcttact tcctagtga agggcaacaa ttaaagccta
16321 tattaaaaat cttacagaga ttatcagact tgttatcacc tgacaaaatt caaaagcgta
```

```
16381 aaattttggc tgacacctgt tgtccaattg gcagcttttg ggtctatcca agcaagtcca
16441 caaggactaa ccattattat gcaagcctta attattggag agacaaagct aataaggtta
16501 agaatactcc tttttcacac ttgataaatt gttcatttcc tgaattttct tcacatacca
16561 gttcagtctc ctctaatcaa caagtgacca attcgaagta tattgtttat ccagaaaata
16621 tcactgaaat aaatgcaaga accagattaa taaattatgg atcaacagct ctacagggga
16681 tggacaccaa gatgccactc tcagagcaaa atctagtcga aaattgtcga ccatcagagg
16741 gcatcagatt caaggacaat caaaaaataa caaaacatga ccagagatgt gagagggagg
16801 aatcttcacc gcaacagatg ttccctgaag ataacatgca gactcctgcg cacatacata
16861 gttcctcccc atttcaaatc cttataaaat cactagatgc acatgaggac tttgatgcct
16921 cgaagataat cttaaattct gaaataaata atcttaacct tacggagtat actcttaata
16981 caaagttatt gacaactcct accaggacag aaatttttaga tacaagtccg ttacaatcct
17041 ctagatattc atcaacttcc agggaacggt ctctactatc cagagaacaa gcttcatatt
17101 tgtacgttga ttgcagtaat attccttcta tctctctaga cccaggtttt cggagtatgt
17161 ctgatcagaa tcaagttcaa atgttaatca ataccctacaa acgtgattta catgcttgtt
17221 ttgatagcaa tcaattctgt cggtttacag gggtagtctc atcaatgcat tacaagcttt
17281 atgatctttt gcctccaggt aaattgaaaa aggcaatttg tttggccgaa gggggaaggaa
17341 gtggtgctcg gttactttttg aagtggaagg aaacggatta tttattcttc aacactttgg
17401 ctacggattc acaacaagaa gccgagattt tgagtggccg ggtaataccg agaatgttgt
17461 ataacataga cagattaagt gctttgcttg aatcaaggag actaatattg aacaacctaa
17521 ctatccaaat tacagatatt acaaatccat tatggctaga ttctgtaata caatatttac
17581 ctgaagatag tgacattctt acaatggacg cagagaccac caaggatgaa acaagggaac
17641 agctttataa aactattgtg aatatttgga cacgtacttc tcctaatatc ccaaaaatta
17701 gcatcatcaa ggtatttttta ttagactatg aagggacttt attcttaatg aagaatgcta
17761 ttcagtatta tgggcaagtt caactcaaga aaccatatag ctcaaatgca aaaaactcag
17821 aatggtactt gtgttgcggt aaacgaagaa ttcaacggct ccaaattgat ttctcagacc
17881 aggtgggaat ttttctgatt tgtaaagcaa tgtcacgcca aagacaagca attccttact
17941 ggttaaaaca tatagaaaag aattatcctg cttcattaca cgagttttct ctaactttgg
18001 gtttcccttc tttagagtca tctttctgcc atcgttatac tattccattc agtgaaggaa
18061 aggctctttt tcacaaggtc cagtcttatg ttcgtcaagg caaacaacat ttacattctc
18121 ttatgttgga ttatgaaaac aattcacctc tactagactt gagaaatcac tttatttgct
18181 cattaagggg aaagataact aaatattaca atgatatatt aaagttaaat ctagtcatca
18241 aggcagtaga aaaaggtaaa aattggtcac aacttgttga gatccttcct aatatgcatt
18301 cagtatgcat agtgcacgtg gatcatgagt gttctggatg cgagaaacgg ttattactta
18361 aattggattt tatcagaaat acaaagatcg cagaacaaaa attacttaac agagtaatcg
18421 ggtatatcct attctttcca ttcggtctgt taaatctgg atcattaagg gcataatttc
18481 aacagagaga acttcattta attcacaaaa acaatctatt taagagtgag ggttacattg
18541 tctaagatat tgtatgagaa gtaataaaat aaataagaaa acgaaaagac tattagacag
18601 cttattttat acaagataat cttatatcgc tttaggcctc acacaagtga gaaaattacg
18661 cgcacagatt aactagtgat tagtgtttgg tcacaccaga ggtaactttt taacgttaat
18721 tactcagatg ttattgctca taattagcat taatattggc acattgggtg aatccttgag
18781 ctttatccct aatatggtgt aagaaattaa ggaaatactg agatacacta gttgaattga
18841 attatgacat accatatatc ataaatataa aaaagtgtct gctgtaatct caagcacct
18901 cttttaaata cattaggaaa agaattaagt taccgttgag atcaaaaaaa ccacgtcatg
18961 ttttctctga tgacaagtga taaaacttcg tagttaaatt tctagaatgt cgatgtgaat
19021 gtaaattaag aaaaaccaat atataaaatt aaaaaattaa aaagcttgga tataagtaac
19081 acaaaacatt cttcatctt tttgtgtgtc c     (SEQ ID NO: 28)
```

*Fig. 10MMMM*

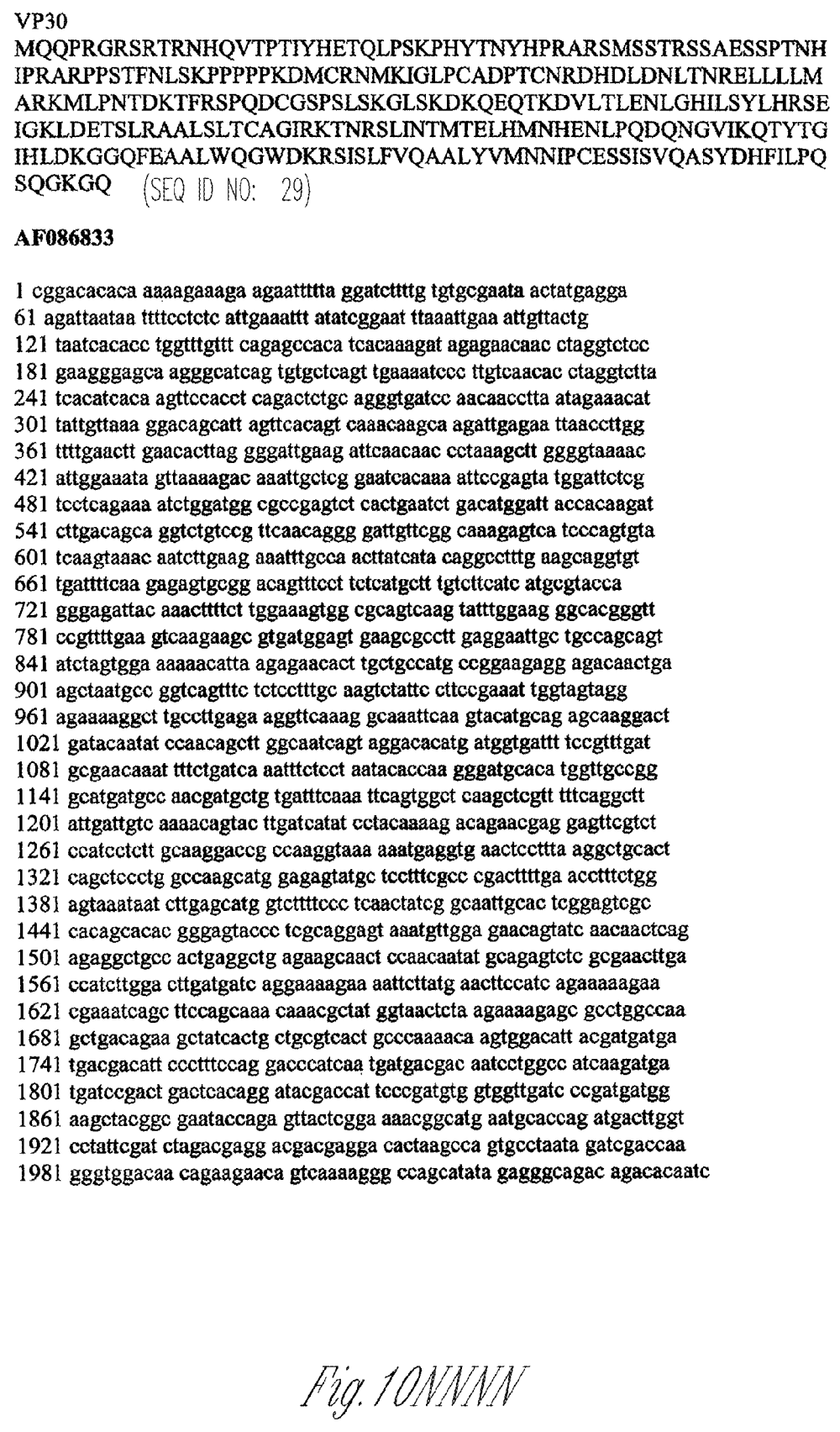

VP30
MQQPRGRSRTRNHQVTPTIYHETQLPSKPHYTNYHPRARSMSSTRSSAESSPTNH
IPRARPPSTFNLSKPPPPPKDMCRNMKIGLPCADPTCNRDHDLDNLTNRELLLLM
ARKMLPNTDKTFRSPQDCGSPSLSKGLSKDKQEQTKDVLTLENLGHILSYLHRSE
IGKLDETSLRAALSLTCAGIRKTNRSLINTMTELHMNHENLPQDQNGVIKQTYTG
IHLDKGGQFEAALWQGWDKRSISLFVQAALYVMNNIPCESSISVQASYDHFILPQ
SQGKGQ (SEQ ID NO: 29)

AF086833

1 cggacacaca aaaagaaaga agaatttttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaacctta atagaaacat
301 tattgttaaa ggacagcatt agttcacagt caaacaagca agattgagaa ttaaccttgg
361 ttttgaactt gaacacttag gggattgaag attcaacaac cctaaagctt ggggtaaaac
421 attggaaata gttaaaagac aaattgctcg gaatcacaaa attccgagta tggattctcg
481 tcctcagaaa atctggatgg cgcccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaacttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg
961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga acctttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt ccctttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc

*Fig. 10NNNN*

```
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttatttttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 cttttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
```

Fig. 100000

```
4801 ttgactcaac tacggccgcc atcatgcttg cttcatacac tatcacccat ttcggcaagg
4861 caaccaatcc acttgtcaga gtcaatcggc tgggtcctgg aatcccggat catccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttaccctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca attttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaaccctcac tagaaaaatt cgcagtgaag agttgtctt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagcacact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
```

Fig. 10PPPP

```
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca ggggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtcttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt taactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc tttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgtaatata
9601 acctgccaag cataccctct gcacaaagtg attcttgtac acaaataatg tttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
```

Fig. 10QQQQ

```
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca ataccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aatttttaca tcaaatgttt ttctggtatg atctggctat tttaactcga
12061 aggggtagat taaatcgagg aaactctaga tcaacatggt tgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccacc tccactttc tcaaccaaaa ttattagtga cttaagtatt
13021 tttataaaag acagagctac cgcagtagaa aggacatgct gggatgcagt attcgagcct
```

Fig. 10RRRR

```
13081 aatgttctag gatataatcc acctcacaaa tttagtacta aacgtgtacc ggaacaattt
13141 ttagagcaag aaaactttc tattgagaat gttcttcct acgcacaaaa actcgagtat
13201 ctactaccac aatatcggaa cttttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa ttctttagt tgaaattaag actggttta agttacgctc agctgtgatg
13801 ggtgacaatc agtgcattac tgttttatca gtcttcccct tagagactga cgcagacgag
13861 caggaacaga gcgccgaaga caatgcagcg agggtggccg ccagcctagc aaaagttaca
13921 agtgcctgtg gaatctttt aaaacctgat gaaacatttg tacattcagg ttttatctat
13981 tttggaaaaa aacaatattt gaatgggtc caattgcctc agtcccttaa aacggctaca
14041 agaatggcac cattgtctga tgcaattttt gatgatcttc aagggaccct ggctagtata
14101 ggcactgctt ttgagcgatc catctctgag acacgacata tctttccttg caggataacc
14161 gcagctttcc atacgttttt ttcggtgaga atcttgcaat atcatcatct cgggttcaat
14221 aaaggtttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tctttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaacccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccct
15361 tcacattact caggaaatat tgttcacagg tacaacgatc aatacagtcc tcattcttc
15421 atggccaatc gtatgagtaa ttcagcaacg cgattgattg tttctacaaa cactttaggt
15481 gagttttcag gaggtggcca gtctgcacgc gacagcaata ttatttttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
```

*Fig. 10SSSS*

```
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttgggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccatttcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 tttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt aagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atggggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
```

*Fig. 10TTTT*

18601 ctttaagatt aagtttttta taattatcat tactttaatt tgtcgtttta aaaacggtga
18661 tagccttaat ctttgtgtaa aataagagat taggtgtaat aaccttaaca tttttgtcta
18721 gtaagctact atttcataca gaatgataaa attaaaagaa aaggcaggac tgtaaaatca
18781 gaaataccct ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtcca (SEQ ID NO: 30)

VP30

MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ ID NO: 31)

AF272001

1 cggacacaca aaaagaaaga agaatttttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaacctta atagaaacat
301 tattgttaaa ggacagcatt agttcacagt caaacaagca agattgagaa ttaaccttgg
361 ttttgaactt gaacacttag ggggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaacttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg
961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga acctttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa

Fig. 10UUUUU

```
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tcccgatgtg gtggttgatc ctgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatt
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca cacccagtc
2401 agaacactcc cttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg ttttcaaag ttcaatttga gtcttaatgc
2881 aaataggcgt taagccacag ttatagccat aattgtaact caatatctca actagcgatt
2941 tatctaaatt aaattacatt atgctttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaagctggt
3121 ctaacaagat gacaactaga acaaagggca ggggccatac tgcggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt ttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
```

```
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttaaag gattgattga tgaaagatca taactaataa cattacaaat aatcctacta
5701 taatcaatac ggtgattcaa atgttaatct ttctcattgc acatacttt tgcccttatc
5761 ctcaaattgc ctgcatgctt acatctgagg atagccagtg tgacttggat tggaaatgtg
5821 gagaaaaat cgggaccccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatatgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccccgg tgccggtatg tgcacaaagt atcaggaacg ggaccgtgtg
6481 ccggagactt tgccttccat aaagagggtg cttctttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggcccttctg ggaaactaaa aaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
```

*Fig. 10WWWW*

```
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggttaa tctgtggggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggattaatt atatgggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagccttt tattaagttg
8401 taataatcag atctgcgaac cggtagagtt tagttgcaac ctaacacaca taaagcattg
8461 gtcaaaaagt caatagaaat ttaaacagtg agtggagaca actttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcaggggtt aagaacattg
9301 gttcctcaat cagataatga ggaagcttca accaacccgg ggacatgctc atggtctgat
9361 gagggtaccc cttaataagg ctgactaaaa cactatataa cctctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgaaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
```

*Fig. 10XXXX*

```
9901  gaggtctgat aagaataaac cttattattc agattaggcc ccaagaggca ttcttcatct
9961  cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa agggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg ccctgcatg gtcaataaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaaccttag caggagccct tggtctgatc tctgattggc tgctaacaac caacactaac
10741 catttcaaca tgcgaacaca acgtgtcaag gaacaattga gcccaaaaat gctgtcgttg
10801 attcgatcca atattctcaa gtttattaac aaattggatg ctctacatgt cgtgaactac
10861 aacggattgt tgagcagtat tgaaattgga actcaaaatc atataatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca atacccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aatttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgctta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
```

Fig. 10YYYY

```
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccaccc tccacttttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaactttc tattgagaat gttctttcct acgcacaaaa actcgagtat
13201 ctactaccac aatatcggaa cttttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gtttttaatt ggatgcatta tacaatccca cagtgttata tgcatgtcag tgattattat
13621 aatccaccac ataacctcac actggagaat cgagacaacc cccccgaagg gcctagttca
13681 tacaggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgttttatca gtcttcccct tagagactga cgcagacgag
13861 caggaacaga gcgccgaaga caatgcagcg aggggtggccg ccagcctagc aaaagttaca
13921 agtgcctgtg gaatctttt aaaacctgat gaaacatttg tacattcagg ttttatctat
13981 tttggaaaaa aacaatattt gaatggggtc caattgcctc agtcccttaa aacggctgca
14041 agaatggcac cattgtctga tgcaattttt gatgatcttc aagggaccct ggctagtata
14101 ggcactgctt ttgagcgatc catctctgag acacgacata tcttttccttg caggataacc
14161 gcagcttcc atacgttttt ttcggtgaga atcttgcaat atcatcatct cgggttcaat
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga ggggaatattc atgggctcat
14941 attttagagg gaagacctct tattggagcc acactcccat gtatgattga gcaattcaaa
15001 gtgttttggc tgaaacccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagatgggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccccct
15361 tcacattact caggaaatat tgttcacagg tacaacgatc aatacagtcc tcattctttc
```

*Fig. 10ZZZZ*

```
15421 atggccaatc gtatgagtaa ttcagcaacg cgattgattg tttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccattcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagaccttat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 tttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 ttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcacttttat tcgtactgca
17941 aaaggacgaa tcacaaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
```

*Fig. 10AAAAA*

18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagttttta taattatcat tactttaatt tgtcgtttta aaaacggtga
18661 tagccttaat ctttgtgtaa aataagagat taggtgtaat aaccttaaca ttttgtctta
18721 gtaagctact atttcataca gaatgataaa attaaaagaa aaggcaggac tgtaaaatca
18781 gaaatacctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttctttttt gtgtgtcca (SEQ ID NO: 32)

VP30
MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ ID NO: 33)

Fig. 10BBBBBB

Known bioactive

| Compound name | IC50 (µM) | CC50 (µM) |
|---|---|---|
| Bepridil Hydrochloride | 1.8 | >10 |
| Clomiphene citrate | 3.1 | >10 |
| Benzotropin mesylate | 2.2 | |
| 7-Deacetoxy-3-deacetyl-7-Oxokhivorin | 0.6 | >10 |
| 1,2alpha-Epoxy-7-Deacetoxy-7-Oxodihxdrogedunin | <0.15 | >10 |
| Epoxygedunin | <0.15 | >10 |
| 1,3-Dideacetly-7-Deacetoxy-7-Oxokhivorin | <0.15 | >10 |
| Gedunin | 0.3 | >10 |
| Tamoxifen Citrate | 0.5 | 9 |
| Fluspirilene | 2.5 | 9 |
| Raloxifene hydrochloride | 0.6 | >10 |
| Bromoenol lactone | 8 | >10 |
| Cortexolone maleate | 4 | >10 |
| (R,R)-cis-Diethyl tetrahydro-2,8-chrysenediol | 5 | >10 |
| MK-866 | 8 | >10 |
| L-687,384 hydrochloride | <0.15 | |
| Cycloheximide | 0.15 | 1.25 |

*Fig. 11*

Maybridge

| Compound name | IC50 (µM) | CC50 (µM) |
|---|---|---|
| HTS00384 | 1.15 | 49.3 |
| NRB03063 | <0.78 | 33.8 |
| CD03565 | 0.64 | 8.7 |
| KM0483 | 0.42 | 30.4 |
| SPB06885 | 0.41 | 4.5 |
| CD04265 | 0.28 | 12.0 |
| CD02075 | <0.78 | 12.5 |
| PD00647 | <0.78 | >50 |
| HTS07940 | 0.20 | >50 |
| HTS13483 | <0.08 | >50 |
| JFD02423 | 0.28 | >50 |
| HTS04029 | 0.09 | >50 |

*Fig. 11 (Cont.)*

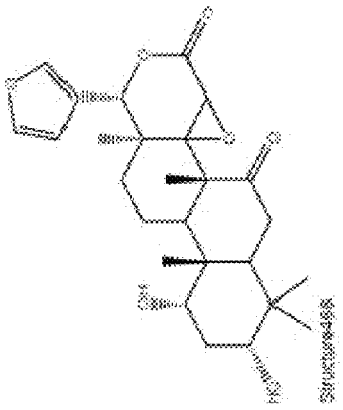
(3) 1,3-Dideacetly-7-Deacetoxy-7-Oxokhivorin
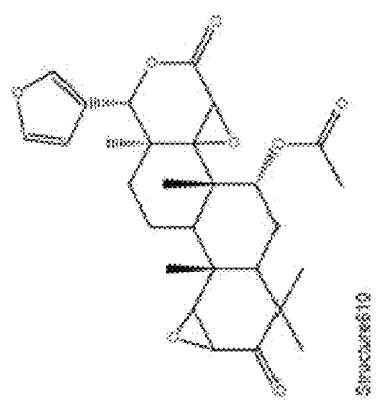
(2) Epoxygedunin
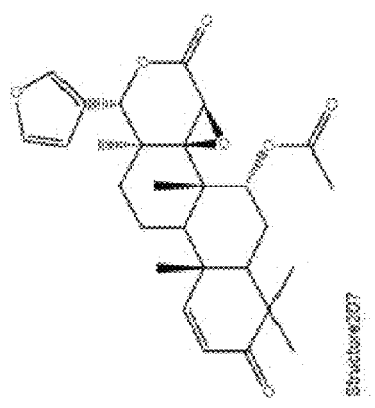
(1) Gedunin
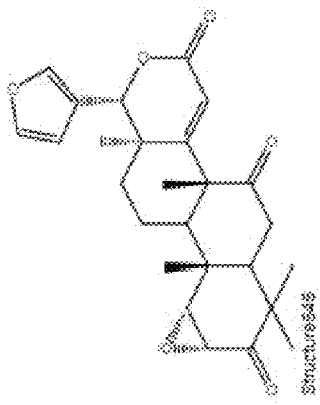
(6) 1,2alpha-Epoxy-7-Deacetoxy-7-Oxodihxdrogedunin
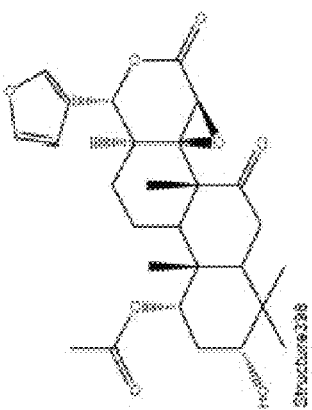
(4) 7-Deacetoxy-3-deacetyk-7-Xokhivorin
Fig. 12

SCREEN FOR INHIBITORS OF FILOVIRUS AND USES THEREFOR

STATEMENT OF GOVERNMENT RIGHTS

The invention was made with a grant from the Government of the United States of America (Grant AI057153 from the National Institutes of Health). The Government has certain rights in the invention.

CROSS-REFERENCE TO RELATED APPLICATION

This application is a nationalization under 35 U.S.C. §371 of PCT/US2009/006019, filed Nov. 6, 2009 and published as WO 2010/053573 on May 14, 2010, which claims the benefit of the filing date of U.S. application Ser. No. 61/112,524, filed on Nov. 7, 2008 and U.S. application Ser. No. 61/150,486, filed on Feb. 6, 2009, the disclosures of which are incorporated by reference herein.

BACKGROUND

Ebolaviruses (family Filoviridae) cause severe hemorrhagic fevers in humans and nonhuman primates, with mortality rates as high as 90% (Sanchez et al., 2007). Ebolaviruses and the closely related Marburgviruses belong to the Filoviridae family (Feldman et al., 2004). Currently, there are no approved vaccines or antivirals for use against filoviruses. Antivirals are not only desirable for local populations in epidemic areas and for health care workers during an outbreak, but also for researchers studying these viruses. Short interfering RNA molecules (Geisbert et al., 2006), and S-adenosylhomocysteine hydrolase inhibitors (Bray et al., 2000; Huggins et al., 1999) have been shown to inhibit Ebola viral growth in vitro and/or in vivo. However, the most effective approach to filovirus control will likely come from a combination of pharmacologic agents with different mechanisms of action (Bray & Paragas, 2002).

High throughput molecular screening (HTS) is an automated, simultaneous testing of thousands of distinct chemical compounds in models of biological mechanisms or disease. Since authentic Ebolaviruses are biosafety level 4 (BSL-4) agents, HTS with the viruses is not feasible. The lack of sufficient BSL-4 space, trained personnel, and the rigors of working in BSL-4 laboratories have severely hampered basic research with Ebolaviruses as well as the development of vaccines. These limitations have prompted examination of various steps in the Ebolavirus viral life cycle in the absence of infectious virus: (i) replication and transcription were studied by use of reporter gene assays that are based on the expression of necessary viral components from plasmids (Boehmann et al., 2005; Groseth et al., 2005; Muhlberger et al., 1999; Modrof et al., 2003; Modrof et al., 2002); (ii) entry and fusion processes were assessed with pseudotyping assays that rely on the use of recombinant vesicular stomatitis or retroviruses (Yonezawa et al., 2005; Wool-Lewis et al., 1998; Takada et al., 1997; Marzi et al., 2006); and (iii) budding was examined using virus-like particles that are generated from viral proteins provided by protein expression plasmids (Jasenosky et al., 2001; Licata et al., 2004; Noda et al., 2002; McCarthy et al., 2006; Johnson et al., 2006). However, several recent findings suggest that data obtained with these artificial systems may not always be reproducible with live, authentic Ebolavirus (Neumann et al., 2005).

SUMMARY OF THE INVENTION

The invention provides a method to identify modulators, e.g., inhibitors, of filovirus infection. The method includes contacting a host cell, e.g., a mammalian cell including a human cell or non-human primate cell, with one or more agents and, in one embodiment, a replication incompetent rhabdovirus having filovirus glycoprotein and a mutant rhabdovirus genome with sequences for a reporter gene product. It is then determined whether the one or more agents inhibit the expression or levels of the reporter gene product, e.g., a reporter protein. In one embodiment, at least one agent inhibits reporter expression or levels by at least 50%, 60%, 70% or more, e.g., 80%, 85%, 90% or more, for instance, by at least 95%, that of reporter expression or levels in a corresponding host cell not contacted with the agent(s). In one embodiment, the host cell is contacted with one agent. In one embodiment, the host cell is contacted with a library of agents. For instance, the host cell may be contacted with a chemically synthesized library, cDNA library or siRNA library. The replication incompetent pseudotyped rhabdovirus may be prepared by contacting a host cell with a vector to express mutant rhabdovirus vRNA with a deletion of rhabdovirus glycoprotein sequences and an insertion of reporter gene sequences. Vectors for protein expression include vectors expressing a filovirus glycoprotein and optionally one or more vectors for protein expression of at least one of P, M, N or L rhabdovirus proteins.

In one embodiment, the invention provides a method to identify one or more agents that inhibit viral infection or replication, e.g., Ebolavirus infection or replication. The method includes contacting a host cell, e.g., a mammalian cell including a human cell or non-human primate cell, with at least one agent and a recombinant negative-sense, single stranded RNA virus, the genome of which contains a deletion of viral sequences, i.e., it is a mutant genome. In one embodiment, the host cell is infected with the virus before being contacted with the one or more agents and in one embodiment, a lysate is prepared, e.g., after contact with the one or more agents. In one embodiment, the deleted viral sequences correspond to those for a viral glycoprotein. In one embodiment, the deleted viral sequences correspond to those for a nonstructural or nonglycosylated viral protein that is essential in trans for viral replication. In one embodiment, the deletion is effective to inhibit or prevent viral replication upon infection of a cell with the recombinant negative-sense, single stranded RNA virus. For example, the deletion may be effective to prevent expression of a functional nonstructural or nonglycosylated protein, or functional glycoprotein, upon infection of a cell with the recombinant negative-sense, single stranded RNA virus. In one embodiment, the deletion may be in filovirus sequences for a viral protein corresponding to Ebola virus VP30. Such a deletion may include a deletion of 1 or more nucleotides, e.g., a deletion of at least 0.1%, 1%, 5%, 10%, 50%, 60%, 70%, 80%, 90%, or any integer in between, and up to 100% of the viral sequences corresponding to those for a nonstructural or nonglycosylated viral protein that is essential in trans for viral replication, e.g., sequences that do not overlap with those for another viral protein encoded by the viral genome. The deletion is one that is stable over multiple passages and is readily detectable, e.g., by RT-PCR. In one embodiment, the deletion may be in rhabdovirus sequences for a rhabdovirus glycoprotein.

As described herein, a biologically contained Ebolavirus (EbolaΔVP30) was employed to identify anti-Ebolavirus candidates using a high throughput screening assay. To determine the steps in the viral life cycle inhibited by an anti-viral compound, an Ebolavirus binding/entry assay and a minigenome replication assay were employed. Anti-viral specificity was defined by using viral growth inhibition tests with EbolaΔVP30, veccinia virus, adenovirus, influenza virus, and vesicular stomatitis virus. Gedunin and gedunin derivatives were identified as anti-Ebolavirus candidates in the high throughput screening assay. These compounds inhibited the growth of EbolaΔVP30 but not that of vaccinia virus, adenovirus, influenza virus, or vesicular stomatitis virus. Further, these compounds inhibited Ebolavirus binding/entry and some also inhibited viral genome replication and protein expression. Thus, gedunin and gedunin derivatives are potent inhibitors of Ebolavirus in vitro. Their inhibitory mechanisms rely mainly upon virus binding/entry.

In one embodiment, an isolated recombinant, biologically contained Ebola virus includes a genome which contains a deletion in sequences corresponding to Ebola virus VP30 sequences. The deletion is effective to inhibit or prevent viral replication, e.g., by preventing expression of a functional protein corresponding to Ebola virus VP30 protein, upon infection of a cell that lacks sequences that encode the functional protein (e.g., the cell that does not express functional VP30 in trans) with the recombinant, biologically contained Ebola virus. In one embodiment, at least 90% of sequences corresponding to VP30 sequences in the viral genome of the virus are deleted. In one embodiment, the genome of the recombinant, biologically contained filovirus further comprises heterologous sequences, for instance, positioned within the deletion. The heterologous sequences may be selected as ones that are not toxic to one or more host cells, e.g., reporter, selectable marker or viral sequences (for instance, neo$^R$, a fluorescent protein such as green fluorescent protein (GFP), luciferase or influenza virus sequences for mammalian cells).

To prepare such virus, a reverse genetics systems for negative-sense RNA viruses was exploited to generate Ebolaviruses that lack the VP30 gene (which encodes an essential transcription factor), termed EbolaΔVP30 virus. These viruses were maintained, genetically stable, and biologically confined to a cell line expressing VP30. Hence, the EbolaΔVP30 virus fulfills several criteria of a vaccine virus: it can be grown to reasonably high titers in helper cells, is genetically stable (as determined by sequence analysis after seven serial passages in VP30-expressing Vero cells), and is safe. Moreover, as described herein, the resultant viruses resemble wild-type virus in their life cycle, their morphology, and their growth properties, but could be handled in a non-BSL-4 laboratory, opening new opportunities for study of the Ebolavirus life cycle and for the identification of effective antiviral compounds.

Other negative-sense, single stranded RNA viruses may likewise be manipulated, e.g., the genome of Nipah virus, Hendravirus, Henipavirus, and the like, may be manipulated to mutate or delete sequences corresponding to those for a nonstructural or nonglycoslyated viral protein that is required for viral replication. Thus, genomes of viruses in the following families may be manipulated to provide for an infectious, biologically contained virus that resembles wild-type virus in its life cycle, morphology, and growth properties, can be grown to reasonably high titers in helper cells, is genetically stable, and is safe: *Bornaviridae, Rhabdoviridae, Filoviridae* (genera Marburgvirus and Ebolavirus), *Paramyxoviridae*, Avulavirus, Henipavirus, Morbillivirus, Respirovirus, or Rubulavirus.

The invention further provides screening methods for anti-virals that employ the recombinant infectious, biologically contained virus. In one embodiment, the methods include those that identify one or more agents that inhibit virus infection or replication. The methods include contacting the recombinant infectious, biologically contained virus of the invention, a host cell, e.g., a helper cell, such as a mammalian cell including a human cell or non-human primate cell, and one or more agents. Then it is determined whether the one or more agents inhibit viral replication or infection. In one embodiment, the one or more identified agents do not substantially decrease host cell viability, e.g., host cell viability is at least 65%, 70%, 75%, 80% or more in the presence of the one or more agents. Further provided is a method to identify one or more agents that inhibit virus infection or replication, which includes contacting a host cell infected with a recombinant infectious, biologically contained filovirus, or a lysate thereof, and one or more agents. Then it is determined whether the one or more agents inhibit viral replication or infection. In one embodiment, the one or more identified agents do not substantially decrease host cell viability, e.g., host cell viability is at least 65%, 70%, 75%, 80% or more. In one embodiment, the anti-viral agent has an $IC_{50}$ of less than about 10.0 μM, e.g., less than 5 μM, 1 μM, or 0.1 μM, e.g., an $IC_{50}$ from 0.001 μM to 10 μM. In one embodiment, the anti-viral agent has a $CC_{50}$ of more than than about 0.1 μM, e.g., more than 1 μM, 5 μM, 10 μM or 50 μM, e.g., a $CC_{50}$ from 0.1 μM to 100 μM. In one embodiment, the agent has an $IC_{50}$ of less than about 10.0 μM, e.g., less than 5 μM, 1 μM, or 0.1 μM and a $CC_{50}$ of more than about 0.1 μM, e.g., more than than 1 μM, 5 μM, 10 μM or 50 μM.

In one embodiment, the screening method identifies inhibitors of filovirus glycoprotein receptor binding or fusion. The method includes contacting a host cell, e.g., a mammalian cell including a human cell or non-human primate cell, with one or more agents and a recombinant replication incompetent pseudotyped rhabdovirus comprising filovirus glycoprotein and a mutant negative sense rhabdovirus genome which lacks sequences for a rhabdovirus glycoprotein but comprises a sequence for a reporter protein, e.g., a fluorescent protein or a bioluminescent protein. At least one agent is identified that inhibits reporter protein levels or expression in the host cell.

Also provided is a method which includes contacting a host cell with a plurality of agents, for example, a composition having the plurality of agents, and recombinant virus, e.g., sequentially or simultaneously.

Further provided are agents identified by the methods and the use of anti-virals in methods to prevent, inhibit or treat viral infection in a mammal, e.g., a human. Agents identified by the method or useful to prevent, inhibit or treat viral, e.g., filovirus, infection, include but are not limited to, an inhibitor of Hsp90, gedunin and gedunin derivatives, a triphenylethylene, an inhibitor of calcium-independent phospholipase $A_2$ and/or of magnesium-dependent phosphatidate phosphohydrolase, an inhibitor of $PGE_2$ synthase, a steroid, dopamine antagonist, or anticholinergic, including a compound of formula (I)-(XIII). Such agents are useful treatments in Ebolavirus infection management and biosafety defense, as well as platforms for developing new chemical entities for use in Ebolavirus treatment.

In addition, the invention provides a method to prevent, inhibit or treat viral infection in a mammal, e.g., a human, by administering a composition having an effective amount of a triphenylethylene, tamoxifen or a derivative thereof such as raloxifene and clomiphene, a calcium channel blocker, a tetranortriterpenoid, an antipsychotic, a sigma receptor agonist, an anticholinergic, a steroid, an inhibitor of calcium-independent phospholipase $A_2$, an inhibitor of magnesium-dependent phosphatidate phosphohydrolase, an inhibitor of the inducible microsomal $PGE_2$ synthase, a Hsp90 inhibitor, a dopamine antagonist, or a compound of formula (I)-(XIII), including compositions having those agents or compounds and pharmaceutically acceptable carriers and/or excipients. In one embodiment a composition for administration in prophylactic or therapeutic methods includes but is not limited to bepridil hydrochloride, clomiphene citrate, benzotropin mesylate, 7-deacetoxy-3-deacetyl-7-oxokhivorin, 1,2alpha-epoxy-7-deacetoxy-7-oxodihxdrogedunin, epoxygedunin, 1,3-dideacetyl-7-deacetoxy-7-oxokhivorin, gedunin, gedunol, dihydrogedunin, 3beta-acetoxydeoxodihydrogedunin, 3alpha-hydroxydeoxodihydrogedunin, deacetoxy-7-oxogedunin, 3beta-hydroxydeoxodihydrogedunin, deacetoxy-7-oxogedunin, 1,2alpha-epoxydeacetoxydihydrogedunin, 3beta-hydroxydeoxydesacetoxy-7-oxogedunin, tridesacetoxykhivorin, 1,3-dideacetylkhivorin, heudelottin C, tamoxifen citrate, fluspirilene, raloxifene hydrochloride, bromoenol lactone, cortexolone maleate, (R,R)-cis,diethyl tetrahydro-2,8-chrysenediol, MK-866, L-687, 384 hydrochloride, cycloheximide, HTS00384, NRB03063, CD03565, KM0483, SPB06885, CD04265, CD02075, PD00647, HTS07940, HTS13483, JFD02423, and/or HTS04029.

Thus, the invention provides compounds for use in medical therapy, such as agents that prevent, inhibit or treat filovirus infection in a mammal, optionally in conjunction with other compounds. Also provided is the use of the compounds for the manufacture of a medicament to prevent, inhibit or treat filovirus infection.

BRIEF DESCRIPTION OF THE FIGURES

FIG. 9. Virus titers in the serum of mice following lethal challenge. Vaccinated (n=3) and control (n=3) mice from groups 1 and 2 were euthanized on day 4 post-challenge. Virus titers from the serum were determined by the plaque assay. ND, not detectable.

FIG. 10A-10BBBBB. Representative filovirus sequences (Accession numbers NC006432, NC004161, AY769362, AY142960, AF522874, AF499101, L11365, NC001608, DQ447652, DQ447649, AB050936, NC002549, NC001608, AF086833 and AF272001, the disclosures of which are incorporated by reference herein; SEQ ID NOs:1-30).

FIG. 11. Compounds screened in an assay of the invention.

FIG. 12. Chemical structures of gedunin (1), epoxygedunin (2), 1,3-Dideacetly-7-Deacetoxy-7-Oxokivorin (3), 7-Deacetoxy-3-deacetyl-7-Oxokhivorin (4), and 1,2alpha-Epoxy-7-Deacetoxy-7-Oxo-Deoxyhydrogedunin (5).

FIG. 13. Growth kinetics of viruses. Compounds were added to cell culture media 2 hours prior to virus infections.

Cells were inoculated with EbolaΔVP30 virus, vaccinia virus, or adenovirus at an MOI of $10^{-3}$, or influenzavirus or VSV at an MOI of $10^{-5}$. Cell culture media (EbolaΔVP30, influenzavirus, and VSV) or cell culture media and cells (vaccinina virus and adenovirus) were collected 24, 48, and 72 hours post-infection for virus titer determinations. Dots and error bars indicate mean titers and standard deviations from three individual experiments, respectively.

Figure 14:
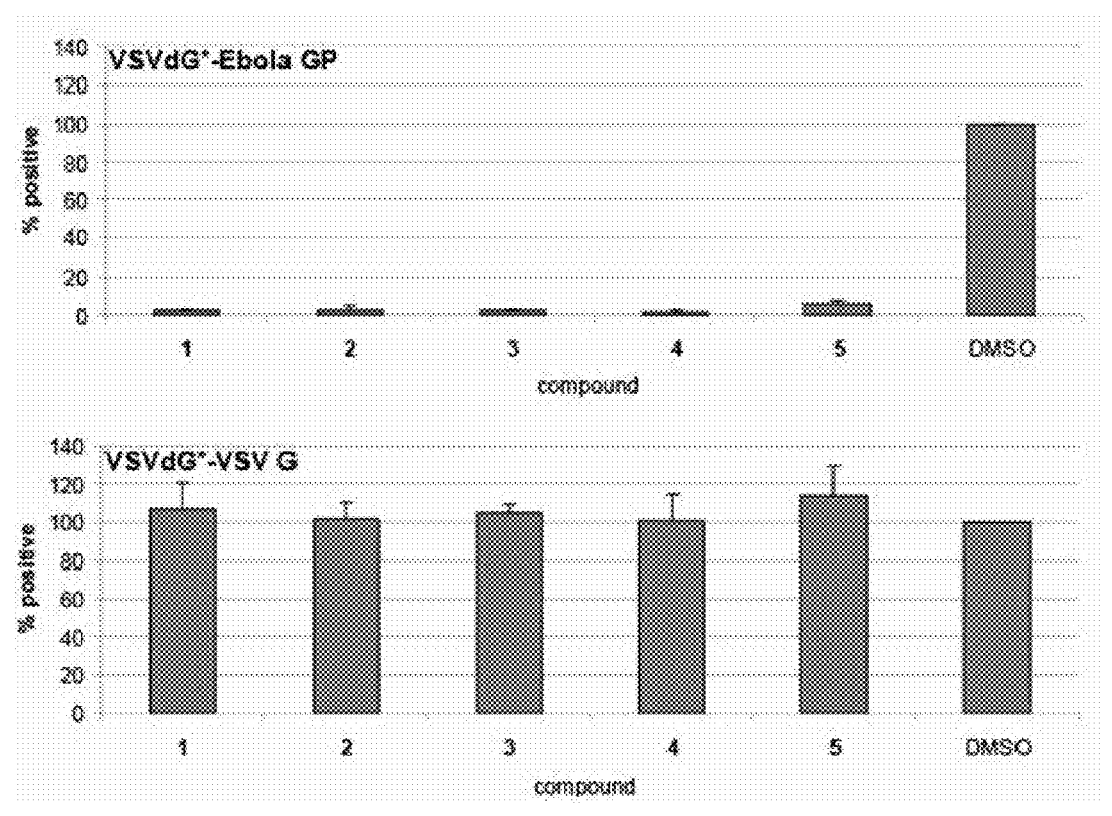

FIG. 14. Gedunin and gedunin-like compounds inhibit Ebolavirus GP-dependent virus entry. Compounds were added to cell culture media at 2 hours prior to VSVΔG*-Ebolavirus GP or VSVΔG*-VSV G virus infection. The number of GFP-positive cells was determined after an overnight incubation. % infectivity=100×number of GFP-positive cells+compound/number of GFP-positive cells+DMSO. Columns and error bars indicate mean % infectivities and standard deviations from four individual experiments, respectively.

Figure 15:
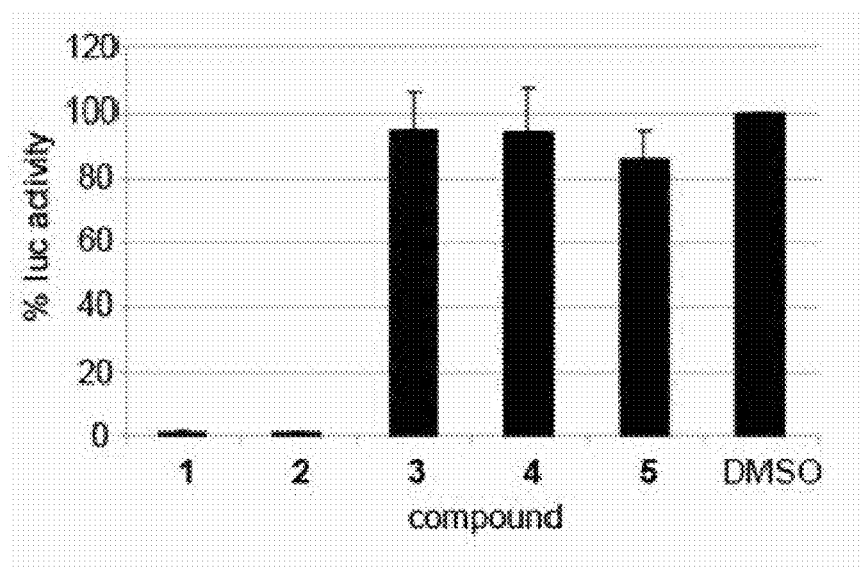

FIG. 15. Gedunin and epoxygedunin inhibit protein expression from the Ebolavirus minigenome. Compounds were added to cell culture media 6.5 hours post-transfection. Luciferase (luc) activities, expressed from the Ebolavirus minigenome, were measured on day 3 post-transfection. % luc activity=100×luc activity+compound/luc activity+DMSO. Columns and error bars indicate mean % luc activities and standard deviations from three individual experiments, respectively.

FIG. 16. Hsp90 inhibitors inhibit protein expression from the Ebolavirus minigenome. (A) Hsp90 inhibitors (10 µM) inhibit growth of EbolaΔVP30-GFP. Dots and error bars indicate mean titers and standard deviations from three individual experiments, respectively. (B) and (C) Hsp90 inhibitors (10 µM) do not substantially reduce Ebolavirus GP-mediated (or VSV-G-mediated) virus binding/entry. (D) Hsp90 inhibitors (10 µM) reduce protein expression from the Ebolavirus minigenome. Columns and error bars indicate mean % infectivities and standard deviations from four individual experiments, respectively.

DETAILED DESCRIPTION OF THE INVENTION

Definitions

The term "isolated" when used in relation to a nucleic acid (e.g., vector or plasmid), peptide, polypeptide or virus refers to a nucleic acid sequence, peptide, polypeptide or virus that is identified and separated from at least one contaminant nucleic acid, polypeptide or other biological component with which it is ordinarily associated in its natural source, e.g., so that it is not associated with in vivo substances, or is substantially purified from in vitro substances. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective (biologically contained), requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include at least a portion of an open reading frame of a gene which is partly or entirely heterologous (i.e., foreign) to the transgenic organism, or may represent at least a portion of an open reading frame of a gene homologous to an endogenous gene of the organism, which portion optionally encodes a polypeptide with substantially the same activity as the corresponding full-length polypeptide or at least one activity of the corresponding full-length polypeptide.

By "transgenic cell" is meant a cell containing a transgene. For example, a cell stably or transiently transformed with a vector containing an expression cassette is a transgenic cell that can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and in one embodiment via a replication-defective viral vector.

The term "heterologous" as it relates to nucleic acid sequences such as gene sequences encoding a protein and control sequences, denotes sequences that are not normally joined together, and/or are not normally associated with a particular cell, e.g., are from different sources (for instance, sequences from a virus are heterologous to sequences in the genome of an uninfected cell). Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," "sequence," "segment," "fragment" or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is, in one embodiment, chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, e.g., at least about 90%, or at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

As used herein, the term "recombinant nucleic acid" or "recombinant DNA sequence, molecule or segment" refers to a nucleic acid, e.g., to DNA, that has been derived or isolated from a source, that may be subsequently chemically altered in vitro, and includes, but is not limited to, a sequence that is naturally occurring, is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

The term "recombinant protein" or "recombinant polypeptide" as used herein refers to a protein molecule that is expressed from a recombinant DNA molecule.

The term "peptide", "polypeptide" and "protein" are used interchangeably herein unless otherwise distinguished.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); such as not less than 9 matches out of 10 possible base pair matches (90%), and, for example, not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more likely homologous if their amino acids are greater than or equal to 50% identical when optimally aligned using the ALIGN program.

The term "corresponds to" is used herein to mean that a polynucleotide sequence is homologous (e.g., is identical, not strictly evolutionarily related) to all or a portion of a reference polynucleotide sequence that encodes a polypeptide or its complement, or that a polypeptide sequence is identical in sequence or function to a reference polypeptide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by using local homology algorithms or by a search for similarity method, by computerized implementations of these algorithms (GAP, BESTFIT, FASTA, and TFASTA Genetics Software Package or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, e.g., at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80% sequence identity, e.g., at least about 90% sequence identity, including at least about 95% percent sequence identity, or at least about 99% sequence identity.

A "protective immune response" and "prophylactic immune response" are used interchangeably to refer to an immune response which targets an immunogen to which the individual has not yet been exposed or targets a protein associated with a disease in an individual who does not have the disease, such as a tumor associated protein in a patient who does not have a tumor.

A "therapeutic immune response" refers to an immune response which targets an immunogen to which the individual has been exposed or a protein associated with a disease in an individual who has the disease.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

As used herein, "substantially pure" means an object species is the predominant species present (i.e., on a molar basis it is more abundant than any other individual species in the composition), and may be a substantially purified fraction is a composition wherein the object species comprises at least about 50 percent (on a molar basis) of all macromolecular species present. Generally, a substantially pure composition will comprise more than about 80 percent of all macromolecular species present in the composition, for example, more than about 85%, about 90%, about 95%, and about 99%. Min one embodiment, the object species is purified to essential homogeneity (contaminant species cannot be detected in the composition by conventional detection methods) wherein the composition consists essentially of a single macromolecular species.

"Transfected," "transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

One diastereomer of a compound disclosed herein may display superior activity compared with the other. When required, separation of the racemic material can be achieved by HPLC using a chiral column or by a resolution using a resolving agent such as camphonic chloride as in Thomas J. Tucker, et al., J. Med. Chem. 1994 37, 2437-2444. A chiral compound of Formula I may also be directly synthesized using a chiral catalyst or a chiral ligand, e.g. Mark A. Huffman, et al., J. Org. Chem. 1995, 60, 1590-1594.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

As used herein, the term "patient" refers to organisms to be treated by the methods of the present invention. Such organisms include, but are not limited to, mammals such as humans. In the context of the invention, the term "subject" generally refers to an individual who will receive or who has received treatment (e.g., administration of a compound of the invention).

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxy. When a substituent is keto (i.e., =O) or thioxo (i.e., =S) group, then 2 hydrogens on the atom are replaced.

"Interrupted" is intended to indicate that in between two or more adjacent carbon atoms, and the hydrogen atoms to which they are attached (e.g., methyl ($CH_3$), methylene ($CH_2$) or methine (CH)), indicated in the expression using "interrupted" is inserted with a selection from the indicated group(s), provided that the each of the indicated atoms' normal valency is not exceeded, and that the interruption results in a stable compound. Such suitable indicated groups include, e.g., non-peroxide oxy (—O—), thio (—S—), carbonyl (—C(=O)—), carboxy (—C(=O)O—), imine (C=NH), sulfonyl (SO) or sulfoxide ($SO_2$).

Specific and preferred values listed below for radicals, substituents, and ranges, are for illustration only; they do not exclude other defined values or other values within defined ranges for the radicals and substituents "Alkyl" refers to a $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-PR, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$).

The alkyl can optionally be substituted with one or more alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. The alkyl can optionally be interrupted with one or more non-peroxide oxy (—O—), thio (—S—), carbonyl (—C(=O)—), carboxy (—C(=O)O—), sulfonyl (SO) or sulfoxide ($SO_2$). Additionally, the alkyl can optionally be at least partially unsaturated, thereby providing an alkenyl.

"Alkenyl" refers to a $C_2$-$C_{18}$ hydrocarbon containing normal, secondary, tertiary or cyclic carbon atoms with at least one site of unsaturation, i.e. a carbon-carbon, sp² double bond. Examples include, but are not limited to: ethylene or vinyl (—CH═CH₂), allyl (—CH₂CH═CH₂), cyclopentenyl (—C₅H₇), and 5-hexenyl (—CH₂CH₂CH₂CH₂CH═CH₂).

The alkenyl can optionally be substituted with one or more alkyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and/or COOR$^x$, wherein each R$^x$ and R$^y$ are independently H, alkyl, alkenyl, aryl, heteroaryl, heterocycle, cycloalkyl or hydroxyl. Additionally, the alkenyl can optionally be interrupted with one or more non-peroxide oxy (—O—), thio (—S—), carbonyl (—C(═O)—), carboxy (—C(═O)O—), sulfonyl (SO) or sulfoxide (SO₂).

"Alkylidenyl" refers to a C₁-C₁₈ hydrocarbon containing normal, secondary, tertiary or cyclic carbon atoms. Examples are methylidenyl (═CH₂), ethylidenyl (═CHCH₃), 1-propylidenyl (═CHCH₂CH₃), 2-propylidenyl (═C(CH₃)₂), 1-butylidenyl (═CHCH₂CH₂CH₃), 2-methyl-1-propylidenyl (═CHCH(CH₃)₂), 2-butylidenyl (═C(CH₃)CH₂CH₃), 1-pentyl (═CHCH₂CH₂CH₂CH₃), 2-pentylidenyl (═C(CH₃)CH₂CH₂CH₃), 3-pentylidenyl (═C(CH₂CH₃)₂), 3-methyl-2-butylidenyl (═C(CH₃)CH(CH₃)₂), 3-methyl-1-butylidenyl (═CHCH₂CH(CH₃)₂), 2-methyl-1-butylidenyl (═CHCH(CH₃)CH₂CH₃), 1-hexylidenyl (═CHCH₂CH₂CH₂CH₂CH₃), 2-hexylidenyl (═C(CH₃)CH₂CH₂CH₂CH₃), 3-hexylidenyl (═C(CH₂CH₃)(CH₂CH₂CH₃)), 3-methyl-2-pentylidenyl (═C(CH₃)CH(CH₃)CH₂CH₃), 4-methyl-2-pentylidenyl (═C(CH₃)CH₂CH(CH₃)₂), 2-methyl-3-pentylidenyl (═C(CH₂CH₃)CH(CH₃)₂), and 3,3-dimethyl-2-butylidenyl (═C(CH₃)C(CH₃)₃).

The alkylidenyl can optionally be substituted with one or more alkyl, alkenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and/or COOR$^x$, wherein each R$^x$ and R$^y$ are independently H, alkyl, alkenyl, aryl, heteroaryl, heterocycle, cycloalkyl or hydroxyl. Additionally, the alkylidenyl can optionally be interrupted with one or more non-peroxide oxy (—O—), thio (—S—), carbonyl (—C(═O)—), carboxy (—C(═O)O—), sulfonyl (SO) or sulfoxide (SO₂).

"Alkenylidenyl" refers to a C₂-C₁₈ hydrocarbon containing normal, secondary, tertiary or cyclic carbon atoms with at least one site of unsaturation, i.e. a carbon-carbon, sp² double bond. Examples include, but are not limited to: allylidenyl (═CHCH═CH₂), and 5-hexenylidenyl (═CHCH₂CH₂CH₂CH═CH₂).

The alkenylidenyl can optionally be substituted with one or more alkyl, alkenyl, alkylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and/or COOR$^x$, wherein each R$^x$ and R$^y$ are independently H, alkyl, alkenyl, aryl, heteroaryl, heterocycle, cycloalkyl or hydroxyl. Additionally, the alkenylidenyl can optionally be interrupted with one or more non-peroxide oxy (—O—), thio (—S—), carbonyl (—C(═O)—), carboxy (—C(═O)O—), sulfonyl (SO) or sulfoxide (SO₂).

"Alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—CH₂—) 1,2-ethyl (—CH₂CH₂—), 1,3-propyl (—CH₂CH₂CH₂—), 1,4-butyl (—CH₂CH₂CH₂CH₂—), and the like.

The alkylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and/or COOR$^x$, wherein each R$^x$ and R$^y$ are independently H, alkyl, alkenyl, aryl, heteroaryl, heterocycle, cycloalkyl or hydroxyl. Additionally, the alkylene can optionally be interrupted with one or more non-peroxide oxy (—O—), thio (—S—), carbonyl (—C(═O)—), carboxy (—C(═O)O—), sulfonyl (SO) or sulfoxide (SO₂). Moreover, the alkylene can optionally be at least partially unsaturated, thereby providing an alkenylene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

The alkenylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and/or COOR$^x$, wherein each R$^x$ and R$^y$ are independently H, alkyl, alkenyl, aryl, heteroaryl, heterocycle, cycloalkyl or hydroxyl. Additionally, The alkenylene can optionally be interrupted with one or more non-peroxide oxy (—O—), thio (—S—), carbonyl (—C(═O)—), carboxy (—C(═O)O—), sulfonyl (SO) or sulfoxide (SO₂).

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, alkylidenyl, alkenylidenyl, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, NR$^x$R$^y$ and COOR$^x$, wherein each R$^x$ and R$^y$ are independently H, alkyl, aryl, heteroaryl, heterocycle, cycloalkyl or hydroxyl.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The term "heterocycle" refers to a saturated or partially unsaturated ring system, containing at least one heteroatom selected from the group oxygen, nitrogen, and sulfur, and optionally substituted with alkyl or $C(=O)OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkenyl, alkoxy, halo, haloalkyl, hydroxy, hydroxyalkyl, aryl, heteroaryl, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. In one specific embodiment of the invention, the nitrogen heterocycle can be 3-methyl-5,6-dihydro-4H-pyrazino[3,2,1-jk]carbazol-3-ium iodide.

Another class of heterocyclics is known as "crown compounds" which refers to a specific class of heterocyclic compounds having one or more repeating units of the formula $[-(CH_2-)_aA-]$ where a is equal to or greater than 2, and A at each separate occurrence can be O, N, S or P. Examples of crown compounds include, by way of example only, $[-(CH_2)_3-NH-]_3$, $[-((CH_2)_2-O)_4-((CH_2)_2-NH)_2]$ and the like. Typically such crown compounds can have from 4 to 10 heteroatoms and 8 to 40 carbon atoms.

The term "alkanoyl" refers to $C(=O)R$, wherein R is an alkyl group as previously defined.

The term "acyloxy" refers to $-O-C(=O)R$, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to $C(=O)OR$, wherein R is an alkyl group as previously defined.

The term "amino" refers to $-NH_2$, and the term "alkylamino" refers to $-NR_2$, wherein at least one R is alkyl and the second R is alkyl or hydrogen. The term "acylamino" refers to $RC(=O)N$, wherein R is alkyl or aryl.

The term "imino" refers to $-C=NH$.

The term "nitro" refers to $-NO_2$.

The term "trifluoromethyl" refers to $-CF_3$.

The term "trifluoromethoxy" refers to $-OCF_3$.

The term "cyano" refers to $-CN$.

The term "hydroxy" or "hydroxyl" refers to $-OH$.

The term "oxy" refers to $-O-$.

The term "thio" refers to $-S-$.

The term "thioxo" refers to (=S).
The term "keto" refers to (=O).

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

The compounds described herein can be administered as the parent compound, a pro-drug of the parent compound, or an active metabolite of the parent compound.

"Pro-drugs" are intended to include any covalently bonded substances which release the active parent drug or other formulas or compounds of the present invention in vivo when such pro-drug is administered to a mammalian subject. Pro-drugs of a compound of the present invention are prepared by modifying functional groups present in the compound in such a way that the modifications are cleaved, either in routine manipulation in vivo, to the parent compound. Pro-drugs include compounds of the present invention wherein a carbonyl, carboxylic acid, hydroxy or amino group is bonded to any group that, when the pro-drug is administered to a mammalian subject, cleaves to form a free carbonyl, carboxylic acid, hydroxy or amino group. Examples of pro-drugs include, but are not limited to, acetate, formate and benzoate derivatives of alcohol and amine functional groups in the compounds of the present invention, and the like.

"Metabolite" refers to any substance resulting from biochemical processes by which living cells interact with the active parent drug or other formulas or compounds of the present invention in vivo, when such active parent drug or other formulas or compounds of the present are administered to a mammalian subject. Metabolites include products or intermediates from any metabolic pathway.

"Metabolic pathway" refers to a sequence of enzyme-mediated reactions that transform one compound to another and provide intermediates and energy for cellular functions. The metabolic pathway can be linear or cyclic.

Obviously, numerous modifications and variations of the present invention are possible in light of the above teachings. It is therefore to be understood that within the scope of the appended claims, the invention may be practiced otherwise than as specifically described herein.

Methods of the Invention

The present invention provides a method for screening for compounds that prevent or inhibit viral infection, e.g., prevent or inhibit viral binding to a host cell surface molecule, e.g., receptor, or prevent or inhibit viral membrane fusion with host cell membrane(s). In one embodiment, the screening method includes contacting cells permissive for viral infection with one or more test agents and a recombinant virus, e.g., a pseudotyed virus or a replication defective, e.g., biologically contained, virus to identify agents that prevent or inhibit viral infection. In one embodiment, cells are first contacted with one or more test agents and then with a recombinant virus to identify agents that prevent or inhibit viral infection. In one embodiment, cells are contacted with a recombinant virus and then with one or more test agents. The methods thus identify compounds that may be used alone or in conjunction with other anti-virals, or other prophylactic or therapeutic compounds.

Agents identified as having anti-viral properties, e.g., agents identified in the screening methods of the invention as having anti-viral properties, are useful in methods to prevent, inhibit or treat viral infection in a mammal. For example, a dopamine antagonist identified as useful to inhibit viral infection or replication in vitro may be employed to prevent, inhibit or treat viral infection in vivo.

Exemplary Viruses Useful in Methods of the Invention

The invention provides isolated vectors, e.g., plasmids, which encode proteins of negative-sense, single stranded RNA viruses and/or express vRNA from recombinant nucleic acid corresponding to sequences for mutant negative-sense, single stranded RNA viruses. In one embodiment, when introduced into a cell, a combination of these vectors is capable of yielding recombinant infectious, biologically contained virus. Thus, the invention includes host cells that produce recombinant infectious, biologically contained virus. In one embodiment, the invention provides isolated vectors, e.g., plasmids, which encode filovirus proteins and/or express mutant filovirus vRNA which, when introduced into a cell, are capable of yielding recombinant infectious, biologically contained filovirus. In one embodiment, the invention provides isolated vectors, e.g., plasmids, which express mutant negative sense vRNA having reporter sequences and lacking viral glycoprotein sequence and vectors that encode filovirus glycoprotein and optionally non-filovirus proteins which, when introduced into a cell, are capable of yielding a pseudotyped recombinant virus. The invention includes host cells that transiently or stably produce the recombinant virus, including helper cells, and isolated recombinant virus prepared by the methods disclosed herein.

Thus, vectors of the invention include those for mRNA production and vRNA production. In one embodiment, the vectors include filovirus DNA, for example, vectors for mRNA production with sequences corresponding to one or more open reading frames encoding filovirus proteins, or vectors for vRNA production that include a deletion of the full-length genomic sequence, which deletion includes internal filovirus sequences corresponding to at least a portion of one open reading frame. The RNA produced from the vRNA vector is capable of being packaged into virions in the presence of filovirus proteins but as part of the resulting virion, is not capable of being replicated and so does not result in virus production when that virion is introduced to a cell that otherwise supports filovirus replication and which cell does not express at least one filovirus protein in trans, e.g., a cell that is not a filovirus helper cell.

For example, Ebolaviruses possess a negative-sense, non-segmented RNA genome, approximately 19 kilobases in length that encodes seven structural proteins and at least one non-structural protein (Sanchez et al., 2007). NP, viral protein (VP)35, VP30, and L, the RNA-dependent RNA polymerase, are components of the nucleocapsid involved in viral replication and transcription (Muhlberger et al., 1999). VP40 is the matrix protein and is involved in viral budding (Harty et al., 2000; Panchal et al., 2003). VP24 is involved in the formation of nucleocapsids composed of NP, VP35 and viral RNA (Huang et al., 2002). The only viral surface glycoprotein, GP, plays a role in viral attachment and entry (Chan et al., 2001; Manicassamy et al., 2005; Shimojima et al., 2006; Chandran et al., 2005). Candidate sequences for deletion/mutation and optional replacement with heterologous sequences include but are not limited to Ebola virus VP30 sequences or corresponding sequences in other negative-sense, single stranded RNA viruses, e.g., sequences for nonstructural, nonpolymerase and/or nonglycosylated viral proteins. Although deletions in other Ebola virus sequences, i.e., in GP and VP40, were prepared, only deletions in VP30 sequences resulted in virus that could be recovered. However, deletions in sequences that do not correspond to VP30 sequences in other negative-sense, single stranded RNA viruses may yield infectious, biologically contained virus that is useful in vaccines or in drug screening.

The vectors may include gene(s) or portions thereof other than those of a negative-sense, single stranded RNA virus such as a filovirus (heterologous sequences), which genes or portions thereof are intended to be expressed in a host cell, either as a protein or incorporated into vRNA. Thus, a vector of the invention may include in addition to viral sequences, for instance, filovirus sequences, a gene or open reading frame of interest, e.g., a heterologous gene for an immunogenic peptide or protein useful as a vaccine or a therapeutic protein.

To express vRNA, e.g., mutant vRNA, the promoter which is operably linked to viral and reporter gene sequences, which may be in antisense (antigenomic orientation for negative-sense viruses), may be, for example, a RNA polymerase I promoter, a RNA polymerase II promoter, a RNA polymerase III promoter, a T7 promoter, or a T3 promoter. The transcription termination sequence may be a RNA polymerase I transcription termination sequence, a RNA polymerase II transcription termination sequence, a RNA polymerase III transcription termination sequence, or a ribozyme.

Any promoter may be employed to express a viral protein. A promoter for the vectors includes but is not limited to a RNA polymerase I promoter, a RNA polymerase II promoter, a RNA polymerase III promoter, a T7 promoter, and a T3 promoter. Each vector comprising an open reading frame may include a transcription termination sequence such as a RNA polymerase I transcription termination sequence, a RNA polymerase II transcription termination sequence, a RNA polymerase III transcription termination sequence, or a ribozyme. Preferred promoters for the vectors for vRNA include, but are not limited to, a RNA polymerase I promoter, a RNA polymerase II promoter, a RNA polymerase III promoter, a T7 promoter, and a T3 promoter. In one embodiment, the vector or plasmid which expresses vRNA comprises a promoter, e.g., a RNA polymerase I, suitable for expression in a particular host cell, e.g., avian or mammalian host cells such as canine, feline, equine, bovine, ovine, or primate cells including human cells. In one embodiment, the RNA polymerase I promoter is a human RNA polymerase I promoter. The vectors or plasmids comprising DNA useful to prepare influenza vRNA may comprise RNA polymerase I transcription termination sequences. Preferred transcription termination sequences for the vectors for vRNA include, but are not limited to, a RNA polymerase I transcription termination sequence, a RNA polymerase II transcription termination sequence, a RNA polymerase III transcription termination sequence, or a ribozyme.

If more than one vector is employed, the vectors may be physically linked or each vector may be present on an individual plasmid or other, e.g., linear, nucleic acid delivery vehicle. The vectors or plasmids may be introduced to any host cell, e.g., a eukaryotic cell such as a mammalian cell, that supports viral replication. Host cells useful to prepare virus of the invention include but are not limited to insect, avian or mammalian host cells such as canine, feline, equine, bovine, ovine, or primate cells including simian or human cells. In one embodiment, the host cell is one that is approved for vaccine production.

The viruses produced by methods described herein are useful in viral mutagenesis studies, drug screening and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). In particular, infectious, biologically contained filovirus of the invention which induces strong humoral and cellular immunity may be employed as a vaccine vector, as they are unlikely to give rise to infectious recombinant virus.

Thus, a virus for use in medical therapy (e.g., for a vaccine or gene therapy) is provided. For example, the invention provides a method to immunize an animal against a pathogen, e.g., a bacteria, virus such as Ebola virus, or parasite, or a malignant tumor. The method comprises administering to the animal an effective amount of at least one isolated virus of the invention which encodes and expresses, or comprises nucleic acid for an immunogenic peptide or protein of a pathogen or tumor, optionally in combination with an adjuvant, effective to immunize the animal.

To prepare expression cassettes for transformation herein, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3□ to 5□ rather than 5□ to 3□). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotropic virus. Such promoters include the CMV promoter, as well as the SV40 late promoter and retroviral LTRs (long terminal repeat elements), e.g., the MMTV, RSV, MLV or HIV LTR, although many other promoter elements well known to the art may be employed in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of *E. coli*, the beta-glucuronidase gene (gus) of the uidA locus of *E. coli*, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al., *Molecular Cloning: A Laboratory Manual* (2002) provides suitable methods of construction.

The recombinant DNA can be readily introduced into the host cells, e.g., mammalian, yeast or insect cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, at least one of the recombinant DNA which is introduced to a cell is maintained extrachromosomally. In one embodiment, at least one recombinant DNA is stably integrated into the host cell genome.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA viral vectors. Viral vectors, e.g., retroviral or lentiviral vectors, have become a widely used method for inserting genes into eukaryotic, such as mammalian, e.g., human, cells. Other viral vectors useful to introduce genes into cells can be derived from poxviruses, e.g., vaccinia viruses, herpes viruses, adenoviruses, adeno-associated viruses, baculoviruses, and the like.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

The recombinant viruses described herein have modifications in genomic sequences relative to a corresponding wild-type viral genome, i.e., the genome of the recombinant virus has a modification which includes a deletion, and optionally an insertion, in a region corresponding to sequences for a viral protein that is associated with transcription, is nonstructural or nonglycosylated, or is a glycoprotein. The mutation in the viral genome is effective to inhibit or prevent production of at least one functional viral protein from that genome when those sequences are present in a nontransgenic cell which supports viral replication. In one embodiment, the deletion includes from 1 up to thousands of nucleotides, e.g., 1%, 10%, 50%, 90% or more of sequences corresponding to the coding region for the viral protein. In one embodiment, the deleted sequences correspond to sequences with a substantial identity, e.g., at least 80% or more, e.g., 85%, 90% or 95% and up to 100% or any integer in between, nucleic acid sequence identity, to VP30 sequences.

In one embodiment, the viral genome in an infectious, replication-incompetent negative-sense, single-stranded RNA virus of the invention includes a deletion in sequences corresponding to those in a wild-type viral genome for a protein that is associated with transcription or is nonstructural or nonglycoslyated, or is a glycoprotein, and includes heterologous sequences that are nontoxic to host cells including cells in an organism to be immunized. In one embodiment, the heterologous sequence is a marker sequence, a selectable sequence or other sequence which is detectable or capable of detection, e.g., GFP or luciferase, or a selectable gene such as an antibiotic resistance gene, e.g., a hygromycin B resistance gene or neomycin phosphotransferase gene, which marker gene or selectable gene is not present in the host cell prior to introduction of the vector.

Pharmaceutical Compositions

Pharmaceutical anti-viral compositions of the present invention, suitable for administration, e.g., nasal, parenteral or oral administration, such as by intravenous, intramuscular, topical or subcutaneous routes, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

In one embodiment, the pharmaceutical composition is part of a controlled release system, e.g., one having a pump, or formed of polymeric materials (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howard et al., *J. Neurosurg.*, 71:105 (1989)). Other controlled release systems are discussed in the review by Langer (*Science*, 249:1527 (1990)).

The pharmaceutical compositions of the present invention comprise a therapeutically effective amount of one or more anti-viral compounds, for instance, those identified by the screening methods of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the virus, such as one in purified form, together with a suitable amount of carrier so as to provide the form for proper administration to the patient. The formulation should suit the mode of administration.

The compositions may be systemically administered, e.g., orally, in combination with a pharmaceutically acceptable vehicle such as an inert diluent. For oral administration, the compound(s) may be combined with one or more excipients and used in the form of ingestible capsules, elixirs, suspensions, syrups, wafers, and the like. Such compositions should contain at least 0.1% of active compound. The percentage of the compositions and preparations may, of course, be varied and may conveniently be between about 2 to about 60% of the weight of a given unit dosage form. The amount of active compound in such useful compositions is such that an effective dosage level will be obtained.

The compositions may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. Various other materials may be present. For instance, a syrup or elixir may contain the virus, sucrose or fructose as a sweetening agent, methyl and propylparabens as preservatives, a dye and flavoring such as cherry or orange flavor. Of course, any material used in preparing any unit dosage form, including sustained-release preparations or devices, should be pharmaceutically acceptable and substantially non-toxic in the amounts employed. The composition also be administered intravenously or intraperitoneally by infusion or injection. Solutions of the compound(s)can be prepared in water or a suitable buffer, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of undesirable microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of undesirable microorganisms can be brought about by various antibacterial and antifungal agents, for example, parabens, chlorobutanol, phenol, sorbic acid, thimerosal, and the like. In many cases, it may be preferable to include isotonic agents, for example, sugars, buffers or sodium chloride.

Sterile injectable solutions are prepared by incorporating the compound(s) in the required amount in the appropriate solvent with various of the other ingredients enumerated above, as required, followed by filter sterilization.

Useful liquid carriers include water, alcohols or glycols or water-alcohol/glycol blends, in which the present compound(s) can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the compositions of the invention can be determined by comparing their in vitro activity and in vivo activity in animal models.

Pharmaceutical Purposes

The administration of the composition may be for either a "prophylactic" or "therapeutic" purpose. When provided prophylactically, the compositions of the invention are provided before any symptom or clinical sign of a pathogen infection becomes manifest. The prophylactic administration of the composition serves to prevent or attenuate any subsequent infection.

When provided therapeutically, the compositions of the invention are provided upon the detection of a symptom or clinical sign of actual infection. The therapeutic administration of the compound(s) serves to attenuate any actual infection.

Thus, a composition of the present invention may be provided either before the onset of infection (so as to prevent or attenuate an anticipated infection) or after the initiation of an actual infection.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of a virus.

The "protection" provided need not be absolute, i.e., the infection need not be totally prevented or eradicated, if there is a statistically significant improvement compared with a control population or set of mammals. Protection may be limited to mitigating the severity or rapidity of onset of symptoms or clinical signs of the virus infection.

Exemplary Compounds and Formulations

Compounds useful in methods of the invention include, but are not limited to, triphenylethylenes, tamoxifen and derivatives thereof such as raloxifene and clomiphene, calcium channel blockers, tetranortriterpenoids, antipsychotics, sigma receptor agonists, anticholinergics, steroids, inhibitor of calcium-independent phospholipase $A_2$, inhibitors of magnesium-dependent phosphatidate phosphohydrolase, inhibitors of the inducible microsomal $PGE_2$ synthase, inhibitors of Hsp90, and dopamine antagonists.

In one embodiment, the compound may be a compound of formula (I):

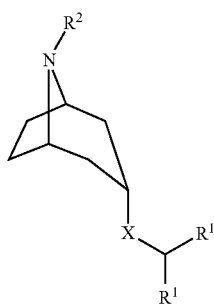

(I)

wherein

X is O or NH;

each $R^1$ is independently aryl, heteroaryl, $(C_1-C_{10})$alkyl, or $(C_1-C_{10})$alkaryl;

$R^2$ is $(C_1-C_{10})$alkyl; and any aryl, heteroaryl, alkyl of $R^1$ and $R^2$ can optionally be substituted with one or more (e.g., one, two, three, four, five, etc.) hydroxy, halo, carboxy, nitro, amino, phenyl, or trifluoromethyl groups;

or a salt thereof.

The various salts of formula I, and of formulas II-VII below, can be formed from, for example, pharmaceutically acceptable acids such as methane sulfonic acid, benzene sulfonic acid, or toluene sulfonic acid. In one specific embodiment, the compound of formula (I) is benztropine mesylate:

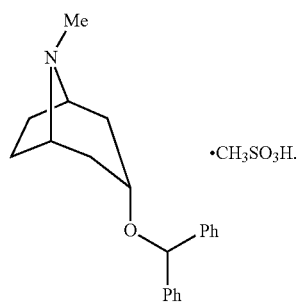 [SMILES: CN1C2CCC1CC(OC(c1ccccc1)c1ccccc1)C2 ; "·CH3SO3H."]

In another embodiment, the compound may be a compound of formula (II):

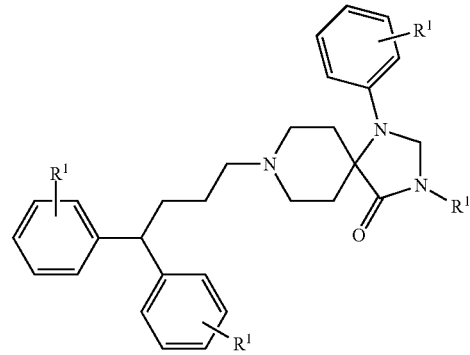

(II)

wherein each $R^1$ is independently hydrogen, hydroxy, halo, carboxy, nitro, amino, trifluoromethyl, aryl, heteroaryl, $(C_1-C_{10})$alkyl, or $(C_1-C_{10})$alkaryl; and any aryl, heteroaryl, or alkyl of $R^1$ can optionally be substituted with one or more (e.g., one, two, three, four, five, etc.) hydroxy, halo, carboxy, nitro, amino, phenyl, or trifluoromethyl groups;

or a salt thereof.

In one specific embodiment, the compound of formula (II) may be Fluspirilene (8-[4,4-bis(4-fluorophenyl)butyl]-1-phenyl-1,3,8-triazaspiro[4.5]decan-4-one):

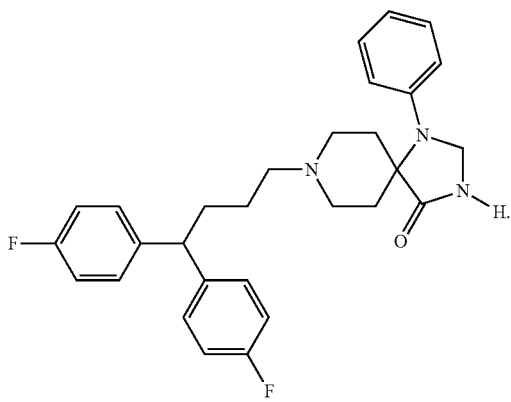

In another embodiment, the compound may be a compound of formula (III):

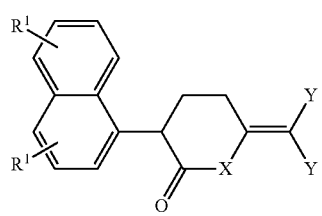

wherein

X is O or NH;

each Y is independently hydrogen or halo;

each $R^1$ is independently hydrogen, hydroxy, halo, carboxy, nitro, amino, trifluoromethyl, aryl, heteroaryl, $(C_1$-$C_{10})$alkyl, or $(C_1$-$C_{10})$alkaryl; and any aryl, heteroaryl, or alkyl of $R^1$ can optionally be substituted with one or more (e.g., one, two, three, four, five, etc.) hydroxy, halo, carboxy, nitro, amino, phenyl, or trifluoromethyl groups;

or a salt thereof.

In one specific embodiment, the compound of formula (III) may be B1552 bromoenol lactone:

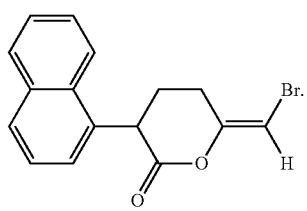 [SMILES: O=C1O/C(=C/Br)CCC1c1cccc2ccccc12]

In another embodiment, the compound may be a compound of formula (IV):

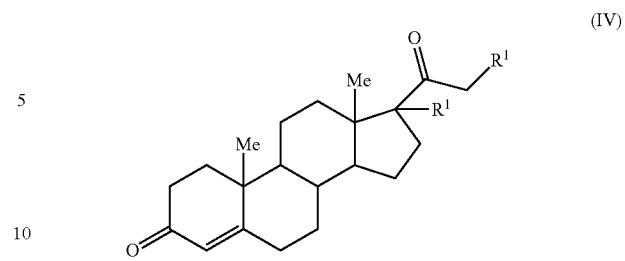

wherein each $R^1$ is independently —X—$R^2$;

each X is independently O, NH, or a direct bond;

each $R^2$ is independently hydrogen, hydroxy, halo, carboxy, nitro, amino, trifluoromethyl, aryl, heteroaryl, $(C_1$-$C_{10})$alkyl, or $(C_1$-$C_{10})$alkaryl; and any aryl, heteroaryl, or alkyl of $R^2$ can optionally be substituted with one or more (e.g., one, two, three, four, five, etc.) hydroxy, halo, nitro, amino, phenyl, or trifluoromethyl groups;

or a salt thereof.

In one specific embodiment, the compound of formula (IV) may be cortexolone:

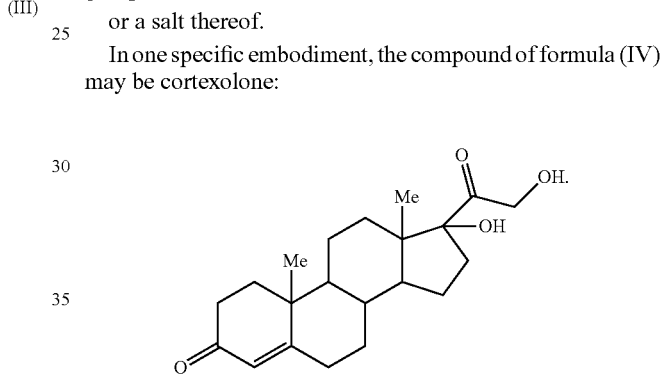

In another embodiment, the compound may be a compound of formula (V):

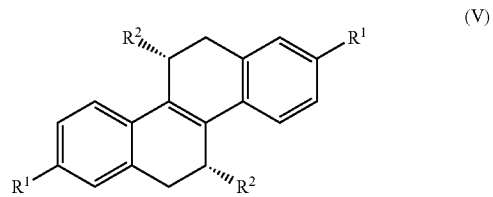

wherein each $R^1$ is independently —X—$R^2$;

each X is independently O, NH, or a direct bond;

each $R^2$ is independently hydrogen, hydroxy, halo, carboxy, nitro, amino, trifluoromethyl, aryl, heteroaryl, $(C_1$-$C_{10})$alkyl, or $(C_1$-$C_{10})$alkaryl; and any aryl, heteroaryl, or alkyl of $R^2$ can optionally be substituted with one or more (e.g., one, two, three, four, five, etc.) hydroxy, halo, carboxy, nitro, amino, phenyl, or trifluoromethyl groups;

or a salt thereof.

In one specific embodiment, the compound of formula (V) may be (R,R)-cis-diethyltetrahydro-2,8-chrysenediol:

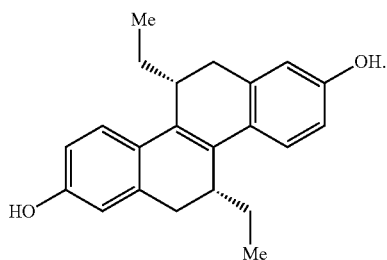 [SMILES: CC[C@@H]1Cc2cc(O)ccc2C2=C1c1ccc(O)cc1C[C@H]2CC]

In another embodiment, the compound may be a compound of formula (VI):

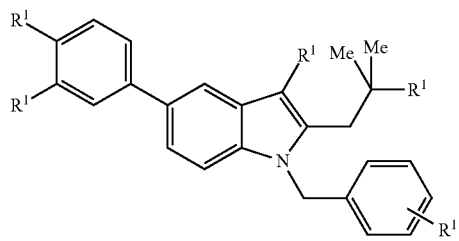

wherein
each $R^1$ is independently —X—$R^2$;
each X is independently O, NH, or a direct bond;
each $R^2$ is independently hydrogen, hydroxy, halo, carboxy, nitro, amino, trifluoromethyl, carboxy, aryl, heteroaryl, ($C_1$-$C_{10}$)alkyl, or ($C_1$-$C_{10}$)alkaryl; and
any aryl, heteroaryl, or alkyl of $R^2$ can optionally be substituted with one or more (e.g., one, two, three, four, five, etc.) hydroxy, halo, carboxy, nitro, amino, phenyl, or trifluoromethyl groups;
or a salt thereof.

In two specific embodiments, the compound of formula (VI) may be:

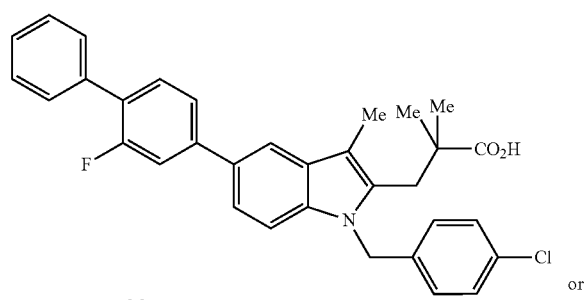

or

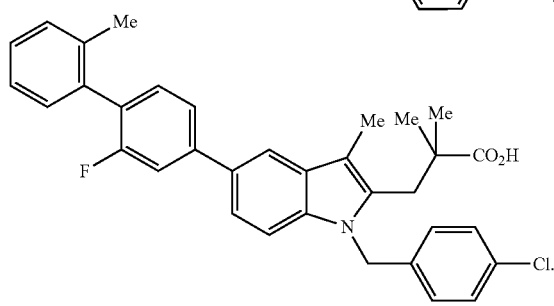

In another embodiment, the compound may be a compound of formula (VII):

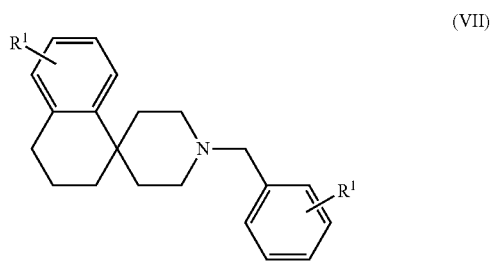

wherein
each $R^1$ is independently —X—$R^2$;
each X is independently O, NH, or a direct bond;
each $R^2$ is independently hydrogen, hydroxy, halo, carboxy, nitro, amino, trifluoromethyl, carboxy, aryl, heteroaryl, ($C_1$-$C_{10}$)alkyl, or ($C_1$-$C_{10}$)alkaryl; and
any aryl, heteroaryl, or alkyl of $R^2$ can optionally be substituted with one or more (e.g., one, two, three, four, five, etc.) hydroxy, halo, carboxy, nitro, amino, phenyl, or trifluoromethyl groups;
or a salt thereof.

In one specific embodiment, the compound of formula (VII) may be L-687,384 (1-benzyl-spiro(1,2,3,4-tetrahydronaphthalene-1,4-piperidine):

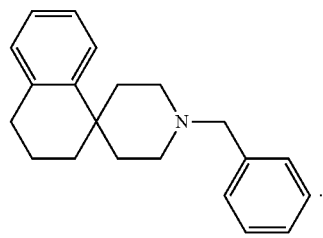 [SMILES: c1ccc(CN2CCC3(CCCc4ccccc43)CC2)cc1]

In another embodiment, the compound may be a compound of formula (VIII)

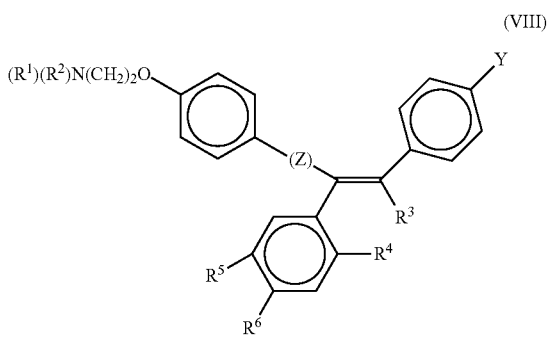

wherein Z is C=O or a covalent bond; Y is H or O($C_1$-$C_4$) alkyl, $R^1$ and $R^2$ are individually ($C_1$-$C_4$)alkyl or together with N are a saturated heterocyclic group, $R^3$ is ethyl or chloroethyl, $R^4$ is H, $R^5$ is I, O ($C_1$-$C_4$)alkyl or H and $R^6$ is I, O($C_1$-$C_4$)alkyl or H with the proviso that when $R^4$, $R^5$, and $R^6$ are H, $R^3$ is not ethyl; or a pharmaceutically acceptable salt, including mixtures thereof.

In another embodiment, the compound can be a compound of formula (IX):

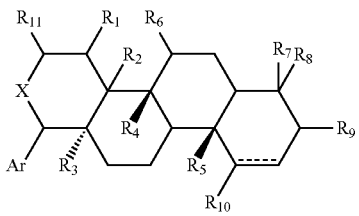

(IX)

wherein

Ar is a substituted or unsubstituted aryl or heteroaryl moiety;

X is —O—, —NH—, —NRx-, —CH$_2$—, —CHRx-, or —C(Rx)$_2$-, wherein Rx is a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; heteroaryloxy; or heteroarylthio moiety;

a dashed line represents either the presence or absence of a bond;

$R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_A$; —C(=O)R$_A$; —CHO; —CO$_2$H; —CO$_2$R$_A$; —CN; —SCN; —SR$_A$; —SOR$_A$; —SO$_2$R$_A$; —NO$_2$; —N$_3$; —NH$_2$; —NHR$_A$; —N(R$_A$)$_2$; —NHC(=O)R$_A$; —NR$_A$C(=O)R$_A$; —NR$_A$C(=O)N(R$_A$)$_2$; —OC(=O)OR$_A$; —OC(=O)R$_A$; —OC(=O)N(R$_A$)$_2$; —NR$_A$C(=O)OR$_A$; or —C(R$_A$)$_3$; wherein each occurrence of $R_A$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —ORB; —C(=O)R$_B$; —CHO; —CO$_2$H; —CO$_2$R$_B$; —CN; —SCN; —SR$_B$; —SORB; —SO$_2$R$_B$; —NO$_2$; —N$_3$; —NH$_2$; —NHR$_B$; —N(R$_B$)$_2$; —NHC(=O)R$_B$; —NR$_B$C(=O)R$_B$; —NR$_B$C(=O)N(R$_B$)$_2$; —OC(=O)N(R$_B$)$_2$; —NR$_B$C(=O)OR$_B$; or —C(R$_B$)$_3$; wherein each occurrence of RB is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety; or $R_1$ and $R_2$ taken together form an epoxide ring, aziridine ring, cyclopropyl ring, or a bond of a carbon-carbon double bond;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_C$; —C(=O)R$_C$; —CHO; —CO$_2$H; —CO$_2$R$_C$; —CN; —SCN; —SR$_C$; —SOR$_C$; —SO$_2$R$_C$; —NO$_2$; —N$_3$; —NH$_2$; —NHR$_C$; —N(R$_C$)$_2$; —NHC(=O)R$_C$; —NR$_C$C(=O)R$_C$; —NR$_C$C(=O)N(R$_C$)$_2$; —OC(=O)OR$_C$; —OC(=O)R$_C$; —OC(=O)N(R$_C$)$_2$; —NR$_C$C(=O)OR$_C$; or —C(R$_C$)$_3$; wherein each occurrence of $R_C$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_D$; —C(=O)R$_D$; —CHO; —CO$_2$H; —CO$_2$R$_D$; —CN; —SCN; —SR$_D$; —SOR$_D$; —SO$_2$R$_D$; —NO$_2$; —N$_3$; —NH$_2$; —NHR$_D$; —N(R$_D$)$_2$; —NHC(=O)R$_D$; —NR$_D$C(=O)R$_D$; NR$_D$C(=O)N(R$_D$)$_2$; —OC(=O)OR$_D$; —OC(=O)R$_D$; —OC(=O)N(R$_D$)$_2$; —OC(=O)OR$_D$; —OC(=O)R$_D$; —OC(=O)N(R$_D$)$_2$; —NR$_D$C(=O)OR$_D$; or —C(R$_D$)$_3$; wherein each occurrence of $R_D$ is independently a hydrogen, a halogen, a protecting group, an aliphatic moiety, a hetero aliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_E$; —C(=O)R$_E$; —CHO; —CO$_2$H; —CO$_2$R$_E$; —CN; —SCN; —SR$_E$; —SOR$_E$; —SO$_2$R$_E$; —NO$_2$; —N$_3$; —NH$_2$; —NHR$_E$; —N(R$_E$)$_2$; —NHC(=O)R$_E$; —NR$_E$C(=O)R$_E$; —NR$_E$C(=O)N(R$_E$)$_2$;—OC(=O)OR$_E$;—OC(=O)R$_E$;—OC(=O)N(R$_E$)$_2$; —NR$_E$C(=O)OR$_E$; or —C(R$_E$)$_3$; wherein each occurrence of $R_E$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_F$; —C(=O)R$_F$; —CHO; —CO$_2$H; —CO$_2$R$_F$; —CN; —SCN; —SR$_F$; —SOR$_E$; —SO$_2$R$_F$; —NO$_2$; —N$_3$; —NH$_2$; —NHR$_E$; —N(R$_F$)$_2$; —NHC(=O)R$_F$; —NR$_F$C(=O)R$_F$; —NR$_F$C(=O)N(R$_F$)$_2$;—OC(=O)OR$_F$;—OC(=O)R$_F$;—OC(=O)R$_F$; —OC(=O)N((R$_F$)$_2$; —NR$_F$C(=O)OR$_F$; or —C(R$_F$)$_3$; wherein each occurrence of RF is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_G$; —C(=O)R$_G$; —CHO; —CO$_2$H; —CO$_2$R$_G$; —CN; —SCN; —SR$_G$; —SOR$_G$; —SO$_2$R$_G$; —NO$_2$; —N$_3$; —NH$_2$; —NHR$_G$; —N(R$_G$)$_2$; —NHC(=O)R$_G$; —NR$_G$C(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —C(R$_G$)$_3$; wherein each occurrence of R$_G$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_8$ is hydrogen; halogen; cyclic or acyclic, substituted or unsubstituted, branched or unbranched aliphatic; cyclic or acyclic, substituted or [mu]nsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_H$; —C(=O)R$_H$; —CHO; —CO$_2$H; —CO$_2$R$_H$; —CN; —SCN; —SR$_H$; —SOR$_H$; —SO$_2$R$_H$; —NO$_2$; —N$_3$; —NH$_2$; —NHR$_H$; —N(R$_H$)$_2$; —NHC(=O)R$_H$; —NR$_H$C(=O)R$_H$; —NR$_H$(C=O)N(2R$_H$)$_2$; —OC(=O)OR$_H$; —O(C=O)R$_H$; —NR$_H$C(=O)OR$_H$; or —C(R$_H$)$_3$; wherein each occurrence of R$_H$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_I$; =O; —C(=O)R$_I$; —CHO; —CO$_2$H; —CO$_2$R$_I$; —CN; —SCN; —SR$_I$; —SOR$_I$; —SO$_2$R; —NO$_2$; —N$_3$; —NH$_2$; —NHR$_I$; —N(R)$_2$; —NHC(=O)R$_I$; —NR$_I$C(=O)R$_I$; —NR$_I$C(=O)N(RI)$_2$; —OC(=O)OR$_I$; —OC(=O)R$_I$; —OC(=O)N(R)$_2$; —NR$_I$C(=O)OR$_I$; or —C(R$_I$)$_3$; wherein each occurrence of R$_I$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or heteroarylthio moiety;

$R_{10}$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OH; —OR$_J$; =O; —C(=O)R$_J$; —CHO; —CO$_2$H; —CO$_2$R$_J$; —CN; —SCN; —SR$_J$; —SOR$_J$; —SO$_2$R$_J$; —NO$_2$; —N$_3$; —NH$_2$; —NHR$_J$; —N(R$_J$)$_2$; —NHC(=O)R$_J$; —NR$_J$C(=O)R$_J$; —NR$_J$C(=O)N(R$_J$)$_2$; —OC(=O)OR$_J$; —OC(=O)R$_J$; —OC(=O)N(R$_J$)$_2$; —NR$_J$C(=O)OR$_J$; or —C(R$_J$)$_3$; wherein each occurrence of R$_J$ is independently a hydrogen, a halogen, a protecting group, an aliphatic moiety, a heteroaliphatic moiety, an acyl moiety; an aryl moiety; a heteroaryl moiety; hydroxy, alkoxy; aryloxy; thioxy; alkylthio; arylthio; amino, alkylamino, dialkylamino, heteroaryloxy; or hetero arylthio moiety;

$R_{11}$ is hydrogen, halo, hydroxy, or a carbonyl;
or a pharmaceutically acceptable salt, stereoisomer, tautomer, or pro-drug thereof.

In yet another embodiment, the compound (e.g., the compound of formula IX) can be a compound of formula (X):

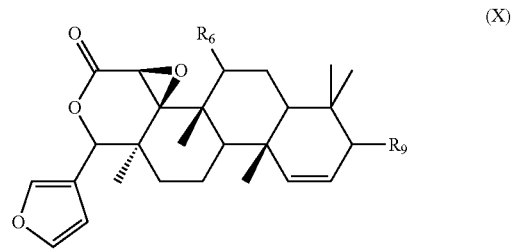

(X)

wherein
$R_6$ is hydrogen; hydroxy; oxo (=O); or acetyl-protected hydroxyl; and
$R_9$ is hydrogen; hydroxy; oxo (=O); or acetyl-protected hydroxyl.

In various embodiments, compounds of formulas (IX) and (X) can include gedunin, gedunol, epoxygedunin, 1,2α-epoxy-7-deacetoxy-7-oxodihydrogedunin, dihydrogedunin, 3β-acetoxydeoxodihydrogedunin, 3α-hydroxydeoxodihydrogedunin, deacetoxy-7-oxogedunin, 3β-hydroxydeoxodihydrogedunin, deacetoxy-7-oxogedunin, 1,2α-epoxydeacetoxydihydrogedunin, 3β-hydroxydeoxydesacetoxy-7-oxogedunin, 7-deacetoxy-3-deacetyl-7-oxokhivorin, 1,3-dideacetyl-7-deacetoxy-7-oxokhivorin, tridesacetoxykhivorin, 1,3-dideacetylkhivorin, and/or Heudelottin C.

In another embodiment, the compound can be a compound of formula (XI):

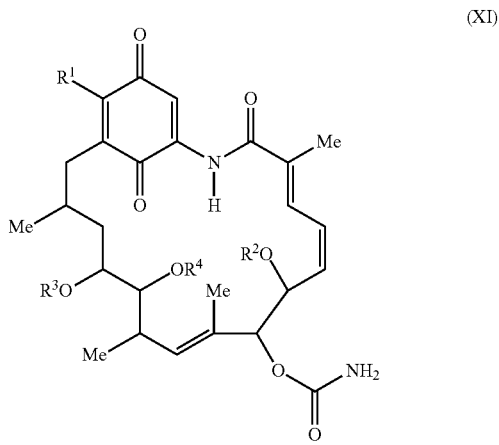

(XI)

wherein
$R^1$ is —X—R$^x$;
X is O, NH, or a direct bond;
$R^x$ is hydrogen, hydroxy, halo, carboxy, nitro, amino, trifluoromethyl, aryl, heteroaryl, (C$_1$-C$_{10}$)alkyl, (C$_1$-C$_{10}$)alkenyl, or (C$_1$-C$_{10}$)alkylaryl;
$R^2$ is hydrogen, trifluoromethyl, aryl, heteroaryl, (C$_1$-C$_{10}$)alkyl, (C$_1$-C$_{10}$)alkenyl, (C$_1$-C$_{10}$)alkylaryl, or an oxygen protecting group;

R[3] is hydrogen, trifluoromethyl, aryl, heteroaryl, ($C_1$-$C_{10}$) alkyl, ($C_1$-$C_{10}$)alkenyl, ($C_1$-$C_{10}$)alkylaryl, or an oxygen protecting group;

R[4] is hydrogen, trifluoromethyl, aryl, heteroaryl, ($C_1$-$C_{10}$) alkyl, ($C_1$-$C_{10}$)alkenyl, ($C_1$-$C_{10}$)alkylaryl, or an oxygen protecting group; and any aryl, heteroaryl, or alkyl (e.g., of $R^x$, $R^2$, $R^3$, or $R^4$) can optionally be substituted with one or more (e.g., one, two, three, four, five, etc.) hydroxy, halo, carboxy, nitro, amino, ($C_1$-$C_{10}$)alkylamino, di($C_1$-$C_{10}$)alkylamino, ($C_1$-$C_{10}$)alkenyl, ($C_1$-$C_{10}$)alkoxy, phenyl, benzyl, or trifluoromethyl groups;

or a salt thereof.

In some embodiments, the compound of formula (XI) may be geldanamycin, 17-AAG, or 17-DMAG.

In another embodiment, the compound can be a compound of formula (XII):

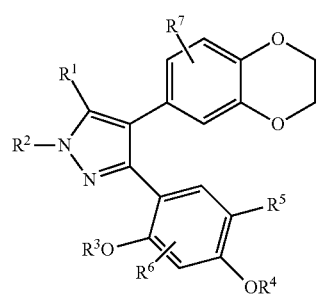

(XII)

wherein $R^1$ is H, ($C_1$-$C_{10}$)alkyl or ($C_1$-$C_{10}$)alkylaryl;

$R^2$ is H, ($C_1$-$C_{10}$)alkyl or ($C_1$-$C_{10}$)alkylaryl;

$R^3$ is hydrogen, trifluoromethyl, aryl, heteroaryl, ($C_1$-$C_{10}$) alkyl, ($C_1$-$C_{10}$)alkylaryl, or an oxygen protecting group;

$R^4$ is hydrogen, trifluoromethyl, aryl, heteroaryl, ($C_1$-$C_{10}$) alkyl, ($C_1$-$C_{10}$)alkylaryl, or an oxygen protecting group;

$R^5$ is H, ($C_1$-$C_{10}$)alkyl or ($C_1$-$C_{10}$)alkylaryl;

$R^6$ is H or —X—$R^x$; X is O, NH, or a direct bond;

$R^7$ is —X—$R^x$; X is O, NH, or a direct bond;

each $R^x$ is independently hydrogen, hydroxy, halo, carboxy, nitro, amino, trifluoromethyl, aryl, heteroaryl, ($C_1$-$C_{10}$) alkyl, or ($C_1$-$C_{10}$)alkaryl; and any aryl, heteroaryl, or alkyl can optionally be substituted with one or more (e.g., one, two, three, four, five, etc.) hydroxy, halo, carboxy, nitro, amino, phenyl, or trifluoromethyl groups;

or a salt thereof.

In one specific embodiment, the compound of formula (XII) may be CCT-018159 (4-[4-(2,3-dihydro-1,4-benzodioxin-6-yl)-5-methyl-1H-pyrazol-3-yl]-6-ethyl-1,3-benzenediol):

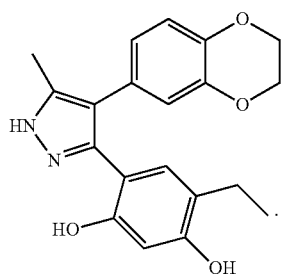 [SMILES: CCc1cc(-c2n[nH]c(C)c2-c2ccc3c(c2)OCCO3)c(O)cc1O]

In another embodiment, the compound can be a compound of formula (XIII):

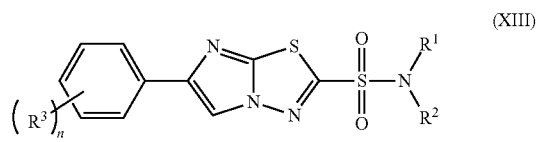

(XIII)

wherein $R^1$ is H, ($C_1$-$C_{10}$)alkyl, aryl, or ($C_1$-$C_{10}$)alkylaryl;

$R^2$ is H, ($C_1$-$C_{10}$)alkyl aryl, or ($C_1$-$C_{10}$)alkylaryl;

each $R^3$ is independently H or —X—$R^x$;

X is O, NH, or a direct bond;

each $R^x$ is independently hydrogen, hydroxy, halo, carboxy, nitro, amino, trifluoromethyl, aryl, heteroaryl, ($C_1$-$C_{10}$) alkyl, or ($C_1$-$C_{10}$)alkylaryl;

any aryl, heteroaryl, or alkyl can optionally be substituted with one or more (e.g., one, two, three, four, five, etc.) hydroxy, halo, carboxy, nitro, amino, phenyl, or trifluoromethyl groups; and n is 1, 2, 3, 4, or 5;

or a salt thereof.

In one specific embodiment, the compound of formula (XIII) may be AEG 3482 (6-phenylimidazo[2,1-b]-1,3,4-thiadiazole-2-sulfonamide):

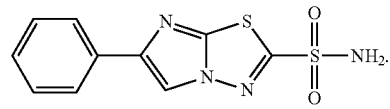 [SMILES: NS(=O)(=O)c1nn2cc(-c3ccccc3)nc2s1]

The compounds of the invention, such as those having formulas (I)-(XIII), can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of the invention can be determined by comparing their in vitro activity and in vivo activity in animal models. Methods for the extrapolation of effective dosages in mice, and other animals, to humans are known to the art; for example, see U.S. Pat. No. 4,938,949.

Generally, the concentration of the compounds of the invention in a liquid composition, such as a lotion, will be from about 0.1-25 wt-%, e.g., from about 0.5-10 wt-%. The concentration in a semi-solid or solid composition such as a gel or a powder will be about 0.1-5 wt-%, e.g., about 0.5-2.5 wt-%.

The amount of the compound, or an active salt or derivative thereof, required for use alone or with other compounds will vary not only with the particular salt selected but also with the route of administration, the nature of the condition being treated and the age and condition of the patient and will be ultimately at the discretion of the attendant physician or clinician.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, such as in the range of 6 to 90 mg/kg/day, or in the range of 15 to 60 mg/kg/day.

The compound may be conveniently administered in unit dosage form; for example, containing 5 to 1000 mg, conveniently 10 to 750 mg, most conveniently, 50 to 500 mg of active ingredient per unit dosage form.

The active ingredient may be administered to achieve peak plasma concentrations of the active compound of from about 0.5 to about 75 μM, e.g., about 1 to 50 μM, such as about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will be further described in the following nonlimiting examples.

EXAMPLE 1

Methods and Materials

Cells and Cell Lines.

Vero cells (green monkey kidney cells) were grown in Eagle's minimal essential medium (MEM) supplemented with 10% fetal calf serum (FCS), L-glutamine, vitamins, nonessential amino acid solution and antibiotics. The VeroVP30 cell line was established by cotransfecting Vero cells with pCAG-VP30 (for the expression of VP30) and pPur, a protein expression plasmid for the puromycin resistance gene (Clontech, Mountain View, Calif.), using the transfection reagent TransIT LT-1 (Mirus, Madison, Wis.). Two days after transfection, puromycin-resistant cells were selected with 5 µg/mL puromycin (Sigma, St. Louis, Mo.). Individual cell clones were screened for VP30 expression by flow cytometry with a polyclonal peptide antibody to VP30.

Human embryonic kidney 293T cells were grown in high-glucose Dulbecco's modified Eagle medium containing 10% FCS, L-glutamine, and antibiotics. All cells were maintained at 37° C. and 5% $CO_2$.

Flow Cytometry.

Cells were detached in phosphate-buffered saline (PBS) containing 0.02% EDTA and then washed once with cold PBS supplemented with 2% FCS and 0.1% sodium azide (wash buffer). Cells were incubated with a VP30 antibody on ice for 20 minutes. After washing in buffer, the cells were further incubated with a secondary antibody labeled with fluorescent isothiocyanate (Zymed Laboratories, Carlsbad, Calif.). They were then washed with buffer and analyzed by FACSCalibur with Cell Quest software (Becton Dickinson, Franklin Lakes, N.J.).

Generation of EbolaΔVP30 Viruses.

Figure 1A:
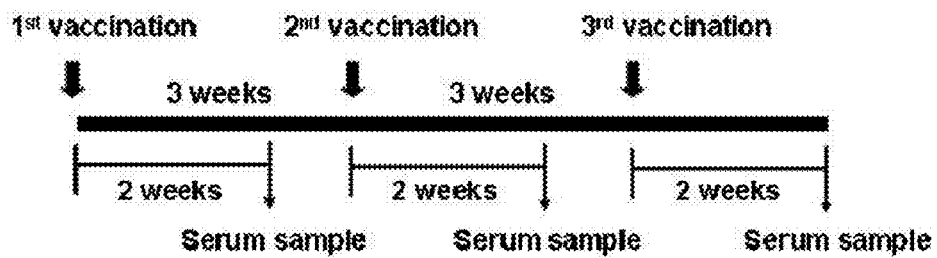
FIG. 1. Schematic diagram of EbolaΔVP30 constructs. (Top row) Schematic diagram of the Ebolavirus genome flanked by the leader sequence (I) and the trailer sequence (t) in positive-sense orientation. Two unique restriction sites for SalI and SacI (positions 6180 and 10942 of the viral antigenome, respectively) allowed the subcloning of a fragment that spans the VP30 gene. The subgenomic fragment was then used to replace the VP30 gene with genes encoding neomycin (neo) or enhanced green fluorescence protein (eGFP), respectively. Using the unique restriction sites, the altered subgenomic fragments were cloned back into the full-length Ebolavirus cDNA construct.
Figure 1B:
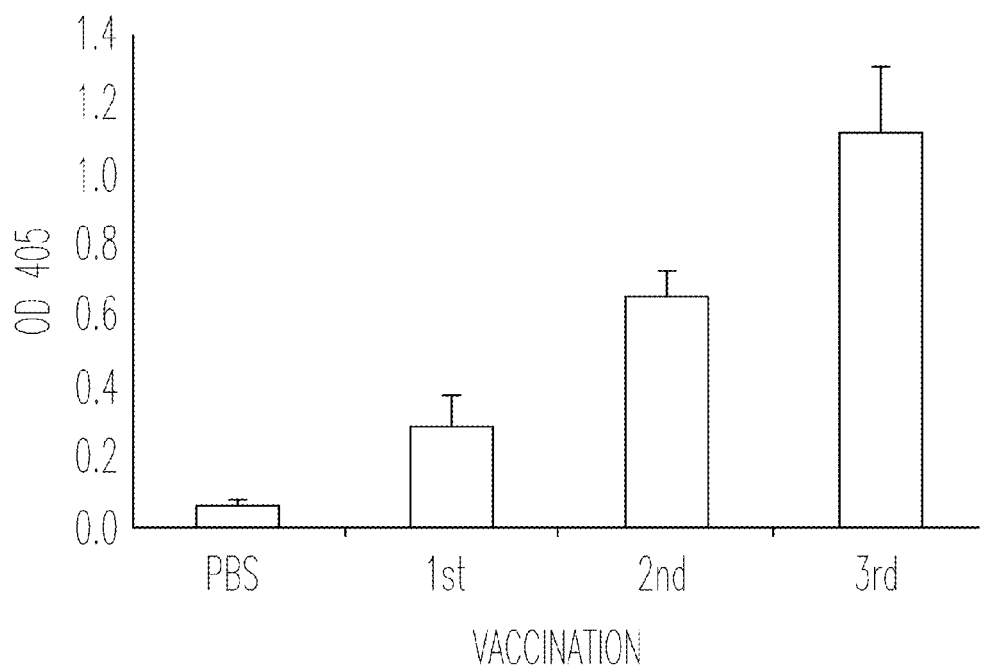

The plasmid pTM-T7G-Ebo-Rib, containing the full-length Ebolavirus cDNA flanked by T7 RNA polymerase promoter and ribozyme sequences, is described in Newmann et al. (2002). First, a fragment encompassing nucleotides 6180 to 10942 (numbers refers to the positive-sense antigenome) was subcloned into a kanamycin-resistant cloning vector. Next, the VP30 ORF was replaced with those encoding neo or eGFP, respectively, by a series of overlapping PCR amplification steps using Pfu Turbo (Stratagene, La Jolla, Calif.). The altered subgenomic fragments were transferred back into the full-length Ebolavirus cDNA plasmid using two unique restriction sites, SalI and SacI (FIG. 1). The resultant plasmids, designated pTM-EbolaΔVP30-neo or -eGFP, were sequenced to verify the replacement of the VP30 ORF and the lack of any unwanted mutations.

To artificially generate Ebolavirus, $5 \times 10^5$ 293T cells were transfected with 1.0 µg pTM-EbolaΔVP30, 2.0 µg pCAG-L, 1.0 µg pCAG-NP, 0.5 µg pCAG-VP35, 0.5 µg pCAG-VP30, and 1.0 µg pCAG-T7 pol, using TransIT LT1 (Mirus, Madison, Wis.) in BSL-4 containment (Neumann et al., 2002). Five days after transfection, the supernatant was harvested, cellular debris removed by low speed centrifugation, and the virus amplified in VeroVP30 cells at 37° C. and 5% $CO_2$ with propagation medium containing 2% FCS in MEM supplemented with L-glutamine, vitamins, nonessential amino acid solution and antibiotics without puromycin.

Plaque Assay and Immunostaining Assay.

To determine the titers of wild-type Ebolavirus or EbolaΔVP30 viruses, tenfold dilutions of the viruses were absorbed to confluent VeroVP30 or wild-type Vero cells for 1 hour at 37° C., after which any unbound virus was removed by washing cells with propagation medium. The cells were then overlaid with propagation medium containing 1.5% methyl cellulose (Sigma). Seven days after infection, cells were fixed with 10% buffered formaldehyde, taken out of BSL-4, permeabilized with 0.25% Triton X-100 in PBS for 10 minutes, and blocked with 4% goat serum and 1% bovine serum albumin (BSA) in PBS for 60 minutes. Cells were then incubated for 60 minutes with a 1:1000 dilution of a mouse anti-VP40 monoclonal antibody, washed with PBS, and incubated for 60 minutes with a 1:1000 dilution of an antimouse IgG-peroxidase-conjugated secondary antibody (Kirkegaard & Perry Laboratories Inc., Gaithersburg, Md.). After washing with PBS, cells were incubated with 3,3'-diaminobenzidine tetrahydrochloride (DAB, Sigma) in PBS. The reaction was stopped by rinsing cells with water.

Western Blotting.

Partially purified virus resuspended in lysis buffer (50 mM Tris-HCl [pH 7.5], 150 mM NaCl, 0.5% Triton X-100, and 0.1% SDS) containing protease inhibitors (complete protease inhibitor cocktails [Roche]) was incubated at 100° C. for 5 minutes, taken out of BSL-4, and separated on 4-20% polyacrylamide gels. Resolved proteins were transferred to Western polyvinylidine difluoride membranes (Schleicher & Schuell, Sanford, Me.) and blocked overnight at 4° C. with 5% skim milk in PBST (0.05% Tween 20 [Sigma] in PBS). Blots were incubated with primary antibodies (a mouse anti-NP antibody, a rabbit anti-VP35 antibody, a rabbit anti-VP40 antibody, a mouse anti-GP antibody, a rabbit anti-VP30 antibody, or a mouse anti-VP24 antibody) for 60 minutes at room temperature, washed three times with PBST, incubated with the appropriate secondary antibody conjugated to horseradish peroxidase (Zymed) for 60 minutes, and finally washed three times with PBST. Blots were then incubated in Lumi-Light Western blotting substrate (Roche, Indianapolis, Ind.) and exposed to X-ray film (Kodak, Rochester, N.Y.).

RNA Isolation and RT-PCR.

Cell culture supernatant from virus-infected VeroVP30 cells was inactivated with guanidinium isothiocyanate buffer and taken out of BSL-4. Viral RNA was isolated with the RNeasy Mini kit (Qiagen, Valencia, Calif.). RT-PCR was carried out with the RobusT One-Step RT-PCR kit (Finnzyme, Espoo, Finland), using 1 µg of isolated RNA and Ebo/avirus-specific primers. The resultant PCR products were cloned into pT7Blue (Novagen, San Diego, Calif.) and sequenced.

Transmission Electron Microscopy.

Ultrathin-section electronmicroscopy was performed as described in Noda et al. (2002). Briefly, at 36 hours postinfection, VeroVP30 cells infected with EbolaΔVP30-neo virus were fixed and inactivated with 2.5% glutaraldehyde in 0.1 M cacodylate buffer, taken out of BSL-4 and posffixed with 2% osmium tetroxide in the same buffer. Cells were then dehydrated with a series of ethanol gradients followed by propylene oxide, before being embedded in Epon 812 Resin mixture (TAAB Laboratories Equipment Ltd., Berkshire, UK). Thin sections were stained with 2% uranyl acetate and Raynold's lead, and examined under a HITACHI H-7500 electron microscope at 80 kV.

Selection of Escape Mutants.

EbolaΔVP30-eGFP was diluted tenfold ($10^{-1}$ to $10^{-6}$) and incubated with the indicated mAbs at a concentration of 250 to 500 µg of mAb/mL at 37° C. for 60 minutes. The virus/ mAb mixtures were inoculated onto VeroVP30 cells for 60 minutes. Viruses were amplified for 5 days in the presence of antibodies. Then, viruses that grew in the presence of mAbs (as determined by GFP expression) were harvested at the highest virus-positive dilution and passaged for a total of 3-6 times in the presence of antibodies. Viral RNA was isolated, RT-PCR amplified, and the GP sequence determined by sequence analysis.

Results

Generation and Passage of EbolaΔVP30-Neo Virus.

Previously a full-length cDNA clone of the Zaire ebolavirus-Mayinga was generated (Newmann et al., 2002). Using a subgenomic fragment that encompasses nucleotides 6180 to 10942 of the viral genome (numbers refers to the positive-sense antigenome), the ORF for VP30 was replaced with that of neomycin (neo), using a series of overlapping PCR amplification steps. After confirmation of the authenticity of the PCR fragments by sequence analysis, the altered subgenomic fragment was inserted into the full-length Ebolavirus cDNA construct via unique SalI and SacI restriction sites (FIG. 1), resulting in an Ebolavirus cDNA genome deficient in the VP30 ORF. The artificial generation of Ebolavirus from plasmids is afforded by flanking this viral cDNA with T7 RNA polymerase promoter and hepatitis delta virus ribozyme sequences (Neumann et al., 2002).

To amplify VP30-deficient Ebola viruses, a stable Vero E6 cell line (designated VeroVP30) was established by cotransfecting Vero cells with two protein expression plasmids encoding VP30 (pCAG-VP30) and puromycin (pPur, Clontech), and selecting cell clones resistant to 5.0 µg/mL of puromycin. VP30 expression in individual clones was determined by flow cytometry with antibodies to VP30. The clone with the highest percentage of VP30-expressing cells (>90% as measured by flow cytometry, data not shown) was used in further studies to amplify EbolaΔVP30 viruses.

EbolaΔVP30-neo virus was rescued under BSL-4 conditions as described for wild-type Ebolavirus (Neumann et al., 2002). All work involving infectious EboΔVP30 viruses and all steps prior to inactivation of biological material were performed under BSL-4 conditions at the National Microbiology Laboratory of the Public Health Agency of Canada.

Figure 2:
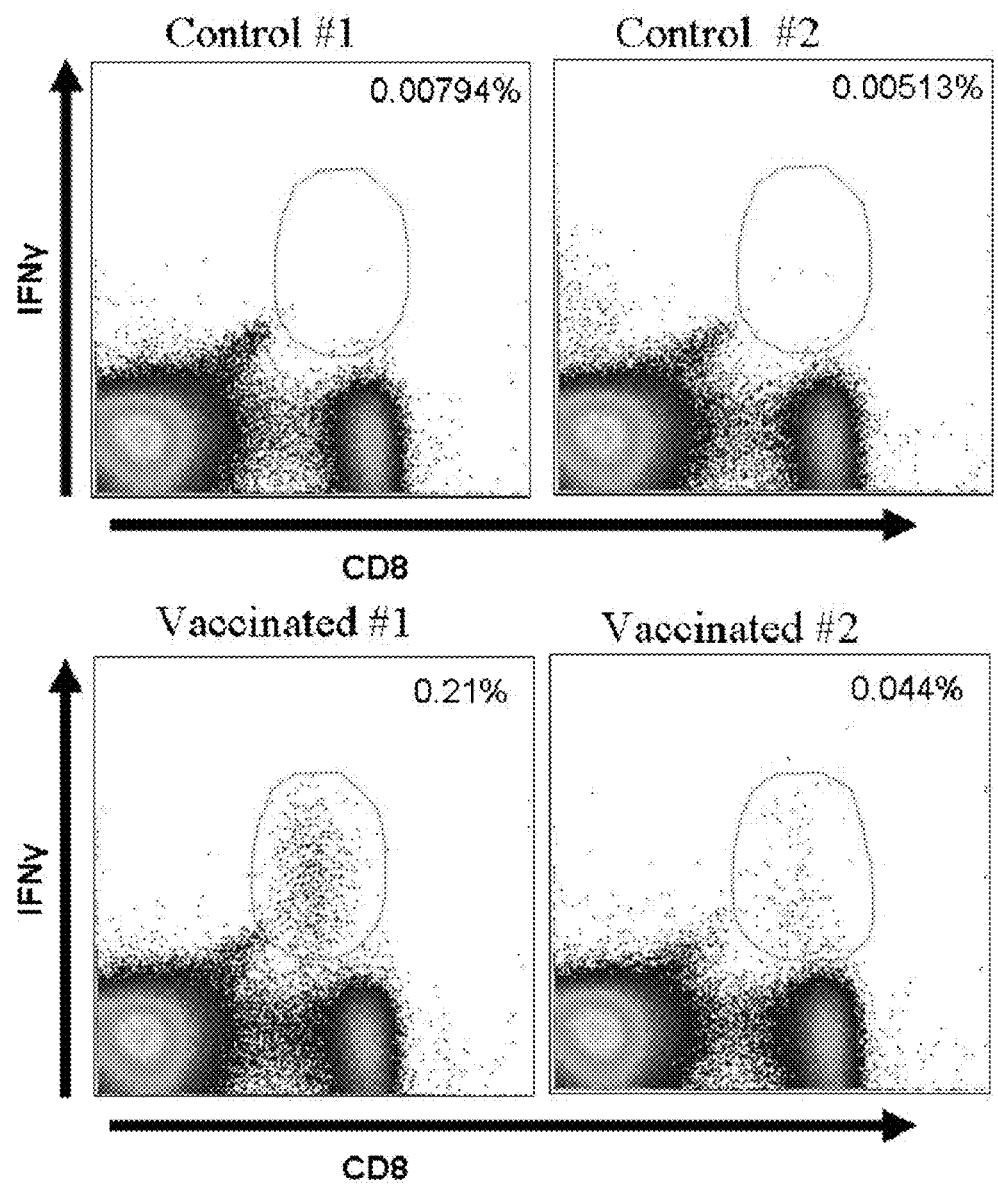
FIG. 2. Characterization of EbolaΔVP30-neo virus. (A) Expression of Ebolavirus antigens by infected VeroVP30 cells. Confluent VeroVP30 cells (left panel) or wild-type Vero cells (right panel) were infected with EbolaΔVP30-neo for 60 minutes, washed, and overlaid with propagation medium with 1.5% methyl cellulose. Seven days later, cells were fixed with 10% buffered formaldehyde and an immunostaining assay with an antibody to Ebolavirus VP40 protein was performed. The formation of plaques in the VeroVP30 cell monolayer (left panel), but not in monolayers of wild-type Vero cells (right panel), illustrates that EbolaΔVP30-neo virus is biologically contained. (B) Detection of EbolaΔVP30-neo viral proteins. Supernatants derived from infected VeroVP30 (labeled '+') or wild-type Vero (labeled '−') cells were collected 5 days after infection and partially purified over 20% sucrose. Protein pellets were suspended in PBS and separated on polyacrylamide gels, transferred to membranes and probed with specific antibodies to Ebolavirus proteins.

Briefly, human embryonic kidney (293T) cells were transfected with a plasmid for the transcription of the VP30-deficient Ebolavirus RNA, with plasmids for the expression of the Ebolavirus NP, VP30, VP35, and L proteins, and with a plasmid for the expression of T7 RNA polymerase. Five days after transfection, VeroVP30 cells were incubated with undiluted supernatant derived from plasmid-transfected cells. Seven days later, the supernatant was harvested, diluted tenfold, and used to infect fresh VeroVP30 cells for the next passage. A total of seven passages were carried out, using the highest dilution of the inoculum that still produced replicating viruses for each passage. The presence of replicating virus was assessed by cytopathic effects (CPE) and immunostaining of infected VeroVP30 cells with an antibody to VP40 (FIG. 2A, left panel). As a control, we also incubated the supernatants from each passage with wild-type Vero cells. As expected, CPE and viral antigens were undetectable in wild-type Vero cells (FIG. 2A, right panel), demonstrating that replicating EbolaΔVP30-neo virus was confined to VeroVP30 cells.

Although the manifestation of a CPE in infected VeroVP30 cells suggested the formation of infectious (but biologically contained) Ebolaviruses, further evidence was sought for the presence of virions in cell culture supernatant derived from infected VeroVP30 cells. Briefly, 5 days after VeroVP30 cells were infected with EbolaΔVP30-neo virus, supernatant was collected and partially purified over 20% sucrose. The pellet was suspended in PBS and separated on a 4-20% polyacrylamide gel. Western blot analyses were carried out with antibodies specific to the respective Ebolavirus protein. All viral proteins (with the exception of L, for which no antibody was available) were detected (FIG. 2B, '+' lanes). Note that VP30 protein in virions originates from VeroVP30 cells while the remaining proteins are encoded by EbolaΔVP30-neo virus. By contrast, no viral proteins were detected in a control sample derived from wild-type Vero cells infected with EbolaΔVP30-neo virus (FIG. 2B, lanes).

Genetic Stability of EbolaΔVP30-Neo Virus.

A major concern with the use of VP30-deficient Ebolaviruses is the potential recombination with VP30 sequences integrated into the genome of the VeroVP30 helper cell line. Thus, to assess the genomic stability of EbolaΔVP30-neo virus, three independent passage experiments were performed (seven passages each). While EbolaΔVP30-neo virus replicated in VeroVP30 cells, viral replication was not observed in wild-type Vero cells. Total viral RNA was isolated from the cell culture supernatant of infected VeroVP30 cells after the seventh passage. A viral genomic fragment spanning the neo gene was amplified by RT-PCR, cloned and sequenced. A total of 20 clones were sequenced, and the sequences were identical to that of the EbolaΔVP30 cDNA construct used for virus generation. Hence, there was no evidence of recombination in any of three independent passage experiments, attesting to the genomic stability of the EbolaΔVP30-neo viral genome.

To further demonstrate the biosafety of EbolaΔVP30-neo virus, EbolaΔVP30-neo virus was collected after seven consecutive passages in VeroVP30 cells and this virus used for three consecutive "blind" passages in wild-type Vero cells. Briefly, Vero cells were infected at a multiplicity of infection (m.o.i.) of 5 with EbolaΔVP30-neo virus (passage 7). Six days later, supernatant was used for the next "blind" passage as well as for Western blot analysis. No viral NP protein was detected after any of the "blind" passages (data not shown). After three consecutive "blind" passages, plaque assays and immunostaining were carried out in wild-type Vero cells to confirm the absence of replicating Ebolavirus. As expected, replicating virus was not detected (data not shown). Collectively, these data further attest to the biosafety of the EbolaΔVP30 system.

Growth Kinetics of EbolaΔVP30-Neo Virus.

Figure 3:
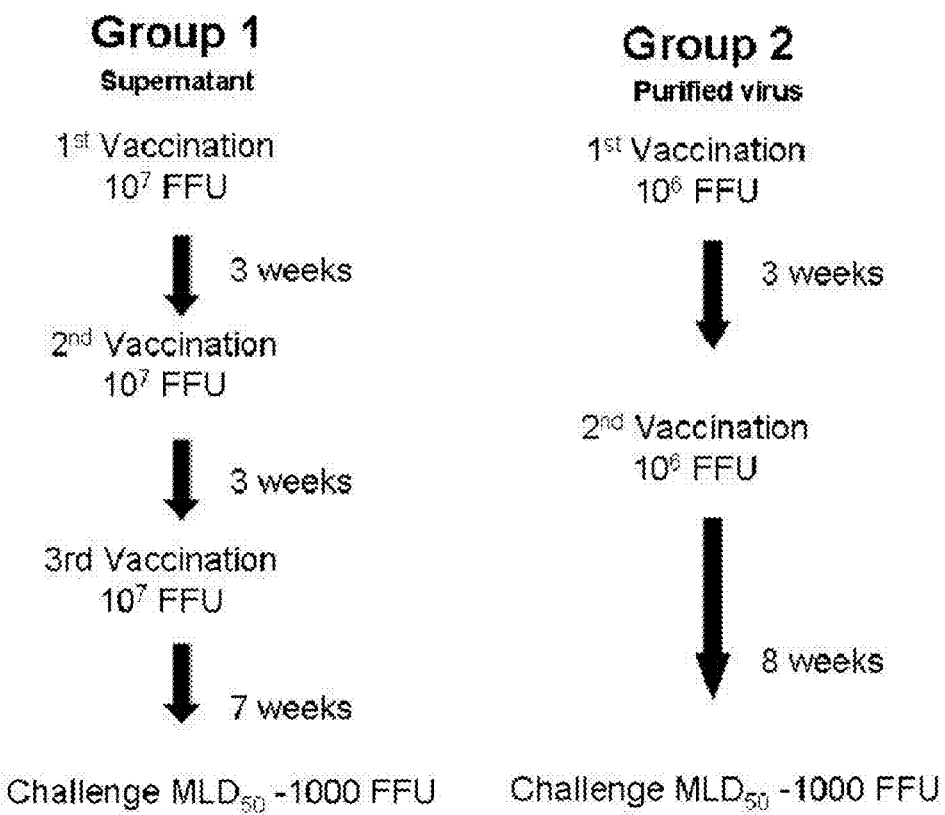
FIG. 3. Replication kinetics of wild-type Ebolavirus and EbolaΔVP30-neo virus. VeroVP30 cells (top panels) and wild-type Vero cells (bottom panels) were infected with Ebolavirus or EbolaΔVP30-neo at a high m.o.i. of 1.0 (left panels) or a low m.o.i. of 0.01 (right panels). Supernatants were harvested every 24 hours postinfection for 6 days. Viral titers of the respective viruses were determined by infecting confluent VeroVP30 cells or wild-type Vero cells with tenfold dilutions of the supernatants and subsequent immunostaining. Virus titers for EbolaΔVP30-neo virus (solid squares) and wild-type Ebolavirus (open circles) were comparable in VeroVP30 cells (top panels). In wild-type Vero cells (bottom panels), no replication was detected for EbolaΔVP30-neo virus (solid squares).

One of the major concerns raised by providing viral proteins in trans is that their amounts, expression kinetics or both may not match those found in cells infected with wild-type virus, leading to reduced virus titers and/or aberrant virion morphology. To address this potential pitfall, the growth kinetics of EbolaΔVP30-neo virus (FIG. 3, solid squares) were compared with that of wild-type Ebolavirus (FIG. 3, open circles). VeroVP30 cells (FIG. 3, top panels) or wild-type Vero cells (FIG. 3, bottom panels) were infected at a high m.o.i. of 1.0 or a low m.o.i. of 0.01 and supernatant was harvested every 24 hours. Virus titers of EbolaΔVP30-neo were determined in VeroVP30 cells, while virus titers of wild-type Ebolavirus were determined in wild-type Vero cells. To determine virus titers, cells were overlaid with 1.5% methylcellulose and 7 days later, assayed for VP40 expression using an immunostaining assay. EbolaΔVP30-neo virus replicated efficiently in VeroVP30 cells at both conditions tested, reaching $10^7$ focal-forming units (FFU)/ml on day 6 postinfection (FIG. 3, top panels, solid squares). No replication of EbolaΔVP30-neo was detected in wild-type Vero cells (FIG. 3, bottom panels, solid squares); the low titers that were detected for up to three days postinfection likely reflect input virus. Together, these findings attest to the biological confinement of the EbolaΔVP30 system. The replication kinetics of EbolaΔVP30-neo in VeroVP30 cells are similar to those of wild-type Ebolavirus in either VeroVP30 (FIG. 3, top panels, open circles) or wild-type Vero cells (FIG. 3, bottom panels, open circles), establishing the described approach as a highly efficient method for generating biologically contained Ebolaviruses.

Morphology of EbolaΔVP30-Neo Virus.

Figure 4A:
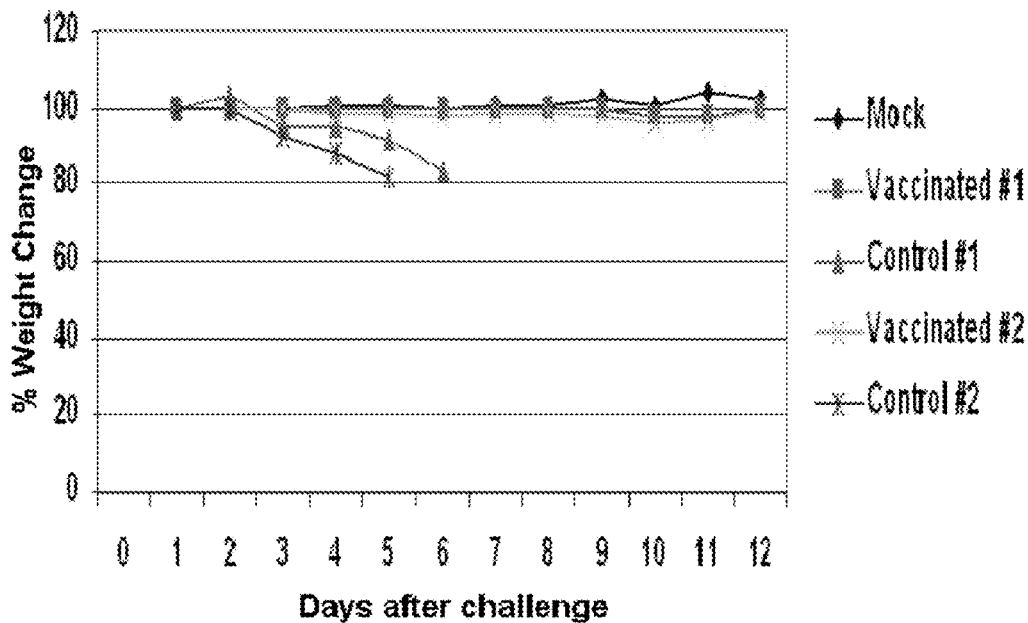
FIG. 4. Morphology of Ebolaviruses budding from infected cells. Vero cells infected with wild-type Ebolavirus (left panels) and VeroVP30 cells infected with EbolaΔVP30-neo virus (right panels) were processed for TEM 3 days postinfection. The pictures show virus budding from infected cells. No significant differences in morphology or budding efficiencies were observed for wild-type Ebolavirus and EbolaΔVP30-neo virus. Top panel, 6,000× magnification; bottom panel, 20,000× magnification of boxed area from top panel.
Figure 4B:
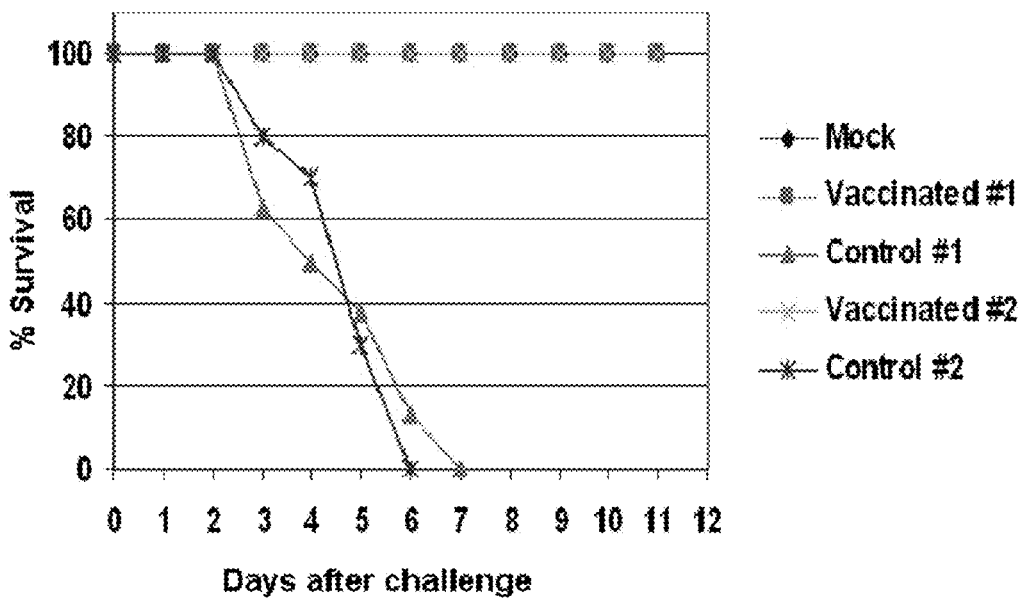

Next, the morphology of EbolaΔVP30-neo virus was assessed by transmission electron microscopy (TEM). VeroVP30 cells were infected with EbolaΔVP30-neo virus and fixed 36 hours later. Samples were processed for TEM as described in Noda et al. (2002). As shown in FIG. 4 (right panels), the particles budding from VeroVP30 cells infected with EbolaΔVP30-neo virus were indistinguishable in their size and shape from wild-type Ebolaviruses (FIG. 4, left panels). Thus, providing VP30 protein in trans does not have a discernable effect on virion morphology, suggesting that the described system would be suitable for studies of virion formation and budding, for example.

Taken together, the above results demonstrate that the EbolaΔVP30-neo virus is biologically contained, replicates to high titers in a helper cell line, is genetically stable, and is morphologically indistinguishable from wild-type virions. Having provided proof-of-concept for the generation of biologically contained Ebolaviruses, the utility of this strategy in basic research and drug screening applications was assessed.

Generation of an EbolaΔVP30-eGFP Virus and its Usefulness for Basic Research Applications.

An EbolaΔVP30 virus encoding enhanced green fluorescence protein (eGFP) instead of VP30 was generated (FIG. 1; designated EbolaΔVP30-eGFP), using the same procedures described above for EbolaΔVP30-neo virus. Analogous to EbolaΔVP30-neo virus, the eGFP variant replicated efficiently with virus titers reaching $8.0 \times 10^7$ FFU/mL. Expression of eGFP was observed as early as 10 hours postinfection (data not shown).

Takada et al. (2003) used replication-competent vesicular stomatitis virus (VSV) pseudotyped with Ebolavirus GP and two neutralizing monoclonal antibodies (mAb), 133/3.16 and 226/8.1, to map Ebolavirus GP epitopes and to generate escape mutants. To confirm with authentic Ebolavirus virions the findings of Takada et al. (2003) based on a VSV-pseudotyping system, escape mutants were generated by amplifying EbolaΔVP30-eGFP virus in the presence of mAb 133/3.16 or 226/8.1. Each of eight escape mutants to mAb 133/3.16 possessed a histidine-to-arginine substitution at position 549 (H549R) in GP, reported by Takada et al. (2003). Using mAb 226/8.1, 12 escape mutants were isolated that all contained an arginine-to-tryptophan substitution at position 134 (R134W), a mutation identical to one identified by Takada et al. (2003). However, the remaining two escape mutations described by Takada et al. (2003) were not detected. Whether this discrepancy in escape mutants reflects differences between the biological systems used or random mutations is presently unclear. Nonetheless, these experiments illustrated one of the ways that biologically contained Ebolaviruses could be used in basic research applications.

In conclusion, biologically contained Ebolaviruses lacking the VP30 gene afford a safe, alternative way to study authentic Ebolavirus, to develop Ebolavirus vaccines, and to screen chemical libraries for compounds that interfere with the Ebolavirus life cycle. Indeed, each of the three different biologically contained viruses generated (encoding neomycin or eGFP instead of VP30) was biologically contained, as demonstrated by their ability to replicate in VeroVP30 (a Vero cell line that stably expresses VP30 in trans), but not in wild-type Vero cells. Moreover, virus titers were in the range of $10^7$ FFU/mL and hence comparable to those obtained for wild-type Ebolavirus (FIG. 3; Volchov et al., 2001; Neumann et al., 2002; Ebihara et al., 2006) while morphological, biochemical, and virological analyses indicated that the tested properties of EbolaΔVP30 viruses were indistinguishable from those of wild-type Ebolavirus.

These physical properties, together with the results of studies to illustrate the potential of biologically contained Ebolaviruses in basic research and drug screening applications, will greatly accelerate current filovirus research efforts.

EXAMPLE 2

Ebola viruses (family Filoviridae), cause severe hemorrhagic fever in humans and nonhuman primates with mortality rates up to 90% (Johnson et al., 1977). Currently, there are no licensed vaccines or antivirals available against Ebola virus. A vaccine against Ebola virus is not only desirable for local populations in the epidemic areas of Africa, but also for health care workers during an outbreak and for post-exposure treatment of laboratory workers after accidental exposure to the virus. A few vaccine candidates have been shown to protect mice, guinea pigs, or nonhuman primates against a lethal challenge of Ebola virus; however, each of these candidates has disadvantages, such as lack of protection in nonhuman primates, preexisting immunity against the vector in humans, or potential central nervous system involvement (Reed et al., 2007). Moreover, the current vaccine candidates are based on virus-like particles (VLPs) or virus-vectored vaccines, none of which express the full components of the viral antigens. On the other hand, the use of live attenuated vaccines may not be feasible for Ebola virus from a biosafety perspective. To overcome these potential limitations, biologically contained viruses offer an attractive option since they are biologically safe but provide all the viral antigens.

Materials and Methods

Cells.

VeroVP30 cells were established as described in Example 1 and grown in Eagle's minimal essential medium (MEM) supplemented with 10% fetal calf serum (FCS), L-glutamine, vitamins, non-essential amino acid solution, and 5 µg/mL puromycin (Sigma, St. Louis, Mo.).

Viruses.

The EbolaΔVP30 virus was generated as described in Example 1. Briefly, using the plasmid containing the full-length Ebola cDNA genome of the Zaire Mayinga strain of Ebola virus (Neumann et al., 2002), the open reading frame (ORF) of VP30 was replaced with the ORF of the drug-resistant gene neomycin. Using Ebola virus reverse genetics (Neumann et al., 2002), the EbolaΔVP30 virus was generated and passaged in a Vero cell line stably expressing VP30. EbolaΔVP30 was propagated in VeroVP30 cells in MEM medium as described above, but supplemented with 2% FCS. The virus was harvested six days after infection of the cells at a multiplicity of infection (MOI) of 1 and directly stored at −80° C. Harvested virus was also partially purified by ultracentrifugation at 27,000 rpm for 2 hours over 20% sucrose. The viral pellet was resuspended in sterile PBS and stored at −80° C. Viral titers were determined by plaque assay in confluent VeroVP30 cells overlaid with 2% FCS-MEM containing 1.5% methyl cellulose (Sigma).

Since wild-type Ebola virus does not kill mice, challenge studies were carried out with a mouse-adapted Ebola virus (Bray et al., 1998). This virus was generated as described in Ebihara et al., 2006 and used under BSL-4 conditions at the Canadian Centre for Human and Animal Health in Winnipeg, Canada.

Antibody Titers.

The levels of Ebola glycoprotein (GP)-specific immunoglobulin G (IgG) antibodies in vaccinated mice were examined by using an enzyme-linked immunosorbent assay (ELISA). Briefly, wells of Immulon 2HB plates (Thermon Labsystems, Franklin, Mass.) were coated with purified Ebola GP (Takada et al., 2001) and blocked with PBS containing 10 mg/mL bovine serum albumin. After incubation of Ebola GP-coated wells with mouse serum from control and vaccinated mice, bound antibodies were detected with goat anti-mouse IgG conjugated to horseradish peroxidase (Kirkegaard & Perry Laboratories Inc., Gaithersburg, Md.) by an ELISA plate reader at an absorbance of 405 nm.

Intracellular Staining and Flow Cytometry.

The number of cytokine-producing CD8$^+$ T cells was determined by intracellular staining as described Murali-Krishna et al. (1998). Briefly, splenocytes were stimulated with the Ebola peptide NP$_{279-288}$(SFKAALSSLA, derived from the nucleoprotein NP; SEQ ID NO: 31) (Olinger et al., 2006; Simmons et al., 2004), VP40$_{171-180}$ (YFTFDLTALK, derived from the matrix protein VP40; SEQ ID NO: 32), or GP$_{161-169}$ (LYDRLASTV, derived from GP; SEQ ID NO: 33) (Olinger et al., 2005; Warfield et al., 2005) for 5 hours in the presence of brefeldin A and IL-2. Following activation, cells were stained for cell surface CD8$^+$ and intracellular IFNγ by using the Cytofix/Cytoperm kit from BD Biosciences (San Jose, Calif.). The number of cytokine-producing CD8$^+$ T cells was determined by using a FACSCalibur flow cytometer (BD Biosciences).

Vaccination and Challenge.

Four-week-old female BALB/c mice (The Jackson Laboratory, Bar Harbor, Me.) were anesthetized with isoflurane and intraperitoneally (IP) inoculated twice at three-week intervals with 10$^6$ focus forming units (FFU) of sucrose-purified EbolaΔVP30 virus (FIG. 7); control mice were simultaneously inoculated with PBS. A second group of mice received three immunizations (at three-week intervals) with 10$^7$ FFU of virus harvested from cell culture supernatant (FIG. 7), or, as a control, 2% FCS-MEM. Vaccinations were conducted at the University of Wisconsin-Madison. Mice were then transported to the BSL-4 laboratory at the National Microbiology Laboratory of the Public Health Agency of Canada, where they were challenged with 1000 mouse lethal doses 50 (MLD$_{50}$; i.e., the dose required to kill 50% of infected animals) of mouse-adapted Ebola virus. Four days after challenge, viral titers were determined in the serum of three control and three vaccinated mice from each group. The remaining mice were monitored for survival for 28 days. All animal experiments were performed in accordance with approved animal use protocols and according to the guidelines set forth by the Canadian Council of Animal Care and the University of Wisconsin-Madison.

Results

Antibody Response of Mice Immunized with EbolaΔVP30 Virus.

Figure 5A:
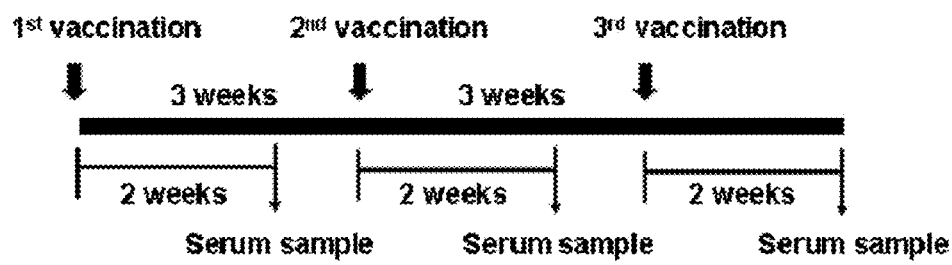
FIG. 5. Ebola ΔVP30 virus generates an antibody response against the Ebola virus glycoprotein, GP. (A) Flow chart of vaccination of 4-week-old Balb/c mice with EbolaΔVP30 virus to determine the antibody titer to Ebola GP. Mice (n=4) were vaccinated three times with $10^7$ FFU of Ebola ΔVP30 at three-week intervals; control mice (n=4) were simultaneously mock-vaccinated. Serum samples were collected two weeks after each vaccination. (B) The amounts of IgG against purified Ebola virus GP in the samples was determined by ELISA. Results are expressed as the mean absorbance at 405 nm (+/− standard deviations) of samples diluted to 1:100.
Figure 5B:
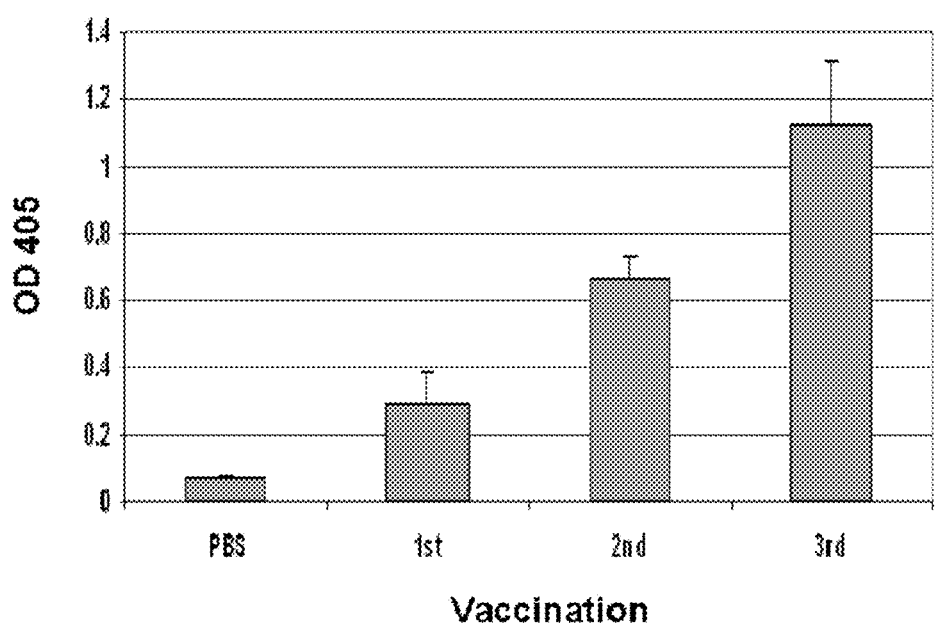

To assess the EbolaΔVP30 virus as a potential vaccine, its immunogenicity in mice was determined. Mice vaccinated with the EbolaΔVP30 virus did not show any signs of disease, demonstrating the lack of pathogenicity of the EbolaΔVP30 virus. When serum samples, collected two weeks after each vaccination to determine the levels of antibodies to the Ebola glycoprotein (GP), were tested for IgG antibody by ELISA with purified GP (FIG. 5), vaccinated animals showed elevated levels of antibody titers against GP after the first vaccination compared to control mice (FIG. 5); these antibody titers further increased after the second and third vaccinations. This finding demonstrates the ability of the biologically contained EbolaΔVP30 virus to elicit antibodies to GP.

CD8$^+$ T-Cell Responses in Vaccinated Mice.

Figure 6:
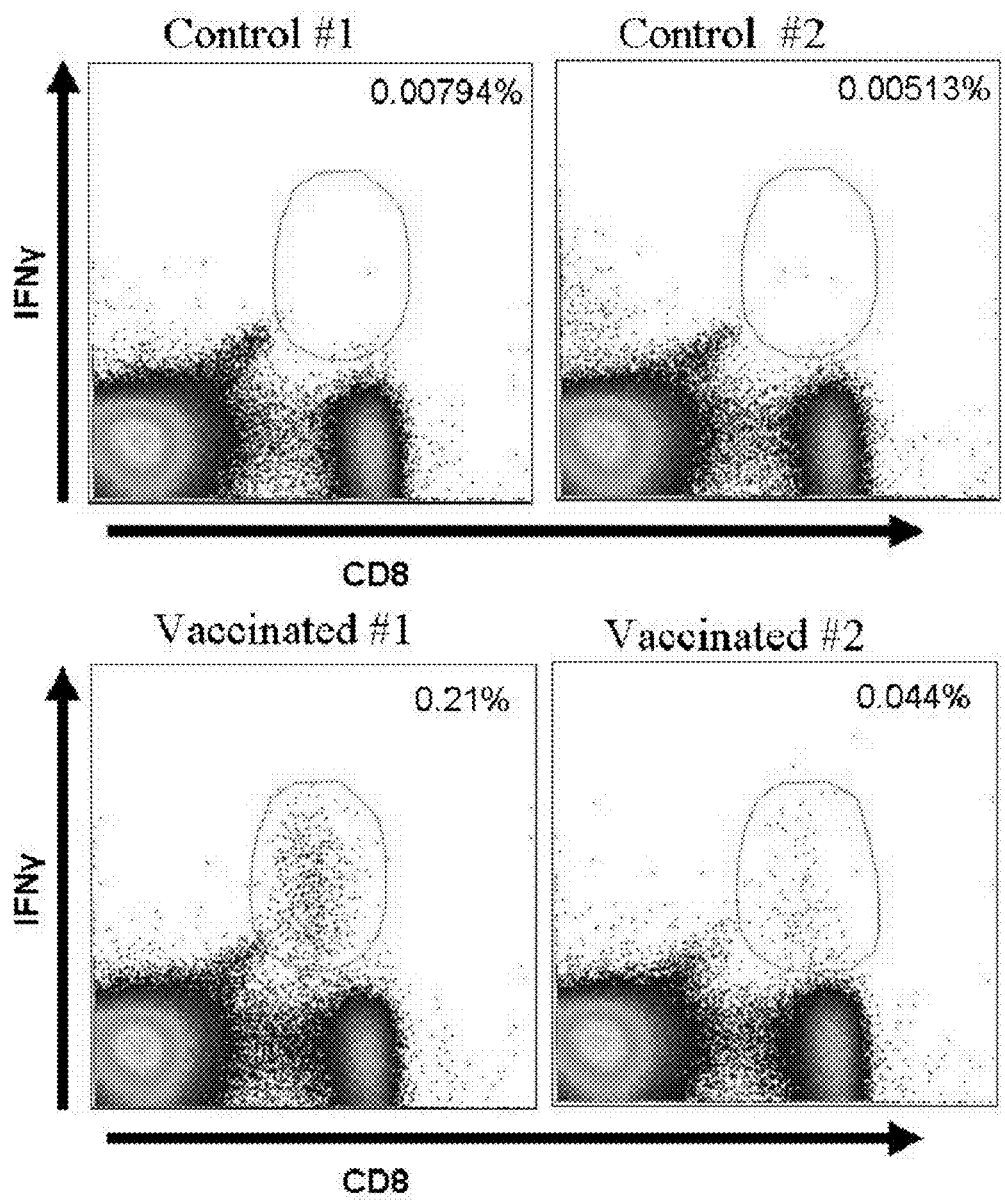
FIG. 6. Cellular immune response in Ebola ΔVP30-vaccinated mice. Mice (n=4) were vaccinated with EbolaΔVP30; control mice (n=2) were simultaneously mock-vaccinated. Splenocytes were collected 8 days after the second vaccination and stimulated with an NP peptide. Cells were stained for the cell surface antigen $CD8^+$ and for intracellular IFNγ. The number of cytokine-producing $CD8^+$ T cells was determined by using a FACSCalibur flow cytometer (BD Biosciences).

The cellular response to vaccination in mice was examined. Mice were vaccinated as described above. Eight days after the second immunization, four vaccinated and two control mice were euthanized and their spleens removed. Splenocytes were isolated and stimulated with the Ebola peptide NP$_{279-288}$(SFKAALSSLA; SEQ ID NO: 31), VP40$_{171-180}$ (YFTFDLTALK; SEQ ID NO: 32) or GP$_{161-169}$ (LYDRLASTV; SEQ ID NO: 33) for 5 hours in the presence of brefeldin A and IL-2. Vaccinated mice had IFNγ-positive CD8$^+$ cells in the range of 0.017% to 0.22% for cells stimulated with Ebola peptide NP$_{279-288}$ (FIG. 6). For control mice, the number of IFNγ-positive CD8$^+$ cells was significantly lower, ranging from 0.00513% to 0.00794% (FIG. 6). No IFNγ-positive CD8$^+$ cells were detected for cells stimulated with Ebola peptide VP40$_{171-180}$ or GP$_{161-169}$ (data not shown).

Protective Efficacy of EbolaΔVP30 Virus in Mice.

Figure 7:
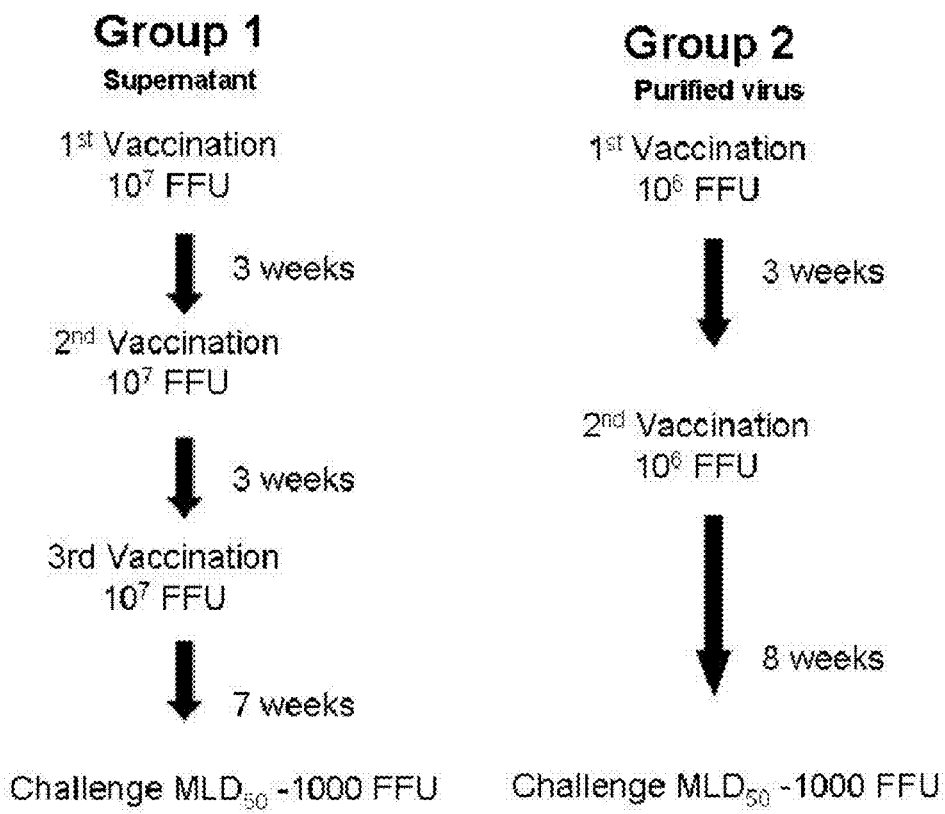
FIG. 7. Flow chart of the vaccination schedule to determine the protective efficacy of the EbolaΔVP30 virus. Four-week-old Balb/c mice were vaccinated with EbolaΔVP30 virus. In group 1, mice (n=14) were vaccinated with nonpurified EbolaΔVP30 virus directly from cell culture supernatant, while control mice (n=8) were mock-vaccinated. In group 2, mice (n=15) were vaccinated with purified EbolaΔVP30 virus, while control mice (n=10) were mock-vaccinated. All mice were challenged with a 1000 $MLD_{50}$ of mouse-adapted Ebola virus.
Figure 8A:
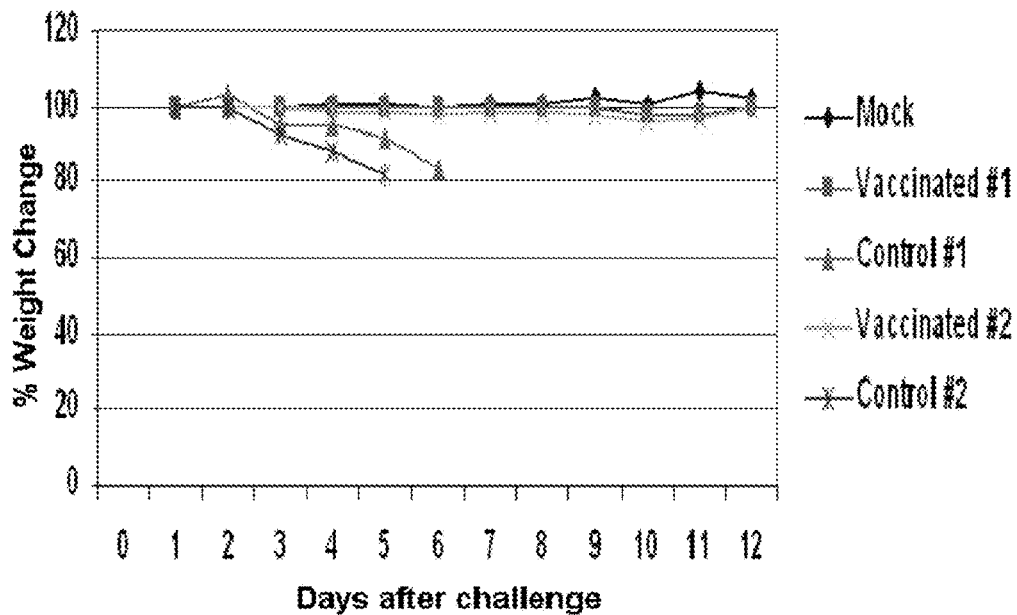
FIG. 8. Body weight changes (A) and Kaplan-Meier survival curve (B) of mice vaccinated with EbolaΔVP30 compared to control mice. Mice from group 1 were vaccinated three times with non-purified EbolaΔVP30 virus while mice from group 2 were vaccinated twice with purified EbolaΔVP30 virus. Mice from the vaccinated groups and control groups were challenged with a 1000 $MLD_{50}$ of mouse-adapted Ebola virus.
Figure 8B:
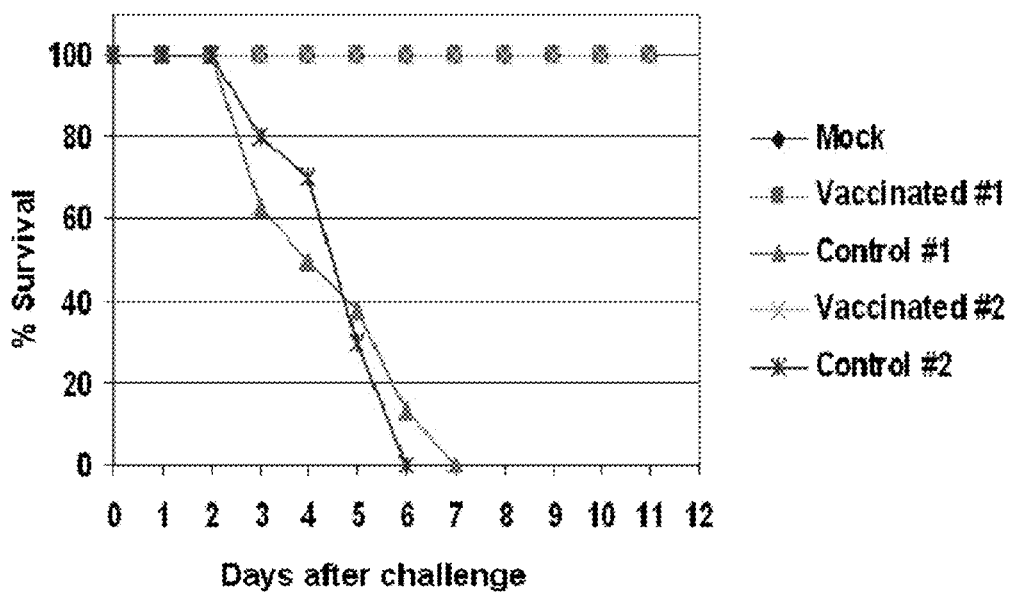

To assess the protective efficacy of the EbolaΔVP30 virus, two groups of 4-week-old mice were intraperitoneally immunized, then subjected to lethal challenge with mouse-adapted Ebola virus (FIG. 7). 'Group 1' mice were immunized three times at three-week intervals with 10$^7$ FFU of non-purified EbolaΔVP30 virus (i.e., virus harvested from cell culture supernatant); eight control mice were inoculated in the same manner with 2% FCS-MEM. Mice from this group were challenged seven weeks after the last immunization with 1000 MLD$_{50}$ of mouse-adapted Ebola virus, which consistently kills mice (Bray et al., 1998; Ebihara et al., 2006). 'Group 2' mice were immunized twice (with a three-week interval) with 10$^6$ FFU of purified EbolaΔVP30 virus; ten control mice were similarly inoculated with PBS. Mice from 'Group 2' were challenged eight weeks after the last immunization with 1000 MLD$_{50}$ of mouse-adapted Ebola virus. No signs of disease or illness were seen in mice vaccinated with purified or non-purified EbolaΔVP30 virus, whereas control mice from both groups began showing signs of sickness (e.g., ruffled fur) along with weight loss on day 3 post-challenge (FIG. 8A). By day 7 post-challenge, all control mice had succumbed to infection (FIG. 8B). By contrast, vaccinated mice from both groups showed no signs of disease, as characterized by ruffled fur and weight loss (FIG. 8A), and were fully protected against lethal challenge (FIG. 8B) up to day 28, when all surviving mice were euthanized. On day 4 post-challenge, mice were sacrificed to determine viral titers in the sera (FIG. 9). Vaccinated mice from both groups showed a 3 to 4 log$_{10}$ reduction in viral titers compared to their respective control mice. Taken together, these data demonstrate that the EbolaΔVP30 virus efficiently protects mice against challenge with a lethal dose of mouse-adapted Ebola virus.

Discussion

Here, it was demonstrated that EbolaΔVP30-immunized mice were completely protected from a lethal challenge with mouse-adapted Ebola virus and that the virus titers in sera from these mice were more than 1000-fold lower than those in control mice. These results show the potential of this biologically contained Ebola virus as a vaccine.

The humoral response to Ebola virus infection is important, as demonstrated by protection from a lethal challenge by passive transfer of antibodies to the viral glycoprotein GP (Gupta et al., 2001; Warfield et al., 2003). However, the ability of a vaccine to elicit an antibody response does not in itself correlate with protection from Ebola virus infection. For example, classical vaccine approaches, such as γ-irradiated Ebola and Marburg viruses, along with GP expressed in baculovirus generate a moderate antibody response; however, they fail to protect mice against a lethal challenge (Ignatyeve et al., 1996; Lupton et al., 1980; Mellquist-Riemenschneider et al., 2003). By contrast, Ebola and Marburg VLPs protect mice from a lethal challenge of Ebola or Marburg virus (Warfield et al., 2003; Warfield et al., 2004; Warfield et al., 2005), and not only elicit a humoral response, but also induce a CD8+ T-cell response, highlighting the importance of the latter response for protection against a lethal challenge of Ebola virus (Warfield et al., 2005). Similarly, in non-human primates (NHPs), full protection from a lethal challenge appears to depend on both the humoral response and a CD8+ cellular response (Sullivan et al., 2000). Vaccine candidates that protect NHPs from a lethal Ebola virus challenge, such as recombinant vesicular stomatitis virus (VSV) (Jones et al., 2005) and adenovirus (Sullivan et al., 2000), induce a CD8+ T-cell response in NHPs, albeit to varying degrees (Jones et al., 2005; Sullivan et al., 2000). The EbolaΔVP30 virus induced both humoral and CD8+ T-cell (specific for an Ebola NP epitope) responses, although the extent of the latter responses varied among animals (FIG. 6). Whether this CD8+ T-cell response is sufficient to provide protection to NHPs from a lethal Ebola virus infection remains to be tested.

Although vaccine candidates such as recombinant VSV or parainfluenza virus offer protection in various animal models (Bukreyev et al., 2006; Jones et al., 2005), there are safety concerns with the use of these vaccines in humans (Bukreyev et al., 2006; Jones et al., 2005; Reed et al., 2007). Preexisting immunity to a vaccine based on recombinant adenovirus is also a concern, as is the large amount of virus ($10^{10}$ particles) needed to confer protection in NHPs (Jones et al., 2005; Sullivan et al., 2000). Ebola and Marburg VLPs have been shown to protect mice and guinea pigs from a lethal challenge of these viruses (Warfield et al., 2004; Warfield et al., 2005). While VLPs are safe and, due to the rarity of Ebola virus infection, preexisting immunity to Ebola or Marburg viruses is not a concern for VLP vaccines, it is difficult to produce large quantities of VLPs from cell culture.

The biologically contained EbolaΔVP30 virus is thus an ideal vaccine candidate since it combines the advantages of VLPs and vectored vaccines (i.e., safety and efficacy), yet it can be propagated to high titers in VeroVP30 cells like standard viruses (Example 1). Further studies will include testing the EbolaΔVP30 virus for its protective efficacy in NHPs. In addition, shorter, single vaccination protocols will be evaluated to determine if the EbolaΔVP30 virus vaccine could elicit fast and effective immunity in the event of an outbreak or bioterrorism attack. This includes evaluating the EbolaΔVP30 virus as a vaccine for post-exposure treatment.

EXAMPLE 3

Generation of Noninfectious Ebola Particles

Materials and Methods
 Cells.
 293 and 293T human embryonic kidney cells were maintained in DMEM supplemented with 10% fetal calf serum, 2% L-glutamine, and penicillin-streptomycin solution (DMEM-FCS) (Sigma). The cells were grown at 37° C. in 5% $CO_2$.
 Construction of Plasmids.
 To generate cDNA constructs encoding the VP40 protein, primers were used that bind to the start and stop codons (positions 4479 and 5459 of the positive-sense antigenomic RNA) to reverse transcribe and PCR-amplify purified viral RNA (Titan RT-PCR Kit, Roche). The PCR product was cloned in the pT7Blue vector (Novagen) resulting in pT7EboZVP40. The cloned Ebola VP40 gene was sequenced to ensure that unwanted nucleotide replacements were not present.

To generate plasmid pETEBoZVP40H is for the expression of 6-histidine-tagged VP40 in *Escherichia coli*, pT7EboZVP40 was used as a template for PCR amplification with the appropriate primers. The PCR product was blunt-end ligated into the SmaI-digested site of vector pM (CLONETECH). This construct was digested with NdeI and EcoRI and the fragment containing VP40 was ligated into the expression vector pET-5a (Promega). To generate plasmids pCEboZVP40, pCEboZVP40AAXY, pCEboZVP40M 14A, pCEboZVP40/1-276, pCEboZVP40/1-226, pCEboZVP40/1-176, pCEboZVP40/50-326, and pCEboZVP40/100-326 (proteins expressed from these plasmids are designated VP40, VP40AAXY, and the like) for expression of VP40 and its mutants in eukaryotic cells, the Ebola Zaire VP40 gene was amplified from pT7EboZVP40 using specific forward primers, each containing an EcoRI site 5' to the start of the coding region, and specific reverse primers, each containing a BglII site 3' to the stop codon for each construct, and blunt-end ligated into the EcoRV-digested site of vector pT7Blue. Each construct was digested with EcoRI and BglII, and the fragment containing the VP40 gene or modified VP40 gene was cloned into the EcoRI and BglII-digested eukaryotic expression vector pCAGGS/MCS (expression controlled by the chicken β-actin promoter) (Kobasa et al., 1997; and Niwa et al., 1991).

Antibody.
 A polyclonal antibody against Ebola Zaire VP40 was produced as follows: BL21 *E. coli* cells were transformed with plasmid pETEBoZVP40His. Expression of the 6-His-tagged VP40 protein was induced with 1 mM IPTG for 3 hours. The *E. coli* cells were lysed and cellular debris was remove by centrifugation. The supernatant was purified over an Ni-NTA agarose column (Qiagen). Expression of VP40 was verified by SDS-PAGE followed by Western blotting using a monoclonal antibody against the histidine tag (Kodak). Rabbits were immunized with approximately 0.5 mg of VP40, and antibody against keratin present in the antiserum was removed with a keratin column (Girault et al., 1989).

Cell Transfection for Expression of VP40 and its Mutants.
 293 or 293T cells (60-mm plates) were transfected with expression vectors with the use of the Trans IT LT-1 liposomal reagent (Panvera) according to the manufacturer's instructions. Briefly, DNA and transfection reagent were mixed (6 μL of Trans IT LT-1 with 3 μg of DNA) in 0.2 mL OPTI-MEM (Gibco-BRL), incubated for 30 minutes at room temperature, and added to the cells. Transfected cells were incubated at 37° C. until harvest of the supernatant and/or cell monolayer.

Particle Formation Assay.
 Particles were assayed by the method of Li et al (1993) with some modifications. Forty-eight hours after transfection of 293T cells with pCEboZVP40, pCEboZVP40AAXY, pCEboZVP40M14A, or pCEboZVP40/1-276, the culture medium was removed and placed on ice. The cell monolayer was washed with phosphate-buffered saline (PBS), scraped into lysis buffer (0.25 M Tris-HCl, pH 8.0, 0.5% Triton X-100) and kept at 4° C. The culture medium (2 mL) was centrifuged at 2,000 rpm in a microcentrifuge for 5 minutes to remove cellular debris, layered over 20% sucrose in STE buffer (0.01 M Tris-Cl, pH 7.5, 0.01 M NaCl, 0.001 M EDTA, pH 8.0) (2 ml), and centrifuged at 150,000×g for 2 hours at 4° C. After centrifugation, the supernatant was removed and added to the cell lysate. This mixture was saved for analysis of total protein expression. The pellet was resuspended in 1 mL STE buffer overnight at 4° C. The resuspended pellet was layered over a 10-50% discontinuous sucrose gradient in STE buffer, centrifuged at 150,000×g for 4 hours at 4° C., and fractions (1 mL) were collected from the top of the gradient. Each fraction was mixed with 0.25 ml of 50% trichloroacetic acid (TCA) (10% TCA), the fractions were incubated for 30 minutes on ice, and the precipitated proteins were pelleted by microcentrifugation for 15 minutes. The pellets were washed once with cold acetone, air-dried, and resuspended in 0.05 ml SDS-PAGE sample buffer. Proteins in the mixture of cell lysate and supernatant from centrifugation through 20% sucrose were precipitated with 10% TCA, washed with acetone, and resuspended in 0.5 mL SDS-PAGE sample buffer. Proteins were separated by 12% SDS-PAGE and detected by Western blotting. Fractions are numbered from the top to the bottom of the gradient.

Protease Protection Assay.

293T cells were transfected with pCEboZVP40 and, at 48 hours post-transfection, the culture medium was removed. The medium was microcentrifuged at 2,000 rpm for 5 minutes to remove cellular debris, layered over a 20% sucrose cushion, and centrifuged at 165,000×g for 1 hour at 4° C. The supernatant was removed and the pellet was resuspended overnight at 4° C. in 0.4 mL STE buffer. This resuspension was divided into six aliquots and treated following a protocol previously described (Mik et al., 1989): Aliquot 1 received no further treatment; aliquot 2 was treated with soybean trypsin inhibitor (Biofluids) to a final concentration of 3 mg/ml; aliquot 3 with triton X-100 to a final concentration of 1%; aliquot 4 with trypsin (Worthington) to a final concentration of 0.1 mg/mL; aliquot 5 with both Triton X-100 to 1% and trypsin to 0.1 mg/ml final concentration; and aliquot 6 with both trypsin inhibitor (3 mg/ml final) and trypsin (0.1 mg/mL final). The samples were incubated at room temperature for 30 minutes, after which an excess of trypsin inhibitor (5 mg/mL) was added to each aliquot. SDS-PAGE sample buffer (6×) was added to each aliquot. Proteins from each aliquot were separated by 12% SDS-PAGE and detected by Western blotting.

Membrane-Association Assay.

The method of Bergmann and Fusco (1988) was used, with some modifications, to determine membrane-association of VP40 and its mutants. Briefly, 48 hours after transfection of 293 cells with pCEboZVP40 or a mutant-VP40 expression plasmid, the culture medium was removed, and the cell monolayer, after a wash with (PBS), was scraped into ice-cold sucrose homogenization buffer (10% wt/wt sucrose, 10 mM Tris-HCl (pH 7.4), 1 mM EDTA, and 10 mM iodoacetamide). Cells were disrupted with 30 strokes of a Dounce homogenizer on ice and microcentrifuged for 3 minutes at 2,000 rpm to remove nuclei. The resulting supernatant was made to 1 M NaCl or left untreated, incubated at room temperature for 20 minutes, made to 80% sucrose (wt/vol), placed at the bottom of a Beckman SW41 centrifuge tube, and overlaid with 5 ml of 65% (wt/vol) sucrose and 2.5 mL of 10% sucrose. The gradient was centrifuged to equilibrium at 150,000×g for 18 hours at 4° C. Fractions (1 mL) were collected from the top of the gradient, diluted 1:1 with TBS-Triton buffer (0.025 M Tris-HCl, pH 7.5, 0.15 M NaCl, 0.5% Triton X-100) or, for experiments involving expression of VP40/100-326, precipitated with TCA (as described for the particle formation assay) owing to the weak signal of this deletion construct in Western analysis, and mixed with SDS-PAGE sample buffer. Proteins from each aliquot were separated by 12% SDS-PAGE and detected by Western blotting.

Triton X-114 Phase Partitioning Analysis.

The method used was essentially that of Bordier (1981). Forty-eight hours post-transfection of 293 cells pCEboZY40, pCEboZVP40/1-276, pCEboZVP40/1-226, pCEboZVP40/1-176, pCEboZP40/50-326, pCEboZVP40/100-326, or, as a control, a vector expressing A/WSN/33 (H1N1) influenza virus hemagglutinin (HA), cells were scraped into cold TN buffer (10 mM Tris-HCl, pH 7.4, 150 mM NaCl), disrupted with 30 strokes in a Dounce homogenizer, and subjected to centrifugation at 2,000 rpm for 3 minutes to remove nuclei. Triton X-114 (Sigma) was added to each supernatant to 1%, and the resulting solution was incubated for 15 minutes at 4° C. with agitation. Unsolubilized material was pelleted by centrifugation in a picofuge for 5 minutes at 4° C., and the supernatant was heated to 37° C. for 5 minutes. The supernatant was layered onto a 37° C. sucrose (6%) cushion in TN buffer containing 0.06% Triton X-114 and centrifuged at 2,000 rpm for 3 minutes at room temperature. The detergent (lower) and aqueous (upper) phases were recovered separately, the aqueous phase was extracted a second time, like phases were pooled, and the detergent phase was diluted in TN buffer. Proteins in each phase were precipitated with 50% acetone and resuspended in SDS-PAGE sample buffer. Proteins were separated by 12% SDS-PAGE and analyzed by Western blotting.

Western Blotting.

Samples in sample buffer (10 µL) were incubated at 100° C. for 5 minutes and separated on 12% polyacrylamide gels. Resolved proteins were transferred to Westran polyvinylidine difluoride membranes (Schleicher & Schuell) and blocked overnight at 4° C. with 5% skim milk in PBST (0.05% Tween 20 (Sigma) in PBS). Blots were incubated in primary antibody for 1 hour at room temperature, washed three times with PBST, incubated in biotinylated anti-rabbit secondary antibody (Vector Laboratories) for 30 minutes, washed three times with PBST, incubated in streptavidin-horseradish peroxidase reagent (Vector Laboratories) for 30 minutes and washed three times with PBST. Blots were then incubated in Lumi-Light Western blotting substrate (Boehringer-Mannheim) for 5 minutes and exposed to x-ray film (Kodak).

Results

Expression of VP40 in Mammalian Cells.

To ensure that VP40 is expressed at efficient levels in human embryonic kidney 293T cells, the cell lysate was analyzed 24 hours after transfection with pCEboZVP40 by Western blotting. Two bands reacting with anti-VP40 polyclonal antibody were found, a small distance apart, in the range of 40 kDa. The lysate from cells transfected with the expression vector alone did not react with the antibody.

VP40 contains an internal start codon at nucleotides 40-42 (codon 14) that is in frame with the first AUG. To determine whether protein synthesis from this internal start codon was responsible for the faster-migrating band on the gel, a construct was generated, pCEboZVP40M14A, which expresses a mutant VP40 with this second AUG changed to GCG, which encodes alanine, and expressed it as described above. Analysis of the cell lysate revealed a single, larger-sized band, suggesting that the second AUG is used as a start codon to an appreciable extent in this system.

To determine whether loss of the PPXY motif at amino acids 10-13 of VP40 affects expression of the protein, 293T cells were transfected with pCEboZVP40AAXY, which expresses a mutant VP40 in which the PPEY sequence at amino acids 10-13 was changed to AAEY. Two bands corresponding to those seen with the expression of wild-type VP40 were detected. However, in contrast to the results obtained with wild-type VP40 expression, where the slower-migrating band was the predominate product, pCEboZVP40AAXY expressed the two products at similar levels, indicating that loss of the PPXY motif affects either the translation of VP40 or its stability.

Production of Membrane-Bound Particles.

To determine whether VP40-associated vesicles are produced when the protein is expressed in the absence of other viral proteins, 293T cells were transfected with pCEboZVP40 and, after 48 hours, collected the supernatant. After removal of cellular debris, the supernatant was subjected to ultracentrifugation over a 20% sucrose cushion. The pellet was resuspended and centrifuged through a 10-50% discontinuous sucrose gradient, and fractions were analyzed by Western blotting. Fractions 6-8 contained VP40, with the majority of the protein found in fraction 7. The VP40 in fractions 6-8 was most likely associated with membrane lipids in a particle-like structure, as the sucrose densities in these fractions ranged from 1.11 to 1.13 g/mL, which corresponds to findings for matrix protein-generated particles of other viruses (Giddings et al., 1998; Sandefur et al., 1998). Bands detected below full-length protein in the total protein fraction are likely degradation products. These data indicate that VP40 expressed in the absence of other viral proteins can produce membrane-bound particles.

Protease Protection Assay.

To confirm the ability of VP40 to produce membrane-bound particles when expressed alone, a trypsin protection assay was employed. Culture supernatant from cells transfected with pCEboZVP40 was centrifuged at 165,000×g through 20% sucrose, and the pellet was resuspended in STE buffer and divided into six equal aliquots. Aliquots 1-3 served as controls (untreated, trypsin inhibitor treated, and triton X-100 treated), aliquot 4 was treated with trypsin, aliquot 5 with trypsin and triton X-100, and aliquot 6 with trypsin inhibitor and trypsin. Trypsin degraded VP40 only in the presence of triton X-100, indicating that the viral protein does induce the production of fully membrane-bound particles; that is, trypsin digestion of VP40 required disruption of the lipid-bilayer surrounding the protein.

VP40 Mutants and Membrane-Bound Particle Formation.

Does the PPXY motif at amino acids 10-13 of VP40 contribute to particle production? To address this question, VP40AAXY was expressed in 293T cells and assayed for particles as described for wild-type VP40. VP40AAXY was not detected in fractions corresponding to the sucrose densities to which wild-type VP40 particles migrated. Since VP40AAXY was synthesized at levels similar to wild-type VP40, this finding indicates that mutation of the PPXY motif markedly disrupts VP40-generated vesicle formation.

A substantial amount of VP40M14A was present in fractions 5-8 in the gradient, and the percentage of total VP40M14A expressed in 293T cells that contributed to membrane-bound particle formation was much greater than the percentage of total wild-type VP40 involved in particle formation. This result is consistent with the finding that the PPXY motif present immediately upstream of the second AUG is critical for VP40-associated particle formation.

To determine whether the C-terminus of VP40 is essential for particle formation, a deletion mutant, VP40/1-276, was assayed which lacks the final 50 amino acids of VP40, for particle generation. Since this deletion mutant was not present at the same sucrose densities that characterized the migration of wild-type VP40, it was concluded that the first 276 amino acids of VP40 are not sufficient for particle formation.

VP40 Association with Cell Membranes and Structural Requirements for Activity.

Flotation analysis was used to determine if VP40 binds cellular membranes efficiently in mammalian cells. In this method, postnuclear membrane fractions in 80% sucrose are loaded at the bottom of a centrifuge tube and overlaid with 65% and 10% sucrose. During centrifugation, cellular membranes and their associated proteins float to the 10-65% sucrose interface, while soluble proteins remain in the dense sucrose fractions at the bottom of the tube.

A large percentage of wild-type VP40 was found at the 10-65% sucrose interface (fraction 3), while the remaining protein was found in the loading zone (fractions 8-12), indicating that VP40 does indeed bind cellular membranes. To clarify the interactions involved in this association, VP40-associated membranes were treated with 1 M NaCl to determine whether electrostatic interactions were required for this association and subjected them to flotation analysis. Salt treatment had a negligible affect on the ability of VP40 to associate with membranes, suggesting that the protein contains at least one hydrophobic domain able to associate with membranes.

To elucidate the domain(s) of VP40 important for membrane association, deletion mutants were generated. Constructs expressing amino acids 50-326 (pCEboZVP40/50-326), amino acids 100-326 (pCEboZVP40/100-326), amino acids 1-176 (pCEboZVP40/1-176), amino acids 1-226 (pCEboZVP40/1-226), and amino acids 1-276 (pCEboZVP40/1-276) of VP40 were expressed in 293 cells and their membrane association in the presence or absence of 1 M NaCl was examined. The mutants with the largest truncations, VP40/1-176 and VP40/100-326, showed the highest level of association with the lipid bilayer. Salt treatment did not affect these interactions. Mutants VP40/1-226 and VP40/50-326 associated with membranes to the extent found with wild-type VP40, and these interactions were also relatively unperturbed by treatment with salt. By contrast, only a small portion of VP40/1-276 associated with the lipid bilayer, and this interaction was eliminated upon treatment with salt. These results indicate that loss of the C-terminal 50 amino acids of VP40 markedly alters the membrane-binding capabilities of VP40, primarily by disrupting hydrophobic interactions. This effect was ameliorated when 50 additional C-terminal amino acids were deleted, and membrane-association was promoted when the protein was further truncated to 176 amino acids. Deletion of the N-terminal 49 amino acids of VP40 did not alter the membrane-binding characteristics of the protein, although truncation of 50 additional N-terminal amino acids did enhance protein-membrane association, as seen with VP40/1-176.

Since particle formation was markedly reduced with VP40AAXY, cells expressing this mutant were subjected to flotation analysis in order to determine whether a decreased ability to bind membranes was involved in this deficiency. The loss of the PPXY motif in VP40 did not affect the ability of the protein to bind membranes, indicating that lack of particle production with this mutant was not due to the loss of membrane association.

Flotation analysis was also used to determine whether the more efficient particle formation induced by VP40M14A, by comparison to wild-type VP40, could be attributed, at least in part, to increased membrane binding by this mutant. The percentage of VP40M14A associated with membranes was only slightly greater than that determined for wild-type VP40, indicating that this mutant relies on another mechanism to increase particle formation.

Triton X-114 Phase Partitioning Analysis.

To probe the nature of the VP40-membrane interaction further, Triton X-114 phase partitioning analysis was used as integral membrane proteins and lipid anchored proteins partition in the detergent phase of a protein extraction and peripheral membrane proteins partition in the aqueous phase. HA, an integral membrane protein, was found entirely in the detergent phase of the extraction, as expected. Only a small portion of total VP40 was found in the detergent phase, while VP40/1-276 was found almost entirely in the aqueous phase. VP40/1-226 and VP40/50-326 partitioned in the detergent phase in proportions similar to that found for wild-type VP40. By contrast, when VP40/1-176 and VP40/100-326 were expressed, large proportions of each partitioned in the detergent phase. These results indicate that wild-type VP40 possesses only minor traits of an integral membrane protein, and that deletion of its C-terminal 50 amino acids (VP40/1-276) abrogates these features. Further truncation of the C-terminus (VP40/1-226 and VP40/1-176) enhances the integral membrane character of protein. Deletion of the N-terminal 49 amino acids of VP40 (VP40/50-326) does not alter the general structural features of the protein, while deletion of amino acids 1-99 (VP40/100-326) appears to increase the extent of anchoring to lipids.

Discussion

Thus, VP40 of Ebola virus, when expressed in the absence of other viral proteins, can induce the formation of membrane-encompassed particles, much in the manner of the matrix proteins of VSV, rabies, and simian immunodeficiency virus (Giddings et al., 1998; Harty et al., 1999; Justice et al., 1995; Li et al., 1993). Cellular proteins containing the WW domain are, in all likelihood, crucial for this process, as VP40 containing an altered version of a PPXY motif at amino acids 10-13 induces little or no particle formation. Harty et al. (1999) demonstrated that the matrix proteins of VSV and rabies viruses, which possess this motif at their N-termini, bind the cellular Yes-kinase-associated and Nedd4 proteins via a PPXY motif-WW domain, interaction, and that the loss of this motif results in impaired virus release from infected cells. Jayakar et al. (2000) recently demonstrated that mutation of the PPXY motif in the matrix protein of VSV impedes budding of fully assembled virions at the plasma membrane. The data described herein provides evidence for an important role of the PPXY motif in particle formation induced by VP40, and suggest that cellular proteins are crucial players in this process.

The efficiency of particle production markedly increased when the second ATG codon of VP40 (codon 14) was changed to GCG (alanine), but the reason for this enhancement remains unclear. This ATG codon immediately follows the PPXY motif. Perhaps the faster-migrating version of VP40, which lacks the PPXY motif, interferes with the assembly or budding of full-length VP40 molecules at the cell surface, or with the interaction between VP40 and a cellular protein. Whether translation from this second ATG occurs in actual viral infection or is an artifact of the system employed in this study is unknown.

Ruigrok et al. (2000) reported that VP40 expressed in *E. coli* can bind liposomes in vitro and that this interaction is largely electrostatic. In mammalian cells, a substantial amount of VP40 bound to the cellular membrane, and that this interaction was disrupted negligibly by the presence of 1 M NaCl, indicating that at least one hydrophobic domain is involved in this interaction. A small but appreciable portion of VP40 partitioned with detergent in the manner of an integral membrane or lipid-anchored protein in Triton X-114 phase-partitioning analysis. This result, together with the inability of 1 M NaCl to dissociate VP40 from the lipid bilayer, indicates that the protein has certain properties of an integral membrane protein, as do a number of matrix proteins of negative-stranded RNA viruses (Chong et al., 1993; Zhang et al., 1996), even though Ebola VP40 does not appear to contain a region of significant length and hydrophobicity to span the cell membrane. Short hydrophobic stretches of VP40 may be able to penetrate the lipid bilayer to some extent, lending modest integral-membrane character to the protein.

Ruigrok et al. (2000) also reported that a deletion mutant of VP40 containing amino acids 31-212 failed to bind liposomes efficiently, indicating that the C-terminus of VP40 is absolutely required for membrane binding. To elucidate the domains involved in the association of VP40 with cellular membranes, carboxy and amino-terminal deletion mutants were constructed. VP40 lacking its C-terminal 50 amino acids demonstrated appreciably reduced membrane association. The Kyte-Doolittle hydrophobicity plot (1982) of VP40 indicates that amino acids 277-326 of the protein are primarily hydrophobic, so that deletion of amino acids 277-326 eliminates a substantial hydrophobic region that is likely important for efficient membrane-binding by the full-length protein. This hypothesis is supported by the fact that 1 M NaCl completely disrupted this association, suggesting that affinity of this deletion construct with the lipid bilayer depends primarily on electrostatic interactions.

When amino acids 227-326 of VP40 were deleted, the resulting truncated protein associated with the lipid bilayer as efficiently as wild-type VP40; moreover, C-terminal deletion of amino acids 177-326 resulted in a protein with much higher affinity for the lipid bilayer than was found for wild-type VP40. Salt treatment did not perturb membrane association of these truncated versions of VP40, indicating the presence of hydrophobic interactions mediated by the N-terminal 176 amino acids of the protein.

The hydrophobicity plot indicates that amino acids 227-276, and particularly amino acids 177-226, are primarily hydrophilic. Deletion of the hydrophilic residues present in this region of VP40 may allow the truncated protein to fold into a structure capable of strong hydrophobic association with the cell membrane, perhaps by effectively exposing the highly hydrophobic central domain of the protein. These results are consistent with data obtained by Triton X-114 extraction analysis. Since VP40 lacking its C-terminal 50 amino acids was unable to produce particles, and these C-terminal residues appear to be required for efficient membrane association of VP40, binding of this highly hydrophobic region to the lipid bilayer may be an essential step in the particle formation process.

The crystal structure of amino acids 31-326 of Ebola virus was recently elucidated by Dessen et al. (2000). It shows VP40 to be distinct from other viral matrix proteins, in that it consists of two similar domains connected by a flexible linker at amino acids 195-200. Ruigrok et al. (2000) showed that amino acids 31-212 of VP40 form hexamers spontaneously in solution. Dessen and associates postulate that, during the life cycle of Ebola virus, VP40 molecules associate with the lipid bilayer through interactions contributed primarily by their C-termini. After membrane binding, the molecules undergo a conformational change that frees their N-termini for hexamerization. These hexamers then form building blocks for a lattice that underlies the plasma membrane, and subsequently may interact with the cytoplasmic tails of viral glycoproteins and/or the ribonucleoprotein complex. This model is based on data demonstrating the hexamerization of VP40 molecules that lack their N-terminal 30 amino acids as well as their C-terminal 114 amino acids. The PPXY motif that appears crucial for membrane-bound particle formation is located at amino acids 10-13 of VP40, and this motif most likely interacts with a cellular protein that exhibits a WW domain during virus particle assembly or budding. It has not yet been demonstrated that VP40 with a truncated C-terminus can form hexamers when the entire N-terminus is present. If hexamerization does occur during virion morphogenesis, the 18 hexamers that form presumably must leave the PPXY motif accessible to cellular proteins that participate in particle formation and/or budding.

EXAMPLE 4

Particles Comprising Filovirus Matrix Protein and Glycoprotein

Materials and Methods

Cells.

293T human embryonic kidney cells were maintained in Dulbecco's modified Eagle medium supplemented with 10% fetal calf serum, L-glutamine and penicillin-streptomycin-gentamicin solution. The cells were grown in an incubator at 37° C. in 5% $CO_2$.

Plasmids.

Full-length cDNAs encoding the Ebola virus (species Zaire) VP40 or GP were cloned separately into a mammalian expression vector, pCAGGS/MCS (Kobasa et al., 1997; Niwa et al., 1991), which contains the chicken β-actin promoter. The resultant constructs were designated pCEboZVP40 and pCEboZGP, respectively.

Cell Transfection for Expression of VP40 and GP.

293T cells ($1\times10^6$) were transfected with plasmids using the Trans IT LT-1 reagent (Panvera, Madison, Wis.) according to the manufacturer's instructions. Briefly, 1 μg of DNA in 0.1 mL Opti-MEM (Gibco-BRL) and 3 μL of the transfection reagent were mixed, incubated for 10 minutes at room temperature, and added to the cells. Transfected cells were incubated at 37° C. for 24 or 48 hours.

Electron Microscopy.

Ultrathin section electron microscopy was performed as follows. Twenty-four hours post-transfection of 293T cells with plasmids, the cells were washed with phosphate-buffered saline (PBS) and fixed for 20 minutes with 2.5% glutaraldehyde (GLA) in 0.1 M cacodylate buffer (pH 7.4). They were scraped off the dish, pelleted by low-speed centrifugation and then fixed for 30 minutes with the same fixative. Small pieces of fixed pellet were washed with the same buffer, postfixed with 2% osmium tetroxide in the same buffer for 1 hour at 4° C., dehydrated with a series of ethanol gradients followed by propylene oxide, embedded in Epon 812 Resin mixture (TAAB) and polymerized at 70° C. for 2 days. For immune electron microscopy, cells were fixed with 4% paraformaldehyde and 0.1% GLA, dehydrated and embedded in LR White Resin (London Resin Company Ltd.). Thin sections were stained with uranil acetate and lead citrate, and examined with a JEM-1200EX electron microscope at 80 Kv.

For negative staining, culture media of 293T cells were collected at 24 hours post-transfection onto a Formvar-coated copper grid, stained with 2% phosphotungstic acid solution (PTA) and examined with a JEM-1200 electron microscope at 80 Kv.

For immune electron microscopy, the samples were absorbed to Formvar-coated nickel grids and washed with PBS containing 0.5% bovine serum albumin (PBS-BSA). The grids were then treated with mouse anti-GP monoclonal antibody (a mixture of ZGP12, ZGP42, and ZGP133 (31); 1:150 in PBS-BSA) or rabbit anti-VP40 polyclonal antibody (1:300 in PBS-BSA), and rinsed six times with PBS, followed by incubation with a goat antimouse immunoglobulin conjugated to 15-nm gold particles (1:50 dilution; BBInternational) or a goat antirabbit immunoglobulin conjugated to 5-nm gold particles (1:100 dilution; BBInternational). After washing, the samples were fixed for 10 min in 2% glutaraldehyde and negatively stained with 2% PTA.

Results

Pleomorphic Particle Formation by GP.

To determine the morphology of vesicles induced by Ebola virus GP expression, GP-expressing cells and their supernatants were analyzed by electron microscopy. The ultrathin sections of these cells showed particle-like structures with surface spikes budding from the plasma membrane; no such structures were observed using cells transfected with the expression vector alone. As previously observed in the recombinant vaccinia virus system (Volchkov et al., 1998), pleomorphic structures similar to virosomes with a range of diameters were apparent in the supernatants of GP-expressing cells. The spikes on the surface of the vesicles reacted with anti-GP monoclonal antibodies, confirming the GP derivation of the structures.

VP40 Induces Filamentous Particle Formation.

To determine how VP40 protein expressed in 293T cells is released into culture medium (Harty et al., 2000; Timmins et al., 2001), the VP40-expressing cells were analyzed by transmission electron microscopy. The ultrathin sections of the cells expressing VP40 showed budding of filamentous structures (approximately 65 nm in diameter) on the cell surface. In some cells, the plasma membranes appeared ruffled and to consist of two bilayers. Aggregated ribosomes were occasionally found in the cytoplasm of cells expressing VP40, as were electron-dense filamentous structures (approximately 45 nm in diameter), which were never seen in cells transfected with the expression vector alone. The budding particles and membrane ruffles reacted with rabbit anti-VP40 polyclonal antibody, confirming that VP40 had contributed to the generation of these structures. In studies to further determine the size and morphology of the VP40 particles released from cells, the supernatants of cells expressing this protein were centrifuged through 20% sucrose, and the pelleted material was negatively stained with 2% PTA and analyzed by electron microscopy. Filamentous particles, which had uniform diameters of approximately 65 nm but varied lengths, were observed. These results indicate that VP40 alone can induce the formation of filamentous particles, which bud from the cell surface.

VP40-GP Interaction in Particle Morphogenesis.

To determine how GP expression affects VP40-driven particle formation, 293T cells were transfected with both VP40- and GP-expressing plasmids. In ultrathin sections of the transfected cells, filamentous particle-like structures of 80-nm external diameter were observed that were budding from the plasma membrane. The structures possessed spikes of approximately 10 nm on their surface, in contrast to the structures observed in cells expressing VP40 alone. Also, unlike the findings with expression of GP alone, few pleomorphic particles were observed. The particle structures were studied in more detail after negative staining of the particles in culture supernatants of cells expressing both VP40 and GP. Filamentous Ebola virus-like particles with surface spikes of approximately 85-nm in external diameter and lengths that ranged to 10 μm were observed. The spikes projected from the particle surface at 5- to 10-nm intervals and were morphologically indistinguishable from those on the Ebola virion surface (Feldmann et al., 1996; Peters et al., 1995). Labeling of the spikes with a mixture of anti-GP monoclonal antibodies conjugated with gold particles confirmed their identity as GP. Furthermore, when treated with 0.03% Triton X-100 and with both the anti-VP40 antibody conjugated to 5-nm gold particles and a mixture of anti-GP monoclonal antibodies conjugated to 15-nm gold particles, the filamentous particles became labeled with both antibodies, demonstrating that the Ebola vires-like particles contained GP as well as VP40 proteins. These results demonstrate GP incorporation into VP40-generated filamentous structures, without affecting filamentous particle formation.

Discussion

A hallmark of Ebola virus is its filamentous virions as featured in its family name Filoviridae. The shape of enveloped viruses are determined by viral proteins in retroviruses (Campbell et al., 1997; Gay et al., 1998; Joshi et al., 2000) or by both viral RNA length and proteins in VSV (Pattnaik et al., 1991). Because specific interactions among viral components are required for the formation of defined virion shapes, understanding of such interactions can lead to the identification of targets for the development of antiviral compounds.

As shown herein by electron microscopy, the expression of VP40 in the absence of any other Ebola virus proteins leads to the formation of filamentous particles, which resemble spikeless virions released into the supernatant of cultured Ebola virus-infected cells (Geisbert et al., 1995). Thus, these results suggest that the Ebola virus VP40 possesses structural information necessary and sufficient to induce the formation of filamentous particles, which then bud from the plasma membrane. Interestingly, some filamentous structures were observed in the cytoplasm of cells expressing VP40 as have been found in the cytoplasm of the cells infected with Ebola virus. Similar structures have also been observed in cells expressing the M1 protein of influenza virus or the GAG protein of retrovirus (Delchambre et al., 1989; Gheyson et al., 1989; Gomez-Puertas et al., 2000). However, the tubular structures observed upon expression of influenza virus M1 alone were not seen during normal viral infection or when M1 was coexpressed with other influenza viral proteins. Thus, VP40 may form intracellular filamentous structures by self-aggregation.

Membrane ruffles containing VP40 protein were observed in some VP40-expressing cells. The M protein of VSV induces similar double-layered membranes at the cell surface when expressed from recombinant Sendai virus (Sakaguchi et al, 1999). IpaC protein secreted by *Shigella flexneri* has also been linked to large-scale membrane extension in macrophages, including lamellipodia and membrane ruffles (Kuwae et al, 2001; Tran Van Nhieu et al., 1999), while *Salmonella typhimurium* triggers the formation of host cell membrane ruffles in nonphagocytic cells (Ginocchio et al., 1994; Zhou et al., 1999). These membrane ruffles are thought to result from interactions between the bacterial proteins, including IpaC, and the actin cytoskeletons of host cells (Tran Van Nhieu et al., 1999; Zhou et al., 1999). In Ebola virus-infected cells, host cell plasma membranes proliferate extensively at the peak stage of viral budding (Geisbert et al, 1995), as observed in cells expressing VP40 alone. Thus, VP40 may interact with actin filaments during the assembly or budding of Ebola virus at the cell surface.

The impact of glycoprotein interaction with the matrix protein on virion morphology differs among viruses. For example, deletion of the cytoplasmic tails of the influenza virus hemagglutinin and neuraminidase alters virus morphology (Jin et al., 1997; Mitnaul et al., 1996), while the characteristic morphology of rabies virus and VSV do not depend on glycoprotein-matrix protein interaction (Mebatsion et al, 1996; Mebatsion et al., 1994; Schnell et al., 1998; Takada et al., 1997). The Ebola virus GP, like VSV-G, was incorporated into filamentous particles without affecting the morphology of the particles. However, such interaction may contribute to the efficiency of budding, as demonstrated by research on VSV (Jayakar et al., 2000; Mebatsion et al., 1999).

In conclusion, VP40 induces VP40 containing-filamentous particle formation and GP spikes are incorporated into VP40 induced-filamentous particles upon coexpression of GP and VP40, resulting in Ebola virus-like particles.

EXAMPLE 5

A Method to Screen for Modulators of Viral Transcription or Replication

To produce viral vectors for an antiviral screening method, vectors were prepared that expressed a rhabdovirus or filovirus protein and a reporter. In one embodiment, a reporter gene replaces rhabdovirus GP sequences in genomic rhabdovirus DNA. In one embodiment, a reporter gene replaces filovirus GP sequences in genomic filoovirus DNA. In one embodiment, viral protein expression vectors useful with the recombinant genomic DNA may include one expressing filovirus GP and optionally one or more vectors expressing one or more of rhabdovirus N, P, M and L. In another embodiment, a reporter gene replaces sequences in genomic filovirus DNA. The Filovirus protein expression vectors, e.g., Marburg virus or Ebola virus vectors, include one or more of the following sequences: sequences for L, NP, VP30 and/or VP35. If more than one vector is employed, the vectors may be physically linked or each vector may be present on an individual plasmid or other, e.g., linear, nucleic acid delivery vehicle.

To develop an antiviral to Ebolavirus, the entry process, including receptor binding and/or fusion, was targeted. To identify compounds that interfere with these steps in the viral life cycle, a replication-incompetent Vesicular Stomatitis Virus (VSV) was employed that lacks the VSV glycoprotein gene and contains the GFP gene instead. This replication-incompetent VSV was pseudotyped with Ebola GP glycoprotein. This pseudotyped virus infects cells once, resulting in GFP gene expression. In the presence of compounds that interfere with Ebola GP-mediated binding or fusion, reporter gene expression is abrogated. This system was used to screen about 6,300 compounds at The National Screening Laboratory for the Regional Centers of Excellence in Biodefense at Harvard University, Boston, Mass., and 144 compounds were identified that reduced reporter gene expression by more than 90%.

To verify whether the compounds indeed inhibit Ebolavirus infection, a biologically contained Ebolavirus expressing GFP protein (EbolaΔVP30-GFP virus) (see Example 2) was employed. 111 of the originally-identified 144 compounds were tested and 24 were identified that reduced the infectivity of the biologically contained Ebolavirus by at least 90% (FIG. 11). For those compounds, the 50% inhibitory concentration ($IC_{50}$) and cytotoxic concentration ($CC_{50}$) were determined. Benztropine mesylate emerged as a lead candidate.

Further studies revealed that benztropine mesylate efficiently reduced the infectivity of VSV pseudotyped with GPs of all known subtypes of Ebolavirus (i.e., Zaire, Reston, Sudan, Ivory Coast); the titers of these pseudotyped viruses were reduced by 98-99%. Benztropin mesylate was also effective against VSV pseudotyped with the GP protein of Marburgvirus, although to a lesser extent (reduction of virus titers of about 75%). On the other hand, benztropine mesylate does not affect the growth of viruses such as VSV and influenza virus, indicating the specificity of this compound for Ebolavirus.

Binding of Ebolavirus to cell surface activates the phosphoinositide-3 (PI3) kinase-Akt pathway. It was determined that benztropine mesylate did not inhibit the phosphoinositide-3 (PI3) kinase-Akt pathway per se. However, benztropine mesylate was found to inhibit infection of VSV pseudotyped with Ebola GP that was bound to cell surfaces at 0-4° C., temperatures that may disrupt endocytosis and vesicle trafficking.

Benztropine mesylate is a known and commercially available inhibitor of the dopamine transporter and is used to treat the symptoms of Parkinsons's disease and other neurological disorders. Since benztropine mesylate is known to bind to receptors for neurotransmitters, Ebolavirus might utilize these receptors as second receptors for entry. Thus, benztropine mesylate might inhibit binding of Ebolavirus to neurotransmitter receptors, resulting in the inhibition of activation of PI3 kinase-Akt pathway for entry. Alternatively, or in addition to blocking neurotransmitter receptors, benztropine mesylate may inhibit fusion of the virus envelope with the cellular membrane.

EXAMPLE 6

Materials and Methods

Cells.

VeroVP30 cells were established as previously described (Halfmann et al., 2008) and grown in Eagle's minimal essential medium (MEM) supplemented with 10% fetal calf serum (FCS). Vero and CV-1 cells were cultured under the same conditions as VeroVP30 cells. 293T cells were maintained in Dulbecco's modified Eagle's medium (DMEM) supplemented with 10% FCS. Madin-Darby canine kidney (MDCK) cells were kept in MEM containing 5% newborn calf serum (NCS). A549 cells were maintained in Kaighn's Modification of Ham's F-12 (F-12K) medium with 10% FCS. All cells were maintained at 37° C. with 5% $CO_2$.

Viruses.

The EbolaΔVP30 expressing GFP (EbolaΔVP30-GFP) and Influenzavirus A/WSN/33 (H1N1) were generated, propagated, and titrated as previously described (Halfmann et al., 2008; Neumann et al., 1999). Vesicular stomatitis virus (VSV) strain Indiana, vaccinia virus, and adenovirus Ad-5 were propagated and titrated in Vero cells, CV-1 cells, and A549 cells, respectively.

High Throughput Screening Assay.

For compound screening, VeroVP30 cells were seeded in 384-well culture plates. After about 2 hours of incubation at 37° C., 5% $CO_2$, compounds dissolved in DMSO were added. The cells were then incubated at 37° C. for another approximate 2 hours, before being inoculated with EbolaΔVP30-GFP virus. All plates included wells to which DMSO was added without any compound for GFP-positive (virus inoculated) and negative (no virus inoculated) controls for the z'-factor calculation. GFP intensities were measured by use of a Safire II plate reader (Tecan Group Ltd., Mannedorf, Switzerland). Cell viabilities were determined by using a CellTiter-Glo™ Luminescent Cell Viability Assay (Promega, Madison, Wis., USA) and compared to GFP-positive controls, which were cells treated with DMSO only and inoculated with virus. The high throughput screen was carried out at the Keck-UWCCC Small Molecule Screening Facility (Madison, Wis.).

Virus Binding and Entry Assay.

Recombinant VSV viruses, VSVΔG*-Ebola virus GP and VSVΔG*-VSV G, were generated as previously described (Ito et al., 1999; Takada et al., 1997). To determine whether the compounds inhibit virus binding/entry, Vero cells in 12-well plates were treated with 500 μL of 2% FCS-MEM containing 10 μM compounds for 2 hours prior to infection with the recombinant viruses. Since the recombinant virus possesses the GFP reporter gene instead of the VSV G gene, cells expressing GFP after virus inoculation indicate that the virus bound, entered, and replicated the protein in the those cells. Therefore, to determine the efficiency of virus binding/ entry mediated by Ebolavirus GP, GFP-positive cells were counted under a fluorescence microscope 16 to 20 hours after virus inoculation and the numbers compared between the two recombinant VSV viruses.

Virus Minigenome Replication Assay.

A plasmid-based minireplicon assay was performed as described by Watanabe et al. (Watanabe et al., 2007). To determine whether the compounds inhibit protein expression from the Ebolavirus minigenome, 293T cells were transfected with plasmids for the expression of Ebolavirus nucleoprotein (NP), L, VP35, VP30, Ebolavirus minigenome encoding firefly luciferase, and T7 polymerase. Compounds were added into the media at a final concentration of 10 μM at 6.5 hours post-transfection. Three days post-transfection, cells were disrupted and mixed with Steady Glo (Promega), and luciferase activities were detected by using Glomax (Promega). A reduction in luciferase activity indicates either inhibition of Ebolavirus RNA-dependent RNA polymerase activity or T7 polymerase activity, which is required for Ebola minigenome expression.

Results

Anti-Ebolavirus High Throughput Compound Screening.

To identify anti-Ebolavirus compounds, Known Bioactive Library 01, which consists of three commercially available collections totaling 4,160 compounds, was screened with the EbolaΔVP30-VeroVP30 system. The z'-factor, a measure of assay quality, was consistently over 0.5 and averaged 0.66 (range; 0.50-0.76), indicating that the EbolaΔVP30-VeroVP30 system was suitable for the HTS assay. Nineteen compounds were identified as anti-Ebolavirus candidates. Six of these were gedunin-like limonoids that shared structural similarities; these six compounds were focused on for further analysis.

Anti-Ebolavirus Activities of Qedunin and Qedunin-Derivatives.

Known Bioactive Library 01 contains 41 gedunin-like limonoids. To assess whether all of these compounds show anti-Ebolavirus activity, 39 accessible compounds were re-screened. For this secondary screening, $1.5 \times 10^4$ cells/30 μL/well were seeded in a 384-well plate, compounds were added at a concentration of 10 μM, and 30 μL of the EbolaΔVP30-GFP virus was added at an MOI of 0.1, so that the final concentration of the compounds was 5 μM. Fourteen of the compounds reduced the GFP intensity by more than 75%, while cell viabilities were maintained at more than 70%, relative to the positive control (cells that received DMSO and inoculated the virus) (Table 1). The other 25 gedunin-like limonoids tested reduced the GFP intensity by less than 45% (range; 45%-negative 49%) or cell viabilities by more than 95%.

TABLE 1

| Compound | % GFP inhibition | % cell viability |
|---|---|---|
| Epoxygedunin* | 103 | 71 |
| Gedunin* | 102 | 77 |
| 1,3-Dideacetyl-7-deacetoxy-7-oxokhivorin* | 100 | 78 |
| Dihydrogedunin | 96 | 79 |
| 7-Deacetoxy-3-deacetyl-7-oxokhivorin* | 92 | 80 |
| 3beta-Acetoxydeoxodihydrogedunin | 90 | 80 |
| Tridesacetoxykhivorin | 89 | 75 |
| 3alpha-Hydroxydeoxodihydrogedunin* | 85 | 94 |
| 1,3-Dideacetylkhivorin | 82 | 78 |
| Deacetoxy-7-oxogedunin | 80 | 79 |
| Gedunol | 79 | 82 |
| 3beta-Hydroxydeoxodihydrogedunin | 75 | 79 |
| 1,2alpha-Epoxydeacetoxydihydrogedunin* | 75 | 77 |
| 3beta-Hydroxydeoxydesacetoxy-7-oxogedunin | 75 | 81 |
| Heudelottin C | 104 | 5 |
| Deacetylgedunin | 45 | 86 |
| Deacetoxy-7-oxisogedunin | 41 | 84 |
| 1,7-Dideacetoxy-1,7-dioxokhivorin | 39 | 88 |
| Isogedunin | 35 | 86 |
| 6-Acetoxyangolensic acid methyl ester | 32 | 88 |
| Tridesacetoxykhivorin | 28 | 94 |
| 7-Deacetoxy-7-oxokhivorin | 26 | 90 |
| 1-Deacetoxy-1-oxo-3,7-dideacetylkhivorin | 19 | 94 |
| 6-Hydroxyangolensic acid methyl ester | 15 | 94 |
| 1,7-Dideacetoxy-1,7-dioxo-3-deacetylkhivorin | 14 | 87 |
| 7-Deacetylkhivorin | 13 | 91 |
| 3-Deacetylkhivorin | 6 | 102 |
| Utilin | 4 | 75 |
| 7-Epikhivorin | 4 | 79 |
| Angolensic acid, methyl ester | 4 | 85 |
| 7-Desacetoxy-6,7-dehydrogedunin | 2 | 70 |
| Khivorin | 0 | 82 |
| Entandrophragmin | −12 | 83 |
| Andirobin | −12 | 91 |
| Prieurianin | −17 | 89 |
| 2,3-Dihydroisogedunin | −17 | 91 |
| 11alpha-Acetoxykhivorin | −47 | 93 |
| Heudelottin E | −49 | 93 |
| 7-Deacetyldihydrogedunin | −30 | 85 |

*These are the compounds selected for further analyses.

Comparison of compounds with and without anti-Ebolavirus activity indicated that those compounds with activity against Ebolavirus had a core structure having four benzene rings and a furan ring. In addition, the 1-Keto group of ring A of these compounds may have reduced virus infectivity. For further analysis, five gedunin-like limonoids were selected (FIG. 12; gedunin, epoxygedunin, 1,3-Dideacetly-7-Deacetoxy-7-Oxokhivorin, 7-Deacetoxy-3-deacetyl-7-Oxokhivorin, and 1,2alpha-Epoxy-7-Deacetoxy-7-Oxo-Deoxyhydrogedunin).

Figure 13:
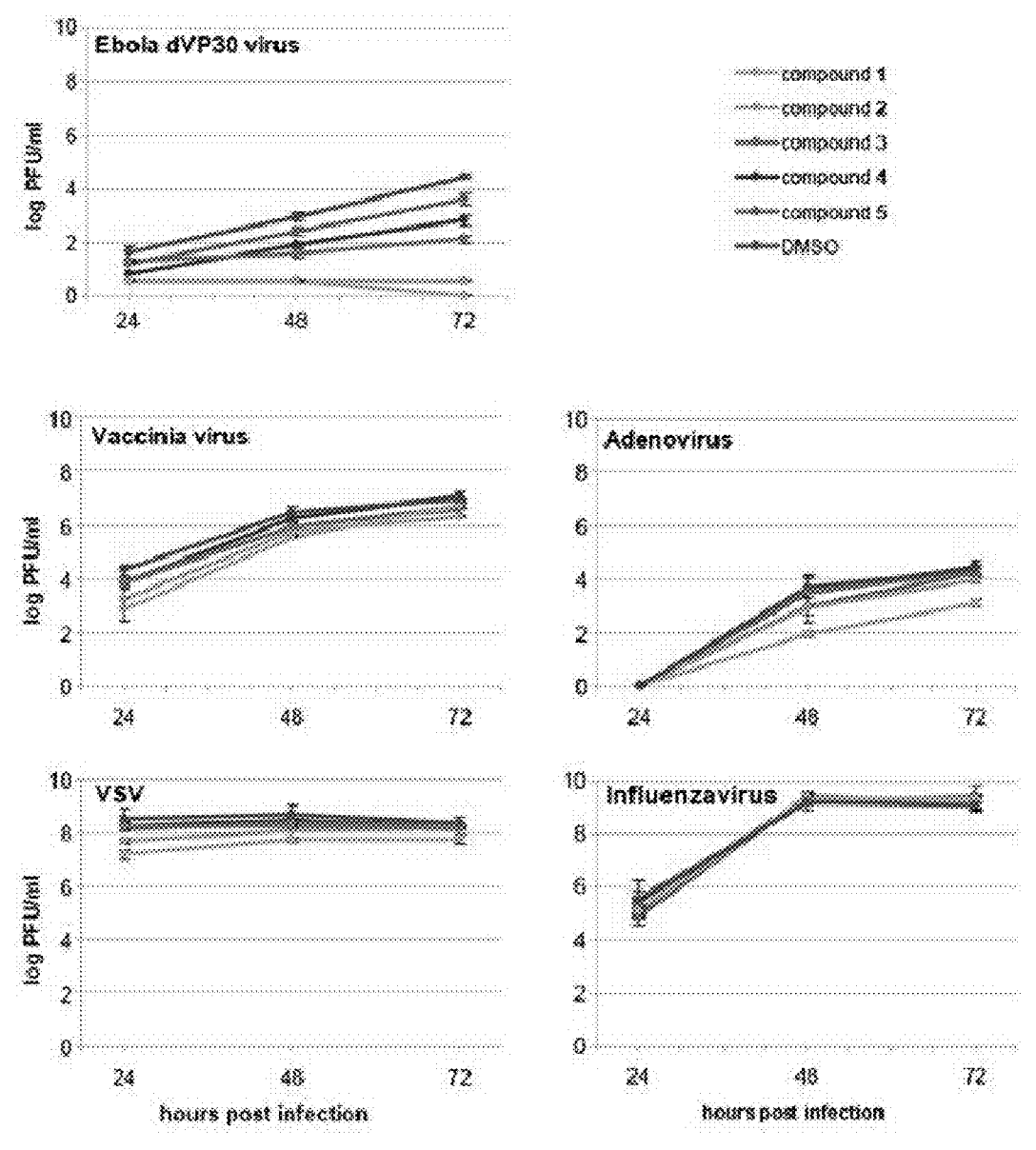

To confirm the anti-Ebolvirus activities of these 5 compounds, the growth kinetics of EbolaΔVP30-GFP were assessed in their presence. The compounds (10 µM) were added to Vero VP30 cell culture medium 2 hours prior to infection (M01=0.001) and the medium was then harvested 24, 48, and 72 hours post-infection. As shown in FIG. 13, all five gedunin-like compounds inhibited the growth of EbolaΔVP30-GFP. Gedunin and epoxygedunin completely inhibited EbolaΔVP30-GFP growth, while the other three compounds reduced virus growth by at least 1 $\log_{10}$ titer (85% reduction) at 72 hours post-infection. These data confirm the anti-Ebolavirus activity of these compounds.

To calculate the anti-Ebolavirus efficacies of the compounds, their 50% inhibitory concentrations ($IC_{50}$) were determined by measuring GFP intensity following virus infection at an MOI of 0.1. The compounds showed significant activity with $IC_{50}$ values of 0.56 µM or lower, with the exception of 1,2alpha-Epoxy-7-Deacetoxy-7-Oxo-Deoxyhydrogedunin (Table 2), whose $IC_{50}$ was 7.12 µM. The 50% cytotoxic concentrations ($CC_{50}$) of the compounds were greater than 10 µM, indicating low toxicity to cell culture.

TABLE 2

$IC_{50}$s and $CC_{50}$s of Gedunin and Gedunin derivatives

| compound | $IC_{50}$ (µM) | $CC_{50}$ (µM) |
|---|---|---|
| Gedunin | 0.33 | >10 |
| Epoxygedunin | <0.15 | >10 |
| 1,3-Dideacetly-7-Deacetoxy-7-Oxokhivorin | <0.15 | >10 |
| 7-Deacetoxy-3-deacetyl-7-Oxokhivorin | 0.56 | >10 |
| 1,2alpha-Epoxy-7-Deacetoxy-7-Oxo-Deoxyhydrogedunin | 7.12 | >10 |

Virus-Specific Inhibition of Compounds.

Gedunin and some gedunin-derivatives have antimalarial (MacKinnon et al., 1997), anti-HIV (http://home.ncifcrf.gov/mtdp/Catalog/compounds/309912.html), anti-insect (Nathan et al., 2005), and anti-cancer (Uddin et al., 2007) activities. Therefore, it was determined whether these five compounds inhibited other viruses, namely vaccinia virus, adenovirus, VSV, and influenza virus. Experiments were carried out with 10 µM compounds and infections at an MOI of 0.001 (vaccinia virus, adenovirus) or 0.00001 (VSV and influenza virus). As shown in FIG. 13, none of the compounds significantly inhibited any of the viruses, although gedunin was slightly inhibitory to adenovirus, indicating that the anti-virus activities of these compounds are not universal.

Inhibition of Ebola GP-Dependent Virus Entry.

The first step of Ebolavirus infection is virus binding and entry into the host cell via its surface glycoprotein (GP). To examine whether gedunin and gedunin-like compounds inhibit virus entry; we adapted a VSV pseudotype system (Ito et al., 2001; Takada et al., 1997). The pseudotype viruses, VSVΔG*-Ebolavirus GP and VSVΔG*-VSV G, possess Ebolavirus GP and VSV G on their surfaces, respectively. Initiation of infection relies upon those surface glycoproteins. In addition, these recombinant viruses possess a GFP reporter gene in place of the VSV G gene, such that infected cells can be distinguished by GFP expression.

Compounds were added 2 hours prior to the pseudotype virus infections, and virus infectivy was determined by counting the number of GFP-positive cells after an overnight incubation at 37° C. All five compounds appreciably reduced the infectivity of VSVΔG*-Ebolavirus GP but not that of VSVΔG*-VSV G (FIG. 14), indicating that these compounds inhibit Ebolavirus GP-dependent virus entry. Interestingly, 2alpha-Epoxy-7-Deacetoxy-7-Oxo-Deoxyhydrogedunin, which inhibited 75% of GFP expression from EbolaΔVP30-GFP virus (Table 2) and had an $IC_{50}$ of 7.12 µM (Table 2), allowed 6.5±1.6% of VSVΔG*-Ebolavirus GP infection, whereas the other four compounds, which inhibited more than 90% of GFP expression of EbolaΔVP30-GFP virus infection (Table 2) and had $IC_{50}$s more than 10 times lower than that of 2alpha-Epoxy-7-Deacetoxy-7-Oxo-Deoxyhydrogedunin, allowed less than 3% of VSVΔG*-Ebolavirus GP infection. These data suggest that the level of Ebolavirus inhibition of these compounds is associated with their ability to inhibit Ebolavirus GP-dependent virus entry.

Inhibition of Protein Expression from the Ebolavirus Minireplicon.

The next steps in Ebolavirus replication are virus genome replication and virus protein expression. To examine whether the tested compounds inhibit Ebolavirus genome replication and protein expression, an Ebolavirus minigenome replication assay was performed. The compounds were added to cell culture media 6.5 hours post-transfection to avoid affecting transfection efficacies. As shown in FIG. 15, gedunin and epoxygedunin significantly reduced firefly luciferase reporter protein expression from the Ebolavirus minireplicon. The luciferase activities in cells treated with these two compounds were 1.3%±0.2% and 1.0%±0.1% of those treated with DMSO, respectively. The other three compounds did not reduce the luciferase activities. Since gedunin and epoxygedunin have a 7-acetate group on their ring B, but the other three compounds do not, this residue may contribute to the inhibition of Ebolavirus genome replication and/or protein expression.

Hsp90 Inhibitors Reduce Protein Expression from the Ebolavirus Minireplicon.

The inhibitor activities of gedunin and some of its derivatives have been tied to the heat shock protein Hsp90 (Hieronymus et al., 2006), suggesting that their Ebolavirus inhibitory mechanisms may involve inhibition of Hsp90 or degradation of its substrate proteins. Therefore, it was determined whether Hsp90 inhibitors have anti-Ebolavirus activity. Four Hsp90 inhibitors, geldanamycin (GM), 17-AAG (17-Allylamino-17-demethoxygeldanamycin), CCT 018159 (4-[4-(2,3-Dihydro-1,4-benzodioxin-6-yl)-5-methyl-1H-pyrazol-3-yl]-6-ethyl-1,3-benzenediol), and AEG 3482 (6-Phenylimidazo[2,1-b]-1,3,4-thiadiazole-2-sulfonamide) were assessed for their anti-Ebolavirus activities by use of an Ebolavirus growth assay, a VSV pseudotype virus assay, and a minireplicon assay.

Figures 16A, 16B, 16C, 16D:
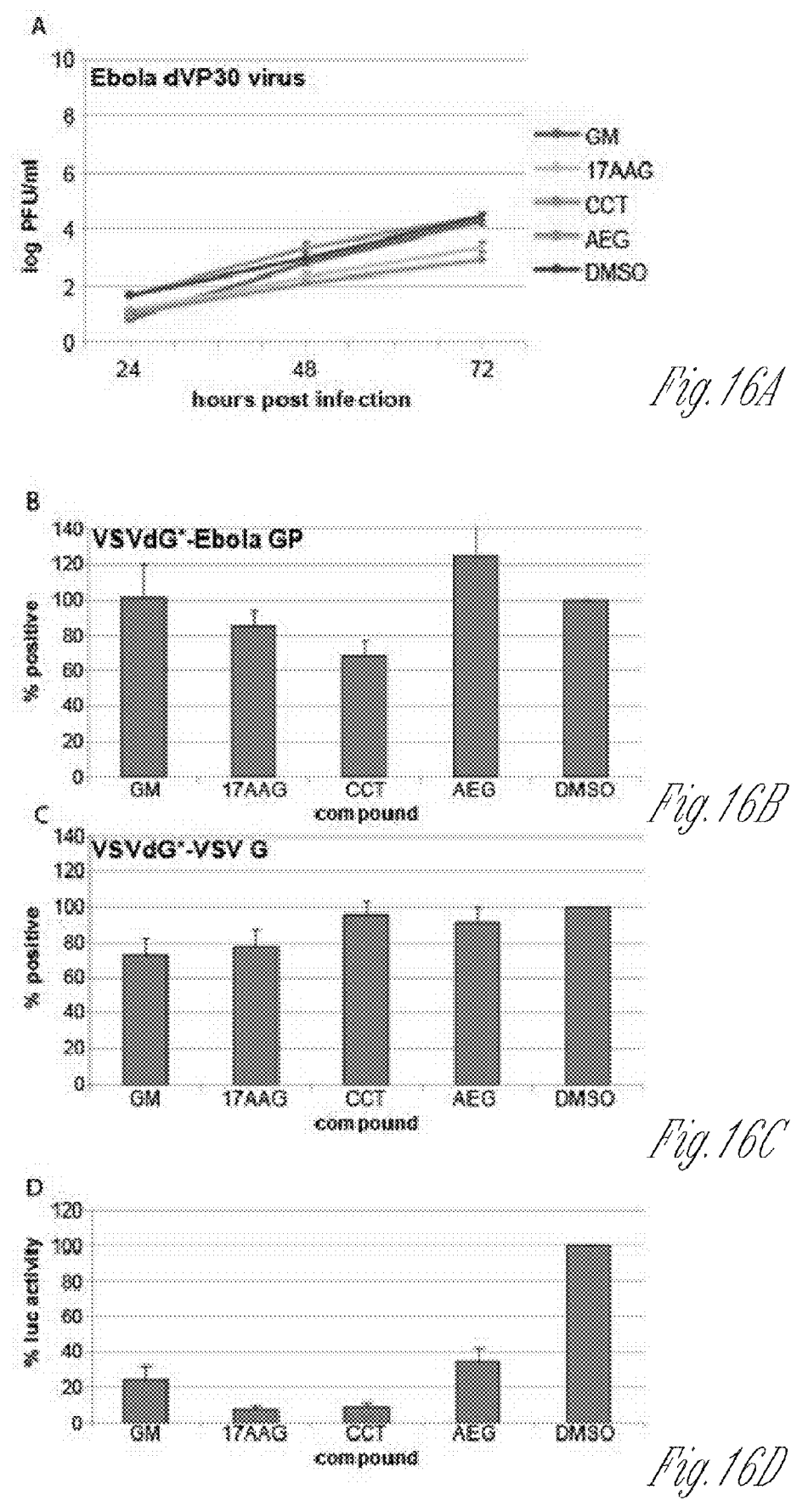

CCT and 17AAG reduced EbolaΔVP30 virus growth (97% and 92% reduction, respectively, at 72 hours post-infection), but GM and AEG did not (30% and 5% reduction, respectively, 72 hours post-infection) (FIG. 16A). Although all five of the gedunin-like compounds significantly reduced virus infection mediated by Ebolavirus GP, only CCT 018159 of the Hsp90 inhibitors slightly reduced the Ebolavirus GP-mediated virus infection (FIGS. 16B and 16C). Infectivities of VSVΔG*-Ebolavirus GP, which were standardized by the infectivities of VSVΔG*-VSV G, were 137% (GM), 110% (17-AAG), 71% (CCT 018159) and 135% (AEG 3482). All four Hsp90 inhibitors reduced reporter protein expression from the Ebolavirus minigenome [luciferase activities were 7.9%±1.5% (17-AAG), 8.8%±2.6% (CCT 018159), 24.7%±7.7% (GM), and 34.0%±8.0% (AEG 3482)] (FIG. 16D). These data demonstrate that Hsp90 inhibitors are potential anti-Ebolavirus agents and that their inhibitory mechanisms likely differ from those of gedunin and its derivatives.

Discussion

A high throughput molecular screen for anti-Ebolavirus agents identified gedunin and its derivatives as anti-Ebolavirus candidates. Further analysis demonstrated that these compounds inhibit Ebolavirus via Ebolavirus GP-dependent virus binding/entry and that some of them also reduce Ebolavirus genome replication and/or protein expression. Gedunin-like limonoids are found in extracts of plants from the Meliaceae (Mahogany) family and have been used in traditional medicine in tropical America and in West and East Africa (Bray et al., 1990), suggesting that there is potential for their use in humans, if in vivo experiments confirm their anti-Ebolavirus activities.

In this study, the specificity of anti-Ebolavirus compounds was assessed by testing their inhibitory activities against influenzavirus, VSV, vaccinina virus, and adenovirus because these compounds are reported to have antimalarial (MacKinnon et al., 1997), anti-HIV (http://home.ncifcrf.gov/mtdp/Catalog/compounds/309912.html), anti-insect (Nathan et al., 2005), and anti-cancer (Uddin et al., 2007) activities. However, none of the compounds tested exhibited significant inhibition of these viruses, although gedunin did slightly delay the propagation of vaccinia virus, adenovirus and VSV. The structural features of these compounds may be a determinant of specificity since only 14 of the 41 gedunin-like limonoids that were screened demonstrated inhibitory activity to Ebolavirus and since 7-deacetoxy-7-hydroxygedunin and 7-deacetoxy-7-oxogeduin had been identified as anti-HIV compounds but the other gedunin-derivatives had not (http://www.stjuderesearch.org/guy/data/parasite_bioactives_screen/MAL_3D7/Results/87.html). These data suggest that gedunin-like limonoids have potential as general antivirals and further screening of these compounds using other microbial assays may be of value.

The mechanisms by which gedunin and its derivatives inhibit Ebolavirus remain unknown; it is not clear whether they interact with host cell components or with Ebolavirus proteins and/or genomes. Since it was previously reported that gedunin and its derivatives express anti-cancer activities via degradation of Hsp90 and/or its substrates (Hieronymus et al., 2006) and DNA and RNA virus propagation can be delayed by Hsp90 inhibitors (Basha et al., 2005; Burch & Weller, 2005; Chase et al., 2008; Connor et al., 2007; Li et al., 2004; Ujino et al., 2009), it seemed possible that Hsp90 inhibitory activities may contribute to the anti-Ebolavirus activities of gedunin and its derivatives. Therefore, the anti-Ebolavirus activities of Hsp90 inhibitors was examined.

Although the four Hsp90 inhibitors tested did not inhibit Ebolavirus GP-dependent virus binding/entry to the same extent as the gedunin-like compounds, they reduced protein expression from the Ebolavirus minireplicon and two of the four Hsp90 inhibitors also delayed EbolaΔVP30-GFP replication. Since structurally different compounds have been found with Hsp90 inhibitors to limit reporter protein expression from the Ebolavirus minireplicon, it has been suggested that this inhibition may be due not to structural binding to Ebolavirus directly, but to Hsp90 inhibitory activities. However, mechanisms other than Hsp90 inhibition should be considered since deacetylegedunin, which shows anti-cancer activity via degradation of Hsp90 substrates (Hieronymus et al., 2006) was one of the 41 gedunin-like limonoids tested, yet it did not show any anti-Ebolavirus activity.

CCT 018159 displayed about a 30% reduction in Ebolavirus GP-dependent virus infection, unlike GM, 17-AAG, and AEG 3482. It has been reported that CCT 018159 binds to the ATP site located in the N-terminal domain of Hsp90; however, GM and 17-AAG also bind at this location via the same main amino acids (Cheung et al., 2005; Stebbins et al., 1997). Therefore, why only CCT 018159 showed inhibitory activity to Ebolavirus binding/entry is unclear. The data suggest that blockage of virus binding/entry mediated by Ebolavirus GP may not rely upon Hsp90 and/or its substrate/signaling.

Inhibitors of S-adenosylhomocysteine hydrolase (SAH) have also shown anti-Ebolavirus activity in vitro and in vivo (Huggins et al., 1999). Their $IC_{50}$ values range from 2 to 64 µM, which is higher than gedunin and its derivatives in this study. Although it is not strictly valid to directly compare these values, since they were determined using different assays, $IC_{50}$ values are not assay-dependent or Ebolavirus strain-dependent (Huggins et al., 1999). Therefore, the anti-Ebolavirus efficacies of gedunin and its derivatives are at least equal to those of SAH inhibitors.

Ebolavirus outbreaks have occurred almost every year in the $21^{st}$ century in Africa, infecting and killing numerous individuals. Moreover, many people and pigs were infected with Ebolavirus Reston in the Philippines in 2008-2009. These reports reflect that Ebolavirus infection is an ongoing threat and that therapeutic and prophylactic options are desperately needed. Gedunin-like limonoids are found in traditional medicine in tropical and subtropical regions, where they have been used to treat humans. The compounds identified in the present screen thus show promise as anti-Ebolavirus agents, and in vivo confirmation of their anti-Ebolavirus activities is warranted.

SUMMARY

A library of compounds (Known Bioactive Library (KB01)) at the Keck-UWCCC Small Molecule Screening Facility, University of Wisconsin-Madison, Madison, Wis.) was screened to determine whether any of the compounds interfered with Ebolavirus replication and infection. The compounds were screened using biologically contained Ebolavirus expressing GFP protein (EbolaΔVP30-GFP virus). In particular, gedunin and gedunin-like compounds were screened. Those compounds are found in extracts of plants from the Meliaceae (Mahogany) family and have been used in traditional medicine for the treatment of fevers in tropical American and in West and East Africa. They are known for their antimalarial, anti-HIV, anti-cancer, and anti-insect activities. Gedunin is an inhibitor of Hsp90.

Through the use of EbolaΔVP30-GFP virus and a follow-up screen, 15 gedunin and gedunin-like compounds were identified that reduced GFP expression by at least 75%.

REFERENCES

Basha et al., *Antivir. Chem. Chemother.*, 16:135 (2005).
Bergmann et al., *J. Cell Biol.*, 107:1707 (1988).
Boehmann et al., *Virology*, 332:406 (2005).
Bray & Paragas, *Antiviral Res.*, 54:1 (2002).
Bray et al., *Antiviral Res.*, 45:135 (2000).
Bray et al., *J. Infect. Dis.*, 178:651 (1998).
Bray et al., *Phytotherapy Research*, 4:29 (1990).
Bukreyev et al., *J. Virol.*, 80:2267 (2006).
Burch & Weller, *J. Virol.*, 79:10740 (2005).
Campbell et al., *J. Virol.*, 71:4425 (1997).
Chan et al., *Cell*, 106:117 (2001).
Chandran et al., *Science*, 308:1643 (2005).
Chase et al., *Virology*, 377:431 (2008).
Cheung et al., *Bioorq. Med. Chem. Lett.*, 15:3338 (2005).
Chong et al., *J. Virol.*, 67:407 (1993).
Connor et al., *Virology*, 362:109 (2007).
Delchambre et al., *EMBO. J.*, 8:2653 (1989).
Dessen et al., *EMBO J.*, 19:4228 (2000).
Ebihara et al., *PloS Pathogens*, 2:0705 (2006).
Ebihara et al., *PLoS. Pathoq.*, 2:e73 (2006).
Feldmann et al., 1996. Marburg and Ebola viruses. P. 1-52. In Maramorosch, K., Murphy, F. A. and Shatkin, A. J. (ed.), Advances in virus research 47, Academic Press.
Feldmann et al., in Virus Taxonomy: Eighth Report of the International Committee of Taxonomy of Viruses, eds. Fauquet, C., Mayo, M. A., Desselberger, U., & Ball, L. A. (Elsevier, London), pp. 645 (2004).
Gay et al., *Virology*, 247:160 (1998).
Geisbert et al., *J. Infect. Dis.*, 193:1650 (2006).
Geisbert et al., *Virus Res.*, 39:129 (1995).
Gheysen et al., *Cell*, 59:103 (1989).
Giddings et al., *Virology*, 248:108 (1998).
Ginocchio et al., *Cell*, 76:717 (1994).
Girault et al., *Anal. Biochem.*, 182:193 (1989).
Gomez-Puertas et al., *J. Virol.*, 74:11538 (2000).
Groseth et al., *J. Virol.*, 79:4425 (2005).
Gupta et al., *J. Virol.*, 75:4649 (2001).
Halfmann et al., In submission (2007).
Halfmann et al., *Proc. Natl. Acad. Sci. USA*, 105:1129 (2008).
Hartman et al., *J. Virol.*, 80:6430 (2006).
Harty et al., *J. Virol.*, 73:2921 (1999).
Harty et al., *Proc. Natl. Acad. Sci. U.S.A.*, 97:13871 (2000).
Hieronymus et al., *Cancer Cell*, 10:321 (2006).
Huang et al., *Mol. Cell*, 10:307 (2002).
Huggins et al., *J. Infect. Dis.*, 179:S240 (1999).
Ignatyeye et al., *J. Biotechnol.*, 44:111 (1996).
Ito et al., *J. Virol.*, 73:8907 (1999).
Ito et al., *J. Virol.*, 75:1576 (2001).
Jasenosky et al., *J. Virol.*, 75:5205 (2001).
Jayakar et al., *J. Virol.*, 74:9818 (2000).
Jin et al., *EMBO. J.*, 16:1236 (1997).
Johnson et al., *Lancet*, 1:569 (1977).
Johnson et al., *Virol. J.* 3:31 (2006).
Jones et al., *Nat. Med.*, 11:786 (2005).
Joshi et al., *J. Virol.*, 74:10260 (2000).
Justice et al., *J. Virol.*, 69:3156 (1995).
Kobasa et al., *J. Virol.*, 71:6706 (1997).
Kuwae et al., *J. Biol. Chem.*, 276:32230 (2001).
Li et al., *Antimicrob. Agents Chemother.* 48:867 (2004).
Li et al., *J. Virol.*, 67:4415 (1993).
Licata et al., *J. Virol.*, 78:7344 (2004).
Lupton et al., *Lancet*, 2:1294 (1980).
MacKinnon et al., *J. Nat. Prod.*, 60:336 (1997).
Manicassamy et al., *J. Virol.*, 79:4793 (2005).
Marzi et al., *Virology*, 352:345 (2006).
McCarthy et al., *J. Virol. Methods*, 137:115 (2006).
Mebatsion et al., *Cell*, 84, 941 (1996).
Mebatsion et al., *J. Virol.* 73:242 (1999).
Mellquist-Riemenschneider et al., *Virus Res.*, 92:187 (2003).
Mitnaul et al., *J. Virol.*, 70:873 (1996).
Modrof et al., *J. Biol. Chem.*, 277:33099 (2002).
Modrof et al., *J. Virol.*, 77:3334 (2003).
Muhlberger et al., *J. Virol.*, 73:2333 (1999).
Murali-Krishna et al., *Immunity*, 8:177 (1998).
Nathan et al., *Acta Trop.*, 96:47 (2005).
Neumann et al., *J. Virol.*, 76:406 (2002).
Neumann et al., *J. Virol.*, 79:10300 (2005).
Neumann et al., *Proc. Natl. Acad. Sci. USA*, 96:9345 (1999).
Niwa et al., *Gene*, 108:193 (1991).
Noda et al., *J. Virol.*, 76:4855 (2002).
Olinger et al., *J. Virol.*, 79:14189 (2005).
Panchal et al., *Proc. Natl. Acad. Sci. USA*, 100:15936 (2003).
Pattnaik et al., *Proc. Natl. Acad. Sci. USA*, 88:1379 (1991).
Peters et al., 1995. *Filoviridae*: Marburg and Ebola viruses. P. 1161-1176. In B. N. Fields, D. M. Knipe, and P. M. Howley (ed.), Fields virology, Lippincott-Raven Publishers, Philadelphia, Pa.
Reed et al., *Vaccine*, 25:1923 (2007).
Ruigrok et al., *J. Mol. Biol.*, 300:103 (2000).
Sanchez et al., in Fields Virology, eds. Knipe, D. M., Howley, P. M., Griffin, D. E., Martin, M. A., Lamb, R. A., Roizman, B., & Straus, S. E. (Lippincott, Williams & Wilkins, Philadelphia), pp. 1409 (2007).
Sanchez et al., *Virus Res.*, 29:215 (1993).
Sandefur et al., *J. Virol.*, 72:2723 (1998).
Schnell et al., *EMBO. J.*, 17:1289 (1998).
Shimojima et al., *J. Virol.*, 80:10109 (2006).
Simmons et al., *Virology*, 318:224 (2004).
Stebbins et al, *Cell*, 89:239 (1997).
Sullivan et al., *Nature*, 408:681 (2000).

Takada et al., *J. Virol.*, 75:2324 (2001).
Takada et al., *Proc. Natl. Acad. Sci. U.S.A.*, 94:14764 (1997).
Takada et al., *Vaccine*, 25:993 (2007).
Takada, *J. Virol.*, 77:1069 (2003).
Theriault et al., *Arch. Virol. Suppl.*, 19:157 (2005).
Timmins et al., *Virology*, 283:1 (2001).
Tran Van Nhieu et al., *EMBO. J.*, 18:3249 (1999).
Uddin et al., *Phytother. Res.*, 21:757 (2007).
Ujino et al., *J. Biol. Chem.*, 284:6841 (2009).
Volchkov et al., *Science*, 291:1965 (2001).
Warfield et al., *J. Immunol.*, 175:1184 (2005).
Warfield et al., *Pro. Natl. Acad. Sci. USA*, 100:15889 (2003).
Warfield et al., *Vaccine*, 22:3495 (2004).
Watanabe et al., *J. Infect. Dis.*, 196:S284 (2007).
Wool-Lewis et al., *J. Virol.*, 72:155 1998).
Yonezawa et al., *J. Virol.*, 79:918 (2005).
Zhang et al., *Virology*, 225:255 (1996).
Zhou et al., *Proc. Natl. Acad. Sci. USA*, 96:10176 (1999).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to inhibit or treat filovirus infection in a mammal, comprising administering to the mammal an effective amount of a compound of formula (IX) or (X), wherein formula (IX) is:

(IX)

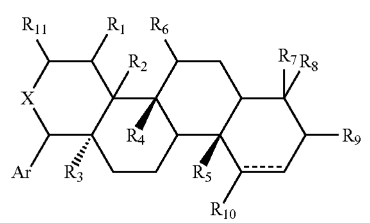

wherein

Ar is a furan;

X is —O;

a dashed line represents either the presence or absence of a bond;

$R_1$ and $R_2$ taken together form an epoxide ring, aziridine ring, cyclopropyl ring, or a bond of a carbon-carbon double bond;

$R_3$ is hydrogen; methyl; ethyl; or propyl;

$R_4$ is hydrogen; methyl; ethyl; or propyl;

$R_5$ is hydrogen; methyl; ethyl; or propyl;

$R_6$ is hydrogen; hydroxy; oxo (═O); acetyl protected hydroxyl; methyl; ethyl; or propyl;

$R_7$ is hydrogen; hydroxy; methyl; ethyl; or propyl;

$R_8$ is hydrogen; hydroxy; methyl; ethyl; or propyl;

$R_9$ is hydrogen; hydroxy; oxo (═O); acetyl protected hydroxyl; methyl; ethyl; or propyl;

$R_{10}$ is hydrogen; hydoxy; oxo (═O); acetyl protected hydroxyl; methyl; ethyl; propyl; or epoxy;

$R_{11}$ is hydrogen, halo, hydroxy, or a carbonyl;

or a pharmaceutically acceptable salt, stereoisomer, or tautomer; and wherein formula (X) is:

(X)

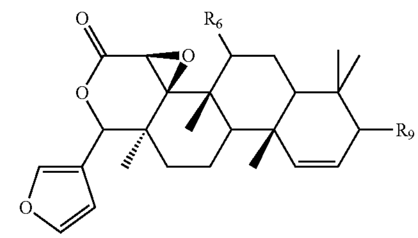

wherein $R_6$ is hydrogen; hydroxy; oxo (═O); or acetyl-protected hydroxyl; and $R_9$ is hydrogen; hydroxy; oxo (═O); or acetyl-protected hydroxyl, or a pharmaceutically acceptable salt, stereoisomer, or tautomer.

2. The method of claim 1 wherein the mammal is a human.

3. A method to inhibit or treat filovirus infection in a mammal, comprising administering to the mammal an effective amount of 7-deacetoxy-3-deacetyl-7-oxokhivorin, 1,2alpha-epoxy-7-deacetoxy-7-oxodihxdrogedunin, epoxygedunin, 1,3-dideacetyl-7-deacetoxy-7-oxokhivorin, gedunin, gedunol, dihydrogedunin, 3beta-acetoxydeoxodihydrogedunin, 3alpha-hydroxydeoxodihydrogedunin, deacetoxy-7-oxogedunin, 3beta-hydroxydeoxodihydrogedunin, 1,2alpha-epoxydeacetoxydihydrogedunin, 3beta-hydroxydeoxydesacetoxy-7-oxogedunin, tridesacetoxykhivorin, 1,3-dideacetylkhivorin, heudelottin C, deacetylgedunin, deacetoxy-7-oxisogedunin, 1,7-dideacetoxy-1,7-dioxokhivorin, isogedunin, or 6-acetoxyangolensic acid methyl ester, or any combination thereof.

4. The method of claim 1 wherein the agent is orally administered.

5. The method of claim 1 wherein the agent is intravenously administered.

6. The method of claim 1 wherein the agent is subcutaneously administered.

7. The method of claim 3 wherein the mammal is a human.

8. The method of claim 3 wherein the agent is orally administered.

9. The method of claim 3 wherein the effective amount is intravenously administered.

10. The method of claim 3 wherein the effective amount is subcutaneously administered.

11. The method of claim 1 wherein $R_3$, $R_4$, $R_5$, $R_7$, or $R_8$ independently is hydrogen or methyl.

12. The method of claim 3 wherein 7-deacetoxy-3-deacetyl-7-oxokhivorin, 1,2alpha-epoxy-7-deacetoxy-7-oxodihxdrogedunin, epoxygedunin, 1,3-dideacetyl-7-deacetoxy-7-oxokhivorin, gedunin, gedunol, dihydrogedunin, 3beta-acetoxydeoxodihydrogedunin, 3alpha-hydroxydeoxodihydrogedunin, deacetoxy-7-oxogedunin, 3beta-hydroxydeoxodihydrogedunin, 1,2alpha-epoxydeacetoxydihydrogedunin, 3beta-hydroxydeoxydesacetoxy-7-oxogedunin, tridesacetoxykhivorin, 1,3-dideacetylkhivorin, or heudelottin C is administered.

13. The method of claim 3 wherein epoxygedunin, 1,3-dideacetyl-7-deacetoxy-7-oxokhivorin, gedunin, gedunol, dihydrogedunin, 3beta-acetoxydeoxodihydrogedunin, 3alpha-hydroxydeoxodihydrogedunin, deacetoxy-7-oxogedunin, 3beta-hydroxydeoxodihydrogedunin, 1,2alpha-epoxydeacetoxydihydrogedunin, 3beta-hydroxydeoxydesacetoxy-7-oxogedunin, 1,3-dideacetylkhivorin, or heudelottin is administered.

14. The method of claim 3 wherein epoxygedunin, 1,3-dideacetyl-7-deacetoxy-7-oxokhivorin, gedunin, or 7-deacetoxy-3-deacetyl-7-oxokhivorin is administered.

15. The method of claim 1 wherein $R_6$ or $R_9$ independently is hydrogen, hydroxyl, oxo (=O), or acetyl-protected hydroxyl.

16. The method of claim 1 wherein $R_{10}$ is hydrogen, hydroxyl or acetyl.

* * * * *